US00RE49435E

(19) United States
(12) Reissued Patent
DeSander et al.

(10) Patent Number: US RE49,435 E
(45) Date of Reissued Patent: Feb. 28, 2023

(54) GLYCAN-INTERACTING COMPOUNDS AND METHODS OF USE

(71) Applicant: Seagen Inc., Bothell, WA (US)

(72) Inventors: Julie DeSander, Arlington, MA (US); Jeffrey Behrens, Newton (TV)

(73) Assignee: Seagen Inc., Bothell, WA (US)

(21) Appl. No.: 16/776,188

(22) Filed: Jan. 29, 2020

Related U.S. Patent Documents

Reissue of:
(64) Patent No.: 9,879,087
Issued: Jan. 30, 2018
Appl. No.: 14/987,432
Filed: Jan. 4, 2016

U.S. Applications:
(63) Continuation-in-part of application No. PCT/US2015/060287, filed on Nov. 12, 2015.

(60) Provisional application No. 62/187,587, filed on Jul. 1, 2015, provisional application No. 62/173,560, filed on Jun. 10, 2015, provisional application No. 62/145,214, filed on Apr. 9, 2015, provisional application No. 62/102,527, filed on Jan. 12, 2015, provisional application No. 62/078,610, filed on Nov. 12, 2014.

(51) Int. Cl.

| | |
|---|---|
| ***A61K 39/00*** | (2006.01) |
| ***C07K 16/30*** | (2006.01) |
| ***A61K 47/68*** | (2017.01) |
| ***A61K 9/00*** | (2006.01) |
| ***A61K 39/395*** | (2006.01) |
| ***A61K 47/02*** | (2006.01) |
| ***C07K 16/44*** | (2006.01) |
| *A61K 47/12* | (2006.01) |

(52) U.S. Cl.
CPC ..... *C07K 16/30* (2013.01); *A61K 9/0019* (2013.01); *A61K 39/39591* (2013.01); *A61K 47/02* (2013.01); *A61K 47/6803* (2017.08); *A61K 47/6851* (2017.08); *A61K 47/6897* (2017.08); *C07K 16/44* (2013.01); *A61K 39/39558* (2013.01); *A61K 47/12* (2013.01); *A61K 2039/505* (2013.01); *C07K 2317/33* (2013.01); *C07K 2317/622* (2013.01); *C07K 2317/73* (2013.01); *C07K 2317/732* (2013.01); *C07K 2317/92* (2013.01)

(58) Field of Classification Search
CPC ..... A61K 47/6897; A61K 39/39591; A61K 47/6803; A61K 47/02; A61K 47/6851; A61K 9/0019; C07K 16/44; C07K 16/30
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,444,887 | A | 4/1984 | Hoffmann |
| 4,474,893 | A | 10/1984 | Reading |
| 4,485,045 | A | 11/1984 | Regen |
| 4,496,689 | A | 1/1985 | Mitra |
| 4,544,545 | A | 10/1985 | Ryan et al. |
| 4,640,835 | A | 2/1987 | Shimizu et al. |
| 4,670,417 | A | 6/1987 | Iwasaki et al. |
| 4,695,198 | A | 9/1987 | Goodacre et al. |
| 4,714,681 | A | 12/1987 | Reading |
| 4,716,111 | A | 12/1987 | Osband et al. |
| 4,791,192 | A | 12/1988 | Nakagawa et al. |
| 4,816,397 | A | 3/1989 | Boss et al. |
| 4,816,567 | A | 3/1989 | Cabilly et al. |
| 4,900,727 | A | 2/1990 | Kattige |
| 4,925,648 | A | 5/1990 | Hansen et al. |
| 4,946,778 | A | 8/1990 | Ladner et al. |
| 4,975,369 | A | 12/1990 | Beavers et al. |
| 4,978,745 | A | 12/1990 | Schoemaker et al. |
| 5,013,556 | A | 5/1991 | Woodle et al. |
| 5,045,532 | A | 9/1991 | Della Valle et al. |
| 5,059,680 | A | 10/1991 | Davis et al. |
| 5,091,513 | A | 2/1992 | Huston et al. |
| 5,158,886 | A | 10/1992 | Kawamura et al. |
| 5,208,020 | A | 5/1993 | Chari et al. |
| 5,225,539 | A | 7/1993 | Winter |
| 5,258,498 | A | 11/1993 | Huston et al. |

(Continued)

FOREIGN PATENT DOCUMENTS

| | | |
|---|---|---|
| EP | 0239400 | 4/1989 |
| EP | 0316818 | 5/1989 |

(Continued)

OTHER PUBLICATIONS

Giusti et al., "Somatic diversification of S107 from an antiphosphocholine to an anti-DNA autoantibody is due to a single base change in its heavy chain variable region," Proc. Natl. Acad. Sci. USA, 84(9), pp. 2926-2930 (May 1987).

(Continued)

*Primary Examiner* — Sharon Turner
*Assistant Examiner* — Padmashri Ponnaluri
(74) *Attorney, Agent, or Firm* — Morrison & Foerster LLP

(57) ABSTRACT

The present invention provides glycan-interacting antibodies and methods for producing glycan-interacting antibodies useful in the treatment and prevention of human disease, including cancer. Such glycan-interacting antibodies include monoclonal antibodies, derivatives, and fragments thereof as well as compositions and kits comprising them. Further provided are methods of using glycan-interacting antibodies to target cells and treat disease.

21 Claims, 6 Drawing Sheets

Specification includes a Sequence Listing.

(56) References Cited

U.S. PATENT DOCUMENTS 5,403,484 A 4/1995 Ladner et al.
5,413,923 A 5/1995 Kucherlapati et al.
5,427,908 A 6/1995 Dower et al.
5,475,092 A 12/1995 Chari et al.
5,516,637 A 5/1996 Huang et al.
5,530,101 A 6/1996 Queen et al.
5,565,332 A 10/1996 Hoogenboom et al.
5,571,698 A 11/1996 Ladner et al.
5,573,920 A 11/1996 Randle
5,580,717 A 12/1996 Dower et al.
5,585,089 A 12/1996 Queen et al.
5,585,499 A 12/1996 Chari et al.
5,601,819 A 2/1997 Wong et al.
5,625,126 A 4/1997 Lonberg et al.
5,633,425 A 5/1997 Lonberg et al.
5,658,727 A 8/1997 Barbas et al.
5,693,761 A 12/1997 Queen et al.
5,693,762 A 12/1997 Queen et al.
5,698,426 A 12/1997 Huse
5,710,038 A 1/1998 Mes-Masson et al.
5,733,743 A 3/1998 Johnson et al.
5,733,920 A 3/1998 Mansuri
5,750,753 A 5/1998 Kimae et al.
5,780,225 A 7/1998 Wigler et al.
5,786,464 A 7/1998 Seed et al.
5,807,715 A 9/1998 Morrison et al.
5,811,510 A 9/1998 Papisov
5,821,047 A 10/1998 Garrard et al.
5,846,545 A 12/1998 Chari et al.
5,849,733 A 12/1998 Kim
5,863,990 A 1/1999 Papisov
5,902,725 A 5/1999 Robbins et al.
5,919,652 A 7/1999 Pang et al.
5,932,448 A 8/1999 Tso et al.
5,939,598 A 8/1999 Kucherlapati et al.
5,951,983 A 9/1999 Bazin et al.
5,958,398 A 9/1999 Papisov
5,969,108 A 10/1999 McCafferty et al.
6,075,181 A 6/2000 Kucherlapati et al.
6,114,148 A 9/2000 Seed et al.
6,114,598 A 9/2000 Kucherlapati et al.
6,180,370 B1 1/2001 Queen et al.
6,300,129 B1 10/2001 Lonberg et al.
6,348,584 B1 2/2002 Hodgson et al.
6,673,901 B2 1/2004 Koide
6,852,533 B1 2/2005 Rafii et al.
6,872,868 B1 3/2005 Wagner et al.
6,936,612 B2 8/2005 Barvian
7,119,200 B2 10/2006 Guzi
7,208,489 B2 4/2007 Barvian
7,345,171 B2 3/2008 Beylin
7,456,168 B2 11/2008 Barvian
7,569,390 B1 8/2009 Eric et al.
7,608,453 B2 10/2009 Cattaneo et al.
7,682,794 B2 3/2010 Varki et al.
7,749,225 B2 7/2010 Chappuis et al.
7,820,797 B2 10/2010 Boons
7,855,211 B2 12/2010 Coates
7,863,278 B2 1/2011 Beylin
7,884,054 B2 2/2011 Zhou et al.
7,897,347 B2 3/2011 Tse et al.
7,994,100 B2 8/2011 Ventresca et al.
8,084,219 B2 12/2011 Varki et al.
823,244 A1 7/2012 Varki et al.
8,232,448 B2 7/2012 Varki et al.
8,298,773 B2 10/2012 Vuskovic et al.
8,399,625 B1 3/2013 Escher
8,440,798 B2 5/2013 Clausen et al.
8,506,966 B2 8/2013 Podda et al.
8,524,214 B2 9/2013 Yurkovetskiy
8,541,231 B2 9/2013 Varki et al.
8,685,383 B2 4/2014 Yurkovetskiy
8,685,980 B2 4/2014 Besong
8,808,679 B2 8/2014 Yurkovetskiy
8,980,311 B2 3/2015 Ingale et al.
9,193,732 B2 11/2015 Calienni
9,254,339 B2 2/2016 Yurkovetskiy
9,273,142 B2 3/2016 Ghaderi et al.
9,423,401 B2 8/2016 Varki
9,555,112 B2 1/2017 Bodyak et al.
9,718,888 B2 8/2017 Magliery
9,879,087 B2 1/2018 DeSander et al.
11,028,181 B2 6/2021 Eavarone et al.
2002/0012660 A1 1/2002 Colman et al.
2002/0192231 A1 12/2002 Zhu et al.
2003/0104402 A1 6/2003 Zauderer et al.
2003/0108548 A1 6/2003 Bluestone et al.
2003/0212027 A1 11/2003 Barbera-Guillem et al.
2003/0235850 A1 12/2003 Cattaneo et al.
2004/0047891 A1 3/2004 Glozman et al.
2004/0115740 A1 6/2004 Benson
2005/0084903 A1 4/2005 Kim
2005/0272107 A1 12/2005 Rabbitts et al.
2005/0276800 A1 12/2005 Rabbitts et al.
2005/0288492 A1 12/2005 Rabbitts et al.
2006/0034834 A1 2/2006 Marasco et al.
2007/0048314 A1 3/2007 Dai et al.
2007/0059769 A1 3/2007 Blixt et al.
2007/0089178 A1 4/2007 Zhu
2007/0116727 A1 5/2007 Hakomori et al.
2007/0265170 A1 11/2007 Blixt et al.
2007/0275409 A1 11/2007 Varki et al.
2008/0019968 A1 1/2008 Blixt et al.
2008/0166805 A1 7/2008 Varki et al.
2008/0193453 A1 8/2008 Monterio et al.
2008/0253963 A1 10/2008 Morin et al.
2008/0279847 A1 11/2008 Hong et al.
2009/0041783 A1 2/2009 Takayama et al.
2009/0099073 A1 4/2009 Rosen et al.
2009/0196916 A1 8/2009 Ingale
2009/0221803 A1 9/2009 Dall'Acqua et al.
2009/0280116 A1 11/2009 Smith et al.
2009/0280128 A1 11/2009 Kamogawa et al.
2009/0326203 A1 12/2009 Adams et al.
2010/0009424 A1 1/2010 Forde et al.
2010/0034825 A1 2/2010 Clausen et al.
2010/0075344 A1 3/2010 Vuskovic et al.
2010/0104572 A1 4/2010 Luria
2010/0143939 A1 6/2010 Rabbitts et al.
2010/0178292 A1 7/2010 Wang et al.
2010/0196983 A1 8/2010 Yang et al.
2010/0221770 A1 9/2010 Varki et al.
2010/0272707 A1 10/2010 Bay et al.
2010/0278818 A1 11/2010 Hubert-Haddad et al.
2010/0292095 A1 11/2010 Laukkanen et al.
2010/0293624 A1 11/2010 Varki et al.
2011/0081356 A1 4/2011 Tahara et al.
2011/0135570 A1 6/2011 Janatpour et al.
2011/0143373 A1 6/2011 Hirvonen et al.
2011/0177614 A1 7/2011 Varki et al.
2011/0195921 A1 8/2011 Varki et al.
2012/0027813 A1 2/2012 Podda et al.
2012/0039984 A1 2/2012 Boons et al.
2012/0045816 A1 2/2012 Ghaderi et al.
2012/0114652 A1 5/2012 Elvin et al.
2012/0142903 A1 6/2012 Varki et al.
2012/0164068 A1 6/2012 Hudson et al.
2012/0177664 A1 7/2012 Yokoseki et al.
2013/0011868 A1 1/2013 Hosaka et al.
2013/0017200 A1 1/2013 Scheer et al.
2013/0039991 A1 2/2013 Varki et al.
2013/0108624 A1 5/2013 Wang et al.
2013/0177579 A1 7/2013 Lin et al.
2013/0236486 A1 9/2013 Boons et al.
2014/0005069 A1 1/2014 Yang et al.
2014/0106449 A1 4/2014 June et al.
2014/0113979 A1 4/2014 Varki et al.
2014/0178365 A1 6/2014 Ghaderi et al.
2015/0110789 A1 4/2015 Liu et al.
2015/0314008 A1 11/2015 Yurkovetskiy
2015/0368349 A1 12/2015 Gonzalez et al.
2016/0022829 A1 1/2016 Yurkovetskiy
2016/0130356 A1 5/2016 DeSander et al.
2016/0168211 A1 6/2016 Ahmed et al.

(56) References Cited

U.S. PATENT DOCUMENTS

| | | | |
|---|---|---|---|
| 2016/0220696 | A1 | 8/2016 | Yurkovetskiy |
| 2017/0305950 | A1 | 10/2017 | Silva et al. |
| 2017/0306046 | A1 | 10/2017 | daSilva et al. |
| 2018/0037663 | A1 | 2/2018 | Magliery |
| 2018/0280504 | A1 | 10/2018 | Silva et al. |
| 2018/0327509 | A1 | 11/2018 | Eavarone et al. |
| 2019/0031780 | A1 | 1/2019 | Eavarone et al. |
| 2019/0276541 | A1 | 9/2019 | Eavarone et al. |
| 2020/0000932 | A1 | 1/2020 | Dransfield et al. |
| 2020/0041517 | A1 | 2/2020 | Eavarone et al. |
| 2020/0247902 | A1 | 8/2020 | Prendergast et al. |
| 2020/0276306 | A1 | 9/2020 | da Silva et al. |
| 2021/0011021 | A1 | 1/2021 | da Silva et al. |
| 2021/0017213 | A1 | 1/2021 | da Silva et al. |

FOREIGN PATENT DOCUMENTS

| | | | |
|---|---|---|---|
| EP | 0313244 | | 8/1990 |
| EP | 0404097 | | 10/1991 |
| EP | 0519596 | | 12/1992 |
| EP | 0316818 | B1 | 5/1993 |
| EP | 0592106 | | 4/1994 |
| EP | 0404097 | B1 | 9/1996 |
| EP | 2287202 | A1 | 2/2011 |
| EP | 2422811 | | 2/2012 |
| EP | 2565268 | A1 | 3/2013 |
| EP | 2703485 | | 3/2014 |
| EP | 3091032 | A1 | 11/2016 |
| WO | 1990002809 | | 3/1990 |
| WO | 1991000360 | | 1/1991 |
| WO | 1991009967 | | 7/1991 |
| WO | 1991010737 | | 7/1991 |
| WO | 1991010741 | | 7/1991 |
| WO | 1991019739 | A1 | 12/1991 |
| WO | 199201047 | | 1/1992 |
| WO | 1992/005793 | | 4/1992 |
| WO | 1992008802 | | 5/1992 |
| WO | 1992018619 | | 10/1992 |
| WO | 1993011161 | | 6/1993 |
| WO | 1993011236 | | 6/1993 |
| WO | 1993017715 | | 9/1993 |
| WO | 1995015982 | | 6/1995 |
| WO | 1995/020401 | | 8/1995 |
| WO | 1995015982 | A3 | 12/1995 |
| WO | 1996033735 | | 10/1996 |
| WO | 1996034096 | | 10/1996 |
| WO | 1998016654 | | 4/1998 |
| WO | 1998024893 | | 6/1998 |
| WO | 1998046645 | | 10/1998 |
| WO | 1998050433 | | 11/1998 |
| WO | 1998050433 | A3 | 2/1999 |
| WO | 1999/014353 | | 3/1999 |
| WO | 1998046645 | A3 | 4/1999 |
| WO | 2000/023573 | | 4/2000 |
| WO | 2000/054057 | | 9/2000 |
| WO | 2011/003896 | | 1/2001 |
| WO | 2001/043778 | | 6/2001 |
| WO | 2001040276 | | 6/2001 |
| WO | 2002/035237 | | 5/2002 |
| WO | 2002/077029 | | 10/2002 |
| WO | 2002/086096 | | 10/2002 |
| WO | 2002/086505 | | 10/2002 |
| WO | 2002/088334 | | 11/2002 |
| WO | 2002/088351 | | 11/2002 |
| WO | 2003/008451 | | 1/2003 |
| WO | 2003/014960 | | 2/2003 |
| WO | 2003016329 | A2 | 2/2003 |
| WO | 2003/040185 | | 5/2003 |
| WO | 2003/062415 | | 7/2003 |
| WO | 2003/077945 | | 9/2003 |
| WO | WO2003/086276 | A2 | 10/2003 |
| WO | 2003/095641 | | 11/2003 |
| WO | 2003/097697 | | 11/2003 |
| WO | 2004/046185 | | 6/2004 |
| WO | 2004/046186 | | 6/2004 |
| WO | 2004/046187 | | 6/2004 |
| WO | 2004/046188 | | 6/2004 |
| WO | 2004/046189 | | 6/2004 |
| WO | 2004/046192 | | 6/2004 |
| WO | 2003062415 | A3 | 6/2004 |
| WO | 2004/099775 | | 11/2004 |
| WO | 2003097697 | A3 | 12/2004 |
| WO | 2005/010485 | | 2/2005 |
| WO | 2005/033303 | | 4/2005 |
| WO | 2003086276 | A3 | 4/2005 |
| WO | 2005/088310 | | 9/2005 |
| WO | 2006002382 | A2 | 1/2006 |
| WO | 2006002382 | A3 | 10/2006 |
| WO | 2006/133356 | | 12/2006 |
| WO | 2006/1333356 | | 12/2006 |
| WO | 2007/059298 | | 5/2007 |
| WO | 2008040362 | A2 | 4/2008 |
| WO | WO2008/070363 | A2 | 6/2008 |
| WO | 2009/018438 | | 2/2009 |
| WO | 2008040362 | A3 | 3/2009 |
| WO | 2009035494 | A2 | 3/2009 |
| WO | 2009035494 | A3 | 4/2009 |
| WO | 2009060129 | A1 | 5/2009 |
| WO | WO2009/091826 | A2 | 7/2009 |
| WO | 2010/004432 | | 1/2010 |
| WO | 2010030666 | | 3/2010 |
| WO | 2010/065818 | | 6/2010 |
| WO | 2013151649 | A1 | 10/2010 |
| WO | 2011/003896 | | 1/2011 |
| WO | 2011/041093 | | 4/2011 |
| WO | 2011/088385 | | 7/2011 |
| WO | 2011089004 | A1 | 7/2011 |
| WO | 2012/007167 | | 1/2012 |
| WO | 2012009474 | A1 | 1/2012 |
| WO | 2012/048332 | | 4/2012 |
| WO | 2012/079000 | | 6/2012 |
| WO | 2012094627 | A2 | 7/2012 |
| WO | 2012106465 | A2 | 8/2012 |
| WO | 2013/023251 | | 2/2013 |
| WO | 2013/033420 | | 3/2013 |
| WO | 2013/040557 | | 3/2013 |
| WO | 2013/055404 | | 4/2013 |
| WO | 2013/074916 | | 5/2013 |
| WO | 2013/092001 | | 6/2013 |
| WO | 2013/126712 | | 8/2013 |
| WO | 2013/138795 | | 9/2013 |
| WO | 2013151649 | A1 | 10/2013 |
| WO | 2014/028560 | | 2/2014 |
| WO | 2014/030780 | | 2/2014 |
| WO | 2014/039513 | | 3/2014 |
| WO | 2014/055771 | | 4/2014 |
| WO | 2014/106639 | | 7/2014 |
| WO | 2014105810 | A1 | 7/2014 |
| WO | 2014/144357 | | 9/2014 |
| WO | 2014/144573 | | 9/2014 |
| WO | 2015048748 | A1 | 4/2015 |
| WO | 2015054600 | A2 | 4/2015 |
| WO | 2015134488 | A1 | 9/2015 |
| WO | 2015159076 | A1 | 10/2015 |
| WO | 2016033284 | A1 | 3/2016 |
| WO | 2016057916 | A1 | 4/2016 |
| WO | 2016077526 | A1 | 5/2016 |
| WO | 2016090034 | A2 | 6/2016 |
| WO | 2016149368 | A1 | 9/2016 |
| WO | 2016201240 | A1 | 12/2016 |
| WO | 2017083582 | A1 | 5/2017 |
| WO | 2018094143 | A1 | 5/2018 |
| WO | 2018094144 | A1 | 5/2018 |

OTHER PUBLICATIONS

Glavey, SV., "The cancer glycome: carbohydrates as mediators of metastasis", Blood Rev., 29(4), pp. 269-279 (2015).

Gussow et al., "Humanization of monoclonal antibodies," Methods in Enzymology, 203, pp. 99-121 (1991).

Hakomori, S., "Tumor Malignancy Defined by Aberrant Glycosylation and Sphingo(glyco)lipid Metabolism," Cancer Research, 56, pp. 5309-5318, Dec. 1, 1996.

(56) References Cited

OTHER PUBLICATIONS

Hakomori, S., "Tumor-associated carbohydrate antigens defining tumor malignancy: basis for development of anti-cancer vaccines", Adv Exp Med Biol 491, pp. 369-402 (2001).
Han et al., "A2780 human ovarian cancer cells with acquired paclitaxel resistance display cancer stem cell properties," Oncology Letters 6; pp. 1295-1298 (2013).
Hauselmann, I., "Altered Tumor-Cell Glycosylation Promotes Metastasis", Front. Oncol., 4, p. 28 (2014).
Hawkins, D. M., "The Problem of Overfitting", Journal of Chemical Information and Computer Sciences, 44(1), pp. 1-12 (2003).
Henry et al., "A prostate-specific membrane antigen-targeted monoclonal antibody-chemotherapeutic conjugate designed for the treatment of prostate cancer," Cancer Res., 64, pp. 7995-8001 (Nov. 1, 2004).
Hinrichs , M., "Antibody Drug Conjugates: Nonclinical Safety Considerations", AAPS J. 17, 1055-1064 (2015).
Hirakawa et al., "Novel Anti-carbohydrate Antibodies Reveal the Cooperative Function of Sulfated N- andO-Glycans in Lymphocyte Homing", Journal of Biological Chemistry, vol. 285, No. 52, 7,pp. 40864-40878 (Oct. 2010).
Hofmann et al., "COSMC knockdown mediated aberrant O-glycosylation promotes oncogenic properties in pancreatic cancer", Mol. Cancer 14, 1-15 (2015).
Holm et al., "Functional mapping and single chain construction of the anti-cytokeratin 8 monoclonal antibody TS1," Mol. Immunol., 44 (6), pp. 1075-1084 (Feb. 2007).
Holmberg et al., "Vaccination with Theratope (STn-KLH) as treatment for breast cancer", Expert Rev Vaccines, 3, pp 655-663 (2004).
Ibrahim et al., "Humoral immune-response to naturally occurring STn in metastatic breast cancer patients (MBC pis) reated with STn-KLH vaccine", Journal of clinical oncology: official journal of the American Society of Clinical Oncology, 22, 2547, 2 pages (2004).
Imada et al., "Sialyl Tn antigen expression is associated with the prognosis of patients with advanced colorectal cancer", Hepatogastroenterology 46, pp. 208-214 (1999).
Imai et al. "Immunohistochemical expression of T, Tn and sialyl-Tn antigens and clinical outcome in human breast carcinoma", Anticancer Research, 21(2B), pp. 1327-1334 (2001).
International Preliminary Report on Patentability in related International Application No. PCT/US2011/021387, dated Jul. 26, 2012 (6 pages).
International Search Report in related International Application No. PCT/US2011/021387, dated Oct. 6, 2011 (5 pages).
International Search Report & Written Opinion dated Apr. 14, 2017 in International Application No. PCT/US2016/061427, dated Mar. 17, 2017 (13 pages).
International Search Report and Written Opinion dated Jun. 9, 2017 in Application No. PCT/US2017/015301, dated Jun. 9, 2017 (13 pages).
International Search Report and Written Opinion for corresponding PCT Application No. PCT/US2017/062155, dated Apr. 17, 2018 (12 pages).
International Search Report and Written Opinion for corresponding PCT Application No. PCT/US2017/062156 dated Feb. 20, 2018 (15 pages).
International Search Report and Written Opinion received in PCT/US2016/036907 dated Sep. 7, 2016 (9 pages).
International Search Report and Written Opinion received in PCT/US2018/020562 dated Jun. 27, 2018 (17 pages).
Ju et al., "The Cosmc connection to the Tn antigen in cancer", Cancer Biomark, 14, pp. 63-81 (2014).
Ju et al., "Tn and SialylTn antigens, Aberrant O-glycomics as Human Disease Markers", Proteomics Clin Appl, 7 pp. 618-631 (2013).
Julien et al., "Expression of Sialyl-Tn antigen in breast cancer cells transfected with the human CMP-Neu5Ac: GalNAc a2,6-sialyltransferase (ST6GalNAc 1) cDNA," Glycoconjugate Journal, 18, pp. 883-893 (2001).
Kim et al. "Combination of Cancer Immunotherapy with Clinically Available Drugs that can Block Immunosupressive Cells", Immunological Investigations, vol. 43, pp. 517-534 (Aug. 1, 2014).
Kim et al., "Implication of Aberrant Glycosylation in Cancer and Use of Lectin for Cancer Biomarker Discovery", Protein & Peptide Letters, 16(5), pp. 499-507 (2009).
Koda et al., "Application of Tyramide Signal Amplification for Detection of N-Glycolylneuraminic Acid in Human Hepatocellular Carcinoma", Int J Clin Oneal, 8(5), pp. 317-321 (2003).
Krishn et al., "Mucins and associated O-glycans based immunoprofile for stratification of colorectal polyps: clinical implication for improved colon surveillance", Oncolarget vol. 8, No. 4 pp. 7025-7038 (2017).
Kulkarni-Datar et al., "Ovarian tumor initiating cell populations persist following paclitaxel and carboplatin chemotherapy treatment in vivo". Cancer Lett, 339, pp. 237-246 (2013).
Li et al., "Prognostic value of cancer stem cell marker CD133 expression in pancreatic ductal adenocarcinoma (PDAC): a systematic review and meta-analysis", Int J Clin Exp Pathol, 8, pp. 12084-12092 (2015).
Liu et al., "PARP inhibitors in ovarian cancer: current status and future promise", Gynecol Oncol, 133, pp. 362-369 (2014).
Long et al., "CD133+ ovarian cancer stem-like cells promote non-stem cancer cell metastasis via CCL5 induced epithelial-mesenchymal transition", Oncotarget, 6, pp. 5846-5859 (2015).
Loureiro et al., "Challenges in Antibody Development against Tn and Sialyl-Tn Antigens", Biomolecules 5, pp. 1783-1809 (2015).
MacCallum et al., "Antibody-antigen interactions: contact analysis and binding site topography," J. Mol. Biol., 262(5), pp 732-745 (Oct. 11, 1996).
Marcos et al., "Role of the Human ST6GalNAc-I and ST6GalNAc-II in the Synthesis of the Cancer-Associated Sialyl-Tn Antigen," Cancer Research, 64, pp. 7050-7057, Oct. 1, 2004.
Mariuzza et al., "The structural basis of antigen-antibody recognition," Annu. Rev. Biophys. Biophys. Chem., 16, pp. 139-159 (1987).
Markman, M., "Rationale for maintenance or consolidation therapy in ovarian cancer", Clin Adv Hematol Oncol, 1, pp. 176-178 (2003).
McDevitt et al., "An alpha-particle emitting antibody ([213Bi]J591) for radioimmunotherapy of prostate cancer," Cancer Res., 60, pp. 6095-6100 (Nov. 1, 2000).
Meetze, et al., "The discovery and development of potent and specific anti-SialylTn antibodies for the treatment of solid tumors (479)", European Journal of Cancer, vol. 50, No. suppl 6, p. 156 (Nov. 1, 2014).
Munkley, J. "The Role of Sialyl-Tn in Cancer" International Journal of Molecular Sciences, vol. 17, pp. 1-9 (Feb. 24, 2016).
O'Boyle et al., "Immunization of Colorectal Cancer Patients with Modified Ovine Submaxillary Gland Mucin and Adjuvants Induces IgM and IgG Antibodies to Sialylated $Tn^{1}$", Cancer Resarch, 52, pp. 5663-5667 (1992).
Oppmann et al., "Novel pl9 Protein Engages IL-12p40 to Form a Cytokine, IL-23, with Biological Activities Similar as Well as Distinct from IL-12", Immunity, 13(5), pp. 715-725 (2000).
Ota et al., "Antitumor effect of monoclonal antibody-carboplatin conjugates in nude mice bearing human ovarian cancer cells," Int J Clin Oncol, 4, pp. 236-240 (1999).
Oza e al. Olaparib combined with chemotherapy for recurrent platinum-sensitive ovarian cancer: a randomised phase 2 trial. Lancet Oncol. 2015, 16(1):87-97; Abstract, p. 91, Fig 2 and its legend.
Ozaki et al., "Enhancement of metastatic ability by ectopic expression of ST6GalNAcl on a gastric cancer cell line in a mouse model", Clin Exp. Metastasis 29, pp. 229-238 (2012).
Ozga et al., "A systematic review of ovarian cancer and fear of recurrence", Palliat Support Care, 13(6), pp. 1771-1780 (2015).
Fujii, Y. et al., Specificities of human heterophilic Hanganutziu and Deicher (H-D) antibodies and avian antisera against H-D antigen-active glycosphingolipids. Mol. Immunol. vol. 19, 1982, pp. 87-94.
Higashi, et al. "Detection of Gangliosides as N-Glycolylneuraminic Acid-Specific Tumor- Associated Hanganutziu-Deicher Antigen in Human Retinoblastoma Cells." Jpn J Cancer Res,79(8):952-956 (1988).

(56) References Cited

OTHER PUBLICATIONS

Schauer, R. Adv. Carbohydr. Chem. Biochem. vol. 40, 1982, pp. 131-234.
Shaw, L. et al. (1988) "The biosynthesis of N-glycoloylneuraminic acid occurs by hydroxylation of the CMP-glycoside of N-acetylneuraminic acid," Biological Chemistry Hoppe-Seyler 369(6), 477-486.
Vazquez, A. M. et al., Generation of a murine monoclonal antibody specific for N-glycolylneuraminic acid-containing gangliosides that also recognizes sulfated glycolipids. Hybridoma vol. 14, 1995, pp. 551-556.
De León, J. et al. (2008) "Differential influence of the tumour-specific non-human sialic acid containing GM3 ganglioside on CD4+CD25? effector and naturally occurring CD4+CD25+ regulatory T cells function," International Immunology 20(4), 591-600.
Drake, P. M. et al. (2010) "Sweetening the Pot: Adding Glycosylation to the Biomarker Discovery Equation," Clinical Chemistry 56(2), 223-236.
Hara, S. et al. (1986) "Highly sensitive determination of N-acetyl- and N- glycolylneuraminic acids in human serum and urine and rat serum by reversed-phase liquid chromatography with fluorescence detection," Journal of chromatography A 377, 111-119.
Hong and Stanley, "Lec3 Chinese Hamster Ovary Mutants Lack UDP-N-Acetylglucosamine 2-Epimerase Activity Because of Mutations in the Epimerase Domain of the Gne Gene." J Biol Chem, 278 (52):53045-53054 (2003).
Kjeldsen, T. et al. (1988) "Preparation and Characterization of Monoclonal Antibodies Directed to the Tumor-associated O-linked Sialosyl-2?6 ?-N-Acetylgalactosaminyl (Sialosyl-Tn) Epitope," Cancer Research 48(8), 2214-2220.
Marquina, Gilda; H. Waki; L. E. Fernandez; K. Kon; A Carr; 0. Valiente; R. Perez; and S. Ando; "Gangliosides Expressed in Human Breast Cancer"; Cancer Research; Nov. 15, 1996; 56; pp. 5165-5171.
Martin et al. Abstract #4182, Blood, (Nov. 16, 2004) vol. 104, No. 11, Part 2, p. 132B. Meeting Info.: 46th Annual Meeting of the American-Society-of-Hematology. San Diego, CA, USA. Dec. 4-7, 2004.
Eavarone et al., "Humanized anti-Sialyl-Tn antibodies for the treatment of ovarian carcinoma," PLoS One 13(7):e0201314, 18 pages, (2018).
Reichert et al., "Development trends for monoclonal antibody cancer therapeutics," Nature Reviews, vol. 6, pp. 349-356, (May 2007).
Blixt et al. "Analysis of Tn antigenicity with a panel of new IgM and IgG1 monoclonal antibodies raised against leukemic cells," Glicobiology 2012, vol. 22, No. 4, pp. 529-542 (2012).
Kim, Y.G. et al., Hybrid restriction enzymes: zinc finger fusions to Fok I cleavage domain. Proc Natl Acad Sci U S A. Feb. 6, 1996;93(3):1156-60.
Malphettes, L. et al., Highly efficient deletion of FUT8 in CHO cell lines using zinc-finger nucleases yields cells that produce completely nonfucosylated antibodies. Biotechnol Bioeng. Aug. 1, 2010;106(5)774-83.
Malykh, Y.N. et al, N-Glycolyineuraminic acid in human tumours. Biochimie. 2001. 83: 623-634.
Motoo, Y. et al., Serum sialyl-Tn antigen levels in patients with digestive cancers. Oncology. 1991;48(4):321-6.
Newsom-Davis, T. et al., Enhanced Immune Recognition of Cryptic Glycan Markers in Human Tumors Cancer Res 2009;69:2018-2025.
Nguyen, D.H. et al., Effects of natural human antibodies against a nonhuman sialic acid that metabolically incorporates into activated and malignant immune cells. J Immunol. Jul. 1, 2005;175(1):228-36.
Ohno, S. et al, Expression of Tn and sialyl-Tn antigens in endometrial cancer: its relationship with tumor-produced cyclooxygenase-2, tumor-infiltrated lymphocytes and patient prognosis. Anticancer Res. Nov.-Dec. 2006;26(6A):4047-53.
Padlan, E.A., A possible procedure for reducing the immunogenicity of antibody variable domains while preserving their ligand-binding properties. Mol Immunol. Apr.-May 1991;28(4-5):489-98.
Pinho, S. et al., Biological significance of cancer-associated sialyl-Tn antigen: modulation of malignant phenotype in gastric carcinoma cells. Cancer Lett. May 8, 2007;249(2):157-70.
Riechmann, L. et al., Reshaping human antibodies for therapy. Nature. Mar. 24, 1998;332(6162):323-7.
Roguska, M.A. et al., Humanization of murine monoclonal antibodies through variable domain resurfacing. Proc Natl Acad Sci U S A. Feb. 1, 1994;91(3):969-73.
Shu, L. et al., Secretion of a single-gene-encoded immunoglobulin from myeloma cells. Proc Natl Acad Sci U S A. Sep. 1, 1993:90(17)7995-9.
Siegwart et al., Combinatorial synthesis of chemically diverse core-shell nanoparticles for intracellular delivery Proc Natl Acad Sci U S A. 2011 108:12996-13001.
Townsend, J.A. et al., High-frequency modification of plant genes using engineered zinc-finger nucleases. Nature. May 21, 2009;459(7245):442-5.
Varki, A., Glycan-based interactions involving vertebrate sialic-acid-recognizing proteins, Nature 2007 446:1023-1029.
Varki, N.M. et al., Biomedical differences between human and nonhuman hominids: potential roles for uniquely human aspects of sialic acid biology. Annu Rev Pathol. 2011. 6: 365-393.
Von Mensdorff-Pouilly, S., et al. Reactivity of natural and induced human antibodies to MUC1 mucin with MUC1 peptides and n-acetylgalactosamine (GalNAc) peptides Int J Cancer. Jun. 1, 2000;86(5):702-12.
Ohno, S. et al., Expression of Tn and sialyi-Tn antigens in endometrial cancer: Its relationship with tumor-produced cyclooxygenase-2, tumor-infiltrated lymphocytes and patient prognosis. Anticancer Res. Nov.-Dec. 2006;26(6A):4047-53.
Padler-Karavani, V. et al., Diversity in specificity, abundance, and composition of anti-Neu5Gc antibodies in normal humans: potential implications for disease. Glycobioiogy. Oct. 2008;18(10):818-30.
Riechmann, L. et al., Reshaping human antibodies for therapy. Nature. Mar. 24, 1988;332(6162):323-7.
Takahashi et al. Immunoglobulin G3 Monoclonal Antibody Directed to Tn Antigen(Tumor-associated alpha-N-ACETYLGALACTASAMINYL Epitope) That Does Not Cross-React with Blood Group A Antigen, Cancer Res 1988;43:4361-4367.
Von Mensdorff-Poullly, S., et al. Reactivity of natural and induced human antibodies to MUC1 mucin with MUC1 peptides and n-acetylgalactosamine (GalNAc) peptides Int J Cancer. Jun. 1, 2000;86(5):702-12.
Ozols et al., "Phase III trial of carboplatin and paclitaxel compared with cisplatin and paclitaxel in patients with optimally resected stage III ovarian cancer: a Gynecologic Oncology Group study", J Clin Oncol 21(17), pp. 3194-3200 (2003).
Padler-Karavani et al. Cross-comparison of protein recognition of sialic acid diversity on two novel sialoglycan microarrays. J BC 2012, vol. 287, No. 27, pp. 22593-22608 (2012).
Padler-Karavani, V., "Aiming at the sweet side of cancer: aberrant glycosylation as possible target for personalized-medicine," Cancer Lett., 352(1), pp. 102-112 (Sep. 28, 2014).
Partial Supplementary European Search Report for corresponding European Application No. 15848503.7 dated Apr. 10, 2018 (16 pages).
Partial Supplementary European Search Report for corresponding European Application No. 16865044.8 dated May 3, 2019 (11 pages).
Partial Supplementary European Search Report dated May 7, 2018 in corresponding European Patent Application No. 15859152.9 (23 pages).
Perez et al., "Antibody-drug conjugates: current status and future directions", Drug Discov. Today, 19, pp. 869-881 (2014).
Petterson et al., "CD47 signals T cell death," J. Immunol., 162(12), pp. 7031-7040 (Jun. 15, 1999).

(56) References Cited

OTHER PUBLICATIONS

Pinato et al., "Evolving concepts in the management of drug resistant ovarian cancer: dose dense chemotherapy and the reversal of clinical platinum resistance", Cancer Treat Rev, 39, pp. 153-160 (2013).
Pitot, H. C., "The Language of Oncology", Fundamentals of Oncology (Dekker, M., Ed.), pp. 15-28, New York, (1978).
Prendergast et al. "Novel Anti-Aialyl-Tn Monoclonal Antibodies and Antibody-Drug Conjugates (ADCs) Demonstrate Tumor Specificity in Vitro and in Vivo Antitumor Efficacy" Poster, Proceedings of the American Association for Cancer Research Annual Meeting 2017, Cancer Research, vol. 77, suppl. 13, 1, pp. 1-13 (Apr. 1, 2017).
Prendergast et al., "Novel anti-Sialyl-Tn monoclonal antibodies and antibody-drug conjugates demonstrate tumor specificity and anti-tumor activity", MABS, pp. 1-13 (Feb. 22, 2017).
Quiles et al., "Synthesis and Preliminary Biological Evaluation of High-Drug-Load-Paclitaxel-Antibody Conjugates for Tumor-Targeted Chemotherapy," J. Med. Chem. 53, pp. 586-594 (2010).
Reis et al., "Intestinal metaplasia of human stomach displays distinct patterns of mucin (MUC1, MUC2, MUC5AC, and MUC6) expression", Cancer Res., 59(5), pp. 1003-1007 (Mar. 1, 1999).
Rho et al., "Discovery of sialyl Lewis A and Lewis X modified protein cancer biomarkers using high density antibody array",. J Proteomics; 96:291-9 (2014).
Rho et al., "High-throughput screening for native autoantigen-autoantibody complexes using antibody microarrays", J Proteome Res. May 3, 2013;12(5):2311-20 (2013).
Ricardo et al., "Detection of glyco-mucin profiles improves specificity of MUC16 and MUC1 biomarkers in ovarian serous tumours", Mol Oncol. 9(2), 503-12 (2015).
Ricci et al., "ALDH enzymatic activity and CD133 positivity and response to chemotherapy in ovarian cancer patients". Am J Cancer Res, 3, pp. 221-229 (2013).
Rudikoff et al., "Single amino acid substitution altering antigen-binding specificity," Proc. Natl. Acad. Sci. USA, 79, pp. 1979-1983 (1982).
Sabbatini, P., "Consolidation therapy in ovarian cancer: a clinical update", Int J Gynecol Cancer, 19 Suppl 2, pp S35-S39 (2009).
Saber et al., "An FDA oncology analysis of antibody-drug conjugates", Regul. Toxicol. Pharmacol. 71, pp. 444-452 (2015).
Schlom et al., "Tumor targeting with monoclonal antibody B72.3", Int. J. Rad. Appl. Instrum. B., 16, pp. 137-142 (1989).
Schlom et al., "Tumor targeting with monoclonal antibody B72.3: experimental and clinical results", Cancer Treat. Res., 51, pp. 313-335 (1990).
Schwarz et al., "A new kind of carhohydrate array, its use for profiling antiglycan antibodies, and the discovery of a novel human cellulose-binding antibody", Glycobiology, Oxford Univ. Press, US, vol. 13, No. 11 pp. 749-754 (Nov. 1, 2003).
Second Examiner's Report dated Mar. 8, 2019 in corresponding Canadian Patent Application No. 2,967,595 (4 pages).
Sedlacek et al., "Neuraminidase and tumor immunotherapy", Klin Wochenschr., 55(5), pp. 199-214. (Mar. 1, 1977).
Sing et al., "ROCR: visualizing classifier performance in R", Bioinformatics, 21(20), pp. 3940-3941 (2005).
Singer et al., "Targeting BACE1 with siRNAs ameliorates Alzheimer disease neuropathology in a transgenic model", Nature Neuroscience, 8(10), pp. 1343-1349 (2005).
Song et al., "A Sialylated Glycan Microarray Reveals Novel Interactions of Modified Sialic Acids with Proteins and Viruses", Journal of Biological Chemistry, vol. 286, No. 36 pp. 31610-31622 (Jul. 12, 2011).
Stancoviski et al., Proceeding of the National Academy of Science USA, 88, pp. 8691-8695 (1991).
Starbuck et al. Eradicating ovarian cancer stem cells by targeting the tumor-associated carbohydrate antigen sialyl Tn. Gynecologic Oncology 2015, 139(3):590, 3 pages.
Takeshita et al., "CMC-544 (inotuzumab ozogamicin), an anti-CD22 immuno-conjugate of calicheamicin, alters the levels of target molecules of malignant B-cells," Leukemia, 23(7), pp. 1329-1336 (Jul. 2009).
Tamura et al. "RNAi-mediated gene silencing of ST6GalNAc I suppresses the metastatic potential in gastric cancer cells", Gastric Cancer, 19(1), pp. 85-97 (Dec. 23, 2014).
Thapa et al., The Importance of CD44 as a Stem Cell Biomarker and Therapeutic Target in Cancer. Stem Cells Int., 2087204, 15 pages (2016).
Tiller et al., "A fully synthetic human Fab antibody library based on fixed VH/VL framework pairings with favorable biophysical properties", mAbs, 5(3), pp. 445-470 (2013).
Tiscornia et al., "Production and purification of lentiviral vectors", Nature Protocols, 1 (1), pp. 241-245 (2006).
Tso et al., "Formation and transport of chylomicrons by enterocytes to the lymphatics," American Journal of Physiology, 250(6 Pt 1), G715-726 (1896).
Vacchelli et al., Trial watch: Tumor-targeting monoclonal antibodies for oncological indications. Oncoimmunology 4, e985940 16 pages (2015).
Vajdos et al., "Comprehensive functional maps of the antigen-binding site of an anti-ErbB2 antibody obtained with shotgun scanning mutagenesis," J. Mol. Biol., 320(2), pp. 415-428 (Jul. 5, 2002).
Welinder et al., "A new murine IgG1 anti-Tn monoclonal antibody with in vivo anti-tumor activity", GLYCOBIOLOGY, 21(8), pp. 1097-1107 (Aug. 2011).
Winkler et al., "Changing the antigen binding specificity by single point mutations of an anti-p24 (HIV-1) antibody," J. Immunol., 165(8), pp. 4505-4514 (Oct. 15, 2000).
Written Opinion in related International Application No. PCT/US2011/021387, dated Oct. 6, 2011 (5 pages).
Yonezawa et al., "Sialosyl-Tn antigen. Its distribution in normal human tissues and expression in adenocarcinomas.", American Journal of Clinical Pathology, 98(2), pp. 167-174 (1992).
Yu et al., "Silencing of ST6GalNAc I suppresses the proliferation, migration and invasion of hepatocarcinoma cells thourgh PI3K/AKT/NF-kB pathway", Tumor Biology, vol. 37(9), pp. 12213-12221 (May 27, 2016).
Zhang et al., "An overview of biomarkers for the ovarian cancer diagnosis", Eur. J. Obstet. Gynecol. Reprod. Biol. 158, pp. 119-123 (2011).
Zhang et al., "Immune sera and monoclonal antibodies define two configurations for the sialyl Tn tumor antigen", Cancer Res., 55, pp. 3364-3368 (1995).
Ghaderi et al. "Production platforms for biotherapeutic glycoproteins. Occurrence, impact, and challaenges of nonhuman sialyation," Biotechnology and Genetic Engineering Reviews, Apr. 15, 2013 (Apr. 15, 2013), vol. 26, pp. 147-176.
Shi, W-X et al., (1996) Sialic Acid 9-O-Acetylation on Murine Erythroleukemia Cells Affects Complement Activation, Binding to l-type Lectins, and Tissue Homing. J of Biol Chem. 271(49): 31526-31532.
Chen et al., (2013) Microarray Glycoprofiling of CA125 Improves Differential Diagnosis of Ovarian Cancer, Journal of proteome research, 12:1408-1418.
An et al., "A Novel Anti-STn Monoclonal Antibody 3P9 Inhibits Human Xenografted Colorectal Carcinomas," J Immunother, vol. 36, No. 1 pp. 20-28 (2013).
Eavarone et al., "Novel Humanized anti-Sialyl-Tn, anti-CD3 bispecific antibodies demostrate tumor and T-cell specificity for immune activation at the tumor site," Cancer Research, vol. 77, No. Suppl. 13, Agstract 3640, Jul. 2017, and Annual Meeting of the AACR, Washington DC on Apr. 1-5, 2017. (3 pages).
Eaverone et al., "Abstract LB-221: Novel anti-Sialyl-Tn monoclonal antibodies and antibody-drug conjugates (ADCs) demonstrate tumor specificity, unique sequence homology and in vitro and in vivo antitumor efficacy," AACR 107 Annual Meeting 2016, Apr. 16-20, 2016, New Orleans, LA, AACR; Cancer Res 2016, vol. 76, 14 Suppl (4 pages).
Extended European Search Report for European Application No. 17871763.3, dated May 29, 2020 (9 pages).

(56) References Cited

OTHER PUBLICATIONS

Extended European Search Report in European Application No. 17872341.7, dated May 27, 2020 (8 pages).
Numa et al., "Tissue Expression of Siayl Tn Antigen in Gynecologic Tumors," J. Obstet. Gynacol. vol. 21, No. 4 pp. 385-389(1995).
Prendergast et al: "Abstract 36: Novel anti-Sialyl-Tn monoclonal antibodies and antibody-drug conjugates (ADCs) demonstrate tumor specificity in vitro and in vivo antitumor efficacy," AACR Annual Meeting 2017, Apr. 1-5, 2017, Washington, DC., AACR, vol. 77, Issue 13 Supplement (4 pages).
Shi et al., "Sialyl-Tn 1 Polysaccharide A1 as an Entirely Carbohydrate Immunogen: Synthesis and Immunological Evaluation," Journal of American Chemical Society, vol. 138, No. 43, pp. 14264-14272 (Oct. 21, 2016).
Adams et al., "Monoclonal antibody therapy of cancer", Nature Biotechnology, 23(9), pp. 1147-1157 (2005).
Andergassen et al. "Glycosyltransferases as Markers for Early Tumorigenesis", Biomed Res. Int. 792672, 12 pages (2015).
Ang et al., "Efficacy of chemotherapy in BRCA1/2 mutation carrier ovarian cancer in the setting of PARP inhibitor resistance: a multi-institutional study", Clin Cancer Res; 19, pp. 5485-5493 (2013).
Anti-STn Antibody, SBH Sciences, https://www.sbhsciences.com/Anti_STn.asp, 1 page, 2019.
Armstrong et al., "Intraperitoneal cisplatin and paclitaxel in ovarian cancer", N Engl J Med. 354(1), 34-43 (2006).
Barrow et al., "Suppression of Core 1 Gal-Transferase Is Associated with Reduction of TF and Reciprocal Increase of Tn, sialyl-Tn and Core 3 Glycans in Human Colon Cancer Cells," PLoS One, 8(3), e59792, p. 106 (Mar. 25, 2013).
Beatson et al., "The Breast Cancer-Associated Glycoforms of MUC1, MUC1-Tn and sialyl-Tn, Are Expressed in COSMC Wild-Type Cells and Bind the C-Type Leclin MGL", PLoS One 10, e0125994, 21 pages (2015).
Bernard et al., "A unique epitope on the CD2 molecule defined by the monoclonal antibody 9-1: epitope-specific modulation of the E-rosette receptor and effects on T-cell functions," Human Immunol., 17, pp. 388-405 (1986).
Berns et al., "The changing view of high-grade serous ovarian cancer", Cancer Res. 72, pp. 2701-2704 (2012).
Blixt, O., "Glycan Microarray Analysis of Tumor-Associates Antibodies" In: Paul Kosma (edit.): "Anticharbohydrate Antibodies", Springer-Verlag, Wien, pp. 290-293 (Nov. 27, 2011).
Braun et a., "Aromatase inhibitors increase the sensitivity of human tumor cells to monocyte-mediated, antibody-lependenl cellular cytotoxicily", American Journal of Surgery, Paul Hoeber, New York, NY, US, vol. 190, No. 4, pp. 570-571 (Oct. 1, 2005).
Bull et al., "Sialic acids sweeten a tumor's life". Cancer Res, 74(12), pp. 3199-3204 (2014).
Burger et al., "Incorporation of bevacizumab in the primary treatment of ovarian cancer", N Engl J Med, 365, pp. 2473-2483 (2011).
Caldas et al., "Humanization of the anti-CD18 antibody 6.7: an unexpected effect of a framework residue in binding to antigen," Mol. Immunol., 39(15), pp. 941-952 (May 2003).
Campbell et al. High-throughput profiling of anti-glycan humoral responses to SIV vaccination and challenge. Plos One, 2013, vol. 8, Issue. 9, pp. 1-12 (2013).
Cao et al., "Thomsen-Friedenreich-related carbohydrate antigens in normal adult human tissues: a systematic and comparative study", Histochemistry and Cell Biology, 106(2), pp. 197-207 (1996).
Casset et al. "A peptide mimetic of an anti-CD4 monoclonal antibody by rational design," Biochem. Biophys. Res. Commun., 307(1), pp. 198-205 (Jul. 18, 2003).
Cazet et al., "Consequences of the expression of sialylated antigens in breast cancer", Carbohydr Res., 345(10), pp. 1377-1383 (2010).
Ceccaldi et al., "A unique subset of epithelial ovarian cancers with platinum sensitivity and PARP inhibitor resistance", Cancer Res; 75, pp. 628-634 (2015).
Chang et al., "Loop-sequence features and stability determinants in antibody variable domains by high-throughput experiments," Structure. 22(1), pp. 9-21 (Jan. 7, 2014).
Chang et al., "Non-invasive phenotyping and drug testing in single cardiomyocytes or beta-cells by calcium imaging and optogenetics," PLoS One 7 (3): e33340; pp. 1-15 (2012).
Chien et al., "Significant structural and functional change of an antigen-binding site by a distant amino acid substitution: proposal of a structural mechanism, "Proc. Natl. Acad Sci. USA., 86(14), pp. 5532-5536 (Jul. 1989).
Choi et al., Platinum and PARP Inhibitor Resistance Due to Overexpression of MicroRNA-622 in BRCA1-Mutant Ovarian Cancer Cell Rep; 14, pp. 429-439 (2016).
Cholleti et al., "Automated Motif Discovery from Glycan Array Data", OMICS A Journal of Integrative Biology, 16 (10) pp. 497-512(2012).
Chothia et al., "Structural repertoire of the human VH segments", J Mol Biol., 227(3), pp. 799-817 (Oct. 5, 1992).
Christiansen et al., "Cell surface protein glycosylation in cancer", Proteomics 14, pp. 525-546 (2014).
Cohen et al., "In 2014, can we do better than CA125 in the early detection of ovarian cancer?", World J. Biol. Chem. 5, pp. 286-300 (2014).
Coleman R.L., "Ovarian cancer in 2015: Insights into strategies for optimizing ovarian cancer care", Nat Rev Clin Oncol. 13(2), pp. 71-72 (2016).
Cooke et al., "Evolution of platinum resistance in high-grade serous ovarian cancer", Lancet Oncol, 12, pp. 1169-1174 (2011).
Curley et al., "CD133 expression defines a tumor initiating cell population in primary human ovarian cancer", Stem Cells, 27, pp. 2875-2883 (2009).
Curley et al., "Evidence for cancer stem cells contributing to the pathogenesis of ovarian cancer", Front Biosci (Landmark Ed), 16, pp. 368-392 (2011).
Davidson et al., "Expression of carbohydrate antigens in advanced-stage ovarian carcinomas and their metastases—A clinicopathologic study", Gynecol Oncol, 77, pp. 35-43 (2000).
De Goeij et al., New developments for antibody-drug conjugate-based therapeutic approaches. Curr Opin Immunol, 40, pp. 14-23 (2016).
De Pascalis et al.,"Grafting of "abbreviated" complementarity-determining regions containing specificity-determining residues essential for ligand contact to engineer a less immunogenic humanized monoclonal antibody," J. Immunol., 169(6), pp. 3076-3084 (2002).
Dearnley et al., "Consolidation therapy in ovarian cancer: where do we stand?", Curr Opin Obstet Gynecol, 18, pp. 3-7 (2006).
Desmetz et al., "Identifying autoantibody signatures in cancer: a promising challenge", Expert Review of Proteomics, 6(4), pp. 377-386 (2009).
Di et al., "Multiple drug resistance due to resistance to stem cells and stem cell treatment progress in cancer (Review)", Exp Ther Med, 9, pp. 289-293 (2015).
Emens, L.A. "Breast Cancer Immunobiology Driving Immunotherapy:Vaccines and Immune Checkpoint Blockade" Expert Review of Anticancer Therapy, vol. 12, pp. 1597-1611 (Dec. 1, 2012).
European Search Report in related EP Application No. EP 13 18 4707, dated Jun. 2, 2014 (13 pages).
Extended European Search Report in related EP Application No. EP 11 73 3477, dated Jun. 25, 2013 (12 pages).
Extended European Search Report dated Aug. 16, 2018 in corresponding European Patent Application No. 15859152.9 (22 pages).
Extended European Search Report dated Jul. 11, 2018 in correspondence European Patent Application No. 15848503.7 (14 pages).
Extended European Search Report dated Jul. 17, 2019 in corresponding European Patent Application No. 16865044.8, 8 pages.
Fawcett, T., "ROC Graphs: Notes and Practical Considerations for Data Mining Researchers", Intelligent Enterprise Technologies Laboratory, (HP Laboratories Palo Alto), pp. 1-27 (2004).
Federici et al., "Selection of carbohydrate antigens in human epithelial ovarian cancers as targets for immunotherapy: serous and mucinous tumors exhibit distinctive patterns of expression", Int J Cancer, 81(2), pp. 193-198(1999).
First Examiner's Report dated Feb. 19, 2018 in corresponding Canadian Patent Application No. 2,967,595 (3 pages).

(56) References Cited

OTHER PUBLICATIONS

Fuster et al., "The sweet and sour of cancer: glycans as novel therapeutic targets", Nat Rev Cancer., 5(7), pp. 526-542 (Jul. 2005).
Gao et al., "High-throughput screening using patient-derived tumor xenografls to predict clinical trial drug response", Nat Med. vol. 21, No. 11, pp. 1318-1328 (2015).
Gao et al., "Identification of Cancer Stem-like Side Population Cells in Ovarian Cancer Cell Line OVCAR-3," Ultrastructual Pathology, 33, pp. 175-181 (2009).
Katari R S et al: "Characterization of the shed form of the human tumor-associated glycoprotein (TAG-72) from serous effusions of patients with different types of carcinomas", Cancer Research, American Asociation for Cancer Research, US, vol. 50, No. 16, Aug. 15, 1990, pp. 4885-4890.
International Search Report for International Application No. PCT/US2013/029240, dated Jun. 21, 2013 (9 pages).
Yin et al., "Hypoxic culture induces expression of sialin, a sialic acid transporter, and cancer-associated gangliosides containing non-human sialic acid on human cancer cells", Cancer Res., 66(6), pp. 2937-2945 (Mar. 15, 2006).
Malphettes, L. et al., Highly efficient deletion of FUT8 in CHO cell lines using zinc-finger nucleases yields cells that produce completely nonfucosyiated antibodies. Biotechnol Bioeng. Aug. 1, 2010;106(5)774-83.
Malykh, Y.N. et al., N-Glycolylneuraminic acid in human tumours. Biochimie. 2001. 83: 623-634.
Agarwal et al., "Site-Specific Antibody-Drug Conjugates: The Nexus of Biorthogonal Chemistry, Protein Engineering, and Drug Development," Bioconjugate Chem., 2015, 26, 176-192 (17 pages).
Al-Alem et al., "Abstract LB-229: Utilizing a novel highly specific sialyl-Tn ELISA as a diagnostic for ovarian cancer," Cancer Research, vol. 79, Issue 13 supplement, Jul. 2019 (2 pages).
Amon et al., "A combined computational experimental approach to define the structural origin of antibody recognition of sialyl-Tn, a tumor associatedcarbohydrate antigen," Scientific Reports, 8:107086, Feb. 2018 (12 pages).
Brinkman-Van der Linden et al., "CD33/Siglec-3 Binding Specificity, Expression Pattern, and Consequences of Gene Deletion in Mice," Molecular and Cellular Biology, vol. 23, No. 12, Jun. 2003, p. 4199-4206 (8 pages).
Dorywalska et al., "Effect of Attachment Site on Stability of Cleavable Antibody Drug Conjugates," Bioconjugate Chem., 2015, 26, 650-659 (10 pages).
Dransfield et al., "Abstract B28: Targeting the tumor-associated carbohydrate antigen STn with humanized anti-Sialyl-Tn monoclonal antibody-drug conjugates inhibits ovarian cancer tumor growth in vitro and in vivo," Clinical Cancer Research, vol. 24, Issue 15 supplement, Aug. 2018 (2 pages).
Eavarone et al. "Abstract 5625: Myeloid derived suppressor cells (MDSCs) express Sialyl Tn (STn) and are a therapeutic target for anti-STn antibody drug conjugates," Cancer Research, vol. 78, Issue 13 supplement, Jul. 2018 (2 pages).
Eavarone et al., "Abstract 3640: Novel humanized anti-Sialyl-Tn, anti-CD3 bispecific antibodies demonstrate tumor and T-cell specificity for immuneactivation at the tumor site," Cancer Research, vol. 77, Issue 13 supplement, Jul. 2017 (2 pages).
Jimeno et al., "Poster 478 Pharmacological disruption of the Astrocytic Elevated Gene-1 (AEG1) in anticancer intervention: PB0412_3 (PB03) as a first-in-class AEG1 interacting agent," Poster Session—Molecular Targeted Agents II, European Journal of Cancer, 50(6):156, Nov. 21, 2014 (1 page).
Kim et al., Abstract: "Session III: Translational Research/Basic Science—I Tetrathiomolybdate mediates the degradation of hypoxia-inducible,factor-1α," Abstracts, Gynecologic Oncology 139 (2015) (1 page).
Kristo et al., Abstract e24279: "Tumor associated carbohydrate antigens in prostatic adenocarcinoma (PAC): Correlation of sialyl-Tn with malignant phenotype," Journal of Clinical Oncology, 36, No. 15 supplemental, Jun. 1, 2018 (2 pages).
McCombs et al., "Antibody Drug Conjugates: Design and Selection of Linker, Payload and Conjugation Chemistry," The AAPS Journal, vol. 17, No. 2, Mar. 2015 (13 pages).
Padler-Karavani et al., "Abstract 67: Expression and antigenicity of tumor-associated Neu5Gc-containing O-glycans in human carcinomas," Conference Abstracts, Joint Meeting of the Society for Glycobiology & American Society for Matrix Biology, Glycobiology, vol. 22, Issue 11, p. 1542 (Nov. 1, 2012).
Padler-Karavani et al., "Expression of the tumor-associated antigen Neu5Gc-Sialyl-Tn in human carcinomas," J Immunol May 1, 2012, 188 (1 Supplement) 74.6 (2 pages).
Partial Extended Search Report issued in European Patent Application No. 18760528.2, dated Mar. 16, 2021 (21 pages).
Patel et al., "OB-BP1/Siglec-6, A Leptin- and Sialic Acid-Binding Protein of the Immunoglobulin Superfamily," The Journal of Biological Chemistry, vol. 274, No. 32, Issue 6, pp. 22729-22738, Apr. 9, 1999 (10 pages).
Prendergast et al., "Novel anti-Sialyl-Tn monoclonal antibodies and antibody-drug conjugates demonstrate tumor specificity and anti-tumor activity," MABS, vol. 9, No. 4, pp. 615-627 (2017).
Prendergast et al., Abstract 183: "Novel anti-Sialyl-Tn monoclonal antibodies and antibody drug conjugates (ADCs) target a cancer stem cell population and demonstrate in vitro and in vivo anti-tumor efficacy," Program and Abstracts for 2016 Annual Meeting of the Society for Glycobiology, Glycobiology, vol. 26, Issue 12, p. 1499, Dec. 1, 2016 (1 page).
Rueda et al., "Abstract MIP-071: Targeting a Chemoresistant Ovariancancer Cell Population Via the Carbohydrate Antigensialyl Tn," Clinical Cancer Research, vol. 23, Issue 11, Jun. 2017 (2 pages).
Starbuck et al., "Treatment of ovarian cancer by targeting the tumor stem cell associated carbohydrate antigen, Sialyl-Thomsen-nouveau," Oncotarget, 2018, vol. 9, (No. 33), pp. 23289-23305 (17 pages).
Graille, M.G. et al., 2000. Crystal structure of a *Staphylococcus aureus* protein A domain complexed with the Fab fragment of a human IgM antibody: Structural basis for recognition of B-cell receptors and superantigen activity. PNAS. 97(10): 5399-404.
Jandus, C. et al., (2014) Interactions between Siglec-7/9 receptors and ligands influence NK cell-dependent tumor immunosurveillance, JCI. pii: 65899 124(4):1810-1820.
Johnson et al., Kabat Database and its applications: 30 years after the first variability plot, Nucleic Acids Res, 28(1), pp. 214-218 (2000).
Matsuda, F. et al., (1998) The Complete Nucleotide Sequence of the Human Immunoglobulin Heavy Chain Variable Region Locus, The Journal of Experimental Medicine. 188(11): 2151-62.
Nelson, A. L., (2010) Antibody fragments Mabs. Jan.-Feb.; 2(1):77-83.
Brinkmann, U. et al., Phage display of disuifide-stabiiized Fv fragments. J Immunol Methods. May 11, 1995;182(1):41-50.
Caron et al., Intracellular delivery of a Tat-eGFP fusion protein into muscle ceils Mol. Ther. 3(3):310-8 (2001).
Carroll, D., Progress and prospects: zinc-finger nucleases as gene therapy agents. Gene Ther. Nov. 2008;15(22):1463-8.
Cathomen, T. et al., Zinc-finger nucleases: the next generation emerges. Mol Ther. Jul. 2008; 16(7):1200-7.
Daugherty, et al., Formulation and delivery issues for monoclonal antibody therapeutics. Adv Drug Deliv Rev. Aug. 7, 2006;58(5-6):686-706.
Davis et al. Evidence of RNAi in humans from systemically administered siRNA via targeted nanoparticles Nature 2010 464:1067-1070.
Davis, M.E. The first targeted delivery of siRNA in humans via a self-assembling, cyciodextrln polymer-based nanoparticle: from concept to clinic Mol Pharm. 2009 6:659-668.
Doyon, Y. et al., Heritable targeted gene disruption in zebrafish using designed zinc-finger nucleases. Nat Biotechnol. Jun. 2008;26(6):702-8.
El-Andaloussi et al., Cell-penetrating peptides: mechanisms and applications Curr. Pharm. Des. 11(28):3597-611 (2003).
Heimburg-Molinaro, J. et al., Cancer vaccines and carbohydrate epitopes. Vaccine. Nov. 8, 2011;29(48):8802-26.

(56) References Cited

OTHER PUBLICATIONS

Higashi, H. et al., Characterization of N-glycolylneuraminic acid-containing gangliosides as tumor-associated Hanganutziu-Deicher antigen in human colon cancer . . . Cancer Res. Aug. 1985;45(8):3796-802.
Hojman, Basic principles and clinical advancements of muscle electrotransfer Curr Gene Ther. 2010 10:128-138.
Ikehara, Y. et al., Cloning and expression of a human gene encoding an N-acetylgalactosamine-alpha2,6-sialyltransferase (ST6GalNAc I): a candidate for synthesis of cancer-associated sialyl-Tn antigens. Glycobiology. Nov. 1999;9(11):1213-24.
Itzkowitz, S.H. et al., Sialosyl-Tn. A novel mucin antigen associated with prognosis in colorectal cancer patients. Cancer. Nov. 1, 1990;66(9):1960-6.
Ju, T. et al., Human tumor antigens Tn and sialyl Tn arise from mutations in Cosmc. Cancer Res. Mar. 15, 2008;68(6):1636-46.
Dransfield, et al. Abstract B114: Humanized anti-Sialyl-Tn monoclonal antibody-drug conjugates inhibit tumor growth in vitro and invivo. Molecular Cancer Therapeutics, Jan. 1, 2018, vol. 17, No. 1 (4 pages).
Nohle, U. et al. (1982) "Uptake, Metabolism and Excretion of Orally and Intravenously Administered, Double-Labeled N-Glycoloylneuraminic Acid and Single-Labeled 2-Deoxy-2,3-dehydro-N-acetylneuraminic Acid in Mouse and Rat," European Journal of Biochemistry 126(3), 543-548.
Oyelaran O; McShane LM; Dodd L; Gildersleeve JC: 'Profiling human serum antibodies with a carbohydrate antigen microarray' J Proteome Res. vol. 8, 2009, pp. 4301-10.
Pearce, O. M. et al. (2010) "Chemo-enzymatic synthesis of the carbohydrate antigen N-glycolylneuraminic acid from glucose," Carbohydrate Research 345(9), 1225-1229.
Sato, Chihiro et al., "Carbohydrates, Lipids, and Other Natural Products: Identification of Oligo-N-Glycolylneuraminic Acid Residues in Mammal-derived Glycoprotiens by a Newly Developed Immunochemical Reagent and Biochemical Methods", J. Biol. Chern. 1998, 273:2575-2582.
Sewell R. et al. (2006) The ST6GalNAc-l Sialyltransferase Localizes throughout the Golgi and Is Responsible for the Synthesis of the Tumor-associated Sialyl-Tn O-Glycan in Human Breast Cancer, Journal of Biological Chemistry 281(6), 3586-3594.
Shaw, L. et al. (1994) "CMP-N-acetylneuraminic acid hydroxylase from mouse liver and pig submandibular glands," European Journal of Biochemistry 219(3), 1001-1011.
Weiss, J. M. et at. (2007) Immunotherapy of Cancer by IL-12-based Cytokine Combinations. Expert Opinion on Biological Therapy 7(11), 1705-1721.
Andreu et al., "FcRgamma activation regulates inflammation—associated squamous carcinogenesis," Cancer Cell vol. 17, 2010, pp. 121-34.
Bedouelle et al., "Diversity and junction residues as hotspots of binding energy in an antibody neutralizing the dengue virus," FEBS Journal, 273, pp. 34-46, 2006 (13 pages).
Brown et al., "Tolerance to Single, but Not Multiple, Amino Acid Replacements in Antibody V H CDR2," The Journal of Immunology, pp. 3285-3291, 1996 (7 pages).
Colman, P. M., "Effects of amino acid sequence changes on antibody-antigen interactions," Research in Immunology, 145:33-36, 1994 (5 pages).
Sinha et al., "Proinflammatory S100 Proteins Regulate the Accumulation of Myeloid-Derived Suppressor Cells," J Immunol. Oct. 1, 2008; 181(7): 4666-4675 (24 pages).
Steplewski et al., "Biological activity of human-mouse IgGI, IgG2, IgG3, and IgG4 chimeric monoclonal antibodies with antitumor specificity," Proc Natl Acad Sci USA 85: 4852-4856 (1988).
Yu et al., "Rationalization and Design of the Complementarity Determining Region Sequences in an Antibody-Antigen Recognition Interface," PLoS ONE 7(3): e33340. doi:10.1371/journal.pone.0033340, Mar. 22, 2012 (15 pages).
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Henry et al. (Cancer Res. Nov. 1, 2004; 64: 7995-8001).*
McDevitt et al. (Cancer Res. Nov. 1, 2000; 60: 6095-6100).*
Takeshita et al. (Leukemia. Jul. 2009; 23 (7): 1329-36).*
Stancoviski et al. (Proceedings of the National Academy of Science USA. 1991; 88: 8691-8695).*
Pettersen et al. (J. Immunol. Jun. 15, 1999; 162 (12): 7031-7040).*
Bernard et al. (Human Immunol. 1986; 17: 388-405).*
Kettleborough, C. A. et al., Isolation of tumor cell-specific single-chain Fv from immunized mice using phage-antibody libraries and the re-construction of whole antibodies from these antibody fragments. Eur J Immunol. Apr. 1994;24 (4):952-8.
Kilgore, B.R. et al., Comparability and monitoring immunogenic N-linked oligosaccharides from recombinant monoclonal antibodies from two different cell lines using HPLC with fluorescence detection and mass spectrometry. Methods Mol Biol. 2008;446:333-46.
Kim, Y.G. et al., Hybrid restriction enzymes: zinc finger fusions to Fok I cleavage domain. Proc Nati Acad Sci U S A. Feb. 6, 1996;93(3):1156-60.
Kirkeby, S. et al., MUC1 and the simple mucin-type antigens: Tn and Sialyl-Tn are differently expressed in salivary gland acini and ducts from the submandibular gland, the vestibular folds, and the soft palate. Arch Oral Biol. Nov. 2010;55(11):830-41.
Kobayashi, H. et al., Serum sialyl Tn as an independent predictor of poor prognosis in patients with epithelial ovarian cancer. J Clin Oncol. Jan. 1992;10(1):95-101).
Kohler, G. et al., Continuous cultures of fused cells secreting antibody of predefined specificity. Nature. Aug. 7, 1975;256(5517):495-7.
Kostelny, S.A. et al., Formation of a bispecific antibody by the use of leucine zippers. J Immunol. Mar. 1, 1992;148 (5):1547-53).
Kozbor, D. et al., A human hybrid myeloma for production of human monoclonal antibodies. J Immunol. Dec. 1984;133(6):3001-5.
Lonberg, N. et al., Human antibodies from transgenic mice. Int Rev Immunol. 1995:13(1):65-93.
Maccioni, H.J. et al., Organization of the synthesis of glycolipid oligosaccharides in the Golgi complex. FEBS Lett. Jun. 6, 2011;585(11):1691-8.
Malphettes, L. et al., Highly efficient deletion of FUT8 in CHO cell lines using zinc-finger nucleases yields cells that produce completely nonfucosylated antibodies. Biotechnol Bioeng, Aug. 1, 2010;106(5):774-33.
Maiykh, Y.N. et al, N-Glycolylneuraminic acid in human tumours. Biochimie. 2001. 83: 623-634.
Manimala, J. et al., Carbohydrate Array Analysis of Anti-Tn Antibodies and Lectins Reveals Unexpected Specificities: Implications for Diagnostic and Vaccine Development ChemBioChem 2005, 6, 2229-2241.
Martin, F.J. et al., Irreversible coupling of immunoglobulin fragments to preformed vesicles. An improved method for liposome targeting. J Biol Chem. Jan. 10, 1982;257(1):286-8.
Massignani, et al., Cellular delivery of antibodies: effective targeted subcellular imaging and new therapeutic tool. Nature Proceedings, May 2010.
McNaughton et al., Mammalian cell penetration, siRNA transfection, and DNA transfection by supercharged proteins Proc. Natl. Acad. Sci. USA 2009 106:6111-6116.
Meng, X. et al., Targeted gene inactivation in zebrafish using engineered zinc-finger nucleases. Nat Biotechnol. Jun. 2008;26(6):695-701.

(56) References Cited

OTHER PUBLICATIONS

Miersch, S. et al., Synthetic antibodies: Concepts, potential and practical considerations. Methods. Aug. 2012;57 (4):486-98.
Morrison, S.L., Transfectomas provide novel chimeric antibodies. Science. Sep. 20 1985;229(4719):1202-7.
Motoo, Y. et al., Serum sialyl-Tn antigen levels in patients with digestive cancers, Oncology. 1991;43(4):321-6.
Newman and Bettinger, Gene therapy progress and prospects: ultrasound for gene transfer Gene Ther. 2007 14:465-475.
Newsome-Davis, T. et al., Enhanced Immune Recognition of Cryptic Glycan Markers in Human Tumors Cancer Res 2009:69:2018-2025.
Nguyen, D.H. et al., Effects of natural human antibodies against a nonhuman sialic acid that metabolically incorporates into activated and malignant immune cells. J Immunol. Jul. 1, 2005 1:175(1):228-36.
Ogata, S. et al., Tumor-associated sialylated antigens are constitutively expressed in normal human colonic mucosa. Cancer Res. May 1, 1995;55(9):1869-74.
Ohno, S. et al, Expression of Tn and sialyl-Tn antigens in endometriai cancer: its relationship with tumor-produced cyclooxygenase-2, tumor-infiltrated lymphocytes and patient prognosis. Anticancer Res. Nov.-Dec. 2006;26 (6A):4047-53.
Radian, E.A., A possible procedure for reducing the immunogenicity of antibody variable domains while preserving their ligand-binding properties. Mol Immunol, Apr.-May 1991;23(4-5):489-98.
Padler-Karavani, V. et al., Diversity in specificity, abundance, and composition of anti-Neu5Gc antibodies in normal humans: potential implications for disease. Glycobiology. Oct. 2008;18(10):818-30.
Padler-Karavani, V. et al., Human xeno-autoantibodies against a non-human sialic acid serve as novel serum biomarkers and immunotherapeutics in cancer. Cancer Res. May 1, 2011;71(9):3352-63.
Persic, L. et al., An integrated vector system for the eukaryotic expression of antibodies or their fragments after selection from phage display libraries. Gene. Mar. 10, 1997;187(1):9-18.
Pinho, S. et al., Biological significance of cancer-associated sialyl-Tn antigen: modulation of rnaiignant phenotype in gastric carcinoma cells. Cancer Lett. May 8, 2007;249(2):157-70.
Porteus, M.H. et al., Chimeric nucleases stimulate gene targeting in human cells. Science, May 2, 2003;300(5620):763.
Riechrnann, L. et al., Reshaping human antibodies for therapy. Nature. Mar. 24, 1988;332(6162):323-7.
Roguska, M.A. et al., Humanization of murine monoclonal antibodies through variable domain resurfacing. Proc Nati Acad Sci U S A. Feb. 1, 1994;91(3):969-73.
Rozema et al., Dynamic PolyConjugates for targeted in vivo delivery of siRNA to hepatocytes Proc Natl Acad Sci U S A. 2007 104:12982-12887.
Sherwood, J.K. et al., Controlled antibody delivery systems Nature Biotechnology 10, 1446-1449 (1992).
Shu, L. et al., Secretion of a single-gene-encoded immunoglobulin from myeloma cells. Proc Natl Acad Sci U S A. Sep. 1, 1993;90(1):7995-9.
Siegwart et al., Combinatorial synthesis of chemically diverse core-shell nanoparticles for intracellular delivery Proc Natl Acad Sci U S A. 2011 108:12996-13001.
Skerra. A. et al., Assembly of a functional immunoglobulin Fv fragment in *Escherichia coli*. Science. May 20, 1988;240(4855):1038-41.
Steentoft, C. et al., Mining the O-glycoproteome using zinc-finger nuclease-glycoengineered SimpleCell lines. Nat Methods. Oct. 9, 2011;8(11):977-82.
Studnicka, G.M. et al., Human-engineered monoclonal antibodies retain full specific binding activity by preserving non-CDR complementarity-modulating residues, Protein Eng. Jun. 1994;7(6):805-14.
Takahashi et al. Immunoglobulin G3 Monoclonal Antibody Directed to Tn Antigen(Tumor-associated alpha-N-acetylgalactasaminyl Epitope) That Does Not Cross-React with Blood Group A Antigen, Cancer Res 1988;48:4361-4367.
Tangvoranuntakul, P. et al., Human uptake and incorporation of an immunogenic nonhuman dietary sialic acid. Proc Natl Acad Sci U S A. Oct. 14, 2003;100(21)12045-50.
Townsend, J.A. et al., High-frequency modification of plant genes using engineered zing-finger nucleases. Nature. May 21, 2009;459(7245):442-5.
Tutt, A. et al., Trispecific F(ab')3 derivatives that use cooperative signaling via the TCR/CD3 complex and CD2 to activate and redirect resting cytotoxic T cells. J Immunol. Jul. 1, 1991;147(1):60-9.
Varki, A. et al., Multiple changes in sialic acid biology during human evolution. Glycoconj J. 2009. 26: 231-245.
Varki, A., Glycan-based interactions involving vertebrate sialic-acid-recognizing proteins, Naure 2007 446:1023-1029.
Varki, N.M. et al., Biomedical differences between human and nonhuman hominids: potential roles for uniquely human aspects of sialic acid bioiogy. Annu Rev Pathol, 2011, 6: 365-393.
von Mensdorff-Pouilly, S., et al., Reactivity of natural and induced human antibodies to MUC1 mucin with MUC1 peptides and n-acetylgalactosamine (GalNAc) peptides Int J Cancer. Jun. 1, 2000;86(5)102-12.
Wang, D., N-glycan Cryptic Antigens as Active Immunological Targets in Prostate.
Wood, A.J. et al., Targeted genome editing across species using ZFNs and TALENs. Science. Jul. 15, 2011;333(6040):307.
Ames, R.S. et al., Conversion of murine Fabs isolated from a combinatorial phage display library to full length immunoglobulins. J Immunol Methods. Aug. 18, 1995;184(2):177-86.
Bardor, M. et al., Mechanism of uptake and incorporation of the non-human sialic acid N-glycolylneuraminic acid into human cells. J Biol Chem. 2005. 280: 4228-4237.
Benoit et al., Synthesis of folate-functionalized RAFT polymers for targeted siRNA delivery Biomacromolecules, 2011 12:2708-2714.
Bibikova, M. et al., Enhancing gene targeting with designed zinc finger nucleases. Science. May 2, 2003;300(5620):764.
Bradbury, A.R. et al., Beyond natural antibodies: the power of in vitro display technologies. Nat Biotechnol. Mar. 2011:29(3)245-54.
Brinkmann, U. et al,, Phage display of disulfide-stabilized Fv fragments. J Immunol Methods. May 11, 1995;182 (1):41-50.
Brinkman-Van der Linden, E.C. et al., New aspects of siglec binding specificities, including the significance of fucosylation and of the sialyl-Tn epitope. Sialic acid-binding immunoglobulin superfamily lectins. J Biol Chem. Mar. 24, 2000;275(12):8625-32.
Brockhausen, I. et al., Pathways of mucin O-glycosylation in normal and malignant rat colonic epithelial cells reveal a mechanism for cancer-associated Sialyl-Tn antigen expression. Biol Chem. Feb. 2001;382(2):219-32.
Cao, Y. et al., Immunodetection of epithelial mucin (MUC1, MUC3) and mucin-associated glycotopes (TF, Tn, and sialosyl-Tn) in benign and malignant lesions of colonic epithelium: apolar localization corresponds to malignant transformation. Virchows Arch. 1997.
Caron et al., Intracellular deiivery of a Tat-eGFP fusion protein into muscle cells Mol. Ther. 3(3):310-8 (2001).
Carroll, D., Progress and prospects: zing-finger nucleases as gene therapy agents. Gene Ther. Nov. 2008;15 (22):1463-3.
Cathomen, T, et al., Zing-finger nucleases: the next generation emerges. Mol Ther. Jul. 2008;16(7):1200-7.
Chao, G. et al., Isolating and engineering human antibodies using yeast surface display. Nat Protoc. 2006;1(2):755-68
Cheever, M.A. et al., The prioritization of cancer antigens: a national cancer institute pilot project for the acceleration of translational research. Clin Cancer Res. Sep. 1, 2009;15(17):5323-37.
Chen, X. et al., Advances in the biology and chemistry of sialic acids, ACS Chem Biol. Feb. 19, 2010;5(2)163-76.
Chung, C.H. et al., Cetuximab-induced anaphylaxis and IgE specific for galactose-alpha-1,3-galactose. N Engl J Med. Mar. 13, 2008;358(11)1109-17.
Cronican et al., Potent delivery of functional proteins into Mammalian cells in vitro and in vivo using a supercharged protein ACS Chem. Biol. 2010 5:747-752.
Daugherty, et al., Formulation and delivery issues for monoclonal antibody therapeutics, Adv Drug Deliv Rev. Aug. 7, 2006;58(5-6):636-706.

(56) References Cited

OTHER PUBLICATIONS

Davis et al. Evidence of RNAi in humans from systemically administered siRNA via targeted nanoparticles Nature 2010 464:1067-1070.
Davis, M.E. The first targeted delivery of siRNA in humans via a self-assembling, cyciodextrin polymer-based nanoparticle: from concept to clinic Mol Pharm. 2009 6:659-668.
Davis, M.E. The first targeted delivery of siRNA in humans via a self-assembling, cyclodextrin polymer-based nanoparticle: from concept to clinic Mol Pharm. 2009 6:659-668.
Deshayes et al., Cell-penetrating peptides: tools for intracellular delivery of therapeutics, Cell. Mol. Life Sci. 62 (16):1839-49 (2005).
Devine, P.L. et al., The breast tumor-associated epitope defined by monoclonal antibody 3E1.2 is an O-linked mucin carbohydrate containing N-glycolylneuraminic acid. Cancer Res. 1991, 51: 5826-5836.
Dharmawardhane, S. et al., Regulation of macropinocytosis by p21-activated kinase-1. Mol Biol Cell. Oct. 2000;11 (10):3341-52.
Diaz, S.L. et al., Sensitive and specific detection of the non-human sialic Acid N-glycolylneuraminic acid in human tissues and biotherapeutic products. PLoS One. 2009, 4: e4241.
Doyon, Y. et al., Heritable targeted gene disruption in zebrafish using designed zinc-finger nucleases, Nat Biotechnol, Jun. 2008;26(6):702-3.
El-Andaloussi et al., Cell-penetrating peptides: mechanisms and applications Curr. Pharm. Des. 11(23):3597-611 (2003).
Eppstein, D.A. et al., Biological activity of liposome-encapsulated murine interferon gamma is mediated by a cell membrane receptor. Proc Natl Acad Sci U S A. Jun. 1985;82(11):3688-92.
Geurts, A.M. et al., Knockout rats via embryo microinjection of zinc-finger nucleases. Science. Jul. 24, 2009;325 (5939):433.
Ghaderi, D. et al., Implications of the presence of N-glycolylneuraminic acid in recombinant therapeutic glycoproteins. Nat Biotechnol. 2010. 28: 863-867.
Gillies, S.D. et al., High-level expression of chimeric antibodies using adapted cDNA variable region cassettes. J Immunol Methods. Dec. 20, 1989;125(1-2):191-202.
Hedlund, M, et al., Evidence for a human-specific, mechanism for diet and antibody-mediated inflammation in carcinoma progression. Proc Natl Acad Sci U S A. Dec. 2, 2008;105(48):18936-41.
Heimburg-Molinaro, J. et al., Cancer vaccines and carbohydrate epitopes. Vaccine. Nov. 8, 2011;29(48):8302-26.
Higashi, H. et al., Characterization of N-glycolylneuraminic acid-containing gangliosides as tumor-associated Hanganutziu-Deicher antigen in human colon cancer.. Caner Res. Aug. 1985;45(8):3796-802.
Hojrnan, Basic principles and clinical advancements of muscle electrotransfer Curr Gene Ther. 2010 10:128-138.
Hollinger et al., Proc. Natl. Acad. Sci. USA, 90:6444-6448 (1993).
Huston, J.S. et al., Protein engineering of single-chain Fv analogs and fusion proteins. Methods Enzymol. 1991;203:46-88.
Hwang, K.J. et al., Hepatic uptake and degradation of unilamellar sphingomyelin/cholesterol liposomes: a kinetic study. Proc Natl Acad Sci U S A. Jul. 1980;77(7):4030-4.
Hwang, K.J. et al., Hepatic uptake and degradation of unilamellar sphingomyelin/cholesterol liposomes: a kinetic study. Proc Natl Acad Sci U S A. Jul. 1980;77(7):40304-4.
Ikehara, Y. et al., Cloning and expression of a human gene encoding an N-acetylgalactosamine-alpha2,6-sialyltransferase (ST6GalNAcI): a candidate for synthesis of cancer-associated sialyl-Tn antigens. Glycobiology. Nov. 1999;9(11):1213-24.
Itzkowitz, S.H. et al., Sialosyl-Tn. A novel rnucin antigen associated with prognosis in colorectal cancer patients. Cancer. Nov. 1, 1990;66(9):1960-6.
Jass, J.R. et al., Distribution of sialosyl Tn and Tn antigens within normal and malignant colorectal epithelium. J Pathol. Jun. 1995;176(2):143-9.
Johannes, L. et al., Clathrin-dependent or not: is it still the question? Traffic. Jul. 2002;3(7):443-51.
Ju, T. et al., Human tumor antigens Tn and sialyl Tn arise from mutaitons in Cosmc. Cancer Res. Mar. 15, 2008;68 (6):1633-46.
Ju, T. et al., Protein glycosylation: chaperone mutation in Tn syndrome. Nature. Oct. 27, 2005;437(7063):1252.
Julien S. et al. Sialyl-Tn in Cancer: (How) Did We Miss the Target? Biomolecules 2012, 2, 435-466.
Julien S. et al. Stable expression of sialyl-Tn antigen in T47-D cells induces a decrease of cell adhesion and an increase of cell migration Breast Cancer Research and Treatment (2005) 90:77-84.
Julien, S. et al., Sialyl-Tn vaccine induces antibody-mediated tumour protection in a relevant murine model, Br J Cancer. Jun. 2, 2009;100(11):1746-54.
Karlen, P. et al., Sialyl-Tn antigen as a marker of colon cancer risk in ulcerative colitis: relation to dysplasia and DNA aneuploidy. Gastroenterology. Dec. 1998;115(6):1395-404.
Kawachi. S, et al., Heterophile Hanganutziu-Deicher antigen in ganglioside fractions of human melanoma tissues. Int Arch Allergy Appl Immunol. 1988. 85: 381-383.
Yin, J. et al., Hypoxic culture induces expression of sialin, a sialic acid transporter, and cancer-associated gangilosides containing non-human sialic acid on human cancer cells. Cancer Res. Mar. 15, 2006;66(6):2937-45.
International Search Report for International Application No. PCT/US2013/029240, dated Jun. 21, 2013.
Zhu et al. Anti-N-glycolylneuraminic acid antibodies identified in healthy human serum. Xenotransplantation. 2002 vol. 9: 376-81.
An, H. J. et al. (2009) Glycomics and disease markers. Current Opinion in Chemical Biology 13(5-6), 601-607.
Andreu P; Johansson M; Affara Ni et al.: FcRgamma activation regulates inflammation-associated squamous carcinogenesis' Cancer Cell vol. 17, 2010, pp. 121-134.
Bergfeld, A. K. et al. (2012) "Metabolism of Vertebrate Amino Sugars with N-Glycolyl Groups: Elucidating the Intracellular Fate of the Non-Human Sialic Acid N-Glycolylneuraminic Acid," Journal of Biological Chemistry 287(34), 28865-28881.
Bork et al, 2009, Increasing the Sialylation of Therapeutic Glycoproteins: The Potential of the Sialic Acid Biosynthetic Pathway. Journal of Pharmaceutical Sciences. 98(10):3499-508.
Brinkman-Vander Linden, Els C. M.; E. R. Sjoberg; L. R. Juneha; P. R. Crocker; N. Varki; and A Varki; "Loss of N-Glycolylneuraminic Acid in Human Evolution"; The Journal of Biological Chemistry; Mar. 24, 2000, vol. 275, No. 12. pp. 8633-8640.
Carlson, D. M. et al. (1968) "Structures and Immunochemical Properties of Oligosaccharides Isolated from Pig Submaxillary Mucins," Journal of Biological Chemistry 243(3), 616-626.
Chou, et al. "A Mutation in Human Cmp-Sialic Acid Hydroxylase Occurred After the Homo-Pan Divergence." Proceedings of the National Academy of Sciences, 95(20):11751-11756 (1998).
Chou, et al. "Inactivation of Cmp-N-Acetylneuraminic Acid Hydroxylase Occurred Prior to Brain Expansion During Human Evolution." Proc Natl Acad Sci USA, 99(18):11736-11741 (2002).
Collins, Brian E.; T. J. Fralich; S. Itonori; Y. Ichiawa; and R. L. Schnaar; "Conversion of cellular sialic acid expression from N-acetyl- to N-glycolylneuraminic acid using a synthetic precursor, N-glycolylmannosamine pentaacetate: inhibition of myelin-associated glycoprotein binding to neural cells" Glycobiology; 2000, vol. 10, No. 1, pp. 11-20.
Conze, T. et al. (2010) "MUC2 mucin is a major carrier of the cancer-associated sialyl-Tn antigen in intestinal metaplasia and gastric carcinomas," Glycobiology 20(2) 199-206.
de León, J. et al. (2008) "Differential influence of the tumour-specific non-human sialic acid containing GM3 ganglioside on CD4+CD25+48 effector and naturally occurring CD4+CD25+ regulatory T cells function," International Immunology 20(4), 591-600.
de Visser, K E. et al. (2005) De novo carcinogenesis promoted by chronic inflammation is B lymphocyte dependent. Cancer Cell 7(5), 411-423.
Drake, P. M. et al. (2010) "Sweetening the Pot: Adding Glycosylation to the Biomarker Discovery Equation," Clinical Chemistry 56(2), 233-236.
Du, J. et al. (2009) "Metabolic glycoengineering: Sialic acid and beyond," Glycobiology 19(12), 1382-1401.

(56) References Cited

OTHER PUBLICATIONS

Eckhardt, A. E. et al. (1997) "The Complete cDNA Sequence and Structural Polymorphism of the Polypeptide Chain of Porcine Submaxillary Mucin," Journal of Biological Chemistry 272(52), 33204-33210.
Ferris, R. L. et al. (2010) "Tumor Antigen-Targeted, Monoclonal Antibody-Based Immunotherapy: Clinical Response, Cellular Immunity, and Immunoescape," Journal of Clinical Oncology 28(28), 4390-4399.
Furukawa, K. et al., Analysis of the expression of N-glycolylneuraminic acid-containing gangliosides in cells and tissues using two human monoclonal antibodies. J Biol. Chem. vol. 263, 1988, pp. 18507-18512.
Goodman, M. The genomic record of Humankind's evolutionary roots. Am. J. Hum. Genet. vol. 64, 1999, pp. 31-39.
Gupta, D. and Lis, C. (2009) "Role of CA125 in predicting ovarian cancer survival—a review of the epidemiological literature," Journal of Ovarian Research 2(1), 13.
Hara, S. et al. (1986) "Highly sensitive determination of N-acetyl- and N-glycolylneuraminic acids in human serum and urine and rat serum by reversed-phase liquid chromatography with fluoroscence detection," Journal of chromatography A 377, 111-119.
Hayakawa, T. et al. (2001) "Alu-mediated inactivation of the human CMP-N-acetylneuraminic acid hydroxylase gene," Proceedings of the National Academy of Sciences 98(20), 11399-11404.
Hedlund, M. et al. (2007) "N-Glycolylneuraminic Acid Deficiency in Mice: Implications for Human Biology and Evolution," Molecular and Cellular Biology 27(12), 4340-4346.
Hirabayashi Y et al: "A new method for purification of anti-glycosphingolipid antibody. Avian anti-hematoside (NeuGc) antibody" Journal of Biochemistry, Japanese Biochemical Society / Oup, Tokyo; JP, vol. 94, No. 1, Jul. 1, 1983 (Jul. 1, 1983), pp. 327-330.
Hong and Stanley, "Lec3 Chinese Hamster Ovary Mutants Lack UDP-N-Acetylglucosamine 2-Epimerase Activity Because of Mutations in the Epimersase Domain of the Gne Gene." J Biol Chem, 278(52):53045-53054 (2003).
Hossler et al, Glycobiology, vol. 19, No. 9, pp. 936-949, 2009, Optimal and consistent protein glycosylation in mammalian cell culture.
Inoue, S. et al., (2010) "Extensive enrichment ofN-glycolylneuraminic acid in extracellular sialoglycoproteins abundantly synthesized and secreted by human cancer cells," Glycobiology 20(6), 752-762.
Irie, A. et al: "The Molecular Basis for the Absence of N-Glycolylneuraminic Acid in Humans", Journal of Biological Chemistry, vol. 273, No. 25, Jun. 19, 1998 (Jun. 19, 1998), pp. 15866-15871.
Johansen, E. et al. (2009) "A Lectin HPLC Method to Enrich Selectively-glycosylated Peptides from Complex Biological Samples," Journal of Visualized Experiments(32), 1398.
Jolles, S. et al. (2005) "Clinical uses of intravenous immunoglobulin," Clinical & Experimental Immunology 142(1), 1-11.
Ju, T. and Cummings, R. D. (2002) A unique molecular chaperone Cosme required for activity of the mammalian core 1 S3-galactosyltransferase, Proceedings of the National Academy of Sciences 99(26), 16613-16618.
Karim, M., et al. 2006 CAB Reviews: Perspectives in Agriculture, Veterinary Science, Nutrition, and Natural Resources 1 (018 ): 1-11.
Kawai T. et al., Quantitative determination of N-glycolylneuraminic acid expression in human cancerous tissues and avian lymphoma cell lines as a tumor-associated sialic acid by gas chromatography-mass spectrometry. Cancer Res. vol. 51, 1991, pp. 1242-1246.
Kawano, T. et al. (1995) "Molecular Cloning of Cytidine Monophospho-N-Acetylneuraminic Acid Hydroxylase. Regulation of Species- and Tissue-Specific Expression of N-Glycolylneuraminic Acid," Journal of Biological Chemistry 270(27), 16458-16463.
Kayser, H. et al., Biosynthesis of a nonphysiological sialic acid in different rat organs, using N-propanoyl-D-hexosamines as precursors. J Biol. Chem. vol. 267, 1992, pp. 16934-16938.
Kjeldsen, T. et al. (1998) "Preparation and Characterization of Monoclonal Antibodies Directed to the Tumor-associated O-linked Sialosyl-2?6 ?-N-Acetylgalactosaminyl (Sialosyl-Tn) Epitope," Cancer Research 48(8), 2214-2220.
Klein, A. et al., New sialic acids from biological sources identified by a comprehensive and sensitive approach: liquid chromatography-electrospray ionization-mass spectrometry (LC-ESI-MS) of SIA quinoxalinones. Glycobiology vol. 7, 1997, pp. 421-432.
Kobata, A. and Amano, J. (2005) "Altered glycosylation of proteins produced by malignant cells, and application for the diagnosis and immunotherapyof tumours," Immunology & Cell Biology 83(4), 429-439.
Kozutsumi, Y.; Kawano, T.; Yamakawa, T.; Suzuki, A J Biochem. vol. 108, 1990, pp. 704-706.
Li, C. et al. (2009) "Pancreatic Cancer Serum Detection Using a Lectin/Glyco-Antibody Array Method," Journal of Proteome Research 8(2), 483-492.
Liu, C.C. et al. (2009) "Integrative disease classification based on cross-platform microarray data," BMC Bioinformatics 10 Suppl 1:S25.
Lofling, J. C. et al. (2009) "A dietary non-human sialic acid may facilitate hemolytic-uremic syndrome," Kidney International 76(2), 140-144.
Marquina, Gilda; H. Waki; L. E. Fernandez; K. Kon; A Carr; 0. Valiente; R. Perez; and S. Ando; "Gangliosides Expressed in Human Breast Cancer"; Cancer Research; Nov. 15, 1996; pp. 5165-5171.
Martin et al. Abstract #4182, Blood, (Nov. 16, 2004) vol. 104, No. 11, Part 2, pp. 132B. Meeting Info.: 46th Annual Meeting of the American-Society-of-Hematology. San Diego, CA, USA. Dec. 4-7, 2004.
Martin. L. T. et al. (2002) Genetically Altered Mice with Different Sialyl transferase Deficiencies Show Tissue-specific Alterations in Sialylation and Sialic Acid 9-O-Acetylation, Journal of Biological Chemistry 277(36), 32930-32938.
Muchmore, Elaine et al, American Journal of Physical Anthropology 107:187-198 (1998); A Structural Difference Between the Cell Surfaces of Humans and the Great Apes.
Muchmore, E. et al., Biosynthesis of N-glycolyneuraminic acid. The primary site of hydroxylation of N-acetylneuraminic acid is the cytosolic sugar nucleotide pool. J Biol. Chem vol. 264, 1989, pp. 20216-20223.
Naito, Y. et al., 2007. Germinal center marker GL7 probes activation-dependent repression of N-glycolylneuraminic acid, a sialic acid species involved in the negative modulation of B-cell activation. Mol Cell Biol. Apr. 2007;27 (8):3008-22.
Nelson, H. D. et al (2009) Screening for Breast Cancer: An Update for the U.S. Preventive Services Task Force, Annals of Internal Medicine 151(10), 727-737.
Nogueira, L. et aL (2009) Prostatic specific antigen for prostate cancer detection. International Braz j urol 35(5), 521-529.
Nohle, U. et al. (1982) "Update, Metabolism and Excretion of Orally and Intravenously Administered, Double-Labeled N-Glycoloylneuraminic Acid and Single-Labeled 2-Deoxy-2,3-dehydro-N-acetylneuraminic Acid in Mouse and Rat, " European Journal of Biochemistry 126(3), 543-548.
Oetke, Cornelia; S. Hinderlich; R. Brossmer; W. Reutter; M. Pawlita; and 0. T. Keppler; "Evidence for efficient uptake and incorporation of sialic acid by eukaryotic cells"; Eur. J. Biochem.; 2001; 265; pp 4553-4561.
Ostrand-Rosenberg, S. (2008) "Immune surveillance: a balance between protumor and antitumor immunity," Current Opinion in Genetics & Development 18(1), 11-18.
Oyelaran O; McShane LM; Dodd L; Gildersleeve JC: 'Profiling human serum antibodies with a carbohydrate antigen microarray' J Proteome Res. vol. 8, 2009, pp. 4301-4310.
Pearce, O. M. et al. (2010) "Chemo-enzymatic synthesis of the carbohydate antigen N-glycolylneuraminic acid from glucose," Carbohydrate Research 345(9), 1225-1229.
Phelps, C. J. et al., "Production of Alpha 1,3-Galactosyltransferase-Deficient Pigs." Science, 299(5605):411-414 (2003).
Saldova, R. et al., 'Glycosylation changes on serum glycoproteins in ovarian cancer may contribute to disease pathogenesis' DIS Markers vol. 25, 2008, pp. 219-232.

(56) References Cited

OTHER PUBLICATIONS

Sato et al. Frequent occurrence of pre-existing alpha 2→8-linked disialic and oligosialic acids with chain lengths up to 7 Sia residues in mammalian brain glycoproteins. Prevalence revealed by highly sensitive chemical methods and anti- di-, oligo-, and poly-Sia antibodies specific for defined chain lengths. J. Bioi. Chem. 2000 vol. 276, p. 15422-15431.
Sato, Chihiro et al., "Carbohydrates, Lipids, and Other Natural Products: Identification of Oligo-N-Glycolylneuraminic Acid Residues in Mammal-derived Glycoproteins by a Newly Developed Immunochemical Reagent and Biochemical Methods", J. Biol. Chern. 1998, 273:2575-2582.
Schröder, F. H. et al. (2009) "Screening and Prostate-Cancer Mortality in a Randomized European Study," New England Journal of Medicine 360(13), 1320-1328.
Schwarzkopf, et al., "Sialylation Is Essential for Early Development in Mice." Proc Natl Acad Sci U S A, 99 (8):5267-5270 (2002).
Sewell R. et al. (2006) The ST6GalNAc-I Sialyltransferase Localizes throughout the Golgi and Is Responsible for the Synthesis of the Tumor-associated Sialyl-Tn O-Glycan in Human Breast Cancer, Journal of Biological Chemistry 281(6), 3586-3594.
Shaw, L. et al. (1994) "CMP-N-acetylneuraminic acid hydroxylase from mouse liver and pig submandibular glads," European Journal of Biochemistry 219(3), 1001-1011.
Sjoberg, Eric R.; L. D. Powell; A Klein; and A Varki; "Natural Ligands of the B Cell Adhesion Molecule CD22j3 can be Masked by 9-0-Acetylation of Sialic Acids"; The Journal of Cell Biology; Jul. 1994; Voo. 126, No. 2., pp. 549-562.
Slovin, S. F. et al. (2005) "Carbohydrate vaccines as immunotherapy for cancer," Immunology & Cell Biology 83(4), 418-428.
Sonnenburg, Justin L.; H. van Halbeek; and A Varki "Characterization of the Acid Stability of Glycosidically Linked Neuraminic Acid"; The Journal of Biological Chemistry; May 17, 2002; vol. 277, No. 20, pp. 17502-17510.
Soussi, T. (2000) "p53 Antibodies in the Sera of Patients with Various Types of Cancer: A Review," Cancer Research 60(7), 1777-1788.
Srivastava, S. and Gopal-Srivastava, R. (2002) "Biomarkers in Cancer Screening: A Public Health Perspective," The Journal of Nutrition 132(8), 2471S-2475S.
Stanley and Ioffe, "Glycosyltransferase Mutants: Key to New Insights in Glycobiology." FASEB J, 9(14):1436-1444 (1995).
Takematsu, H. et al., (1994) "Reaction Mechanism Underlying CMP-N-Acetylneuraminic Acid Hydroxylation in Mouse Liver: Formation of a Ternary Complex of Cytochrome b5, CMP-N-Acetylneuraminic Acid, and a Hydroxylation Enzyme," J. Biochem. (Tokyo) 115(3), 381-386.
Taylor, R. E. et al. (2010) "Novel mechanism for the generation of human xeno-autoantibodies against the nonhuman sialic acid N-glycolylneuraminic acid," The Journal of Experimental Medicine 207(8), 1637-1646.
Thompson I.M. et al. (2005) "Operating characteristics of prostate-specific antigen in men with an initial psa level of 3.0 ng/ml or lower," JAMA: The Journal of the American Medical Association 294(1), 66-70.
Uygur-Bayramicli, O. et al. (2007) "Type 2 diabetes mellitus and CA 19-9 levels," World Journal of Gastroenterology 13 (40), 5357-5359.
Vamecq, J.et al., Subcellular distribution of glycolyltransferases in rodent liver and their significance in special reference to the synthesis of N-glycolyneuraminic acid. J Biochem vol. 111, 1992, pp. 579-583.
Varki "Sialic Acids in Human Health and Disease." Trends Mol Med, 14(8):351-360 (2008).
Varki, A "N-glycolylneuraminic acid deficiency in humans", Biochimie 83 (2001) 615-622.
Varki, A. "Loss of N-Glycolylneuraminic Acid in Humans: Mechanisms, Consequences, and Implications for Hominid Evolution" Yearbook of Physical Anthropology 44:54-69 (2001).
Varki, A. (2010) "Uniquely human evolution of sialic acid genetics and biology," Proceedings of the National Academy of Sciences 107(Supplement 2), 8939-8946.
Varki, A. et al. (2009) Glycosylation Changes in Cancer, in Essentials of Glycobiology. Ch 44, pp. 617-632, Cold Spring Harbor Laboratory Press, Cold Spring Harbor, New York.
Varki, A. et al. (2009) In Essentials of Glycobiology (Varki, A., et al., Eds.), Ch. 14, pp. 199-218, Cold Spring Harbor Laboratory Press, Cold Spring Harbor, NY.
Varki, Ajit; "Sialic acids such as ligands in recognition phenomena" The FASEB Journal; Mar. 1997; vol. 111 pp. 248-255.
Wang, B. et al. (2001) "Concentration and distribution of sialic acid in human milk and infant formulas," American Journal of Clinical Nutrition 74(4), 510-515.
Wang, B. et al. (2007) "Dietary sialic acid supplementation improves learning and memory in piglets," American Journal of Clinical Nutrition 85(2), 561-569.
Weiss, J. M. et al. (2007) Immunotherapy of Cancer by IL-12-based Cytokine Combinations. Expert Opinion on Biological Therapy 7(11), 1705-1721.
Wong, N.S. et al, 2010. An Investigation of Intracellular Glycosylation Activities in CHO Cells: Effects of Nucleotide Sugar Precursor Feeding. Biotechnology and Bioengineering. 107(2):321-36.
Wright, et al., "Piscine Islet Xenotransplantation." ILAR J, 45(3):314-323 (2004).
Wu, X. et al. (2004) "A New Homobifunctional p-Nitro Phenyl Ester Coupling Reagent for the Preparation of Neoglycoproteins," Organic Letters 6(24), 4407-4410.
Wu. C.-Y. et al. (2009) New development of glycan arrays, Organic & Biomolecular Chemistry 7(11), 2247-2254.
Yu, H. et al. (2005) A Multifunctional Pasteurella multocida Sialyltransferase: A Powerful Powerful Tool for the Synthesis of Sialoside Libraries, Journal of the American Chemical Society 127(50), 17618-17619.
Yu, H. et al. (2006) Highly Efficient Chemoenzymatic Synthesis of Naturally Occurring and Non-Natural a-2,6-Linked Sialosides: A P. damsela a-2,6-Sialyltransferase with Extremely Flexible Donor-Substrate Specificity, Angewandte Chemie International Edition 45(24), 3938-3944.
Yu, H. et al. (2006) One-pot three-enzyme chemoenzymatic approach to the synthesis of sialosides containing natural and non-natural functionalities. Nature Protocols 1(5), 2485-2492.
Yu, H. et al. (2007) "Efficient chemoenzymatic synthesis of biotinylated human serum albumin-sialoglycoside conjugates containing O-acetylated sialic acids," Organic & Biomolecular Chemistry 5(15), 2458-2463.
Zhang, D.Y. et al. (2009) "Proteomics, pathway array and signaling network-based medicine in cancer," Cell Division 4 (1), 20.
Angata, T. et al. (2002) "Chemical Diversity in the Sialic Acids and Related α-Keto Acids; An Evolutionary Perspective," Chemical Reviews 102(2), 439-470.
Asaoka, H. et al. "Two chicken monoclonal antibodies specific for heterophil Hanganutziu-Deicher antigens." Immunol. Lett vol. 32, 1992, pp. 91-96.
Candefjord, S. et al. (2009) "Technologies for localization and diagnosis of prostate cancer," Journal of Medical Engineering & Technology 33(8), 585-603.
Carr, et al. "A Mouse IgG1 Monoclonal Antibody Specific for N-Glycolyl Gm3 Ganglioside Recognized Breast and Melanoma Tumors." Hybridoma, 19(3):241-247 (2000).
Cavadas, V. et al. (2010) "Prostate Cancer Prevention Trial and European Randomized Study of Screening for Prostate Cancer Risk Calculators: A Performance Comparison in a Contemporary Screened Cohort," European Urology 58(4), 551-558.
Chenu, et al. "Reduction of Cmp-N-Acetylneuraminic Acid Hydroxylase Activity in Engineered Chinese Hamster Ovary Cells Using an Antisense-RNA Strategy." Biochim Biophys Acta, 1622(2):133-144 (2003).
Dai, et al., "Targeted Disruption of the Alpha1,3-Galactosyltransferase Gene in Cloned Pigs." Nat Biotechnol, 20(3):251-255 (2002).
Desmetz, C. et al. (2009) "Humoral response to cancer as a tool for biomarker discovery," Journal of Proteomics 72(6), 982-988.

(56) References Cited

OTHER PUBLICATIONS

Diaz, A. et al., (2003) "Immune responses in breast cancer patients immunized with an anti-idiotype antibody mimicking NeuGc-containing gangliosides," Clin. Immunol. 107(2), 80-89.
Dube, D. H. and Bertozzi, C. R. (2005) "Glycans in cancer and inflammation—potential for therapeutics and diagnostics," Nature Reviews Drug Discovery 4(6), 477-488.
Finn, O. J. (2008) "Cancer Immunology," New England Journal of Medicine 358(25), 2704-2715.
Fujii, Y. et al., Specificities of human heterophilic Hanganutziu and Deicher (H-D) antibodies and avian antisera H-D antigen-active glycosphingolipids. Mol. Immunol. vol. 19, 1982, pp. 87-94.
Greene, K. L. et al. (2009) "Prostate Specific Antigen Best Practice Statement: 2009 Update," The Journal of Urology 182(5), 2232-2241.
Heiskanen, et al., "N-Glycolylneuraminic Acid Xenoantigen Contamination of HumanEmbryonic and Mesenchymal Stem Cells Is Substantially Reversible." Stem Cells, 25(1):197-202 (2007).
Higashi, et al. "Detection of Gangliosides as N-Glycolylneuraminic Acid-Specific Tumor-Associated Hanganutziu-Deicher Antigen in Human Retinoblastoma Cells." Jpn J Cancer Res,79(8):952-956 (1998).
Higashi, H. et al., Antigen of "serum sickness" type of heterophile antibodies in human sera: indentification as gangliosides with N-glycolylneuraminic acid. Biochem. Biophys. Res. Comm. vol. 79, 1977, pp. 388-395.
Hirabayashi Y et al: "Occurrence of Tumor-Associated Ganglioside Antigens With Hanganutziu-Deicher Antigenic Activity on Human Melanomas" Japanese Journal of Cancer Research, Japanese Cancer Association, Tokyo, JP, vol. 78, No. 6, Jan. 1, 1987, pp. 614-620.
Hirabayashi, et al. "Specific Expression of Unusual Gm2 Ganglioside with Hanganutziu-Deicher Antigen Activity on Human Colon Cancers." 78(3):251-260 (1987).
Juneja, L. R. et al. Large-scale preparation of sialic acid from chalaza and egg-yolk membrane. Carbohydr. Res. vol. 214, 1991, pp. 179-186.
Kasai N et al: "Preparation and specificity of avian anti-GM2(NeuGc) ganglioside antiserum", Biochemical and Biophysical Research Communications, Academic Press Inc. Orlando, FL, US, vol. 129, No. 2, Jun. 14, 1985 (Jun. 14, 1985) , pp. 334-341.
Kim, G. E. et al. (2002) "Aberrant expression of MUC5AC and MUC6 gastric mucins and sialyl Tn antigen in intraepithelial neoplasms of the pancreas," Gastroenterology 123(4), 1052-1060.
Kim, Y. and Varki, A. (1997) "Perspectives on the significance of altered glycosylation of glycoproteins in cancer," Glycoconjugate Journal 14(5), 569-576.
Lee, J.-O., et al. Production of N-acetylneuraminic acid from N-acetylglucosamine and pyruvate using recombinant human renin binding protein and sialic acid aldolase in one pot. 2004. Enzyme and Microbial Technology 35(2-3): 121-125.
Lewartowska Aleksandra et al: "Ganglioside reactive antibodies of IgG and IgM class in sera of patients with differentiated thyroid cancer", Immunology Letters, vol. 80, No. 2, Feb. 1, 2002 (Feb. 1, 2002), pp. 129-132.
Lowe and Marth, "A Genetic Approach to Mammalian Glycan Function." Annu Rev Biochem,72:643-691 (2003).
Ludwig, J. A. and Weinstein, J. N. (2005) "Biomarkers in Cancer Staging, Prognosis and Treatment Selection," Nature Reviews Cancer 5(11), 845-856.
Marcial, V. A. (1977) "Carcinoma of the cervix. Present status and future," Cancer 39(Supplement S2), 945-958.
Mechref, Y. et al. (2009) "Quantitative Serum Glycomics of Esophageal Adenocarcinoma and Other Esophageal Disease Onsets," Journal of Proteome Research 8(6), 2656-2666.
Merrick, J. M.et al., Characterization of the Hanganutziu-Deicher (serum-sickness) antigen as gangliosides containing n-glycolylneuraminic acid. Int. Arch. Allergy Appl. Immunol. vol. 57, 1978, pp. 477-480.
Morito T et al. 1986. "Studies on Hanganutziu-Deicher antigens-antibodies. I. Hanganutziu-Deicher antibodies of IgG class in liver diseases", International Archives of Allergy and Applied Immunology. 81(3): 204-208.
Nelson, A. E. et al. (2009) "Population screening and early detection of ovarian cancer in asymptomatic women," Australian & New Zealand Journal of Obstetrics & Gynaecology 49(5), 448-450.
Nohle, U. et al. (1981) "Uptake, metabolism and excretion of orally and intravenously administered, 14C- and 3H-labeled N-acetylneuraminic acid mixture in the mouse and rat," Hoppe-Seylers Zeitschriftfur Physiologische Chemie 362(11), 1495-1506.
Nossov, V. et al. (2008) "The early detection of ovarian cancer: from traditional methods to proteomics. Can we really do better than serum CA-125?," American Journal of Obstetrics and Gynecology 199(3), 215-223.
Ogata, S. et al. (1998) "Different modes of sialyl-Tn expression during malignant transformation of human colonic mucosa," Glycoconjugate Journal 15(1), 29-35.
Parkin, D. M. et al. (2001) "Cancer burden in the year 2000. The global picture," European Journal of Cancer 37, Supplement 8(0), 4-66.
Prehn, R. T. and Prehn, L. M. (2008) "The flip side of immune surveillance: immune dependency," Immunological Reviews 222(1), 341-356.
Raedle, J. et al. (1998) "Clinical evaluation of autoantibodies to p53 protein in patients with chronic liver disease and hepatocellular carcinoma," European Journal of Cancer 34(8), 1198-1203.
Ransohoff, D. F. (2004) "Rules of evidence for cancer molecular-marker discovery and validation," Nature Reviews Cancer 4(4), 309-314.
Schauer, R. et al. (2009) "Low incidence ofN-glycolylneuraminic acid in birds and reptiles and its absence in the platypus," Carbohydrate Research 344(12), 1494-1500.
Schauer, R. Adv. Carbohydr. Chem. Biochem. Biochem. vol. 40, 1982, pp. 131-234.
Shaw, L. et al. (1998) "The biosynthesis of N-glycoloylneuraminic acid occurs by hydroxylation of the CMP-glycoside of N-acetylneuraminic acid," Biological Chemistry Hoppe-Seyler 369(6), 477-486.
Stacker, S. A. et al., (1985) "A new breast carcinoma antigen defined by a monoclonal antibody," J. Natl. Cancer Inst. 75(5), 801-811.
Tan, H. T. et al. (2009) "Serum autoantibodies as biomarkers for early cancer detection," FEBS Journal 276(23), 6880-6904.
Traving and Schauer "Structure, Function and Metabolism of Sialic Acids." Cell Mol Life Sci,54(12):1330-1349 (1998).
Tzanakakis, et al., "Determination and Distribution of N-Acetyl- and N-Glycolylneuraminic Acids in Culture Media and Cell-Associated Glycoconjugates from Human Malignant Mesothelioma and Adenocarcinoma Cells." Biomed Chromatogr, 20(5):434-439 (2006).
Vamecq, J. et al., Studies on the metabolism of glycolyl-CoA. Biochem. Cell Biol. vol. 68, 1990, pp. 846-851.
van Leeuwen, P. J. et al. (2010) "Prostate cancer mortality in screen and clinically detected prostate cancer: Estimating the screening benefit," European Journal of Cancer 46(2), 377-383.
Varki, A. et al., The release and purification of sialic acids from glycoconjugates: methods to minimize the loss and migration of O-acetyl groups. Anal. Biochem. vol. 137, 1984, pp. 236-247.
Vaquez, A. M. et al., Generation of a murine monoclonal antibody specific for N-glycolylneuraminic acid-containing gangliosides that also recognizes sulfated glycolipids. Hybridoma vol. 14, 1995, pp. 551-556.
Warren, L. 1963. The Distribution of Sialic Acids in Nature. Comp. Biochem. Physiol. 10: 153-71.
International Search Report for PCT/US2014/060079 dated Mar. 27, 2015.
International Search Report for PCT/US2015/054877 dated Feb. 9, 2016.
International Search Report for PCT/US2015/054936 dated Feb. 4, 2016.
International Search Report for PCT/US2015/060287 dated Mar. 31, 2016.

(56) References Cited

OTHER PUBLICATIONS

Padler-Karavani et al. "Human Xeno-Autoantibodies against a Non-Human Sialic Acid Serve as Novel Serum Biomarkers and Immunotherapeutics in Cancer", Cancer Research, Apr. 19, 2011 (Apr. 19, 2011), vol. 71, pp. 3352-3363.
Ghaderi et al. "Production platforms for biotherapeutic glycoproteins. Occurrence, impact, and challanges of non-human sialyation," Biotechnology and Genetic Engineering Reviews, Apr. 15, 2013 (Apr. 15, 2013), vol. 26, pp. 147-176.
Alderson, K.L. et al., (2011) Clinical Cancer Therapy by NK Cells via Antibody-Dependent Cell-Mediated Cytotoxicity, J Biomed Biotechnol. 2011:379123.
Allavena, P. et al., (2010) Engagement of the Mannose Receptor by Tumoral Mucins Activates an Immune Suppressive Phenotype in Human Tumor-ssociatedMacrophages Clin Dev Immunol. 2010:547179.
Al-Lazikani, B. et al., (1997) Standard Conformations for the Canonical Structures of Immunoglobulins J. Mol. Biol. 273 (4):927-48.
Arafat et al., (2000) Antineoplastic effect of anti-erbB-2 intrabody is not correlated with scFv affinity for its target Cancer Gene Ther. 7:1250-6.
Biocca, Neuberger and Cattaneo (1990) Expression and targeting of intracellular antibodis in mammalian cells EMBO J. 9:101-108.
Carrascal, M.A. et al., (2014) Sialyl Tn-expressing bladder cancer cells induce a tolerogenic phenotype in innate and adaptive immune cells Molecular Oncology. 8(3): 753-65.
Casadesus, A.V. et al., A shift from N-glycolyl- to N-acetyl-sialic acid in the GM3 ganglioside impairs tumor development in mouse lymphocytic leukemia cells, 2013. Glycoconj J. 30(7):687-99.
Chen et al., (1994) Combined intra- and extracellular immunization against human anti-gp120 antibody Proc. Natl. Acad. Sci. USA 91:5932-5936.
Chothia and Lesk, (1987) Canonical Structures for the Hypervariable Regions of Immunoglobulins, J. Mol. Biol. 196:901-917.
Chothia et al., (1989) Conformations of immunoglobulin hypervariable regions, Nature 342:877-883.
Chu et al., (2000) CpG Oligodeoxynucleotides Act as Adjuvants for Pneumococcal Polysaccharide-Protein Conjugate Vaccines and Enhance Antipolysaccharide Immunoglobulin G2a (IgG2a) and IgG3 Antibodies, Infection Immunity 68 (3):1450-1456.
Cohen, et al., (1998) Characterization of a new intrabody directed against the N-terminal region of human p53, Oncogene 17:2445-2456.
Colby et al., (2004) Potent inhibition of huntingtin aggregation and cytotoxicity by a disulfide bond-free single-domain intracellular antibody, Proc. Natl. Acad. Sci. U.S.A. 101(51):17616-17621.
Colcher, D. et al., 1981. A spectrum of monoclonal antibodies reactive with human mammary tumor cells PNAS 78(5): 3199-203.
der Maur et al., (2002) Direct in Vivo Screening of Intrabody Libraries Constructed on a Highly Stable Single-chain Framework, J. Biol. Chem. 277(47):45075-45085.
Edwards, B.M. et al., (2003) The Remarkable Flexibility of the Human Antibody Repertoire; Isolation of Over One Thousand Different Antibodies to a Single Protein, BLyS, JMB. 334:103-18.
Engelmann et al., (2008) MCF7 Side Population Cells with Characteristics of Cancer Stem/Progenitor Cells Express the Tumor Antigen MUC1, Cancer Research, 68(7):2419-2426.
Finney, et al., (2004) Activation of Resting Human Primary T Cells with Chimeric Receptors: Costimulation from CD28, Inducible Costimulator, CD134, and CD137 in Series with Signals from the TCR Chain, J. Immunology, 172:104-113.
Graille, M.G. et al., 2000. Crystal structure of a *Staphylococcus aureus* protein A domain complexed with the Fab fragment of a human IgM antibody: Structural basis for recognition of B-cell receptors and superantigen activity. PNAS. 37(10): 5399-404.
Hamilton, T.C. et al., (1983) Characterization of a Human Ovarian Carcinoma Cell Line (NIH:OVCAR-3)1 with Androgen and Estrogen Receptors, Cancer Res. 43: 5379-89.
Hassanzadeh, et al., (1998) The regulated expression of an intrabody produces a mutant phenotype in *Drosophila*, FEBS Lett. 437:81-86.
Honegger, A. and Pluckthun, A. (2001) Yet Another Numbering Scheme for Immunoglobulin Variable Domains: An Automatic Modeling and Analysis Tool, J. Mol. Biol. 309(3):657-70.
Ibrahim, N.K. et al., (2013) Survival Advantage in Patients with Metastatic Breast Cancer Receiving Endocrine Therapy plus Sialyl Tn-KLH Vaccine: Post Hoc Analysis of a Large andomized Trial, Journal of Cancer 4(7): 577-584.
Ishida, A. et al., Mucin-induced apoptosis of monocyte-derived dendritic cells during maturation, 2008. Proteomics. 8:3342-9.
Jandus, C. et al., (2014) Interactions between Siglec-7/9 receptors and ligands influence NK cell-dependent tumor immunosurveilance, JCI. pii: 65899 124(4):1810-1820.
Johnson, G. et al., (2000) Interactions between Siglec-7/9 receptors and ligands influence NK cell-dependent tumor immunosurveilance , Nucleic Acids Res. 28(1): 214-218.
Lefranc, M.P., (2005) IMGT, the international ImMunoGeneTics information system®: a standardized approach for immunogenetics and immunoinformatics, Immunome Res. 1:3.
Liang, D. et al., (2012) The hypoxic microenvironment upgrades stem-like properties of ovarian cancer cells, BMC Cancer. 12: 201.
Mack et al, (1995) A small bispecific antibody construct expressed as a functional single-chain molecule with high tumor cell cytotoxicity, Proc. Natl. Acad. Sci., 92: 7021-7025.
Marasco et al., (1993) Design, intracellular expression, and activity of a human anti-human immunodeficiency virus type 1 gpl20 single-chain antibody, Proc. Natl. Acad. Sci. USA 90:7889-7893.
Marasco, (1995) Intracellular antibodies (intrabodies) as research reagents and therapeutic molecules for gene therapy, Immunotech, 1:1-19.
Marasco (1997) Intrabodies: turning the humoral immune system outside in for intracellular immunization, Gene Ther. 4:11-15.
Marvin, J.S. et al., (2005) Recombinant approaches to IgG-like bispecific antibodies, Acta Pharmacologica Sinica. 26 (6):649-58.
Matusda, F. et al., (1998) The Complete Nucleotide Sequence of the Human Immunoglobulin Heavy Chain Variable Region Locus, The Journal of Experimental Medicine. 188(11): 2151-62.
McCafferty, et al., Recovery From Hip Fracture in Eight Areas of Function, 1990. Nature. 348:552-4.
Meunier, L. et al., (2010) Effect of Ovarian Cancer Ascites on Cell Migration and Gene Expression in an Epithelial Ovarian Cancer In Vitro Model, Transl Oncol. 3(4): 230-238.
Mhashilkar et al., (2002) Intrabody-mediated phenotypic knockout of major histocompatibility complex class I expression in human and monkey cell lines and in primary human keratinocytes, Gene Ther. 9:307-319.
Mhashilkar, et al., (1995) Inhibition of HIV-1 Tat-mediated LTR transactivation and HIV-1 infection by anti-Tat single Chain intrabodies, EMBO J. 14:1542-1551.
Mortezai, N. et al., (2013) Tumor-associated Neu5Ac-Tn and Neu5Gc-Tn antigens bind to C-type lectin CLEC10A (CD301, MGL), Glycobiology 23(7):844-852.
Mukherjee, K. et al., O-Acetylation of GD3 Prevents its Apoptotic Effect and Promotes Survival of Lymphoblasts in Childhood Acute Lymphoblastic Leukaemia, 2008. J Cell Biochem. 105: 724-34.
Mukherjee, K. et al., Co-expression of 9-O-acetylated sialoglycoproteins and their binding proteins on lymphoblasts of childhood acute lymphoblastic leukemia: an anti-apoptotic role, 2009. Biol Chem. 390: 325-35.
Muraro, R. et al., (1988) Generation and Characterization of B72.3 Second Generation Monoclonal Antibodiws Reactive with the Tumor-associated Glycoprotein 72 Antigen, Cancer Res. 48: 4588-4596.
Nielson, A. L., (2010) Antibody fragments Mabs. Jan.-Feb.; 2(1):77-83.
Nikoloudis, D. et al., (2014) A complete,multi-level conformational clustering of antibody complementarity-determining regions PeerJ. 2:e456.
Nollau, P. et al., (2013) A complete, multi-level conformational clustering of antibody complementarity-determining regions, J Histochem Cytochem. 61(3):199-205.
Ohage and Steipe, Intrabody Construction and Expression. I. The Critical Role of VL Domain Stability, 1999, J. Mol. Biol. 291:1119-1128.

(56) References Cited

OTHER PUBLICATIONS

Ohage et al., Intrabody Construction and Expression. II. A Synthetic Catalytic Fv Fragment, 1999, J. Mol. Biol. 291:1129-1134.
Panowski, S. et al., Site-specific antibody drug conjugates for cancer therapy, 2014. mAbs 6:1, 34-45.
Park J.G. et al., Characteristics of Cell Lines Established from Human Gastric Carcinoma, 1990. Cancer Res. 50: 2773-80.
Pershad, K. et al., (2010) Generating a panel of highly specific antibodies to 20 human SH2 domains by phage display, Protein Engineering Design and Selection 23:279-288.
Porter, et al., (2011) Chimeric Antigen Receptor-Modified T Cells in Chronic Lymphoid Leukemia, N. Engl. J. Med. 365:725-733
Proba et al., (1998) Antibody scFv Fragments Without Disulfide Bonds Made by Molecular Evolution, J. Mol. Biol. 275:245-253.
Richardson et al., (1998) Intrabody-mediated knockout of the high-affinity IL-2 receptor in primary human T cells using a bicistronic lentivirus vector, Gene Ther. 5:635-644.
Riethmuller, G. (2012) Symmetry breaking: bispecific antibodies, the beginnings, and 50 years on, Cancer Immunity. 12:12-18.
Schaefer, W. et al., (2011) Immunoglobulin domain crossover as a generic approach for the production of bispecific IgG antibodies. PNAS. 108(27):11187-11192.
Schofield, D. et al., (2007) Application of phage display to high throughput antibody generation and characterization. Genome Biol 8:R254.
Sen et al., (2006) Immunization of Aged Mice with a Pneumococcal Conjugate Vaccine Combined with an Unmethylated CpG-Containing Oligodeoxynucleotide Restores Defective Immunoglobulin G Antipolysaccharide Responses and Specific CD4-T-Cell Priming to Young Adult Levels. Infection Immunity 74(3):2177-86.
Shi, W-X. et al., (1996) Sialic Acid 9-O-Acetylation on Murine Erythroleukemia Cells Affects Complement Activation, Binding to I-type Lectins, and Tissue Homing. J of Biol Chem. 271(49):31526-31532.
Sjoberg, E.R. et al. (1994) Natural Ligands of the B Cell Adhesion Molecule CD22/3 can be Masked by 9-O-Aeetylation of Sialic Acids, JCB 126(2): 549-562.
Steinberger et al., (2000) Functional deletion of the CCR5 receptor by intracellular immunization produces cells that are refractory to CCR5-dependent HIV-1 infection and cell fusion, Proc. Natl. Acad. Sci. USA 97:805-810.
Strohl, W.R., (2012) Antigen combining (binding) site and CDRs, Therapeutic Antibody Engineering. Woodhead Publishing, Philadelphia PA. Ch. 3, p. 47-54.
Toda, M. et al., (2008) Down-modulation of B cell signal transduction by ligation of mucins to CD22, Biochem Biophys Res Commun. 372(1):45-50.
van Vliet, SJ. et al., (2008) The C-Type Lectin Macrophage Galactose-Type Lectin Impedes Migration of Immature APCs, J Immunol. 181(5):3148-55.
van Vliet, SJ., (2007) Novel insights into MGL-glycan interactions in the immune system, Amsterdam: Vrije Universiteit. p. 1-232.
Wheeler et al., (2003) Intrabody-based strategies for inhibition of vascular endothelial growth factor receptor-2: effects on apoptosis, cell growth, and angiogenesis. FASEB J. 17:1733-1735.
Wirtz and Steipe, (1999) Intrabody construction and expression III: Engineering hyperstable VH domains, Protein Sci. 8:2245-2250.
Wu, T.T. et al., (1970) An Analysis of the Sequences of the Variable Regions of Bence Jones Proteins and Myeloma Light Chains and Their Implications for Antibody Complementarity, JEM, 132(2):211-50.
Zhu et al., (1999) Extended half-life and elevated steady-state level of a single-chain Fv intrabody are critical for specific intracellular retargeting of its antigen, caspase-7, J. Immunol. Methods 231:207-222.
Acres et al., (2005) MUC1 as a target antigen for cancer immunotherapy, Expert review of vaccines, 4:493:502.
Bapat, S. A. (2010) Human ovarian cancer stem cells. Reproduction 140:33-41.
Burgos-Ojeda et al., (2012) Ovarian cancer stem cell markers: Prognostic and therapeutic implications, Cancer letters, 322:1-7.
Cazet et al., (2010) Tumour-associated carbohydrate antigens in breast cancer, Breast cancer research: BCR, 12:204.
Chen et al., (2013) Microarray Glycoprofifing of CA125 Improves Differential Diagnosis of Ovarian Cancer, Journal of proteome research, 12:1408-1418.
Curry et al., (2013) The Use of a Novel MUC1 Antibody to Identify Cancer Stem Cells and Circulating MUC1 in Mice and Patients With Pancreatic Cancer, Journal of surgical oncology, 107:713-722.
Ferreira et al., (2013) Overexpression of tumour-associated carbohydrate antigen sialyl-Tn in advanced bladder tumours, Molecular oncology, 7: 719-731.
Foster et al., (2013) Ovarian cancer stem cells: Working towards the root of stemness, Cancer letters, 338:147-157.
Gill et al., (2013) Initiation of GalNAc-type O-glycosylation in the endoplasmic reticulum promotes cancer cell invasiveness, Proceedings of the National Academy of Sciences of the United States of America 2013, 110: E3152-3161.
Gupta et al., (2009) Cancer stem cells: mirage or reality?, Nature medicine, 15:1010-1012.
Zoller, (2011) CD44: can a cancer-initiating cell profit from an abundantly expressed molecule?, Cancer, 11:254-267.
Julien et al., (2006) ST6GalNAc I expression in MDA-MB-231 breast cancer cells greatly modifies their O-glycosylation pattern and enhances their tumourigenicity, Glycobiology 16:54-64.
Karsten and Goletz, (2013) What makes cancer stem cell markers different?, SpringerPlus, 2:301.
Kinney et al., (1997) The Prognostic Significance of Sialyl-Tn Antigen in Women Treated with Breast Carcinoma Treated with Adjuvant Chemotherapy, Cancer, 80:2240-2249.
Kobayashi et al., (1991) Clinical Evaluation of Circulating Serum Sialyl Tn Antigen Levels in Patients with Epithelial Ovarian Cancer, Journal of clinical oncology: official journal of the American Society of Clinical Oncology, 9:983-987.
Kobayashi et al., (1992) Serum sialyl Tn as an independent predictor of poor prognosis in patients with epithelial ovarian cancer, Journal of clinical oncology: official journal of the American Society of Clinical Oncology, 10:95-101.
Leth-Larsen et al., (2012) Functional Heterogeneity within the CD44 High Human Breast Cancer Stem Cell-Like Compartment Reveals a Gene Signature Predictive of Distant Metastasis, Molecular medicine, 18:1109-1121.
Lobo et al., (2007) The Biology of Cancer Stem Cells, Annu. Rev. Cell Dev. Biol. 23:675-699.
McCann et al., (2011) Inhibition of Hedgehog Signaling Antagonizes Serous Ovarian Cancer Growth in a Primary Xenograft Model, PloS one, 6:e28077.
Medema et al., (2013) Cancer stem cells: The challenges ahead, Nature cell biology, 15:338-344.
Miles et al., (2011) Phase III Multicenter Clinical Trial of the Sialyl-TN (STn)-Keyhole Limpet Hemocyanin (KLH) Vaccine for Metastatic Breast Cancer, The oncologist, 16:1092-1100.
Naor et al., (2008) Involvement of CD44, a molecule with a thousand faces, in cancer dissemination, Seminars in cancer biology, 18:260-267.
Negi et al., (2012) Role of CD44 in tumour progression and strategies for targeting, Journal of drug targeting, 20:561-573.
Rabu et al., (2012) Glycans as targets for therapeutic antitumor antibodies, Future oncology, 8:943-960.
Schultz et al., (2012) Regulation of the metastatic cell phenotype by sialylated glycans, Cancer metastasis reviews, 31:501-518.
Siegel et al., (2013) Cancer statistics, CA: a cancer journal for clinicians 63:11-30.
Zhang et al., (2008) Identification and Characterization of Ovarian Cancer-Initiating Cells from Primary Human Tumors, Cancer research, 68:4311-4320.
Reddish M A et al: "Specificities of anti-sialyl-Tn and anti-Tn monoclonal antibodies generated using novel clustered synthetic blycopeptide epitopes", Glycoconjugate Journal, Chapman & Hall, Boston, vol. 14, No. 5, Aug. 1, 1997, pp. 549-560.

(56) References Cited

OTHER PUBLICATIONS

Yi Cao et al: "Expression of CD175 (Tn), CD175s (sialsyl-Tn) and CD176 (Thomsen-Friedenreich antigen) on malignant human hematopoietic cells", International Journal of Cancer, vol. 123, No. 1, Jan. 1, 2008.
Kjelsen T et al: "Preparation and characterization of monoclonal antibodies directed to the tumor-associated 0-linked sialosyl 2 6 alpha-N-acetylgalactosaminyl (sialosyl-TN) epitope", Cancer Research, American Association for Cancer Research, US, vol. 48, No. 8, Apr. 15, 1988.
Katari R S et al: "Characterization of the shed form of the human tumor-associated glycoprotein (TAG-72) from serous effusions of patients with different types of carcinomas", Cancer Research, American Association for Cancer Research, US, vol. 50, No. 16, Aug. 15, 1990, pp. 4885-4890.
Keshab D Pant et al: "Immunohistochemical Examination of Anti-STn Monoclonal Antibodies LLU9B4, B72.3 and B35.2 for Their Potential use as Tumor Markers", Digestive Diseases and Sciences, Kluwer Academic Publishers-Plenum Publishers, NE, vol. 53, No. 8, Feb. 26, 2008, pp. 2189-2194.
Jillian M Prendergast et al: "Novel anti-Sialyl-Tn monoclonal antibodies and antibody-drug conugates demonstrate tumor specificity and anit-tumor activity", MABS, Feb. 22, 2007, pp. 1-13.
Extended European Search Report dated May 17, 2017, received in EP Application No. 14852277.4.

* cited by examiner

STn Binding Specificity (Group 1)

Detected epitope (largest ellipse)

STn Binding Specificity (Group 2)

Detected epitope (largest ellipse)

STn Binding Specificity (Group 3)

Detected epitope (largest ellipse)

STn Binding Specificity (Group 4)

Detected epitope (largest ellipse)

S3F; 8C2-2D6; 4G8-1E3; 2G12-2B2
OVCAR3 Cell Binding
% Cells with Positive Binding
80
70
60
50
40
30
20
10
0
300
60
12
2.4
0.48
0.096
0.0192
0
[Ab] nM S3F; 8C2-2D6; 4G8-1E3; 2G12-2B2
SNU-16 Cell Binding
% Cells with Positive Binding
100
80
60
40
20
0
300
60
12
2.4
0.48
0.096
0.0192
0
[Ab] nM

GLYCAN-INTERACTING COMPOUNDS AND METHODS OF USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is *a reissue application of U.S. Pat. No. 9,879,087, issued on Jan. 30, 2018, from U.S. application Ser. No. 14/987,432, which is* a continuation-in-part of International Application No. PCT/US2015/060287 filed Nov. 12, 2015 entitled Glycan-Interacting Compounds and Methods of Use, which claims priority to U.S. Provisional Patent Application No. 62/078,610 filed Nov. 12, 2014 entitled Glycan-Interacting Compounds and Methods of Use, U.S. Provisional Patent Application No. 62/102,527 filed Jan. 12, 2015 entitled Glycan-Interacting Compounds and Methods of Use, U.S. Provisional Patent Application No. 62/145,214 filed Apr. 9, 2015 entitled Compositions and Methods for Targeting Cancer Stem Cells, U.S. Provisional Patent Application No. 62/173,560 filed Jun. 10, 2015 entitled Glycan-Interacting Compounds and Methods of Use, and U.S. Provisional Patent Application No. 62/187,587 filed Jul. 1, 2015 entitled Glycan-Interacting Compounds and Methods of Use, the contents of each of which are herein incorporated by reference in their entirety.

GOVERNMENT SUPPORT

This invention was made with government support under Grant No. 1R43CA186326-01A1 awarded by the Department of Health and Human Services. The United States government may have certain rights in the invention.

SEQUENCE LISTING

The instant application contains a Sequence Listing which has been submitted electronically in ASCII format and is hereby incorporated by reference in its entirety. Said ASCII copy, created on Jan. 4, 2016, is named 20331012USCIP_SL.txt and is 144,844 bytes in size.

FIELD OF THE INVENTION

This invention relates to methods for the development of compounds and compositions, including, but not limited to antibodies for the detection and/or removal of glycosylated matter from an organism.

BACKGROUND OF THE INVENTION

Aberrant glycosylation accompanies some of the other mutations commonly observed in carcinomas. It has been estimated that about 80% of all carcinomas express the truncated glycans, the Tn Antigen and the sialylated form, Sialyl Tn (STn). With few exceptions, Tn and STn are not expressed in normal, healthy tissues. Furthermore, the non-human immunogenic sialic acid, N-glycolylneuraminic acid (Neu5Gc), seems to be differentially expressed on carcinomas such as breast cancer in the form of Neu5Gc-STn (GcSTn).

Multiple aberrant glycosylation forms have been described in human cancers, identifying specific glycans as a class of cell surface molecules suitable for specific tumor targeting (Cheever, M. A. et al., Clin Cancer Res. 2009 Sep. 1; 15(17):5323-37). For example, various human cancer types (such as bladder, breast, cervical, colon, lung, and ovarian cancer among others) show high expression of STn antigen, which is rare in normal human tissues (Karlen, P. et al., Gastroenterology. 1998 December; 115(6):1395-404; Ohno, S. et al, Anticancer Res. 2006 November-December; 26(6A):4047-53). In addition, the presence of STn on tumor-associated mucins relates to cancer with poor prognosis and is therewith considered an attractive epitope for cancer detection and targeted therapy (Cao, Y. et al., Virchows Arch. 1997 September; 431(3):159-66; Julien, S. et al., Br J Cancer. 2009 Jun. 2; 100(11):1746-54; Itzkowitz, S. H. et al., Cancer. 1990 Nov. 1; 66(9):1960-6; Motoo, Y. et al., Oncology. 1991; 48(4):321-6; Kobayashi, H. et al., J Clin Oncol. 1992 January; 10(1):95-101). Tn and STn formation is associated with somatic mutations in the gene Cosmc that encodes a molecular chaperon required for the formation of the activate T-synthase (Ju, T. et al., Nature. 2005 Oct. 27; 437(7063):1252; Ju, T. et al., Cancer Res. 2008 Mar. 15; 68(6):1636-46). It can also result from increased expression of the sialyl transferase, ST6GalNAc-I (Ikehara, Y. et al., Glycobiology. 1999 November; 9(11):1213-24; Brockhausen, I. et al., Biol Chem. 2001 February; 382(2):219-32). De-novo expression of STn can modulate carcinoma cells, change the malignant phenotype, and lead to more aggressive cell behaviors (Pinho, S. et al., Cancer Lett. 2007 May 8; 249(2):157-70). Although STn is highly expressed in malignant tissues, low levels are also found on healthy human cells Pass, J. R. et al., J Pathol. 1995 June; 176(2): 143-9; Kirkeby, S. et al., Arch Oral Biol. 2010 November; 55(11):830-41). STn alone has attracted attention as a target for cancer detection and therapy (Cheever, M. A. et al., Clin Cancer Res. 2009 Sep. 1; 15(17):5323-37). STn is also present in mucins associated with cancer stem cells (Engelmann et al., Cancer research, 2008, 68, 2419-2426) and STn is implicated in immune suppression (Carrascal, M. A., et al., Molecular Oncology. 2014. 8(3): 753-65).

In addition to the presence of STn, other glycosylation changes have been described in cancer. One of them involves Neu5Gc. N-acetylneuraminic acid (Neu5Ac) and Neu5Gc are the two major sialic acids on mammalian cell surfaces. Neu5Ac and Neu5Gc differ only in that Neu5Gc comprises an additional oxygen atom associated with chemical group attached to carbon 5. Due to the loss of a functional gene, humans can only synthesize sialic acid in the form of Neu5Ac, but not Neu5Gc. However Neu5Gc can be metabolically incorporated into humans from animal-derived dietary sources such as red meats (Tangvoranuntakul, P. et al., Proc Natl Acad Sci USA. 2003 Oct. 14; 100(21):12045-50; Nguyen, D. H. et al., J Immunol. 2005 Jul. 1; 175(1):228-36; U.S. Pat. No. 7,682,794, U.S. Pat. No. 8,084,219, US2012/0142903, WO2010030666 and WO2010030666). Neu5Gc is significantly abundant among human tumors (Higashi, H. et al., Cancer Res. 1985 August; 45(8):3796-802; Miyoshi I. et al., Mol Immunol. 1986. 23: 631-638; Hirabayashi, Y. et al., Jpn J Cancer Res. 1987. 78: 614-620; Kawachi. S, et al., Int Arch Allergy Appl Immunol. 1988. 85: 381-383; Devine, P. L. et al., Cancer Res. 1991. 51: 5826-5836; Malykh, Y. N. et al, Biochimie. 2001. 83: 623-634 and Inoue, S. et al., 2010. Glycobiology. 20(6):

752-762) and remarkably low in normal human tissues, which had been overlooked for several decades (Diaz, S. L. et al., PLoS One. 2009. 4: e4241; Tangvoranuntakul, P. et al., Proc Natl Acad Sci USA. 2003. 100: 12045-12050; Varki, A. et al., Glycoconj J. 2009. 26: 231-245). The increased metabolic accumulation of diet-derived Neu5Gc in cancer tissue compared to healthy human tissues is likely explained by at least three factors: rapid growth with underproduction of competing endogenous Neu5Ac, enhanced macropinocytosis induced by growth factors (Dharmawardhane, S. et al., Mol Biol Cell. 2000 October; 11(10):3341-52; Simonsen, A. et al., Curr Opin Cell Biol. 2001 August; 13(4):485-92; Johannes, L. et al., Traffic. 2002 July; 3(7):443-51; Amyere, M. et al., Int J Med Microbiol. 2002 February; 291(6-7): 487-94), and the upregulation of gene expression of the lysosomal sialic acid transporter gene sialin by hypoxia (Yin, J. et al., Cancer Res. 2006 Mar. 15; 66(6):2937-45). In addition, all humans tested to date comprise a polyclonal antibody reservoir against non-human Neu5Gc, which makes it the first example of a xeno-autoantigen (Padler-Karavani, V. et al., Glycobiology. 2008 October; 18(10): 818-30; Varki, N. M. et al., Annu Rev Pathol. 2011; 6:365-93). The accumulation of dietary Neu5Gc in malignant tumors in the face of an anti-Neu5Gc response was shown to facilitate tumor progression by inducing a low-grade chronic inflammation (Hedlund, M. et al., Proc Natl Acad Sci USA. 2008 Dec. 2; 105(48):18936-41). Thus, Neu5Gc containing glycan epitopes on human tumors represent a valuable possibility for drug targeting. A recent study suggests the existence of antibodies against Neu5Gc-containing STn (GcSTn), but not Neu5Ac-STn (AcSTn), in cancer patients and explores their potential as a specific biomarker for cancer detection (Padler-Karavani, V. et al., Cancer Res. 2011 May 1; 71(9):3352-63).

There remains a need in the art for antibodies capable of binding glycans, including glycans associated with disease and diseased cells and tissues. Such antibodies could be used to target tumor cells and cancerous tissues and to treats subjects suffering from cancer. Further, there remains a need for better methods to develop such antibodies as well as methods for specific characterization of epitopes bound by glycan-interacting antibodies. The present invention meets this need by providing antibodies that target glycans, by providing methods of developing anti-glycan antibodies, and by providing methods of using anti-glycan antibodies to identify and target cancerous cells and tissues in the diagnosis and treatment of disease.

SUMMARY OF THE INVENTION

In some embodiments, the present invention provides an antibody comprising a variable domain, the variable domain comprising at least 95% amino acid sequence identity to an amino acid sequence selected from the group consisting of SEQ ID NOs: 15-52 or a fragment thereof. In some cases, such antibodies comprise a variable domain pair selected from the group consisting of SEQ ID NO:29 and SEQ ID NO:30; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:31 and SEQ ID NO:32; SEQ ID NO:35 and SEQ ID NO:36; SEQ ID NO:37 and SEQ ID NO:38; SEQ ID NO:39 and SEQ ID NO:40; SEQ ID NO:42 and SEQ ID NO:32; SEQ ID NO:44 and SEQ ID NO:45; SEQ ID NO:46 and SEQ ID NO:32; SEQ ID NO:47 and SEQ ID NO:32; SEQ ID NO:48 and SEQ ID NO:50; SEQ ID NO:48 and SEQ ID NO:49; and SEQ ID NO:51 and SEQ ID NO:52.

Some antibodies of the invention comprise at least one complementarity determining region (CDR) comprising from about 60% to about 95% sequence identity to an amino acid sequence selected from the group consisting of SEQ ID NOs: 81-148, SEQ ID NOs: 152-155, and SEQ ID NOs: 159-164. In some cases, such antibodies comprise a CDR with a heavy chain variable domain (VH) CDR (CDR-H) comprising at least 70% sequence identity to an amino acid sequence selected from the group consisting of SEQ ID NOs: 81-99, SEQ ID NOs: 143-148, and SEQ ID NOs: 152-155. Some antibodies comprise a CDR-H3 comprising an amino acid sequence selected from the group consisting of SEQ ID NOs: 90-99, and SEQ ID NOs: 152-155. In some cases, antibodies comprise a light chain variable domain (VL) CDR (CDR-L) comprising at least 70% sequence identity to an amino acid sequence selected from the group consisting of SEQ ID NOs: 100-142, and SEQ ID NOs: 159-164. Such antibodies may comprise a CDR-L3 comprising an amino acid sequence selected from the group consisting of SEQ ID NOs: 127-142.

In some embodiments, the present invention provides an antibody comprising: (1) a CDR-L1 selected from the group consisting of SEQ ID NOs: 100-114, and SEQ ID NOs: 159-167; (2) a CDR-L2 selected from the group consisting of SEQ ID NOs: 115-126, and SEQ ID NOs: 168-170; (3) a CDR-L3 selected from the group consisting of SEQ ID NOs: 127-142, and SEQ ID NOs: 171-173; (4) a CDR-H1 selected from the group consisting of SEQ ID NOs: 81-83, SEQ ID NO: 143, and SEQ ID NO: 144; (5) a CDR-H2 selected from the group consisting of SEQ ID NOs: 84-89, and SEQ ID NOs: 145-151; and (6) a CDR-H3 selected from the group consisting of SEQ ID NOs: 90-99, and SEQ ID NOs: 152-158.

Some antibodies of the invention are monoclonal antibodies. Some antibodies comprise an IgG1 isotype. Other antibodies comprise an IgG2 isotype. In some cases, antibodies of the invention belong to an antibody group selected from the group consisting of a Group 1 antibody, a Group 2 antibody, a Group 3 antibody and a Group 4 antibody. Some antibodies specifically target an antigen selected from the group consisting of N-acetylneuraminic sialyl Tn antigen (AcSTn) and N-glycolylneuraminic sialyl Tn antigen (GcSTn). Such antibodies may target antigens comprising a 9-O-acetyl group. Some antibodies bind to a cluster of two or more glycans. Further antibodies comprise bispecific antibodies.

In some embodiments, antibodies of the invention comprise an antibody-drug conjugate. Some antibody-drug conjugates comprise a therapeutic agent. Some antibody-drug conjugates comprise a cytotoxic agent. In some cases, cytotoxic agents are conjugated to antibodies directly. In some cases, cytotoxic agents are conjugated to antibodies via a linker. Such linkers may include cleavable linkers or non-cleavable linkers. In some cases, the cytotoxic agent is a DNA damaging agent. In some cases, the cytotoxic agent is a cytoskeletal inhibitor.

According to some embodiments, antibodies of the invention bind a tumor-associated carbohydrate antigen (TACA). Such TACAs may include Tn antigen, sialylated Tn antigen (STn,) Thomsen-Friedenreich antigen, Lewis$^{Y}$ (Le$^{Y}$) antigen, Lewis$^{X}$ (Le$^{X}$) antigen, Sialyl Lewis$^{X}$ (SLe$^{X}$) antigen, Sialyl Lewis$^{A}$ (SLe$^{A}$) antigen, Globo H, stage-specific embryonic antigen-3 (SSEA-3,) a glycosphingolipid comprising sialic acid, ganglioside GD2, ganglioside GD3, ganglioside GM2, fucosyl GM1, ganglioside Neu5GcGM3, or a polysialic acid-related antigen.

In some embodiments, the present invention provides a method of killing a tumor cell comprising contacting the tumor cell with an antibody of the invention.

According to other embodiments, the present invention provides a method of treating cancer in a subject in need thereof, the method comprising administering to the subject an antibody of the invention. In some cases, such methods are used to treat an epithelial cancer. Such epithelial cancers may include breast, colon, lung, bladder, cervical, ovarian, stomach, prostate, and/or liver cancer.

In some aspects, the present invention provides compositions comprising at least one of the antibodies of the invention. Further provided are kits comprising such compositions and instructions for use thereof.

In some embodiments, the present invention provides methods of reducing tumor volume in a subject comprising administering to said subject a composition of the invention. In some cases, methods of the invention may be used to increase anti-tumor cell immune activity by contacting at least one immune-resistant tumor cell with an antibody of the invention. Such anti-tumor cell immune activity may include innate immune activity (e.g., natural killer (NK) cell anti-tumor cell activity). In some cases, anti-tumor cell activity includes adaptive immune activity (e.g., B cell anti-tumor cell activity or dendritic cell (DC) anti-tumor cell activity). In some cases, compositions of the invention may increases DC expression of one or more factor selected from the group consisting of CD80, CD86, IL-12, and TNF-α. Further methods of the invention include treating an immune-resistant tumor in a subject in need thereof by administering a composition of the invention.

According to some embodiments, the present invention provides methods of reducing or eliminating cancer stem cells (CSCs) in a subject comprising administering to the subject an antibody of the invention. In some cases, the CSCs are present in breast, ovarian, pancreatic, bladder, cervical, colon and/or lung tissue. In some cases the CSCs comprise CD133 and/or CD44 biomarkers. In some cases, methods of reducing or eliminating CSCs further comprise the administration of at least one chemotherapeutic agent. Such chemotherapeutic agents may be selected from paclitaxel and carboplatin.

In some aspects, the present invention provides intrabodies comprising a variable domain comprising at least 95% amino acid sequence identity to an amino acid sequence selected from the group consisting of SEQ ID NO: 15-52 and a fragment thereof. Some intrabodies comprise a variable domain pair selected from the group consisting of SEQ ID NO:29 and SEQ ID NO:30; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:31 and SEQ ID NO:32; SEQ ID NO:35 and SEQ ID NO:36; SEQ ID NO:37 and SEQ ID NO:38; SEQ ID NO:39 and SEQ ID NO:40; SEQ ID NO:42 and SEQ ID NO:32; SEQ ID NO:44 and SEQ ID NO:45; SEQ ID NO:46 and SEQ ID NO:32; SEQ ID NO:47 and SEQ ID NO:32; SEQ ID NO:48 and SEQ ID NO:50; SEQ ID NO:48 and SEQ ID NO:49; and SEQ ID NO:51 and SEQ ID NO:52.

In other aspects, the present invention provides a chimeric antigen receptor (CAR) comprising a variable domain comprising at least 95% amino acid sequence identity to an amino acid sequence selected from the group consisting of SEQ ID NOs: 15-52 and a fragment thereof. Some CARs comprise a variable domain pair selected from the group consisting of SEQ ID NO:29 and SEQ ID NO:30; SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:31 and SEQ ID NO:32; SEQ ID NO:35 and SEQ ID NO:36; SEQ ID NO:37 and SEQ ID NO:38; SEQ ID NO:39 and SEQ ID NO:40; SEQ ID NO:42 and SEQ ID NO:32; SEQ ID NO:44 and SEQ ID NO:45; SEQ ID NO:46 and SEQ ID NO:32; SEQ ID NO:47 and SEQ ID NO:32; SEQ ID NO:48 and SEQ ID NO:50; SEQ ID NO:48 and SEQ ID NO:49; and SEQ ID NO:51 and SEQ ID NO:52.

In some embodiments, the present invention provides constructs encoding antibodies of the invention. Such constructs may comprise at least one nucleotide sequence having at least 95% sequence identity to a nucleotide sequence selected from the group consisting of SEQ ID NOs: 192-233 and a fragment thereof. In some cases, constructs of the invention encode intrabodies or CARs of the invention.

Further provided are cells comprising one or more constructs of the invention. Also provided are viruses comprising constructs of the invention.

According to some embodiments, the present invention provides methods of identifying cells and/or tissues expressing STn with antibodies of the invention. Further provided are methods of identifying cancerous cells in tissues or organs with antibodies of the invention. Such tissues or organs may include breast, ovary, and pancreas.

In some embodiments, the present invention provides antibody variants comprising sequence analysis-informed variants of antibodies of the invention. Such antibody variants may comprise improved epitope specificity and/or affinity. Some antibody variants comprise a CDR length modification (e.g., a CDR-H3 length modification). Some antibody variants comprise a substitution of one or more amino acids in one or more CDRs. In some cases, antibody variants comprise at least one germline gene modification. Some antibody variants comprise an scFv, monobody, diabody, intrabody, CAR, or antibody mimetic.

In some aspects, the present invention provides a method of developing an antibody fragment display library comprising: (1) aligning variable domain amino acid sequences among two or more antibodies of the invention; (2) identifying conserved and variable amino acids among the aligned antibodies, and (3) constructing an antibody fragment display library, wherein variability among library members is limited to amino acid variation of the variable amino acids identified. Further embodiments provide antibody fragment display libraries produced according to such methods. Additional embodiments provide antibodies comprising variable domains isolated from such antibody fragment display libraries. Such antibodies may include an scFv, monobody, diabody, intrabody, CAR, or antibody mimetic.

In some embodiments, the present invention provides a method of reducing tumor volume comprising administering an antibody to a subject in need thereof, wherein the antibody is administered at a dose of from about 0.25 mg/kg to about 25 mg/kg and wherein the antibody comprises a variable domain having an amino acid sequence comprising at least 95% amino acid sequence identity to an amino acid sequence selected from the group consisting of SEQ ID NOs: 15-52. In some cases, the antibody includes a variable domain pair selected from the group consisting of SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:35 and SEQ ID NO:36; SEQ ID NO:37 and SEQ ID NO:38; SEQ ID NO:39 and SEQ ID NO:40; SEQ ID NO:42 and SEQ ID NO:32; SEQ ID NO:44 and SEQ ID NO:45; SEQ ID NO:46 and SEQ ID NO:32; SEQ ID NO:47 and SEQ ID NO:32; SEQ ID NO:48 and SEQ ID NO:50; SEQ ID NO:48 and SEQ ID NO:49; and SEQ ID NO:51 and SEQ ID NO:52. In some cases, the antibody is a monoclonal antibody. In some embodiments, the antibody is an IgG1 isotype antibody. In other embodiments, the antibody is an IgG2 isotype antibody.

In some embodiments, the present invention provides a method of reducing tumor volume comprising administering an antibody to a subject in need thereof, wherein the antibody is administered at a dose of from about 0.25 mg/kg to about 25 mg/kg and wherein the antibody comprises an antibody-drug conjugate. In some cases, the antibody-drug conjugate comprises a cytotoxic agent. The cytotoxic agent, in some cases, is monomethyl auristatin E.

According to some methods of the invention, administration of anti-glycan antibodies at a dose of from about 0.25 mg/kg to about 25 mg/kg is sufficient to reduce tumor volume by at least 20%. In some cases, tumor volume is reduced by from about 80% to about 99%. In other embodiments, the percent tumor growth inhibition (% T/C) is from about 2% to about 20%.

In some embodiments, the present invention provides a composition comprising: (1) an anti-glycan antibody with a variable domain having an amino acid sequence comprising at least 95% amino acid sequence identity to an amino acid sequence selected from the group consisting of SEQ ID NOs: 15-52; and (2) an excipient, the excipient comprising from about 2 mM to about 100 mM citrate and from about 10 mM to about 300 mM NaCl. In some cases, the antibody includes a variable domain pair selected from the group consisting of SEQ ID NO:15 and SEQ ID NO:16; SEQ ID NO:17 and SEQ ID NO:18; SEQ ID NO:19 and SEQ ID NO:20; SEQ ID NO:21 and SEQ ID NO:22; SEQ ID NO:23 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:35 and SEQ ID NO:36; SEQ ID NO:37 and SEQ ID NO:38; SEQ ID NO:39 and SEQ ID NO:40; SEQ ID NO:42 and SEQ ID NO:32; SEQ ID NO:44 and SEQ ID NO:45; SEQ ID NO:46 and SEQ ID NO:32; SEQ ID NO:47 and SEQ ID NO:32; SEQ ID NO:48 and SEQ ID NO:50; SEQ ID NO:48 and SEQ ID NO:49; and SEQ ID NO:51 and SEQ ID NO:52. In some cases, the antibody in such compositions is an antibody-drug conjugate.

In some embodiments, the present invention provides a method of treating cancer comprising administering an antibody composition of the invention to a subject in need thereof. In some cases, such antibody compositions include an antibody-drug conjugate. In other embodiments, the antibody-drug conjugate is monomethyl auristatin E.

BRIEF DESCRIPTION OF THE FIGURES

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

FIG. 2A is a bar graph presenting antibody binding results with OVCAR3 cells. FIG. 2B is a bar graph presenting antibody binding results with SNU-16 cells.

DETAILED DESCRIPTION

Introduction

Figure 1A:
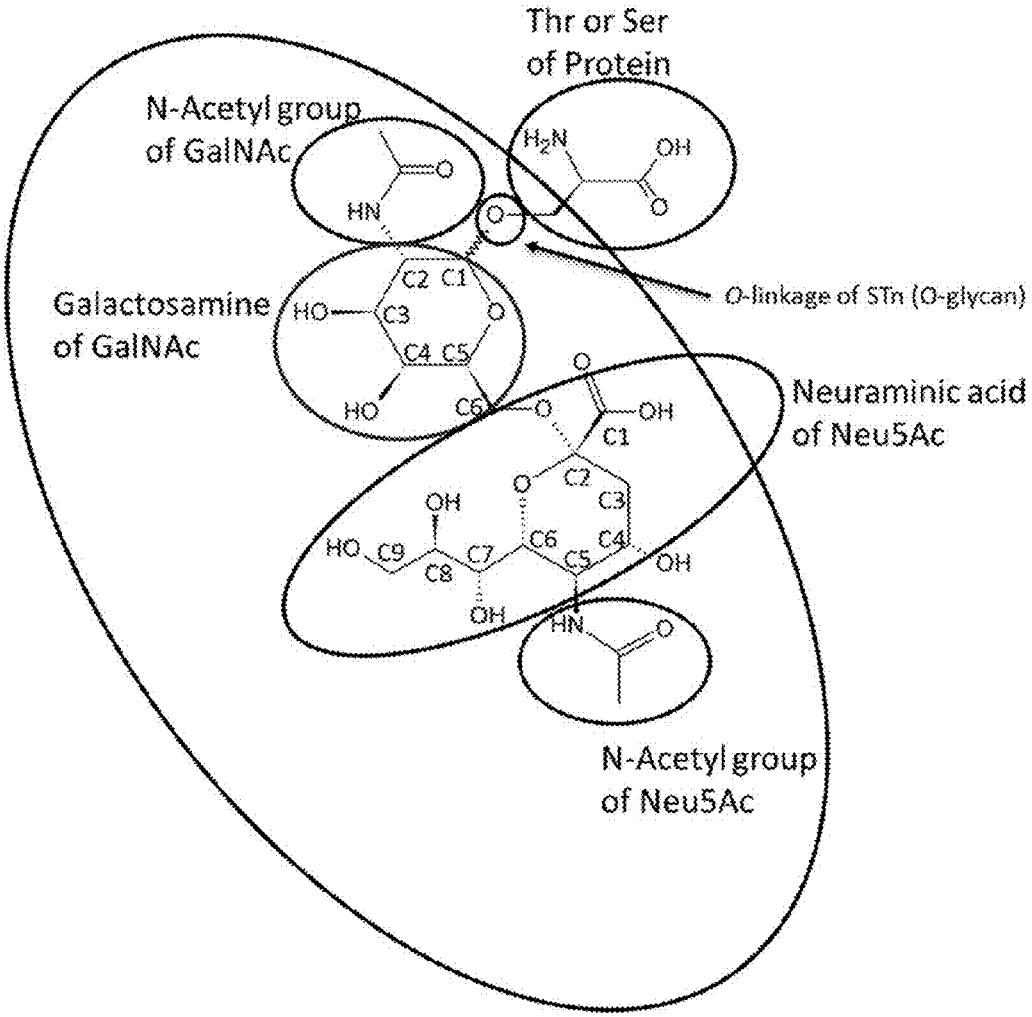
FIGS. 1A-1D are diagrams depicting α2,6-sialylated N-acetylgalactosamine (STn) and indicating putative epitopes involved in anti-STn antibody binding. The largest ellipse in each diagram indicates the specific region of STn targeted by each of 4 antibody groups. These groups include Group 1 antibodies (binding to the large elliptical region indicated in FIG. 1A), Group 2 antibodies (binding to the large elliptical region indicated in FIG. 1B), Group 3 antibodies (binding to the large elliptical region indicated in FIG. 1C) and Group 4 antibodies (binding to the large elliptical region indicated in FIG. 1D).

According to the present invention are antibodies specific for or which interact with epitopes comprising carbohydrate groups referred to herein as glycans. Some glycan-interacting antibodies described herein may be used as biotherapeutics. Other embodiments provide methods for generating such glycan-interacting antibodies.

In nature, glycans may be sialylated with N-acetylneuraminic acid (Neu5Ac) or N-glycolylneuraminic acid (Neu5Gc). Glycan-interacting antibodies according to the present invention may be directed to cancer-related glycans comprising α2,6-sialylated N-acetylgalactosamine (STn). Such antibodies may target any STns (pan-STn antibodies), glycans comprising STns having Neu5Ac specifically (Ac-STn) or glycans having STns comprising Neu5Gc specifically (GcSTn). In some embodiments, glycan-interacting antibodies of the present invention target other cancer-related glycan antigens.

In some embodiments, the present invention provides methods of producing glycan-interacting antibodies. Such methods may comprise the use of mice for generating an immune response to one or more antigens comprising STn (e.g. AcSTn and/or GcSTn). As described herein, a number of methods may be utilized in order to manipulate the resulting antibodies produced through mouse immunization. Such methods may include varying the strain and/or gender of the mice being immunized, varying the antigen used, varying the type and dose of adjuvant included in antigen administration and time course of immunization before initiation of hybridoma fusion.

In some embodiments, the present invention provides methods for eliminating cancer stem cells using glycan-interacting antibodies. In other embodiments, the present invention provides methods for treating cancer in a subject by eliminating cancer stem cells using glycan-interacting antibodies. In some aspects, glycan-interacting antibodies may be used alone. In other aspects, glycan-interacting antibodies are used in combination with chemotherapeutic agents.

Further provided are optimized, humanized, and conjugated forms of glycan-interacting antibodies. Additionally, kits, assays and reagents comprising antibodies and/or methods of the present invention are presented.

Definitions

Adjacent: As used herein, the term "adjacent" refers to something that is adjoining, neighboring or next to a given entity. In some embodiments, "adjacent residues" are sugar residues within a glycan chain that are linked to one another. In some embodiments, "adjacent glycans" are glycan chains that next to each other either in direct contact or within close proximity and without another glycan in between the two.

Administered in combination: As used herein, the term "administered in combination" or "combined administration" means that a subject is simultaneously exposed to two or more agents administered at the same time or within an interval of time such that the subject is at some point in time simultaneously exposed to both and/or such that there may be an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administration of individual doses of one or more glycan-interacting antibodies, as described herein, are spaced sufficiently closely together such that a combinatorial (e.g., a synergistic) effect is achieved.

Amino acid: As used herein, the terms "amino acid" and "amino acids" refer to all naturally occurring L-alpha-amino acids as well as non-naturally occurring amino acids. Amino acids are identified by either the one-letter or three-letter designations as follows: aspartic acid (Asp:D), isoleucine threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antibody: As used herein, the term "antibody" is used in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies are primarily amino-acid based molecules but may also comprise one or more modifications such as with sugar moieties.

Antibody fragment: As used herein, the term "antibody fragment" refers to a portion of an intact antibody, preferably comprising an antigen binding region thereof. Examples of antibody fragments include Fab, Fab', $F(ab')_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an $F(ab')_2$ fragment that has two antigen-binding sites and is still capable of cross-linking antigen. Glycan-interacting antibodies may comprise one or more of these fragments. For the purposes herein, an antibody may comprise a heavy and light variable domain as well as an Fc region.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biomolecule: As used herein, the term "biomolecule" is any natural molecule which is amino acid-based, nucleic acid-based, carbohydrate-based or lipid-based, and the like.

Bispecific antibody: As used herein, the term "bispecific antibody" refers to an antibody capable of binding two different antigens. Such antibodies typically comprise regions from at least two different antibodies. Bispecific antibodies may include any of those described in Riethmuller, G. 2012. Cancer Immunity. 12:12-18, Marvin, J. S. et al., 2005. Acta Pharmacologica Sinica. 26(6):649-58 and Schaefer, W. et al., 2011. PNAS. 108(27):11187-92, the contents of each of which are herein incorporated by reference in their entirety.

Branch: As used herein, the term "branch" refers to an entity, moiety or appendage that is linked or extends out from a main entity or source. In some embodiments, a "branch chain" or "branching chain" comprises one or more residues (including, but not limited to sugar residues) that extend from a parent chain. As used herein, a "parent chain" is used to refer to a chain of residues (including, but not limited to sugar residues) from which a branching chain is linked. In the case of a glycan with multiple branches, the parent chain may also refer to the source chain from which all such branches are directly or indirectly attached. In the case of a polysaccharide comprising a chain of hexose residues, parent chain linkages typically occur between carbons 1 and 4 of adjacent residues while branching chains are attached to a parent chain through a linkage between carbon 1 of the branching residue and carbon 3 of the parent residue from which the branch extends. As used herein, the term "branching residue" refers to the residue attached to the parent chain in a branching chain.

Cancer stem cells: As used herein, cancer stem cells (CSCs) refer to a subset of tumor cells that have the ability to self-renew. CSCs may be able to regenerate diverse cell types. In some cases, these cells are difficult or impossible to remove through surgical or chemical treatment of a tumor.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form. In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Cyclic or Cyclized: As used herein, the term "cyclic" refers to the presence of a continuous loop. Cyclic molecules need not be circular, only joined to form an unbroken chain of subunits.

Cytidine monphosphate-N-acetylneuraminic acid hydroxylase: As used herein, the term "cytidine monophosphate-N-acetylneuraminic acid hydroxylase" or "CMAH" refers to an enzyme, absent in humans, but present in most other mammals (including, but not limited to mice, pigs and chimpanzees) that catalyzes the formation of N-glycolylneuraminic acid from N-acetylneuraminic acid. The absence of the enzyme in humans is due to a frameshift mutation resulting in the premature termination of the CMAH transcript and the production of a non-functional protein.

Cytotoxic: As used herein, the term "cytotoxic" is used to refer to an agent that kills or causes injurious, toxic, or deadly effects on a cell (e.g., a mammalian cell (e.g., a human cell)), bacterium, virus, fungus, protozoan, parasite, prion, or a combination thereof.

Delivery: As used herein, "delivery" refers to the act or manner of transporting a compound, substance, entity, moiety, cargo or payload to an intended destination.

Delivery Agent: As used herein, "delivery agent" refers to any substance which facilitates, at least in part, the in vivo delivery of a compound, substance, entity, moiety, cargo or payload.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Display library: As used herein, the term "display library" refers to a tool used in scientific discovery to identify biomolecular interactions. Different variations of display libraries exist that include the utilization of bacteriophages, yeast and ribosomes. In each case, proteins within a given library (also referred to herein as "library members") are linked (physically or through association with a host) to the nucleic acid which encodes the protein. When a target molecule is incubated with the members of a display library, any library members that bind to the target may be isolated and the sequences encoding the bound protein may be determined through analysis of the linked nucleic acid. In some embodiments, display libraries are "phage display libraries" wherein the display library is made up of bacteriophage viral particles (also referred to herein as "phage particles") wherein nucleic acids have been incorporated into the phage genome resulting in the production of viral coat proteins that are fused to proteins encoded by the nucleic acids that have been introduced. Such fused proteins are "displayed" on the outer surface of the assembled phage particles where they may interact with a given target.

Distal: As used herein, the term "distal" means situated away from the center or away from a point or region of interest.

Engineered: As used herein, embodiments of the invention are "engineered" when they are designed to have a feature or property, whether structural or chemical, that varies from a starting point, wild type or native molecule. Thus, engineered agents or entities are those whose design and/or production include an act of the hand of man.

Epitope: As used herein, an "epitope" refers to a surface or region on a molecule that is capable of interacting with components of the immune system, including, but not limited to antibodies. In some embodiments, an epitope may comprise a target site. Epitopes may comprise a region on an antigen or between two or more antigens that is specifically recognized and bound by a corresponding antibody. Some epitopes may comprise one or more sugar residues along one or more glycan. Such epitopes may comprise 1, 2, 3, 4, 5, 6, 7, 8, 9 or at least 10 sugar residues. Epitopes may also comprise one or more regions of interaction between entities. In some embodiments, epitopes may comprise a junction between two sugar residues, between a branching chain and a parent chain or between a glycan and a protein.

Ether bond: As used herein, an "ether bond" refers to a chemical bond comprising an oxygen bonded between two carbon atoms. In some embodiments, ether bonds link sugar residues to other entities, including, but not limited to other sugar residues to form a glycan chain. Such bonds are also referred to as "glycosidic bonds" or "glycosidic linkages". In the context of at least one sugar residue, the terms "link" and/or "linkage" are also used herein when referring to a glycosidic linkage. In some embodiments, linkages may link glycans to other entities, including, but not limited to proteins, lipids, phospholipids and sphingolipids. In some embodiments, sugar residues may be linked to protein, typically forming a link between a sugar residue and an amino acid residue. Such amino acid residues include serine and threonine. In some embodiments, ether bonds link glycans to a glycan array comprising a carbohydrate linker that participates in bond formation. Glycosidic linkages may differ in their stereochemical properties. In some embodiments, alpha oriented glycosidic linkages (also referred to herein as "alpha linkages") result in an axial orientation between the bonded oxygen of the ether bond and the cyclohexane ring of the sugar reside. In some embodiments, beta oriented glycosidic linkages (also referred to herein as "beta linkages") result in an equatorial orientation between the bonded oxygen of the ether bond and the cyclohexane ring of the sugar residue.

Expression: As used herein, "expression" may refer to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein (e.g., by glycosylation).

Feature: As used herein, a "feature" refers to a characteristic, a property, or a distinctive element.

Formulation: As used herein, a "formulation" refers to a material or mixture prepared according to a formula and which may comprise at least one antibody, compound, substance, entity, moiety, cargo or payload and a delivery agent, carrier or excipient.

Functional: As used herein, a "functional" biological molecule is a biological entity with a structure and in a form in which it exhibits a property and/or activity by which it is characterized. As used herein, a "functional group" or "chemical group" refers to a characteristic group of atoms or chemical bonds that are part of a larger molecule. In some embodiments, functional groups may be associated with different molecules, but may participate in similar chemical reactions regardless of the molecule of which they are a part. Common functional groups include, but are not limited to carboxyl groups (—COOH), acetyl groups (—COH), amino groups (—$NH_2$), methyl groups (—$CH_3$), sulfate groups (—$SO_3H$) and acyl groups. In some embodiments, the addition of one or more functional group to a molecule may be conveyed using terms that modify the name of the functional group with the ending "-ylated", e.g., acetylated, methylated and sulfated.

Glycan: As used herein, the terms "glycan", "oligosaccharide" and "polysaccharide" are used interchangeably and refer to polymers made up of sugar monomers, typically joined by glycosidic bonds also referred to herein as linkages. In some embodiments, the terms "glycan", "oligosaccharide" and "polysaccharide" may be used to refer to the carbohydrate portion of a glycoconjugate (e.g., glycoprotein, glycolipid or proteoglycan).

Glycan chain: As used herein, the term "glycan chain" refers to a sugar polymer comprising two or more sugars. In some embodiments, glycan chains are covalently linked to proteins through serine or threonine residues on the protein.

Glycan-rich composition: As used herein, the term "glycan-rich composition" refers to composition comprising a large percentage of glycans. In some embodiments, glycans within a glycan-rich composition may comprise from about 1% to about 10%, from about 5% to about 15%, from about 20% to about 40%, from about 30% to about 50%, from about 60% to about 80%, from about 70% to about 90% or at least 100% of the total weight of the composition.

Glycosidic bond: As used herein, the term "glycosidic bond" refers to a covalent bond formed between a carbohydrate and another chemical group. In some embodiments, glycosidic bonds are formed between the reducing end of one sugar molecule and the non-reducing end of a second sugar molecule or polysaccharide chain. Such glycosidic bonds are also known as O-glycosidic bonds due to the oxygen (or ether bond) between the joined sugars. In some embodiments, a glycosidic bond between two sugars or between a sugar and a linker may also be referred to as a "linkage".

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Kit: As used herein, the term "kit" refers to a set comprising one or more components adapted for a cooperative purpose and instructions for use thereof.

Knockout: As used herein, the term "knockout" refers to an organism wherein an existing gene has been inactivated through a process that typically involves the hand of man. In a knockout organism, a gene that has been inactivated is said to have been "knocked out". In some embodiments, the knocked out gene may be inactivated through the insertion of a nucleotide sequence into the gene or through replacement of the gene entirely.

Linker: As used herein, a "linker" refers to a moiety that connects two or more domains, moieties or entities. In one embodiment, a linker may comprise 10, 11, 12, 13, 14, 15 or more atoms. In a further embodiment, a linker may comprise a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. In some embodiments, the linker may comprise an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent) or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bonds include an amido bond which may be cleaved for example by the use of tris(2-carboxyethyl)phosphine (TCEP), or other reducing agents, and/or photolysis, as well as an ester bond which may be cleaved for example by acidic or basic hydrolysis. In some embodiments, a linker is a carbohydrate moiety used to link glycans to a substrate, such as in a glycan array. Such carbohydrate linkers include, but are not limited to $—O(CH_2)_2CH_2HN_2$ and $—O(CH_2)_3NHCOCH_2(OCH_2CH_2)_6NH_2$.

Mucin: As used herein, the term "mucin" refers to a family of proteins that are heavily glycosylated. In some embodiments mucins are produced by the submaxillary glands and are found in saliva and mucous.

Negative selection: As used herein, the term "negative selection" refers to the selection of library members from a display library based on their ability to bind entities and/or components of a composition that do not comprise a target antigen. In some embodiments, negative selection is used prior to positive selection to remove elements that might bind non-specifically to the target.

Off-target: As used herein, "off target" refers to any unintended effect on any one or more target, gene, or cellular transcript.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Peptide: As used herein, "peptide" is a protein or polypeptide which is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than active agents (e.g., as described herein) present in a pharmaceutical composition and having the properties of being substantially nontoxic and non-inflammatory in a patient. In some embodiments, a pharmaceutically acceptable excipient is a vehicle capable of suspending or dissolving the active agent. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety. Pharmaceutically acceptable solvate: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Positive selection: As used herein, the term "positive selection" refers to the selection of a given entity from a group of unique entities. Such entities and groups thereof may be, for example antibodies. In some cases they may be antibody fragments or antibody fragments expressed in association with an agent capable of expressing such fragments (e.g. library members from a display library). Selection may be based on the ability of selected entities to bind to a desired target or epitope. In some embodiments, positive selection may be used with phage display libraries to identify phage particles expressing scFvs that bind to the desired target. In other embodiments, positive selection may refer to the selection of antibody candidates from among a pool of antibodies. In some embodiments, entities may be cells, cell lines or clones as in the selection of clones during hybridoma selection. In such cases, positive selection may refer to clonal selection based on one or more features of antibodies (e.g. specificity for one or more desired epitopes) produced by such clones. In some cases, desired epitopes in positive selection methods may comprise STn (e.g. AcSTn and/or GcSTn).

Conversely, "negative selection," as used herein, included the same principles and examples described for positive selection, but with the distinguishing characteristic that it is used for removal of undesired entities from a group of unique entities.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Proximal: As used herein, the term "proximal" means situated nearer to the center or to a point or region of interest.

Region of interaction: As used herein, the term "region of interaction" refers to a region along any of two or more entities where such entities interact or overlap. In some embodiments, a region of interaction may comprise one or more sugar residues along a glycan chain that contacts a second glycan chain. In some embodiments, the glycan chains are branching chains from the same parent chain. In some embodiments, a region of interaction may occur between two glycan chains wherein one chain is a branching chain and the second chain is a parent chain. In the case of glycan chains, regions of interaction may comprise 1, 2, 3, 4, 5, 6, 7, 8, 9 or at least 10 sugar residues. In some embodiments, regions of interaction may also occur between glycans and proteins or between glycans and lipids.

Residue: As used herein, the term "residue" refers to a monomer associated with or capable of associating with a polymer. In some embodiments, residues comprise sugar molecules including, but not limited to glucose, galactose, N-acetylglucosamine, N-acetylgalactosamine, sialic acids. In some embodiments, residues comprise amino acids.

Sample: As used herein, the term "sample" refers to an aliquot or portion taken from a source and/or provided for analysis or processing. In some embodiments, a sample is from a biological source such as a tissue, cell or component part (e.g. a body fluid, including but not limited to blood, mucus, lymphatic fluid, synovial fluid, cerebrospinal fluid, saliva, amniotic fluid, amniotic cord blood, urine, vaginal fluid and semen). In some embodiments, a sample may be or comprise a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample comprises a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Sialyl: As used herein, the prefix "sialyl" as well as the term "sialylated" describe compounds comprising sialic acid.

Single-chain variable fragment: As used herein, the term "single-chain variable fragment" or "scFv" refers to a fusion protein comprising antibody variable regions connected by a linker. In some embodiments, scFvs are utilized in conjunction with phage display methods where they may be expressed in association with a phage coat protein and used in the identification of high affinity peptides for a given antigen.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Submaxillary glands: As used herein, the term "submaxillary glands" or "submandibular glands" refers to mucous producing glands located beneath the mouth floor. These glands are capable of producing mucins and in some embodiments, may be extracted from mammals as a source of mucin.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Target: As used herein, the term "target" refers to an object or entity to be affected by an action. In some embodiments, targets refer to antigens to be used for the development of antibodies that specifically bind the antigens.

Target screening: As used herein, the term "target screening" refers to the use of a target substance to identify binding partners for that substance.

Target site: As used herein, the term "target site" refers to a target on or within one or more glycans, biomolecules and/or biostructures within a cell, the extracellular space, a tissue, an organ and/or an organism. In some embodiments, glycan target sites may reside exclusively on one sugar residue or may be formed by two or more residues. In some embodiments, target sites are formed between two or more glycans. In some embodiments, target sites are formed between branching chains of the same glycan or between one or more branching chains and a parent chain.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Terminal residue: As used herein, the term "terminal residue" refers to the last residue in a polymeric chain. In some embodiments, terminal residues are sugar residues located at the non-reducing end of a polysaccharide chain.

Therapeutic agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transgenic: As used herein, the term "transgenic" refers to an organism that comprises one or more genes incorporated within the organisms genome that are not naturally found in that organism.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Variable region: As used herein, the term "variable region" or "variable domain" refers to specific antibody domains that differ extensively in sequence among antibodies and are used in the binding and specificity of each particular antibody for its particular antigen.

Whole IgG: As used herein, the term "whole IgG" refers to a complete IgG molecule. In some embodiments, whole IgG molecules comprise regions found naturally in two or more other organisms.

Wild type: As used herein, the term "wild type" refers to an organism comprising a natural genome (free from genes derived from other organisms).

I. Compositions of the Invention

The present invention provides compounds as well as compositions that comprise at least one glycan-interacting antibody. Within a glycan, monosaccharide monomers may all be the same or they may differ. Common monomers include, but are not limited to trioses, tetroses, pentoses, glucose, fructose, galactose, xylose, arabinose, lyxose, allose, altrose, mannose, gulose, iodose, ribose, mannoheptulose, sedoheptulose and talose. Amino sugars may also be monomers within a glycan. Glycans comprising such sugars are herein referred to as aminoglycans. Amino sugars, as used herein, are sugar molecules that comprise an amine group in place of a hydroxyl group, or in some embodiments, a sugar derived from such a sugar. Examples of amino sugars include, but are not limited to glucosamine, galactosamine, N-acetylglucosamine, N-acetylgalactosamine, sialic acids (including, but not limited to, N-acetylneuraminic acid and N-glycolylneuraminic acid) and L-daunosamine.

As used herein the term "glycan-interacting antibody" refers to an antibody that can interact with a glycan moiety. Glycan-interacting antibodies may function to bind to, alter, activate, inhibit, stabilize, degrade and/or modulate a glycan or a glycan-associated molecule or entity. In so doing, glycan-interacting antibodies may function as a therapeutic, whether palliative, prophylactic or as an ongoing treatment composition. In some embodiments, glycan-interacting antibodies may comprise conjugates or combinations with other molecules. In some embodiments, glycan-interacting antibodies are directed toward glycans comprising one or more amino sugar. In a further embodiment, one or more amino sugars is a sialic acid. In a further embodiment, one or more sialic acids is N-acetylneuraminic acid and/or N-glycolylneuraminic acid.

Antibodies

Glycan-interacting antibodies may comprise entire antibodies or fragments thereof. As used herein, the term "antibody" is used in the broadest sense and specifically covers various embodiments including, but not limited to monoclonal antibodies, polyclonal antibodies, multispecific antibodies (e.g., bispecific antibodies formed from at least two intact antibodies), antibody conjugates (including, but not limited to antibody-drug conjugates), antibody variants [including, but not limited to antibody mimetics, chimeric antibodies (e.g. antibodies with amino acid sequences derived from more than one species), and synthetic variants] and antibody fragments such as diabodies so long as they exhibit a desired biological activity. Antibodies are primarily amino-acid based molecules but may also comprise one or more modifications such as with sugar moieties.

As used herein, the term "antibody fragment" refers to a portion of an intact antibody or fusion-protein thereof, in some cases comprising at least one antigen binding region. Examples of antibody fragments include Fab, Fab', $F(ab')_2$, Fv fragments, single-chain variable fragments (scFvs); diabodies; tri(a)bodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an $F(ab')_2$ fragment that has two antigen-binding sites and is still capable of cross-linking antigen. Glycan-interacting antibodies may comprise one or more of these fragments.

"Native antibodies" are usually heterotetrameric glycoproteins of about 150,000 Daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 103(12: 4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains comprise hypervariable regions. As used herein, the term "hypervariable region" refers to a region within a variable domain comprising amino acid residues responsible or antigen binding. The amino acids present within the hypervariable regions determine the structure of the complementarity determining regions (CDRs) that become part of the antigen-binding site of the antibody. As used herein, the term "CDR" refers to a region of an antibody comprising a structure that is complimentary to its target antigen or epitope. Other portions of the variable domain, not interacting with the antigen, are referred to as framework (FW) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments can also be used based on comparisons with other antibodies (Strohl, W. R. Therapeutic Antibody Engineering. Woodhead Publishing, Philadelphia Pa. 2012. Ch. 3, p 47-54, the contents of which are herein incorporated by reference in their entirety). Determining residues making up CDRs may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989) and Al-Lazikani, B. et al., 1997, J. Mol. Biol. 273(4):927-48, the contents of each of which are herein incorporated by reference in their entirety], Lefranc (Lefranc, M. P. et al., 2005, Immunome Res. 1:3) and Honegger (Honegger, A. and Pluckthun, A. 2001. J. Mol. Biol. 309(3):657-70, the contents of which are herein incorporated by reference in their entirety).

VH and VL domains have three CDRs each. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs have favored canonical structures with the exception of the CDR-H3, which comprises amino acid sequences that may be highly variable in sequence and length between antibodies resulting in a variety of three-dimensional structures in antigen-binding domains (Nikoloudis, D. et al., 2014. Peed. 2:e456). In some cases, CDR-H3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia Pa. 2012. Ch. 3, p 47-54, the contents of which are herein incorporated by reference in their entirety).

As used herein, the term "Fv" refers to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain [to form a single chain Fv (scFv)] or through the introduction of a disulfide bridge between heavy and light chain variable domains (Strohl, W. R. Therapeutic Antibody Engineering. Woodhead Publishing, Philadelphia Pa. 2012. Ch. 3, p 46-47, the contents of which are herein incorporated by reference in their entirety).

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2a, IgG2b, IgG2c, IgG3, IgG4, IgA1, and IgA2.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen.

The term "diabodies" refers to small antibody fragments with two antigen-binding sites, which fragments comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "intrabody" refers to a form of antibody that is not secreted from a cell in which it is produced, but instead target one or more intracellular protein. Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more construct for intrabody-based therapy. In some cases, intrabodies of the invention may target one or more glycated intracellular protein or may modulate the interaction between one or more glycated intracellular protein and an alternative protein.

The term "chimeric antigen receptor" or "CAR" as used herein, refers to artificial receptors (also known as "chimeric immunoreceptors," "artificial T cell receptors" or "chimeric T cell receptors") that are engineered to be expressed on the surface of immune effector cells resulting in specific targeting of such immune effector cells to cells expressing entities that bind with high affinity to the artificial receptors. CARs may be designed to include one or more segments of an antibody, scFv, antibody variable domain, and/or antibody CDRs, such that when such CARs are expressed on immune effector cells, the immune effector cells bind and clear any cells that are recognized by the antibody portions of the CARs. In some cases, CARs are designed to specifically bind cancer cells, leading to immune-regulated clearance of the cancer cells. The phrases "have antigen specificity" and "elicit antigen-specific response" as used with respect to CARs means that the CAR can specifically bind to and immunologically recognize an antigen to elicit an immune response.

The term "monoclonal antibody" as used herein refers to an antibody obtained from a population of substantially homogeneous cells (or clones), i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen.

The modifier "monoclonal" indicates the character of the antibody as being obtained from a substantially homogenous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity.

In some embodiments, glycan-interacting antibodies of the present invention may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. No. 6,673,901; U.S. Pat. No. 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure and/or function comprising some differences in their amino acid sequence, composition or structure as compared to a native antibody.

Antibody Development

Glycan-interacting antibodies of the present invention are developed to bind antigens such as those described herein. As used herein, an "antigen" is an entity which induces or evokes an immune response in an organism. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen. In some cases, methods of immunization may be altered based on one or more desired immunization outcomes. As used here, the term "immunization outcome" refers to one or more desired effects of immunization. Examples include high antibody titers and/or increased antibody specificity for a target of interest.

Antigens of the invention may comprise glycans, glycoconjugates (including, but not limited to glycoproteins and glycolipids), peptides, polypeptides, fusion proteins, or any of the foregoing and may be conjugated or complexed to one or more separate adjuvants or heterologous proteins. In some embodiments, antigens used according to methods of the present invention may comprise sialylated glycans, such as STn. Antigens comprising STn may comprise mucins. Mucins are a family of proteins that are heavily glycosylated. They are a component of many tumors originating from epithelial cells (Ishida, A. et al., 2008. Proteomics. 8: 3342-9, the contents of which are herein incorporated by reference in their entirety). They are highly expressed by submaxillary glands and can be found at high levels in saliva and mucous Animal-derived submaxillary mucins may be used as antigens to generate anti-STn antibodies in immunogenic hosts. Submaxillary mucin from different species differ in their STn content with regard to AcSTn versus GcSTn forms. Porcine submaxillary mucin (PSM) is particularly rich in GcSTn, which makes up about 90% of total STn. STn from bovine submaxillary mucin (BSM) comprises roughly equal percentages of GcSTn and AcSTn. Ovine submaxillary mucin (OSM) is particularly rich in AcSTn, which makes up about 90% of total STn. In some cases, solutions prepared for immunization may be modified to include one or more of PSM, BSM and OSM depending on the desired target of antibodies resulting from such immunization. PSM may be used in immunizations to generate antibodies in immunogenic hosts that are more likely to be specific for GcSTn. PSM is rich in Neu5Gc-containing mucin-type, glycoproteins that are decorated with GcSTn. Among the currently known sources of high Neu5Gc content is red meat; especially submaxillary glands were previously described as a rich source of Neu5Gc due to the high expression of the CMAH enzyme, which catalyzes the reaction to produce the Neu5Gc precursor, CMP-Neu5Ac. In some cases, PSM may be used to prevent a pan-anti-Neu5Gc response and induce a more specific immune response against GcSTn. OSM may be used in immunizations to generate antibodies in immunogenic hosts that are more likely to be specific for AcSTn.

In one embodiment, the present invention provides a glycan-interacting antibody that is GcSTn-specific. The antibody has little cross-reactivity to Neu5Ac-STn or Tn. The antibody can bind GcSTn but has reduced affinity for AcSTn.

In some embodiments, antigens may be subjected to enzymatic digestion prior to immunization to modulate the resulting immune response in immunogenic hosts. In one example, submaxillary mucins may be treated with trypsin or proteinase K enzymes prior to immunization. The activity of such enzymes may help to cleave off and thereby reduce the percentage and variability of non-STn epitopes. Glycan moieties may shield regions of the peptide where they are attached from enzymatic proteolysis and thereby remain intact. Antibody titers resulting from immunizations may comprise different levels depending on the type and amount of antigen used in such immunizations. In some cases, certain antigens may be selected for use in immunizations based on the expected titer.

As used herein, an "adjuvant" is a pharmacological or immunological agent that modifies the effect of other agents. Adjuvants according to the present invention include, but are not limited chemical compositions, biomolecules, therapeutics, and/or therapeutic regimens. Adjuvants may include Freund's adjuvant (complete and/or incomplete), immunostimulatory oligonucleotides [e.g. CpG oligodeoxynucleotides (ODNs)], mineral-containing compositions, bacterial ADP-ribosylating toxins, bioadhesives, mucoadhesives, microparticles, lipids, liposomes, muramyl peptides, N-oxidized polyethylene-piperazine derivatives, saponins and/or immune stimulating complexes (ISCOs). In some embodiments, adjuvants may comprise oil-in-water emulsions (e.g. sub-micron oil-in-water emulsions). Adjuvants according to the present invention may also include any of those disclosed in US Patent Publication No. US20120027813 and/or U.S. Pat. No. 8,506,966, the contents of each of which are herein incorporated by reference in their entirety.

Antibodies of the present invention may be polyclonal or monoclonal or recombinant, produced by methods known in the art or as described in this application. In some embodiments, the antibodies of the present invention may be labeled for purposes of detection with a detectable label known by one of skill in the art. The label can be a radioisotope, fluorescent compound, chemiluminescent compound, enzyme, or enzyme co-factor, or any other labels known in the art. In some aspects, the antibody that binds to a desired antigen is not labeled, but may be detected by binding of a labeled secondary antibody that specifically binds to the primary antibody.

Antibodies of the present invention (e.g., glycan-interacting antibodies) include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. Antibodies of the present invention (e.g., glycan-interacting antibodies) can be from any animal origin including birds and mammals. Preferably, such antibodies are of human, murine (e.g., mouse and rat), donkey, sheep, rabbit, goat, guinea pig, camel, horse, or chicken origin. The antibodies of the present invention can be monospecific or multispecific (e.g., bispecific, trispecific, or of greater multispecificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tutt, A. et al., Trispecific F(ab)3 derivatives that use cooperative signaling via the TCR/CD3 complex and CD2 to activate and redirect resting cytotoxic T cells. J Immunol. 1991 Jul. 1; 147(1):60-9; U.S. Pat. Nos. 4,474,893; 4,714,681; 4,925,648; 5,573,920; 5,601,819; and Kostelny, S. A. et al., Formation of a bispecific antibody by the use of leucine zippers. J Immunol. 1992 Mar. 1; 148(5): 1547-53).

Glycan-interacting antibodies of the present invention comprising monoclonal antibodies can be prepared using well-established methods known by those skilled in the art. In one embodiment, the monoclonal antibodies are prepared using hybridoma technology (Kohler, G. et al., Continuous cultures of fused cells secreting antibody of predefined specificity. Nature. 1975 Aug. 7; 256(5517):495-7). For hybridoma formations, first, a mouse, hamster, or other appropriate host animal, is typically immunized with an immunizing agent (e.g., a target antigen of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, J. W., Monoclonal Antibodies: Principles and Practice. Academic Press. 1986; 59-1031). Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, D. et al., A human hybrid myeloma for production of human monoclonal antibodies. J Immunol. 1984 December; 133(6):3001-5; Brodeur, B. et al., Monoclonal Antibody Production Techniques and Applications. Marcel Dekker, Inc., New York. 1987; 33:51-63).

In some embodiments, myeloma cells may be subjected to genetic manipulation. Such manipulation may be carried out using zinc-finger nuclease (ZFN) mutagenesis as described herein. Alternatively, transfection methods known in the art may be used. NSO myeloma cells or other mouse myeloma cell lines may be used. For example, Sp2/0-Ag14 can be an alternative cell line for hybridoma development.

Transcription Activator-Like Effector Nucleases (TALENs)-induced gene editing provides an alternative gene knock out method. TALENs are artificial restriction enzymes generated by fusing the TAL effector DNA binding domain to a DNA cleavage domain. Similar to ZFNs, TALENs induce double-strand breaks at desired loci that can be repaired by error-prone NHEJ to yield insertions/deletions at the break sites (Wood, A. J. et al., Targeted genome editing across species using ZFNs and TALENs. Science. 2011 Jul. 15; 333(6040):307). Cellectis Bioresearch (Cambridge, Mass.) provides the service of TALEN design and plasmid construction. The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known by those skilled in the art. The binding specificity of the monoclonal antibody can, for example, be determined by Scatchard analysis (Munson, P. J. et al., Ligand: a versatile computerized approach for characterization of ligand-binding systems. Anal Biochem. 1980 Sep. 1; 107(1):220-39). In some cases, antibody specificity for regions of a given antigen may be characterized by chemically modifying the antigens prior to assaying for antibody binding. In one example, periodate treatment may be used to destroy the C6 side chain of sialic acids. Assays may be conducted with and without periodate treatment to reveal whether or not binding in untreated samples is sialic acid-specific. In some cases, antigens comprising 9-O-acetylated sialic acid may be subjected to mild base treatment (e.g. with 0.1 M NaOH) to destroy 9-O-acetyl groups. Assays may be conducted with and without mild base treatment to reveal whether or not binding in untreated samples depends on 9-O-acetylation of sialic acid.

After the desired hybridoma cells are identified, the clones may be subcloned by limiting dilution procedures and grown by standard methods. Suitable culture media for this purpose include, for example, Dulbecco's Modified Eagle's Medium or RPMI-1640 medium. Alternatively, the hybridoma cells may be grown in vivo as ascites in a mammal.

Alternative methods to clone hybridomas may include those provided by kits from STEMCELL Technologies (Vancouver, BC, Canada), e.g. CLONACELL™-HY kit, containing methylcellulose-based semi-solid medium and other media and reagents, to support the selection and growth of hybridoma clones. However, the media in this kit contain FCS, which provides an exogenous source for Neu5Gc incorporation. Though the machinery for endogenous Neu5Gc synthesis is destroyed in $Cmah^{-/-}$ hybridoma, Neu5Gc incorporated from the culture media may also pose a problem in some cases (Bardor, M. et al., Mechanism of uptake and incorporation of the non-human sialic acid N-glycolylneuraminic acid into human cells. J Biol Chem. 2005. 280: 4228-4237). In such instances, the culture media may be supplemented with Neu5Ac to eliminate Neu5Gc incorporation by metabolic competition (Ghaderi, D. et al., Implications of the presence of N-glycolylneuraminic acid in recombinant therapeutic glycoproteins. Nat Biotechnol. 2010. 28: 863-867).

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In another embodiment, the monoclonal antibodies of the present invention can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiments, antibodies of the present invention (e.g., glycan-interacting antibodies) may be produced by various procedures known by those skilled in the art. For the production of polyclonal antibodies in vivo, host animals, such as rabbits, rats, mice, cows, horses, donkeys, chickens, monkeys, sheep or goats, are immunized with either free or carrier-coupled antigens, for example, by intraperitoneal and/or intradermal injection. In some embodiments, injection material may be an emulsion containing about 100 μg of antigen or carrier protein. In some embodiments, injection materials comprise a glycan-rich composition such as non-human mammalian submaxillary mucin in solution. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, TITERMAX® (CytRx Corp, Los Angeles, Calif.), keyhole limpet hemocyanins, dinitrophenol, and potentially useful human adjuvants such as BCG (bacille Calmette-Guerin) and corynebacterium parvum. Such adjuvants are also well known in the art. Several booster injections may be needed, for instance, at intervals of about two weeks, to provide a useful titer of antibody which can be detected, for example, by ELISA assay using glycans and/or free peptide adsorbed to a solid surface. The titer of antibodies in serum from an immunized animal can be increased by selection of antibodies, e.g., by adsorption of antigens onto a solid support and elution of the selected antibodies according to methods well known in the art.

Glycan-interacting antibodies, variants and fragments thereof may be selected and produced using high throughput methods of discovery. In one embodiment, glycan-interacting antibodies comprising synthetic antibodies, variants and fragments thereof are produced through the use of display libraries. The term "display" as used herein, refers to the expression or "display" of proteins or peptides on the surface of a given host. The term "library" as used herein, refers to a collection of unique cDNA sequences and/or the proteins that are encoded by them. A library may contain from as little as two unique cDNAs to hundreds of billions of unique cDNAs. In a preferred embodiment, glycan-interacting antibodies comprising synthetic antibodies are produced using antibody display libraries or antibody fragment display libraries. The term "antibody fragment display library" as used herein, refers to a display library wherein each member encodes an antibody fragment containing at least one variable region of an antibody. Such antibody fragments are preferably Fab fragments, but other antibody fragments such as single-chain variable fragments (scFvs) are contemplated as well. In an Fab antibody fragment library, each Fab encoded may be identical except for the amino acid sequence contained within the variable loops of the complementarity determining regions (CDRs) of the Fab fragment. In an alternative or additional embodiment, amino acid sequences within the individual $V_H$ and/or $V_L$ regions may differ as well.

Display libraries may be expressed in a number of possible hosts including, but not limited to yeast, bacteriophage, bacteria and retroviruses. Additional display technologies that may be used include ribosome-display, microbead-display and protein-DNA linkage techniques. In a preferred embodiment, Fab display libraries are expressed in yeast or in bacteriophages (also referred to herein as "phages" or "phage particles". When expressed, the Fabs decorate the surface of the phage or yeast where they can interact with a given antigen. An antigen comprising a glycan or other antigen from a desired target may be used to select phage particles or yeast cells expressing antibody fragments with the highest affinity for that antigen. The DNA sequence encoding the CDR of the bound antibody fragment can then be determined through sequencing using the bound particle or cell. In one embodiment, positive selection is used in the development of antibodies. In some embodiments, negative selection is utilized in the development of antibodies. In some embodiments, both positive and negative selection methods are utilized during multiple rounds of selection in the development of antibodies using display libraries.

In yeast display, cDNA encoding different antibody fragments are introduced into yeast cells where they are expressed and the antibody fragments are "displayed" on the cell surface as described by Chao et al. (Chao, G. et al., Isolating and engineering human antibodies using yeast surface display. Nat Protoc. 2006; 1(2):755-68). In yeast surface display, expressed antibody fragments contain an additional domain comprising the yeast agglutinin protein, Aga2p. This domain allows the antibody fragment fusion protein to attach to the outer surface of the yeast cell through the formation of disulphide bonds with surface-expressed Aga1p. The result is a yeast cell, coated in a particular antibody fragment. Display libraries of cDNA encoding these antibody fragments are utilized initially in which the antibody fragments each have a unique sequence. These fusion proteins are expressed on the cell surface of millions of yeast cells where they can interact with a desired antigenic target antigen, incubated with the cells. Target antigens may be covalently or otherwise modified with a chemical or magnetic group to allow for efficient cell sorting after successful binding with a suitable antibody fragment takes place. Recovery may be by way of magnetic-activated cell sorting (MACS), fluorescence-activated cell sorting (FACS) or other cell sorting methods known in the art. Once a subpopulation of yeast cells is selected, the corresponding plasmids may be analyzed to determine the CDR sequence.

Bacteriophage display technology typically utilizes filamentous phage including, but not limited to fd, F1 and M13 virions. Such strains are non-lytic, allowing for continued propagation of the host and increased viral titres. Examples of phage display methods that can be used to make the antibodies of the present invention include those disclosed in Miersch et al. (Miersch, S. et al., Synthetic antibodies: Concepts, potential and practical considerations. Methods. 2012 August; 57(4):486-98), Bradbury et al. (Bradbury, A. R. et al., Beyond natural antibodies: the power of in vitro display technologies. Nat Biotechnol. 2011 March; 29(3): 245-54), Brinkman et al. (Brinkmann, U. et al., Phage display of disulfide-stabilized Fv fragments. J Immunol Methods. 1995 May 11; 182(1):41-50); Ames et al. (Ames, R. S. et al., Conversion of murine Fabs isolated from a combinatorial phage display library to full length immunoglobulins. J Immunol Methods. 1995 Aug. 18; 184(2):177-86); Kettleborough et al. (Kettleborough, C. A. et al., Isolation of tumor cell-specific single-chain Fv from immunized mice using phage-antibody libraries and the re-construction of whole antibodies from these antibody fragments. Eur J Immunol. 1994 April; 24(4):952-8); Persic et al. (Persic, L. et al., An integrated vector system for the eukaryotic expression of antibodies or their fragments after selection from phage display libraries. Gene. 1997 Mar. 10; 187(1):9-18); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety. Antibody fragment expression on bacteriophages may be carried out by inserting the cDNA encoding the fragment into the gene expressing a viral coat protein. The viral coat of filamentous bacteriophages is made up of five coat proteins, encoded by a single-stranded genome. Coat protein pIII is the preferred protein for antibody fragment expression, typically at the N-terminus. If antibody fragment expression compromises the function of pIII, viral function may be restored through coexpression of a wild type pIII, although such expression will reduce the number of antibody fragments expressed on the viral coat, but may enhance access to the antibody fragment by the target antigen. Expression of viral as well as antibody fragment proteins may alternatively be encoded on multiple plasmids. This method may be used to reduce the overall size of infective plasmids and enhance the transformation efficiency.

As described above, after selection of a host expressing a high affinity antibody or antibody fragment, (e.g., glycan-interacting antibodies) the coding regions from the antibody or antibody fragment can be isolated and used to generate whole antibodies, including human antibodies, or any other desired antigen binding fragment, and expressed in any desired host, including mammalian cells, insect cells, plant cells, yeast, and bacteria, e.g., as described in detail below.

The DNA sequence encoding a high affinity antibody can be mutated for additional rounds of selection in a process known as affinity maturation. The term "affinity maturation", as used herein, refers to a method whereby antibodies are produced with increasing affinity for a given antigen through successive rounds of mutation and selection of antibody- or antibody fragment-encoding cDNA sequences. In some cases, this process is carried out in vitro. To accomplish this, amplification of CDR coding sequences may be carried out using error-prone PCR to produce millions of copies containing mutations including, but not limited to point mutations, regional mutations, insertional mutations and deletional mutations. As used herein, the term "point mutation" refers to a nucleic acid mutation in which one nucleotide within a nucleotide sequence is changed to a different nucleotide. As used herein, the term "regional mutation" refers to a nucleic acid mutation in which two or more consecutive nucleotides are changed to different nucleotides. As used herein, the term "insertional mutation" refers to a nucleic acid mutation in which one or more nucleotides are inserted into a nucleotide sequence. As used herein, the term "deletional mutation" refers to a nucleic acid mutation in which one or more nucleotides are removed from a nucleotide sequence. Insertional or deletional mutations may include the complete replacement of an entire codon or the change of one codon to another by altering one or two nucleotides of the starting codon.

Mutagenesis may be carried out on CDR-encoding cDNA sequences to create millions of mutants with singular mutations in CDR heavy and light chain regions. In another approach, random mutations are introduced only at CDR residues most likely to improve affinity. These newly generated mutagenic libraries can be used to repeat the process to screen for clones that encode antibody fragments with even higher affinity for the target antigen. Continued rounds of mutation and selection promote the synthesis of clones with greater and greater affinity (Chao, G. et al., Isolating and engineering human antibodies using yeast surface display. Nat Protoc. 2006; 1(2):755-68).

Examples of techniques that can be used to produce antibodies and antibody fragments, such as Fabs and scFvs, include those described in U.S. Pat. Nos. 4,946,778 and 5,258,498; Miersch et al. (Miersch, S. et al., Synthetic antibodies: Concepts, potential and practical considerations. Methods. 2012 August; 57(4):486-98), Chao et al. (Chao, G. et al., Isolating and engineering human antibodies using yeast surface display. Nat Protoc. 2006; 1(2):755-68), Huston et al. (Huston, J. S. et al., Protein engineering of single-chain Fv analogs and fusion proteins. Methods Enzymol. 1991; 203:46-88); Shu et al. (Shu, L. et al., Secretion of a single-gene-encoded immunoglobulin from myeloma cells. Proc Natl Acad Sci USA. 1993 Sep. 1; 90(17):7995-9); and Skerra et al. (Skerra, A. et al., Assembly of a functional immunoglobulin Fv fragment in Escherichia coli. Science. 1988 May 20; 240(4855):1038-41), each of which is incorporated herein by reference in its entirety.

For some uses, including the in vivo use of antibodies (e.g., glycan-interacting antibodies) in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (Morrison, S. L., Transfectomas provide novel chimeric antibodies. Science. 1985 Sep. 20; 229 (4719):1202-7; Gillies, S. D. et al., High-level expression of chimeric antibodies using adapted cDNA variable region cassettes. J Immunol Methods. 1989 Dec. 20; 125(1-2):191-202.; and U.S. Pat. Nos. 5,807,715; 4,816,567; and 4,816,397, which are incorporated herein by reference in their entirety).

Humanized antibodies are antibody molecules from nonhuman species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (U.S. Pat. Nos. 5,693,762 and 5,585,089; Riechmann, L et al., Reshaping human antibodies for therapy. Nature. 1988 Mar. 24; 332(6162):323-7, which are incorporated herein by reference in their entireties). Antibodies can be humanized using a variety of techniques known in the art, including, for example, CDR-grafting (EP 239,400; PCT publication WO 91/09967; U.S. Pat. Nos. 5,225,539; 5,530,101; and 5,585,089); veneering or resurfacing (EP 592,106; EP 519,596; Padlan, E. A., A possible procedure for reducing the immunogenicity of antibody variable domains while preserving their ligand-binding properties. Mol Immunol. 1991 April-May; 28(4-5):489-98; Studnicka, G. M. et al., Human-engineered monoclonal antibodies retain full specific binding activity by preserving non-CDR complementarity-modulating residues. Protein Eng. 1994 June; 7(6):805-14; Roguska, M. A. et al., Humanization of murine monoclonal antibodies through variable domain resurfacing. Proc Natl Acad Sci USA. 1994 Feb. 1; 91(3):969-73); and chain shuffling (U.S. Pat. No. 5,565,332); each of which is incorporated herein by reference in their entirety. Humanized antibodies of the present invention may be developed for desired binding specificity, complement-dependent cytotoxicity, and antibody-dependent cellular-mediated cytotoxicity, etc.

Completely human antibodies (e.g., glycan-interacting antibodies) are particularly desirable for therapeutic treatment of human patients, so as to avoid or alleviate immune reaction to foreign protein. Human antibodies can be made by a variety of methods known in the art, including the antibody display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies (e.g., glycan-interacting antibodies) can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a glycan, glycoconjugate and/or polypeptide of the invention.

Thus, using such a technique, it is possible to produce useful human IgG, IgA, IgM, IgD and IgE antibodies. For an overview of the technology for producing human antibodies, see Lonberg and Huszar (Lonberg, N. et al., Human antibodies from transgenic mice. Int Rev Immunol. 1995; 13(1): 65-93). For a detailed discussion of the technology for producing human antibodies and human monoclonal antibodies and protocols for producing such antibodies, see, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, each of which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the present invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The affinity between an antibody and a target or ligand (such as an antigen used to generate a given antibody) may be measured in terms of $K_D$ using one or more binding assays as described herein. Depending on the desired application for a given antibody, varying $K_D$ values may be desirable. High affinity antibodies typically form ligand bonds with a $K_D$ of about $10^{-5}$M or less, e.g. about $10^{-6}$M or less, about $10^{-7}$M or less, about $10^{-8}$M or less, about $10^{-9}$M or less, about $10^{10}$M or less, about $10^{-11}$M or less or about $10^{-12}$M or less.

In some embodiments, antibodies of the invention may be characterized according to their half maximal effective or inhibitory concentration ($EC_{50}$ or $IC_{50}$, respectively). In some cases, this value may represent the concentration of antibody necessary to inhibit cells expressing STn (e.g. kill, reduce proliferation and/or reduce one or more cell function) at a level equal to half of the maximum inhibition observed with the highest concentrations of antibody. Such $IC_{50}$ values may be from about 0.001 nM to about 0.01 nM, from about 0.005 nM to about 0.05 nM, from about 0.01 nM to about 1 nM, from about 0.05 nM to about 5 nM, from about 0.1 nM to about 10 nM, from about 0.5 nM to about 25 nM, from about 1 nM to about 50 nM, from about 5 nM to about 75 nM, from about 10 nM to about 100 nM, from about 25 nM to about 250 nM, from about 200 nM to about 1000 nM or more than 1000 nM.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

Targets

Glycan-interacting antibodies of the present invention exert their effects via binding (reversibly or irreversibly) to one or more glycan or glycan-associated or glycan-related targets. In some embodiments, glycan-interacting antibodies can be prepared from any region of the targets taught herein. In some embodiments, targets of the present invention comprise glycans. Glycans used for generating antibodies may comprise a chain of sugars comprising at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 residues. Preferably, glycans used for generating antibodies comprise from about 2 residue to about 5 residues.

In some embodiments, glycan-interacting antibody target antigens comprise sialic acids. N-acetylneuraminic acid (Neu5Ac) and N-glycolylneuraminic acid (Neu5Gc) are the major sialic acids on mammalian cell surfaces. Of these, Neu5Ac is naturally produced in humans. Neu5Gc is naturally produced in most mammals with the exception of humans due to a mutation in the cytidine monophosphate (CMP)-N-acetylneuraminic acid hydroxylase (CMAH) gene responsible for CMP-Neu5Gc production from CMP-Neu5Ac. Neu5Gc in humans is in fact immunogenic with nearly all humans expressing anti-Neu5Gc antibodies. Despite a lack of production, most human systems comprise some level of Neu5Gc due to dietary intake. These foreign products are subsequently incorporated into human glycoproteins. Such glycoproteins are contemplated as targets of the invention. Glycan target antigens of the present invention, include, but are not limited to those listed in Table 1.

TABLE 1

| Glycan target antigens<br>Glycan |
|---|
| GalNAcα-R |
| Galα1,3Galβ1,4GlcNAcβ-R |
| Galβ1,3GalNAcβ-R |
| Galβ1,3GlcNAcα-R |
| Galβ1,3GlcNAcβ1,3Galβ1,4Glcβ-R |
| Galβ1,3GlcNAcβ-R |
| Galβ1,4GlcNAc6Sβ-R |
| Galβ1,4GlcNAcβ-R |
| Galβ1,4Glcβ-R |
| KDNα2,8Neu5Acα2,3Galβ1,4Glcβ-R |
| KDNα2,8Neu5Gcα2,3Galβ1,4Glcβ-R |
| Neu5,9Ac2α2,3Galβ1,3GalNAcα-R |
| Neu5,9Ac2α2,3Galβ1,3GalNAcβ-R |
| Neu5,9Ac2α2,3Galβ1,3GlcNAcβ-R |
| Neu5,9Ac2α2,3Galβ1,4GlcNAcβ-R |
| Neu5,9Ac2α2,3Galβ1,4Glcβ-R |
| Neu5,9Ac2α2,3Galβ-R |
| Neu5,9Ac2α2,6GalNAcα-R |
| Neu5,9Ac2α2,6Galβ1,4GlcNAcβ-R |
| Neu5,9Ac2α2,6Galβ1,4Glcβ-R |
| Neu5,9Ac2α2,6Galβ-R |
| Neu5Acα2,3Galβ1,3GalNAcα-R |
| Neu5Acα2,3Galβ1,3GalNAcβ-R |
| Neu5Acα2,3Galβ1,3GlcNAcβ1,3Galβ1,4Glcβ-R |
| Neu5Acα2,3Galβ1,3GlcNAcβ-R |
| Neu5Acα2,3Galβ1,4(Fucα1,3)GlcNAc6Sβ-R |
| Neu5Acα2,3Galβ1,4(Fucα1,3)GlcNAcβ-R |
| Neu5Acα2,3Galβ1,4GlcNAc6Sβ-R |
| Neu5Acα2,3Galβ1,4GlcNAcβ-R |
| Neu5Acα2,3Galβ1,4Glcβ-R |
| Neu5Acα2,3Galβ-R |
| Neu5Acα2,6(KDNα2,3)Galβ1,4Glcβ-R |
| Neu5Acα2,6(Neu5Acα2,3)Galβ1,4Glcβ-R |
| Neu5Acα2,6(Neu5Gcα2,3)Galβ1,4Glcβ-R |
| Neu5Acα2,6GalNAcα-R |
| Neu5Acα2,6Galβ1,4GlcNAcβ-R |
| Neu5Acα2,6Galβ1,4Glcβ-R |
| Neu5Acα2,6Galβ-R |
| Neu5Acα2,8KDNα2,6Galβ1,4Glcβ-R |
| Neu5Acα2,8Neu5Acα2,3Galβ1,4Glcβ-R |
| Neu5Acα2,8Neu5Acα2,3Galβ1,4Glcβ-R |
| Neu5Acα2,8Neu5Acα2,6Galβ1,4Glcβ-R |
| Neu5Acα2,8Neu5Acα2,8Neu5Acα2,3Galβ1,4Glcβ-R |
| Neu5Acα2,8Neu5Acα2,8Neu5Acα2,3Galβ1,4Glcβ-R |
| Neu5Acα2,8Neu5Gcα2,3Galβ1,4Glcβ-R |
| Neu5Acα2,8Neu5Gcα2,6Galβ1,4Glcβ-R |
| Neu5Gc9Acα2,3Galβ1,4Glcβ-R |
| Neu5Gc9Acα2,6Galβ1,4Glcβ-R |
| Neu5Gc9Acα2,3Galβ1,3GalNAcα-R |
| Neu5Gc9Acα2,3Galβ1,3GalNAcβ-R |
| Neu5Gc9Acα2,3Galβ1,3GlcNAcβ-R |
| Neu5Gc9Acα2,3Galβ1,4GlcNAcβ-R |
| Neu5Gc9Acα2,3Galβ-R |
| Neu5Gc9Acα2,6GalNAcα-R |
| Neu5Gc9Acα2,6Galβ1,4GlcNAcβ-R |
| Neu5Gc9Acα2,6Galβ-R |
| Neu5GcOMeα2,8Neu5Acα2,3Galβ1,4Glcβ-R |
| Neu5Gcα2,3Galβ1,3GalNAcα-R |
| Neu5Gcα2,3Galβ1,3GalNAcβ-R |
| Neu5Gcα2,3Galβ1,3GlcNAcβ1,3Galβ1,4Glcβ-R |
| Neu5Gcα2,3Galβ1,3GlcNAcβ-R |
| Neu5Gcα2,3Galβ1,4(Fucα1,3)GlcNAc6Sβ-R |
| Neu5Gcα2,3Galβ1,4(Fucα1,3)GlcNAcβ-R |
| Neu5Gcα2,3Galβ1,4GlcNAc6Sβ-R |
| Neu5Gcα2,3Galβ1,4GlcNAcβ-R |
| Neu5Gcα2,3Galβ1,4Glcβ-R |
| Neu5Gcα2,3Galβ-R |
| Neu5Gcα2,6GalNAcα-R |
| Neu5Gcα2,6Galβ1,4GlcNAcβ-R |
| Neu5Gcα2,6Galβ1,4Glcβ-R |
| Neu5Gcα2,6Galβ-R |
| Neu5Gcα2,8Neu5Acα2,3Galβ1,4Glcβ-R |
| Neu5Gcα2,8Neu5Gcα2,3Galβ1,4Glcβ-R |

The following abbreviations are used herein: Glc—glucose, Gal—galactose, GlcNAc—N-acetylglucosamine, GalNAc—N-acetylgalactosamine, GlcNAc6S—6-Sulfo-N-acetylglucosamine, KDN—2-keto-3-deoxy-D-glycero-D-galactonononic acid, Neu5,9Ac2—N-acetyl-9-O-acetylneuraminic acid, Fuc—fucose and Neu5GcOMe—2-O-methyl-N-glycolylneuraminic acid. O-glycosidic bonds are present between each residue in the glycans listed with α and β indicating the relative stoichiometry between the two residues joined by the bond, wherein α indicates an axial orientation and β indicates an equatorial orientation. The numbers following α and/or β, in the format x,x, indicated the carbon number of each of the carbons from each of the adjoined residues that participate in bond formation. While the glycans listed in Table 1 represent individual glycan target antigens contemplated, the present invention also includes embodiments wherein the above presented glycans comprise different combinations of α and β-oriented O-glycosidic bonds than the ones presented. Also in Table 1, R represents an entity that the glycan may be coupled with. In some embodiments, R is a protein wherein the glycan is linked typically to a serine or threonine residue. In some embodiments, R is a linker molecule used to join the glycan to a substrate, such as in a glycan array. In some embodiments, R may be a linker comprising $—(CH_2)_2CH_2NH_2$ or $—(CH_2)_3NHCOCH_2(OCH_2CH_2)_6NH_2$. In some embodiments, R may be biotin, albumin, $ProNH_2$, —CH—, —OH, $—OCH_3$, $—OCH_2CH_3$, —H, hydrido, hydroxy, alkoxyl, oxygen, carbon, sulfur, nitrogen, polyacrylamide, phosphorus, $NH_2$, $ProNH_2{=}O(CH_2)_2CH_2NH_2$, $(OCH_2CH_2)_6NH_2$, $O(CH_2)_3NHCOCH_2(OCH_2CH_2)_6NH_2$, the fluorescent labels 2-aminobenzamide (AB) and/or 2-aminobenzoid acid (AA), 2-aminobenzamide analog that contains an alkyl amine (AEAB), aminooxygroups, methylaminooxygroups, hydrazide groups, amino lipid 1,2-dihexadecyl-sn-glycero-3-phosphoethanolamine (DHPE), aminooxy (AO) functionalized DHPE and glycosylphosphatidylinositol (GPI). Without intending to limit the source or nature of R, this may include structures that affect the physical spacing of glycan residue. In some embodiments, the R group may comprise a combination of the R groups presented here, e.g. a biotinylated polyacrylamide. In some embodiments, the R group in combination with underlying substrates effect glycan residue spacing.

Glycan targets of the present invention may comprise regions of antibody recognition. As used herein, the term "region of antibody recognition" refers to one or more regions located on any part of the molecule, an attached group or located on a region of interaction between the glycan and another molecule, including, but not limited to another glycan. In some embodiments, regions of antibody recognition are located at interchain target sites, wherein the term interchain means within the present polymeric chain. Interchain target sites may comprise regions of antibody recognition comprising 1, 2, 3, 4, 5, 6, 7, 8, 9 or at least 10 residues, bonds between residues or combinations of residues and bonds. In some embodiments, regions of antibody recognition are located at regions of interaction between one or more glycan chains. Such regions may be between 2, 3, 4 or at least 5 glycan chains.

In some embodiments, regions of antibody recognition are located at regions of interaction between glycan branch chains connected to a common parent chain. In some embodiments, regions of antibody recognition are located at regions of interaction between a glycan branch chain and a parent chain. In some embodiments, regions of antibody recognition are located at regions of interaction between glycans and proteins. Such regions of interaction may comprise chemical bonds between the glycan and the protein, including, but not limited to covalent bonds, ionic bonds, hydrostatic bonds, hydrophobic bonds and hydrogen bonds. In some embodiments, regions of antibody recognition are located at regions of interaction between glycans and other biomolecules including, but not limited to lipids and nucleic acids. Such regions of interaction may comprise chemical bonds between the glycan and the biomolecule, including, but not limited to covalent bonds, ionic bonds, hydrostatic bonds, hydrophobic bonds and hydrogen bonds.

In some embodiments, glycan targets of the present invention are components of glycoconjugates. As used herein, the term "glycoconjugate" refers to any entity comprising a glycan moiety. In some embodiments, glycoconjugates are glycolipids. As used herein, the term "glycolipid" refers to a class of lipids wherein a carbohydrate moiety is covalently attached. In some embodiments, carbohydrate moieties present on glycolipids comprise glycans. In some embodiments, lipid components of glycolipids comprise ceramide moieties. Examples of glycolipids contemplated as targets of the present invention include, but are not limited to glyceroglycolipids (including, but not limited to galactolipids and sulfolipids), glycosphingolipids (including, but not limited to cerebrosides (e.g., galactocerebrosides, glucocerebrosides and sulfatides), gangliosides, globosides and glycophosphosphingolipids) and glycosylphosphatidylinositols. When located within cell membranes, glycan moieties of glycolipids are located on the extracellular side of the membrane where they may interact with other cells as well as cell signaling ligands (Maccioni, H. J. et al., Organization of the synthesis of glycolipid oligosaccharides in the Golgi complex. FEBS Lett. 2011 Jun. 6; 585(11):1691-8).

In some embodiments, glycoconjugate targets of the present invention are glycoprotein and/or proteoglycans. Glycoproteins refer to any proteins that are covalently bonded with glycans. Proteoglycans are a class of proteins that are heavily glycosylated with glycans that often carry a negative charge. This property makes them very hydrophilic and important components of connective tissue.

Recombinant Antibodies

Recombinant antibodies (e.g., glycan-interacting antibodies) of the invention may be generated using standard techniques known in the art. In some embodiments, recombinant antibodies may be anti-glycan antibodies. Further antibodies may be anti-STn antibodies (e.g. anti-GcSTn or anti-AcSTn antibodies). Recombinant antibodies of the invention may be produced using variable domains obtained from hybridoma cell-derived antibodies produced according to methods described herein. Heavy and light chain variable region cDNA sequences of antibodies may be determined using standard biochemical techniques. Total RNA may be extracted from antibody-producing hybridoma cells and converted to cDNA by reverse transcriptase (RT) polymerase chain reaction (PCR). PCR amplification may be carried out on resulting cDNA to amplify variable region genes. Such amplification may comprise the use of primers specific for amplification of heavy and light chain sequences. In other embodiments, recombinant antibodies may be produced using variable domains obtained from other sources. This includes the use of variable domains selected from one or more antibody fragment library, such as an scFv library used in antigen panning. Resulting PCR products may then be subcloned into plasmids for sequence analysis. Once sequenced, antibody coding sequences may be placed into expression vectors. For humanization, coding sequences for human heavy and light chain constant domains may be used to substitute for homologous murine sequences. The resulting constructs may then be transfected into mammalian cells for large scale translation.

Anti-Tn Antibodies

In some embodiments, recombinant antibodies of the invention (e.g., glycan-interacting antibodies) may be anti-Tn antibodies. Such antibodies may bind to targets comprising Tn. Anti-Tn antibodies may be specific for Tn or may bind other modified forms of Tn, such as Tn linked to other moieties, including, but not limited to additional carbohydrate residues. In some cases anti-Tn antibodies may be anti-sialyl-Tn antibodies. Such antibodies may bind to targets comprising sialylated Tn comprising Neu5Ac and/or targets comprising sialylated Tn comprising Neu5Gc. Some anti-Tn antibodies may bind specifically to clusters of Tn antigen.

Anti-STn Antibodies

Figure 1B:
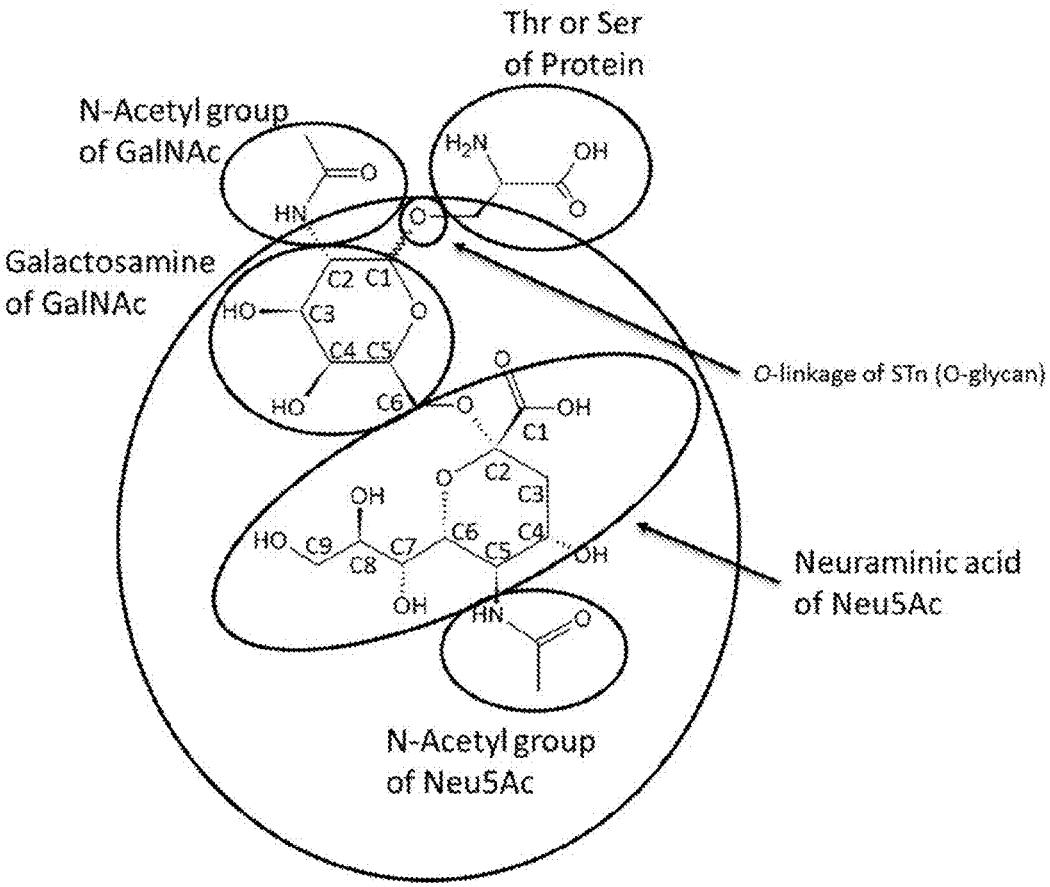
Figure 1C:
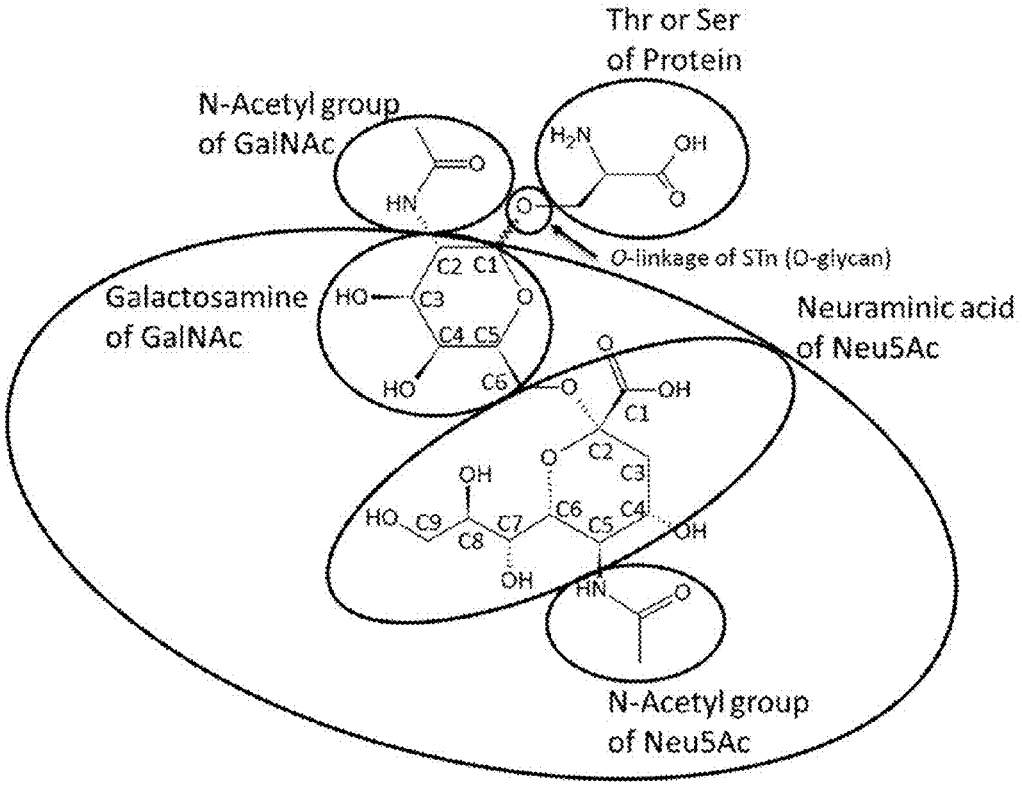
Figure 1D:
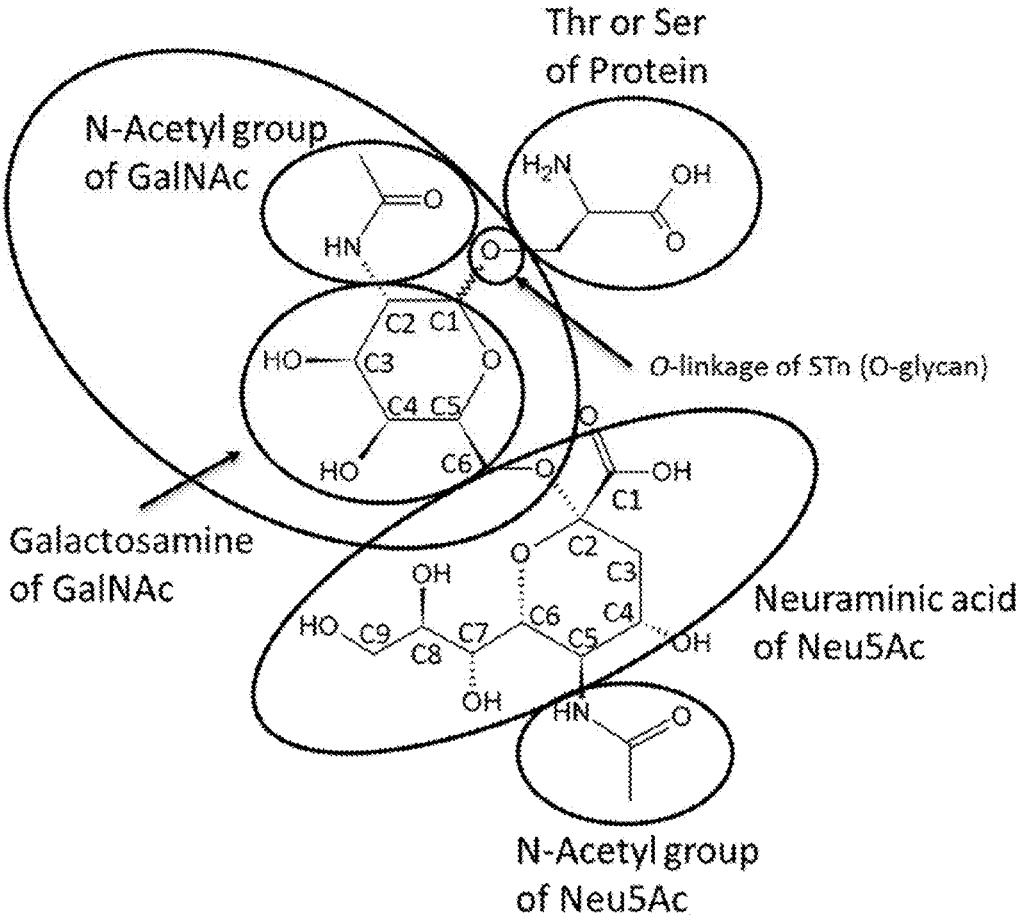

In some embodiments, antibodies of the invention (e.g., glycan-interacting antibodies) may specifically bind to antigens comprising STn. Anti-STn antibodies of the invention may be categorized by their binding to specific portions of STn antigens and/or by their specificity for AcSTn versus GcSTn. In some cases, anti-STn antibodies of the invention are Group 1 antibodies. "Group 1" antibodies according to the invention are antibodies capable of binding AcSTn and GcSTn. Such antibodies may also be referred to herein as pan-STn antibodies due to their ability to associate with a wider range of STn structures. In some embodiments, Group 1 antibodies may associate with the portion of STn indicated by the large oval in FIG. 1A. In some cases, anti-STn antibodies of the invention are Group 2 antibodies. "Group 2" antibodies, according to the invention, are antibodies capable of binding STn as well as some related structures that include an O-linkage to serine or threonine. In some embodiments, Group 2 antibodies may associate with glycans comprising a sialylated galactose residue. In some cases, Group 2 antibodies may associate with the portion of STn indicated by the large oval in FIG. 1B. Some Group 2 antibodies preferably bind to structures with AcSTn over structures with GcSTn. Further anti-STn antibodies may be Group 3 antibodies. As referred to herein, "Group 3" antibodies are antibodies capable of binding STn, but may also bind a broader set of related structures. Unlike Group 2 antibodies, Group 3 antibodies do not require that such structures have an O-linkage to serine or threonine. In some embodiments, Group 3 antibodies may associate with the portion of STn indicated by the large oval in FIG. 1C. Finally, some anti-STn antibodies of the invention may be Group 4 antibodies. As referred to herein, "Group 4" antibodies are capable of binding to both AcSTn and GcSTn as well as the un-sialylated Tn antigen, and therefore have broader specificity. In some embodiments, Group 4 antibodies may associate with the portion of STn indicated by the large oval in FIG. 1D.

In some cases, anti-STn antibodies of the invention may bind specifically to clusters of STn on a particular antigen or cell surface. Some such antibodies may recognize epitopes formed by the clustering of STn, including epitopes that include areas of contact between neighboring STn structures. Such epitopes may be formed by the clustering of 2, 3, 4, 5, 6, 7, 8, 9, 10 or more STn structures.

Antibody Components

In some cases, antibodies or antigen binding fragments thereof of the invention may comprise variable domain and/or CDR amino acid sequences provided herein. Some antibodies or antigen binding fragments may comprise different combinations of such sequences. In some cases, antibodies or antigen binding fragments of the invention may comprise one or more of the variable domain sequences listed in Table 2. Residues indicated with an "X" may be absent or selected from any amino acid residues. Light chain variable domains presented in the Table may be expressed with or without a C-terminal arginine residue. This residue typically links light chain variable domains with light chain constant domains and may be expressed as part of the light chain constant domain instead of the light chain variable domain. In some cases, antibodies or antigen binding fragments thereof may comprise an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the variable domain sequences listed in Table 2 or a fragment thereof (e.g., an N-terminal fragment, C-terminal fragment, or internal fragment).

TABLE 2

Variable domain sequences

| Antibody ID Number | Variable domain | Sequence | SEQ ID NO |
|---|---|---|---|
| 18D2 | Heavy chain | QVTLKESGPGILQPSQTLSLTCSFSGFSLSTSNMGIG WIRQPSGKGLEWLAHIWWHDDKYYNPSLKSRLTIS KDISNNQVFLKITSVDTADTATYYCAQVPFYYGTSF DVWGTGTTVTVSS | 1 |
| 18D2 | Light chain 1 | DIVMTQSPATLSVTPGDRVSLSCRASQSISDYLHWY QQKSHESPRLLIKYASQSISGIPSRFSGSGSGSDFTLSI NSVEPEDVGVYYCQNGHSFPLTFGAGTKLELK | 2 |
| 18D2 | Light chain 2 | QIVLTQSPAIMSASPGETVTMTCSASSSITYMHWYQ QKPGTSPKRWIYDTSKLASGVPARFSGSGSGTSYSL TISSMEAEDAATYYCHQRSSYTFGGGTKLEIKR | 3 |
| 18C7 | Heavy chain | QVTLKESGPGILQPSQTLSLTCSFSGFSLSTFGMGVG WIRQPSGKGLEWLAHIWWDDDKYYNPALKSRLTIS KDTSKNQVFLKIANVDTADTATYYCARIAYYYGSE RDYWGQGTTLTVSS | 4 |

TABLE 2 -continued

| Variable domain sequences | | | |
|---|---|---|---|
| Antibody ID Number | Variable domain | Sequence | SEQ ID NO |
| 18C7 | Light chain | QIVLTQSPAIMSASPGEKVTMTCSASSSISYMHWYH QKPGTSPKRWIYDTSKLASGVPARFSGSGSGTSYSL TISSMEAEDAATYYCHQRSSYTFGGGTKLEIKR | 5 |
| 10A5-2A12 | Heavy chain | QVQLKESGPGLVAPSQSLSITCTVSGFSLTSYGVSW VRQPPGKGLEWLGVIWGDGSTNYHSSLISRLSISKD NSKSQVFLKLNSLQTDDTATYYCARAFVYWGQGT LVTVSA | 6 |
| 10A5-2A12 | Light chain | QIVLTQSPAIMSASPGEKVTMTCSASSSVSYIHWYQ QKSGTSPKRWIYDTSKLASGVPARFSGSGSGTSYSL TISSMEAEDAATYYCQQWSSNPPMLTFGAGTKLEL K | 7 |
| 8C11-1D10 | Heavy chain | QVQLKESGPGLVAPSQSLSITCTVSGFSLTSYGVSW VRQPPGKGLEWLGVIWGDGSTNYHSALISRLIISKD NSKSQVFLKLNSLQTDDTATYYCTKGFTYWGQGTL VTVSA | 8 |
| 8C11-1D10 | Light chain | QIVLTQSPAIMSASPGEKVTMTCSASSSVSYMHWY QQKSGTSPKRWIFDTSKLASGVPARFSGSGSGTSYS LTISSMEAEDAATYYCQQWSSNLLTFGAGTKLELK | 9 |
| 2D4-1B4 | Heavy chain | QVQLQESGPGLVAPSQSLSITCTVSGFSLISYGVNW VRQPPGKGLEWLGVIWGDGSTNYQSALISRLIISKD NSKSQVFLKLNSLQTDDTATYYCTKGFAYWGQGT LVTVSA | 10 |
| 2D4-1B4 | Light chain | QIVLTQSPAIMSASPGEKVTMTCSASSSVSYMHWFQ QKSGTSPKRWIYDTSKLASGVPARFSGSGSGTSYSL TISSMEAEDAATYYCQQWSSNLLTFGAGTKLELK | 11 |
| 7G9-1A8 | Heavy chain | QVQLKESGPGLVAPSQNLSITCTVSGFSLTSYGVNW VRQPPGKGLEWLGVIWGDGSTNYHSALISRLIISKE NSKSQVFLKLNSLQTNDTATYYCTKGFVYWGQGT LVTVSA | 12 |
| 7G9-1A8 | Light chain | QIVLTQSPAIMSASPGEKVTMTCSASSSVSYMHWY QQKSGTSPKRWIFDTSKLASGVPARFSGSGSGTSYS LTISSMEAEDAATYYCQQWSSNLLTFGAGTKLELK | 9 |
| 1A12-2B2 | Heavy chain | QVQLKESGPGLVAPSQSLSITCTVSGFSLTSYGVSW VRQPPGKGLKWLGVIWGDGSTNYHSALISRLSISKD NSKSQVFLKLNSLQTDDTATYYCAKGGYFDYWGQ GTTLTVSS | 13 |
| 1A12-2B2 | Light chain | QIVLTQSPAVMSASPGEKVAITCSASSSVSYMHWFQ QKPGTSPKLWIYSTSNLASGVPARFSGSGSGTSYSLT ISRMEAEDAATYYCQQRSSYPWTFGGGTKLEIK | 14 |
| 7D3-2C10 | Heavy chain | QVQLLQYDAELVKPGGSVKISCKASGYTFTDHAIH WVKQKPEQGLEWIGYFSPGNDDIKYSEKFKGKATL TADKSSSTAYMQLNSLTSEDSAVYFCKRSITTPYWG QGTLVTVSA | 15 |
| 7D3-2C10 | Light chain | DIQMNQSPSSLSASLGDTITITCHASQNINVWLSWY QQKPGNIPKLLIYKVSNLHTGVPSRFSGSGSGTGFTL TISSLQPEDIATYYCQQDQSYPYTFGGGTKLKK | 16 |
| A5-2G12 | Heavy chain | QVQLLQYDAELVKPGASVKISCKASGYTFTDHAIH WVKQKPEQGLEWIGYISPGNDDIKYSEKFKGKATL TADKSSSTAYMQLNSLTSEDSAVYFCKRSITTPYWG QGTLVTVSA | 17 |
| A5-2G12 | Light chain | NIVMTQSPKSMSMSVGERVTLTCKASENVVIYVSW YQQKPEQSPKLLIYGASNRYTGVPDRFTGSGSATDF TLTISSVQAEDLADYHCGQGYSYPYTFGGGTKLEIKR | 18 |
| 1A5-2C9 | Heavy chain | QVQLQQSDAELVKPGASVKISCKASGYTFTDHAIH WVKQKPEQGLEWIGYVSPGNGDIKYNEKFKGKAT LTADKSSSTAYMQLNSLTSEDSAVYFCKRSLIGDY WGQGTTLTVSS | 19 |

TABLE 2 -continued

Variable domain sequences

| Antibody ID Number | Variable domain | Sequence | SEQ ID NO |
|---|---|---|---|
| 1A5-2C9 | Light chain | OIVMTQSOKFMSSSVGDRVTITCKASONVGTAVAW YQQKPGQSPKFLIYSASNRYTGVPDRFTGSGSGTDF TLTISNMQSEDLADYFCOOYSSYRLTFGGGTKLEIK | 20 |
| 4D9-2C11 | Heavy chain | QVQLQQSDAELVKPGASVKISCKASGYTFTDHAIH WVKQKPEOGLEWIGYLSPGNDDIKYSEKFKDKATL TADKSSSTAYMOLNSLTSEDSAVYFCKRSIGGDHW GQGTTLTVSS | 21 |
| 4D9-2C11 | Light chain | DIOMNQSPSSLSASLGDTITITCHASQNINVWLNWY QQKPGNIPKLLIYKASNLHTGVPSRFSGSGSGTGFTL TIGSLQPED1ATYYCQQGQSYPFTFGGGTKLEIKR | 22 |
| 2F4-1E2 | Heavy chain | QVQLQQSDAELVKPGASVKISCKASGYTFTDHAIH WVKQKPEQGLEWIGYISPGNGDIKYNEKFKGKATL TADKSSSTAYMQLNSLTSEDSAVYFCQRQLGQGY WGQGTTLTVSS | 23 |
| 2F4-IE2 | Light chain | DVVMTQTPLSLPVSLGDQASISCRSSQSLVHSYGNT YLHWYLQKPGQSPKLLIYKVSNRFSGVPDRFSGSGS GTDFTLKISRVEAEDLGVYFCSQNTHVPYTFGGGTK LEIKR | 24 |
| 2F4-1H8 | Heavy chain | QVQLQQSDAELVKPGASVKISCKASGYTFTDHAIH WVKQKPEQGLEWIGYISPGNGDIKYNEKFKGKATL TADKSSSTAYMQLNSLTSEDSAVYFCQRQLGQGY WGQGTTLTVSS | 23 |
| 2F4-1H8 | Light chain | DVVMTQTPLSLPVSLGDQASISCRSSQSLVHSYGNT YLHWYLQKPGQSPKLLIYKVSNRFSGVPDRFSGSGS GTDFTLKISRVEAEDLGVYFCSQNTHVPYTFGGGTK LEIKR | 24 |
| 2C6-2F11 | Heavy chain | QVQLQQSDAHLGKPGASVKISCKASGYTFSDHAIH WVKQKPEQGLEWIGYISPGNDDIKYNEKFKGKATL TADKSSSTAYMQLNSLTSEDSAVYFCERSMIGVYW GQGTLVTVSA | 25 |
| 2C6-2F11 | Light chain | DVVMTQTPLSLTVSLGDQASISCRFSOSLVOSNGNT YLQWYLQKPGOSPKLLIYKV'SNRI CGVPDRI'SGSGS GTDFTLKISRVEAEDLGVYFCSQSTHAPLTFGAGTK LELK | 26 |
| 2B2-2A7 | Heavy chain | QVQLQQSDAELVKPGASVKISCKTSGYTFTDHAIH WVKQKPEQGLEWIGYISPGNGDIKYNEKFKGKATL TADKSSSTAYMQLSSLTPEDSAVYFCKISYYGIWGQ GTTLTVSS | 27 |
| 2B2-2A7 | Light chain | OIOMTQSPASLSVSVGESVTITCRLSEDIYSNLAWFO QRPGKSPQLLVYKATNLADGVPSRFSGSGSGTQYSL KINSLQSEDFGTYYCQHFWGTPFTFGSGTKVEIK | 28 |
| 5G2-IB3 | Heavy chain | QVQLQQSDAELVKPGASVKISCKASGYTFTDHAIH WVKQKPE0GLEWIGYFSPGNDD1KYNEKFKVKATL TADKSSSTAYMQLTSLTSEDSAVYFCKRSYYGDWG QGTTLTVSS | 29 |
| 5G2-1B3 | Light chain | DIQMTQSPASLSVSVGETVTITCRASENIYSHLAWY QQKQGKSPQLLVYGATNLADGVPSRFSGSGSGTQF SLKIHSLQSEDFGSYYCQHFWGAP1 TFGSGTKLEIK | 30 |
| 7A6-2A2 | Heavy chain | QIQLQQSDAELVKPGTSVKMSCKASGYTFTDHAIH WVKQKPEQGLEWIGYFSPGNDD1KYNVKFKGKATL TADKSSSTAYMQLNSLTSEDSAVYFCSVGYALDYW GLGTTLTVSS | 31 |
| 7A6-2A2 | Light chain | NIVMTQSPKSMSMSVGERVTLTCKASENVVTYVSW YQQKPEQSPKLLIYGASNRYTGVPDRFTGSGSATDF TLTISSVQAEDLADYHCGQGYSYPYTFGGGTKLEIK R | 32 |
| 10C9-2G7 | Heavy chain | QVQLQQSDAELVKPGTTVKISCKASGYTFTDHAIH WVKEKPEQGLEWIGYISPGNDDIKYSEKFKGKATLT ADKSSSTAYMQLNSLTSDDSAVYFCKRSLSTPYWG QGTLVTVSA | |
| 10C9-2G7 | Light chain | Unknown | |
| 1011-2G9 | Heavy chain | Unknown | |
| 1C11-2G9 | Light chain | DIVMTOSPSSLTVTAGEKVTMSCRSSOSLLNSGNQK NYLTWYQQKPGQPPKLLIYWASTRESGYPDRFTGS GSGTDFTLTISSVQAEDLAVYYCQNDYSYPYTFGG GTKLE1KR | 34 |

TABLE 2 -continued

Variable domain sequences

| Antibody ID Number | Variable domain | Sequence | SEQ ID NO |
|---|---|---|---|
| 1F6-1B7 (also sequence of 1F6-1C10) | Heavy chain | QVQLQQSDAELVKPGASVKISCKASGYTFTDHAIH WVMOMPEQGLEWIGYISPGNGDVKYSERFKGRAT LTADKSSSSAYMQLNSLTSEDSAVYFCKRSLSTPYW GQGTLVTVS | 35 |
| 1F6-IB7 (also sequence of 1F6-1CI0) | Light chain | DIVMTQSPSSLTVTAGERVTMSCKSSQSLLNSGNQK | |
| 2G12-2B2 | Heavy chain | QVOLQQSDXELVKPGASVKISCKASGYTFTDHAIH WVKQKPEQGLEWIGYFSPGNDDIKYNEKFRGKATL TADKSSSTAYMQLNSLSSDDSAVYFCKRSLSTPYW GQGTLXTVSA | 37 |
| 2G12-2B2 | Light chain | DIVMTQSPSSLTVTAGEKVTMSCKSSQSLLNRGNH KNYLTWYRQKPGLPPKLLIYWASTRESGVPDRFTG SGSGTDFALTISSVQAEDLAVYYCQNDYTYPYTFG GGTKLEIKR | 38 |
| 5E6-2E7 | 1 leavy chain | QVQLQQSDAELVKPGASMKISCKASGYTFTDHAIH WVKQKPEQGLEWIGYISPGNGDIKYNEKFKVKATL TADKSSSTAYMQLNSLTSEDSAVYFCKRSITTPYWG QGTLVTVSA | 39 |
| 5E6-2E7 | Light chain | DIVMTQSPSSLTVTAGEKVTMSCKSSQSLLNSGKTK NYLTWYQQKPGQPPKLLIYWASTRESGVPDRFTGS GSGTDFTLTISSVQAEDLAVYYCKNDYSYPYTFGG GTKLEIKR | 40 |
| 9E5-1A8 | Heavy chain | OVOLQOSDAELVKPGASVKISCKTSGYTFTDHAIH WVKQKPEQGLEWIGYlSPGNODiKYTEKFKGKVTL TADKSSSTAYMQLNSLTSEDSAVYFCKRSITTPYWG QGTLVTVSA | 41 |
| 9E5-1A8 | Light chain | Unknown | |
| 9F1I-1F7 | Heavy chain | QVQLQQSDAELVKPGASMKISCKASGYTFTDHAIH WVKQKPEQGLEWIGYISPGNGDIKYNEKFKVKATL TADKSSSTAYMQLNSLTSEDSAVYFCKRSITTPYWG QGTLVTVSA | 39 |
| 9F11-1F7 | Light chain | DIVVITQSPSSLTVTAGEKVTMSCKSSQSLLNSGKTK NYLTWYQQKPGQPPKLLIYWASTRESGVPDRFTGS GSGTDFTLTISSVQAEDLAVYYCKNDYSYPYTFGG GTKLEIKR | 40 |
| 10F4-2F2 | Heavy chain | QVQLQQSDAELVKPGASVKISCKASGYTFTDHAIH WVKQKPEQGLEWIGYISPGNGDIKYDEKFKGKATL TADKSSSTAYMQLNSLTSEDSAVYFCKRSITTSYWG QGTLVTVSA | 42 |
| 10F4-2F2 | Light chain | NIVMTQSPKSMSMSVGERVTLTCKASENVVTYVSW YQQKPEQSPKLLIYGASNRYTGVPDRFTGSGSATDF TLTIS S VQ AEDL AD YHCGQG Y S YP YTFGG GTKLEIK R | 32 |
| 2B8-2F10 | Heavy chain | QVQLQQSDAELVKPGASVKISCKASGYTFTDHAIH WVKQKPEQGLEWIGYISPGNDDIKYNEKFKGKATL TADKSSSTAYMQLNSLTSEDSAVFFCKRSITTSYWG QGTLVTVSA | 43 |
| 2B8-2FI0 | Light chain | Unknown | |
| 4G8-1E3 | Heavy chain | QVQLQQSDAELVKPGASVKISCKASGYIFTDHAIHW VKQKPEQGLEWIGYISPGNGDIKYNEKFKGKATLT ADKSSSTAYMHLNSLTSEDSAVYFCKRSITTSYWG ()(IH\I\S\ | 44 |
| \4G8-IE3 | Light chain | DIOMNQSPSSI SASI.GDITI 1 1(11 \SQI IIM AVI S\\ YQ QKPGNIPKLLIYKASNLHTGVPSRFSGSGSGTGFTLT ISSLLPEDVATYYCQQDQSYPYMFGGGTKLEIKR | 45 |
| 6B11-2E3 | Ileavy chain | QVQLQQSDAELVKPGASVKISCKASGYTFTDHAIH WVKQKPEQGLEWIGYISPGNDDIKYNEKFKGKATL TADKSSSTAYMLLNSLTSEDSAVYFCKRSITTSYWG QGTLVTVSA | 46 |
| 6BU-2E3 | Light chain | NIVYITQSPKSMSMSVGERVTI 1 ( K ASIA\ VTYVStt YQQKPEQSPKLLIYGASNRYTGVPDRFTGSGSATDF TLTISSVQAEDLADYHCGQGYSYPYTFGGGTKLEIK R | |
| 8C2-2D6 | 1 leavy chain | QVQLQQSDAELVKPGASVKISCKASGYTFTDHAIH WVKOKPi:OGI.i:\VIGYISPGNGDIKYNFKFKGKATL TADTSSTTAYMQLNSLTSEDSAMYFCKRSITTSYW GQGTLVTVSA | 47 |
| 8C2-2D6 | Light chain | NIVMTQSPKSMSMSVGERVTLTCKASENVVTYVSW YQQKPEQSPKLLIYGASNRYTGVPDRFTGSGSATDF TLTISSVQAEDLADYHCGQGYSYPYTFGGGTKLEIK R | 32 |
| 7D4-2A2-2F2 | Heavy chain | QVQLQQSDAELVKPGASVKISCKASGYIFTDHAIHW VKQKPEQGLEWIGYISPGNGDIKYIEKFRGKATLTA DKSSSTAYMQLNSLTSEDSAVYFCKRSLSTPYWGQ GTLVTVSA | 48 |

TABLE 2 -continued

| Variable domain sequences | | | |
|---|---|---|---|
| Antibody ID Number | Variable domain | Sequence | SEQ ID NO |
| 7D4-2A2-2F2 | Light chain | \ii.mtospks\ismsvgi-:rvtltckasenvvnyvsw yqqkpeqspkllifgasnrysgvpdrftgsgsatdf tltissvqaedladyhcgskwitsypytfgggtkle IKR | •1*1 |
| 7D4-1H12-2B3 | 1 leavy chain | QVQLQQSDAELVKPGASVKISCKASGYIFTDHAIHW VKQKPEQGLEWIGYISPGNGDIKYIEKFRGKATLTA DKSSSTAYMQLNSLTSEDSAVYFCKRSLSTPYWGQ GTLVTVSA | 48 |
| 7D4-1H12-2B3 | Light chain | NILMTQSPKSMSMSVGERVTLTCKASENVVNYVSW YQQKPEQSPKLLIYGASNRYSGVPDRFTGSGSATDF TLTISSVQAEDLADYHCGARVTSYPYTFGGGTKLEI KR | 50 |
| 2C2-2C5 | Heavy-chain | QVOLQOSDAELVKPGTSVKISCRASGYTFTDHAIH WVKQKPEQGLEWIGYISPGNGDIKYNEKFKGKATL TADKSSSTAYMQLNSLTSDDSAVYFCKRSITTPYW GQGTTLTVSS | 51 |
| 2C2-2C5 | Light chain | SFVMTQTPKFLLVSAGDRVTITCKASQSVNNNVAW YQQKPGQSPKQLIYYASNRYTGVPDRFTGSGYGTD FTFTIYTVQAEDLAVYFCQQGYSSPWTFGGGTKLK | 52 |
| Heavy 10F4-2A9 chain QGTLVTVSA | | QVQLQQSDAELVKPGASVKISCKASGYTFTDHAIH WVKQKPEQGLEWIGYISPGNGDIKYDEKFKGKATL TADKSSSTAYMQLNSLTSEDSAVYFCKRSITTSYWG | 42 |
| 3F1 chain | Heavy | QVQLQQSDAELVKPGASVKISCKASGYTFTDHAIH WVKQKPEQGLDWIGYISPGNGDIKYNEKFKDKVTL TADKSSSTACMHLNSLTSEDSAVYFCKRSLLALDY WGQGTTLTVSS | 53 |
| 3F1 chain | Light | DIVMTQSHKFMSTSVGDRVSITCKASQDVGTNIAW YQQKPGRSPKVLIYSASTRHTGVPDRFTGSGSGTDF TLTISNVQSEDLTDYFCQQYSSFPLTFGVGTKLELK | 54 |

In some embodiments, antibodies of the invention may be developed using one or more CDRs derived from any of the variable domain sequences presented in the previous Table. In some cases, CDR sequences are determined from a variable domain sequence through the use of one or more numbering schemes including, but not limited to, those taught by Kabat [Wu, T. T. et al., 1970, JEM, 132(2):211-50 and Johnson, G. et al., 2000, Nucleic Acids Res. 28(1):214-8, the contents of each of which are herein incorporated by reference in their entirety], Chothia [Chothia and Lesk, J. Mol. Biol. 196, 901 (1987), Chothia et al., Nature 342, 877 (1989) and Al-Lazikani, B. et al., 1997, J. Mol. Biol. 273(4):927-48, the contents of each of which are herein incorporated by reference in their entirety], Lefranc (Lefranc, M. P. et al., 2005, Immunome Res. 1:3) and Honegger (Honegger, A. and Pluckthun, A. 2001. J. Mol. Biol. 309(3):657-70, the contents of which are herein incorporated by reference in their entirety).

In some cases, antibodies or antigen binding fragments thereof of the invention may comprise one or more of the CDR amino acid sequences listed in Table 3. Residues indicated with an "X" may be absent or selected from any amino acid residues. In some cases, antibodies or antigen binding fragments thereof may comprise an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed in Table 3. In some cases, antibodies or antigen binding fragments thereof of the invention may comprise an amino acid sequence comprising one or more fragments of any of the sequences listed in Table 3. In the Table, "consensus" refers to an antibody sequence derived from alignment of multiple sequences wherein the most conserved residues were used to form the consensus sequence. B72.3 (Thermo Fisher Scientific, Waltham, Mass.) and CC49 (see Muraro, R. et al., 1988. Cancer Res. 48: 4588-96) are commercially available antibodies.

TABLE 3

| CDR sequences | | | |
|---|---|---|---|
| Antibody ID Number | CDR | Sequence | SEQ ID NO |
| 18D2 | CDR-H1 | GFSLSTSNMG | 55 |
| 18C7 | CDR-H1 | GFSLSTFGMG | 56 |
| 10A5-2A12 | CDR-H1 | GFSLTSYG | 57 |
| 8C11-1D10 | CDR-H1 | GFSLTSYG | 57 |
| 2D4-1B4 | CDR-H1 | GFSLISYG | 58 |
| 7G9-1A8 | CDR-H1 | GFSLTSYG | 57 |
| 1A12-2B2 | CDR-H1 | GFSLTSYG | 57 |
| 18D2 | CDR-H2 | IWWHDDK | 59 |
| 18C7 | CDR-H2 | IWWDDDK | 60 |
| 10A5-2A12 | CDR-H2 | IWGDGST | 61 |

TABLE 3-continued

CDR sequences

| Antibody ID Number | CDR | Sequence | SEQ ID NO |
|---|---|---|---|
| 8C11-1D10 | CDR-H2 | IWGDGST | 61 |
| 2D4-1B4 | CDR-H2 | IWGDGST | 61 |
| 7G9-1A8 | CDR-H2 | IWGDGST | 61 |
| 1A12-2B2 | CDR-H2 | IWGDGST | 61 |
| 18D2 | CDR-H3 | AQVPFYYGTSFDV | 62 |
| 18C7 | CDR-H3 | ARIAYYYGSERDY | 63 |
| 10A5-2A12 | CDR-H3 | ARAFVY | 64 |
| 8C11-1D10 | CDR-H3 | TKGFTY | 65 |
| 2D4-1B4 | CDR-H3 | TKGFAY | 66 |
| 7G9-1A8 | CDR-H3 | TKGFVY | 67 |
| 1A12-2B2 | CDR-H3 | AKGGYFDY | 68 |
| 18C7 | CDR-L1 | SSISY | 69 |
| 10A5-2A12 | CDR-L1 | SSVSY | 70 |
| 8C11-1D10 | CDR-L1 | SSVSY | 70 |
| 2D4-1B4 | CDR-L1 | SSVSY | 70 |
| 7G9-1A8 | CDR-L1 | SSVSY | 70 |
| 1A12-2B2 | CDR-L1 | SSVSY | 70 |
| 18D2 | CDR-L1 | QSISDY | 71 |
| 18D2 | CDR-L1 | SSITY | 72 |
| 18C7 | CDR-L2 | DTS | 73 |
| 10A5-2A12 | CDR-L2 | DTS | 73 |
| 8C11-1D10 | CDR-L2 | DTS | 73 |
| 2D4-1B4 | CDR-L2 | DTS | 73 |
| 7G9-1A8 | CDR-L2 | DTS | 73 |
| 1A12-2B2 | CDR-L2 | STS | 74 |
| 18D2 | CDR-L2 | YAS | 75 |
| 18D2 | CDR-L2 | DTS | 73 |
| 18C7 | CDR-L3 | HQRSSYT | 76 |
| 10A5-2A12 | CDR-L3 | QQWSSNPPMLT | 77 |
| 8C11-1D10 | CDR-L3 | QQWSSNLLT | 78 |
| 2D4-1B4 | CDR-L3 | QQWSSNLLT | 78 |
| 7G9-1A8 | CDR-L3 | QQWSSNLLT | 78 |
| 1A12-2B2 | CDR-L3 | QQRSSYPWT | 79 |
| 18D2 | CDR-L3 | QNGHSFPLT | 80 |
| 18D2 | CDR-L3 | HQRSSYT | 76 |
| 7A6-2A2 | CDR-H1 | GYTFTDHAIHWV | 81 |
| 2B2-2A7 | CDR-H1 | GYTFTDHAIHWV | 81 |

TABLE 3-continued

CDR sequences

| Antibody ID Number | CDR | Sequence | SEQ ID NO |
|---|---|---|---|
| 5G2-1B3 | CDR-H1 | GYTFTDHAIHWV | 81 |
| 4D9-2C11 | CDR-H1 | GYTFTDHAIHWV | 81 |
| 2F4-1E2 | CDR-H1 | GYTFTDHAIHWV | 81 |
| 2F4-1H8 | CDR-H1 | GYTFTDHAIHWV | 81 |
| 1A5-2C9 | CDR-H1 | GYTFTDHAIHWV | 81 |
| 1F6-1B7 (also sequence of 1F6-1C10) | CDR-H1 | GYTFTDHAIHWV | 81 |
| 2C2-2C5 | CDR-H1 | GYTFTDHAIHWV | 81 |
| 2G12-2B2 | CDR-H1 | GYTFTDHAIHWV | 81 |
| 10C9-2G7 | CDR-H1 | GYTFTDHAIHWV | 81 |
| 2C6-2F11 | CDR-H1 | GYTFSDHAIHWV | 82 |
| 7D4-2A2-2F2 | CDR-H1 | GYIFTDHAIHWV | 83 |
| 7D4-1H12-2B3 | CDR-H1 | GYIFTDHAIHWV | 83 |
| 7D3-2C10 | CDR-H1 | GYTFTDHAIHWV | 81 |
| 8C2-2D6 | CDR-H1 | GYTFTDHAIHWV | 81 |
| 9E5-1A8 | CDR-H1 | GYTFTDHAIHWV | 81 |
| 5E6-2E7 | CDR-H1 | GYTFTDHAIHWV | 81 |
| 9F11-1F7 | CDR-H1 | GYTFTDHAIHWV | 81 |
| 4G8-1E3 | CDR-H1 | GYIFTDHAIHWV | 83 |
| 10F4-2F2 | CDR-H1 | GYTFTDHAIHWV | 81 |
| 10F4-2A9 | CDR-H1 | GYTFTDHAIHWV | 81 |
| 6B11-2E3 | CDR-H1 | GYTFTDHAIHWV | 81 |
| 2B8-2F10 | CDR-H1 | GYTFTDHAIHWV | 81 |
| 7A5-2G12 | CDR-H1 | GYTFTDHAIHWV | 81 |
| 7A6-2A2 | CDR-H2 | FSPGNDDIKY | 84 |
| 2B2-2A7 | CDR-H2 | ISPGNGDIKY | 85 |
| 5G2-1B3 | CDR-H2 | FSPGNDDIKY | 84 |
| 4D9-2C11 | CDR-H2 | LSPGNDDIKY | 86 |
| 2F4-1E2 | CDR-H2 | ISPGNGDIKY | 85 |
| 2F4-1H8 | CDR-H2 | ISPGNGDIKY | 85 |
| 1A5-2C9 | CDR-H2 | VSPGNGDIKY | 87 |
| 1F6-1B7 (also sequence of 1F6-1C10) | CDR-H2 | ISPGNGDVKY | 88 |
| 2C2-2C5 | CDR-H2 | ISPGNGDIKY | 85 |
| 2G12-2B2 | CDR-H2 | FSPGNDDIKY | 84 |
| 10C9-2G7 | CDR-H2 | ISPGNDDIKY | 89 |
| 2C6-2F11 | CDR-H2 | ISPGNDDIKY | 89 |

TABLE 3-continued

CDR sequences

| Antibody ID Number | CDR | Sequence | SEQ ID NO |
|---|---|---|---|
| 7D4-2A2-2F2 | CDR-H2 | ISPGNGDIKY | 85 |
| 7D4-1H12-2B3 | CDR-H2 | ISPGNGDIKY | 85 |
| 7D3-2C10 | CDR-H2 | FSPGNDDIKY | 84 |
| 8C2-2D6 | CDR-H2 | ISPGNGDIKY | 85 |
| 9E5-1A8 | CDR-H2 | ISPGNDDIKY | 89 |
| 5E6-2E7 | CDR-H2 | ISPGNGDIKY | 85 |
| 9F11-1F7 | CDR-H2 | ISPGNGDIKY | 85 |
| 4G8-1E3 | CDR-H2 | ISPGNGDIKY | 85 |
| 10F4-2F2 | CDR-H2 | ISPGNGDIKY | 85 |
| 10F4-2A9 | CDR-H2 | ISPGNGDIKY | 85 |
| 6B11-2E3 | CDR-H2 | ISPGNDDIKY | 89 |
| 2B8-2F10 | CDR-H2 | ISPGNDDIKY | 89 |
| 7A5-2G12 | CDR-H2 | ISPGNDDIKY | 89 |
| 7A6-2A2 | CDR-H3 | SVGYALDY | 90 |
| 2B2-2A7 | CDR-H3 | KISYYGI | 91 |
| 5G2-1B3 | CDR-H3 | KRSYYGD | 92 |
| 4D9-2C11 | CDR-H3 | KRSIGGDH | 93 |
| 2F4-1E2 | CDR-H3 | QRQLGQGY | 94 |
| 2F4-1H8 | CDR-H3 | QRQLGQGY | 94 |
| 1A5-2C9 | CDR-H3 | KRSLIGDY | 95 |
| 1F6-1B7 (also sequence of 1F6-1C10) | CDR-H3 | KRSLSTPY | 96 |
| 2C2-2C5 | CDR-H3 | KRSITTPY | 97 |
| 2G12-2B2 | CDR-H3 | KRSLSTPY | 96 |
| 10C9-2G7 | CDR-H3 | KRSLSTPY | 96 |
| 2C6-2F11 | CDR-H3 | ERSMIGVY | 98 |
| 7D4-2A2-2F2 | CDR-H3 | KRSLSTPY | 96 |
| 7D4-1H12-2B3 | CDR-H3 | KRSLSTPY | 96 |
| 7D3-2C10 | CDR-H3 | KRSITTPY | 97 |
| 8C2-2D6 | CDR-H3 | KRSITTSY | 99 |
| 9E5-1A8 | CDR-H3 | KRSITTPY | 97 |
| 5E6-2E7 | CDR-H3 | KRSITTPY | 97 |
| 9F11-1F7 | CDR-H3 | KRSITTPY | 97 |
| 4G8-1E3 | CDR-H3 | KRSITTSY | 99 |
| 10F4-2F2 | CDR-H3 | KRSITTSY | 99 |
| 10F4-2A9 | CDR-H3 | KRSITTSY | 99 |
| 6B11-2E3 | CDR-H3 | KRSITTSY | 99 |

TABLE 3-continued

CDR sequences

| Antibody ID Number | CDR | Sequence | SEQ ID NO |
|---|---|---|---|
| 2B8-2F10 | CDR-H3 | KRSITTSY | 99 |
| 7A5-2G12 | CDR-H3 | KRSITTSY | 99 |
| 7A6-2A2 | CDR-L1 | ENVVTY | 100 |
| 2B2-2A7 | CDR-L1 | EDIYSN | 101 |
| 5G2-1B3 | CDR-L1 | ENIYSH | 102 |
| 4D9-2C11 | CDR-L1 | QNINVW | 103 |
| 2F4-1E2 | CDR-L1 | QSLVHSYGNTY | 104 |
| 2F4-1H8 | CDR-L1 | QSLVHSYGNTY | 104 |
| 1A5-2C9 | CDR-L1 | QNVGTA | 105 |
| 1F6-1B7 (also sequence of 1F6-1C10) | CDR-L1 | QSLLNSGNQKSY | 106 |
| 2C2-2C5 | CDR-L1 | QSVNNN | 107 |
| 2G12-2B2 | CDR-L1 | QSLLNRGNHKNY | 108 |
| 2C6-2F11 | CDR-L1 | QSLVQSNGNTY | 109 |
| 7D4-2A2-2F2 | CDR-L1 | ENVVNY | 110 |
| 7D4-1H12-2B3 | CDR-L1 | ENVVNY | 110 |
| 7D3-2C10 | CDR-L1 | QNINVW | 103 |
| 8C2-2D6 | CDR-L1 | ENVVTY | 100 |
| 5E6-2E7 | CDR-L1 | QSLLNSGKTKNY | 111 |
| 9F11-1F7 | CDR-L1 | QSLLNSGKTKNY | 111 |
| 4G8-1E3 | CDR-L1 | QHINFW | 112 |
| 10F4-2F2 | CDR-L1 | ENVVTY | 100 |
| 10F4-2A9 | CDR-L1 | ENVVTY | 100 |
| 6B11-2E3 | CDR-L1 | ENVVTY | 100 |
| 7A5-2G12 | CDR-L1 | ENVVIY | 113 |
| 1C11-2G9 | CDR-L1 | QSLLNSGNQKNY | 114 |
| 7A6-2A2 | CDR-L2 | GASNRYT | 115 |
| 2B2-2A7 | CDR-L2 | KATNLAD | 116 |
| 5G2-1B3 | CDR-L2 | GATNLAD | 117 |
| 4D9-2C11 | CDR-L2 | KASNLHT | 118 |
| 2F4-1E2 | CDR-L2 | KVSNRFS | 119 |
| 2F4-1H8 | CDR-L2 | KVSNRFS | 119 |
| 1A5-2C9 | CDR-L2 | SASNRYT | 120 |
| 1F6-1B7 (also sequence of 1F6-1C10) | CDR-L2 | WASTRDS | 121 |
| 2C2-2C5 | CDR-L2 | YASNRYT | 122 |
| 2G12-2B2 | CDR-L2 | WASTRES | 123 |

TABLE 3-continued

CDR sequences

| Antibody ID Number | CDR | Sequence | SEQ ID NO |
|---|---|---|---|
| 2C6-2F11 | CDR-L2 | KVSNRFC | 124 |
| 7D4-2A2-2F2 | CDR-L2 | GASNRYS | 125 |
| 7D4-1H12-2B3 | CDR-L2 | GASNRYS | 125 |
| 7D3-2C10 | CDR-L2 | KVSNLHT | 126 |
| 8C2-2D6 | CDR-L2 | GASNRYT | 115 |
| 5E6-2E7 | CDR-L2 | WASTRES | 123 |
| 9F11-1F7 | CDR-L2 | WASTRES | 123 |
| 4G8-1E3 | CDR-L2 | KASNLHT | 118 |
| 10F4-2F2 | CDR-L2 | GASNRYT | 115 |
| 10F4-2A9 | CDR-L2 | GASNRYT | 115 |
| 6B11-2E3 | CDR-L2 | GASNRYT | 115 |
| 7A5-2G12 | CDR-L2 | GASNRYT | 115 |
| 1C11-2G9 | CDR-L2 | WASTRES | 123 |
| 7A6-2A2 | CDR-L3 | GQGYSYPYT | 127 |
| 2B2-2A7 | CDR-L3 | QHFWGTPFT | 128 |
| 5G2-1B3 | CDR-L3 | QHFWGAPFT | 129 |
| 4D9-2C11 | CDR-L3 | QQGQSYPFT | 130 |
| 2F4-1E2 | CDR-L3 | SQNTHVPYT | 131 |
| 2F4-1H8 | CDR-L3 | SQNTHVPYT | 131 |
| 1A5-2C9 | CDR-L3 | QQYSSYRLT | 132 |
| 1F6-1B7 (also sequence of 1F6-1C10) | CDR-L3 | QSDYSYPYT | 133 |
| 2C2-2C5 | CDR-L3 | QQGYSSPWT | 134 |
| 2G12-2B2 | CDR-L3 | QNDYTYPYT | 135 |
| 2C6-2F11 | CDR-L3 | SQSTHAPLT | 136 |
| 7D4-2A2-2F2 | CDR-L3 | GSKWITSYPYT | 137 |
| 7D4-1H12-2B3 | CDR-L3 | GARVTSYPYT | 138 |
| 7D3-2C10 | CDR-L3 | QQDQSYPYT | 139 |
| 8C2-2D6 | CDR-L3 | GQGYSYPYT | 127 |
| 5E6-2E7 | CDR-L3 | KNDYSYPYT | 140 |
| 9F11-1F7 | CDR-L3 | KNDYSYPYT | 140 |
| 4G8-1E3 | CDR-L3 | QQDQSYPYM | 141 |
| 10F4-2F2 | CDR-L3 | GQGYSYPYT | 127 |
| 10F4-2A9 | CDR-L3 | GQGYSYPYT | 127 |
| 6B11-2E3 | CDR-L3 | GQGYSYPYT | 127 |
| 7A5-2G12 | CDR-L3 | GQGYSYPYT | 127 |
| 1C11-2G9 | CDR-L3 | QNDYSYPYT | 142 |

TABLE 3-continued

CDR sequences

| Antibody ID Number | CDR | Sequence | SEQ ID NO |
|---|---|---|---|
| 8C2-2D6 | CDR-H1 | GYTFTDHAIH | 143 |
| 4G8-1E3 | CDR-H1 | GYIFTDHAIH | 144 |
| 2G12-2B2 | CDR-H1 | GYTFTDHAIH | 143 |
| 5G2-1B3 | CDR-H1 | GYTFTDHAIH | 143 |
| 5E6-2E7 | CDR-H1 | GYTFTDHAIH | 143 |
| 2C2-2C5 | CDR-H1 | GYTFTDHAIH | 143 |
| 3F1 | CDR-H1 | GYTFTDHAIH | 143 |
| CC49 | CDR-H1 | GYTFTDHAIH | 143 |
| B72.3 | CDR-H1 | GYTFTDHAIH | 143 |
| Consensus | CDR-H1 | GYTFTDHAIH | 143 |
| 8C2-2D6 | CDR-H2 | YISPGNGDIKYNEKFKG | 145 |
| 4G8-1E3 | CDR-H2 | YISPGNGDIKYNEKFKG | 145 |
| 2G12-2B2 | CDR-H2 | YFSPGNDDIKYNEKFRG | 146 |
| 5G2-1B3 | CDR-H2 | YFSPGNDDIKYNEKFKV | 147 |
| 5E6-2E7 | CDR-H2 | YISPGNGDIKYNEKFKV | 148 |
| 2C2-2C5 | CDR-H2 | YISPGNGDIKYNEKFKG | 145 |
| 3F1 | CDR-H2 | YISPGNGDIKYNEKFKD | 149 |
| CC49 | CDR-H2 | YFSPGNDDFKYNEKFKG | 150 |
| B72.3 | CDR-H2 | YISPGNDDIKYNEKFKG | 151 |
| Consensus | CDR-H2 | YISPGNGDIKYNEKFKG | 145 |
| 8C2-2D6 | CDR-H3 | SITTSY | 152 |
| 4G8-1E3 | CDR-H3 | SITTSY | 152 |
| 2G12-2B2 | CDR-H3 | SLSTPY | 153 |
| 5G2-1B3 | CDR-H3 | SYYGD | 154 |
| 5E6-2E7 | CDR-H3 | SITTPY | 155 |
| 2C2-2C5 | CDR-H3 | SITTPY | 155 |
| 3F1 | CDR-H3 | SLLALDY | 156 |
| CC49 | CDR-H3 | SLNMAY | 157 |
| B72.3 | CDR-H3 | SYYGH | 158 |
| Consensus | CDR-H3 | SITTSY | 152 |
| 8C2-2D6 | CDR-L1 | KASENVVTYVS | 159 |
| 4G8-1E3 | CDR-L1 | HASQHINFWLS | 160 |
| 2G12-2B2 | CDR-L1 | KSSQSLLNRGNHKNYLT | 161 |
| 5G2-1B3 | CDR-L1 | RASENIYSHLA | 162 |
| 5E6-2E7 | CDR-L1 | KSSQSLLNSGKTKNYLT | 163 |
| 2C2-2C5 | CDR-L1 | KASQSVNNNVA | 164 |
| 3F1 | CDR-L1 | KASQDVGTNIA | 165 |

TABLE 3-continued

| CDR sequences | | | |
|---|---|---|---|
| Antibody ID Number | CDR | Sequence | SEQ ID NO |
| CC49 | CDR-L1 | KSSQSLLYSGNQKNYLA | 166 |
| B72.3 | CDR-L1 | RASENIYSNLA | 167 |
| 8C2-2D6 | CDR-L2 | GASNRYT | 115 |
| 4G8-1E3 | CDR-L2 | KASNLHT | 118 |
| 2G12-2B2 | CDR-L2 | WASTRES | 123 |
| 5G2-1B3 | CDR-L2 | GATNLAD | 117 |
| 5E6-2E7 | CDR-L2 | WASTRES | 123 |
| 2C2-2C5 | CDR-L2 | YASNRYT | 122 |
| 3F1 | CDR-L2 | SASTRHT | 168 |
| CC49 | CDR-L2 | WASARES | 169 |
| B72.3 | CDR-L2 | AATNLAD | 170 |
| 8C2-2D6 | CDR-L3 | GQGYSYPYT | 127 |
| 4G8-1E3 | CDR-L3 | QQDQSYPYM | 141 |
| 2G12-2B2 | CDR-L3 | QNDYTYPYT | 135 |
| 5G2-1B3 | CDR-L3 | QHFWGAPFT | 129 |
| 5E6-2E7 | CDR-L3 | KNDYSYPYT | 140 |

TABLE 3-continued

| CDR sequences | | | |
|---|---|---|---|
| Antibody ID Number | CDR | Sequence | SEQ ID NO |
| 2C2-2C5 | CDR-L3 | QQGYSSPWT | 134 |
| 3F1 | CDR-L3 | QQYSSFPLT | 171 |
| CC49 | CDR-L3 | QQYYSYPLT | 172 |
| B72.3 | CDR-L3 | QHFWGTPYT | 173 |

In some cases, antibodies or antigen binding fragments of the invention may be encoded by a nucleotide sequence comprising one or more of the variable domain sequences listed in Table 4. Residues labeled "N" may be absent or selected from nucleotides A, C, G or T. In some cases, antibodies or antigen binding fragments thereof may be encoded by a nucleotide sequence comprising a sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, f$_{rom\ a}$bout 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the variable domain sequences listed in Table 4. In some cases, antibodies or antigen binding fragments thereof of the invention may be encoded by a nucleotide sequence comprising one or more fragments of any of the sequences listed in Table 4.

TABLE 4

| Variable domain nucleotide sequences | | | |
|---|---|---|---|
| Antibody ID Number | Variable chain | Sequence | SEQ ID NO |
| 18D2 | Heavy chain | CAGGTTACTCTGAAAGAGTCTGGCCCTGGGATA<br>TTGCAGCCCTCCCAGACCCTCAGTCTGACTTGTT<br>CTTTCTCTGGGTTTTCACTGAGCACTTCTAATAT<br>GGGTATAGGCTGGATTCGTCAGCCTTCAGGGAA<br>GGGTCTAGAGTGGCTGGCACACATTTGGTGGCA<br>TGATGATAAGTACTATAACCCATCCCTGAAGAG<br>CCGGCTCACAATCTCCAAGGATATCTCCAACAA<br>CCAGGTATTCCTCAAGATCACCAGTGTGGACAC<br>TGCAGATACTGCCACGTACTACTGTGCTCAAGTC<br>CCGTTTTACTACGGAACCTCGTTCGATGTCTGGG<br>GCACAGGGACCACGGTCACCGTCTCCTCA | 174 |
| 18D2 | Light chain 1 | GACATTGTGATGACTCAGTCTCCAGCCACCCTGT<br>CTGTGACTCCAGGAGATAGAGTCTCTCTTTCCTG<br>CAGGGCCAGCCAGAGTATTAGCGACTACTTACA<br>CTGGTATCAACAAAAATCACATGAGTCTCCAAG<br>GCTTCTCATCAAATATGCTTCCCAATCCATCTCT<br>GGGATCCCCTCCAGGTTCAGTGGCAGTGGATCA<br>GGGTCAGATTTCACTCTCAGTATCAACAGTGTG<br>GAACCTGAAGATGTTGGAGTGTATTACTGTCAA<br>AATGGTCACAGCTTTCCTCTCACGTTCGGTGCTG<br>GGACCAAGCTGGAGCTGAAAC | 175 |
| 18D2 | Light chain 2 | CAAATTGTTCTCACCCAGTCTCCAGCAATCATGT<br>CTGCATCTCCAGGGGAGACGGTCACCATGACCT<br>GCAGTGCCAGCTCAAGTATAACTTACATGCACT<br>GGTACCAGCAGAAGCCAGGCACCTCCCCCAAAA<br>GATGGATTTATGACACATCCAAACTGGCTTCTG<br>GAGTCCCTGCTCGCTTCAGTGGCAGTGGGTCTG<br>GGACCTCTTATTCTCTCACAATCAGCAGCATGGA | 176 |

TABLE 4 -continued

Variable domain nucleotide sequences

| Antibody ID Number | Variable chain | Sequence | SEQ ID NO |
|---|---|---|---|
| | | GGCTGAAGATGCTGCCACTTATTACTGCCATCA<br>GCGGAGTAGTTACACGTTCGGAGGGGGGACCAA<br>GCTGGAAATAAAACG | |
| 18C7 | Heavy chain | CAGGTTACTCTGAAAGAGTCTGGCCCTGGGATA<br>TTGCAGCCCTCCCAGACCCTCAGTCTGACTTGTT<br>CTTTCTCTGGGTTTTCACTGAGCACTTTTGGTAT<br>GGGTGTAGGCTGGATTCGTCAGCCTTCAGGGAA<br>GGGTCTGGAGTGGCTGGCACACATTTGGTGGGA<br>TGATGATAAGTACTATAACCCAGCCCTGAAGAG<br>TCGGCTCACAATCTCCAAGGATACCTCCAAAAA<br>CCAGGTATTCCTCAAGATCGCCAATGTGGACAC<br>TGCAGATACTGCCACATACTACTGTGCTCGAAT<br>AGCCTATTACTACGGTAGCGAGAGGGACTACTG<br>GGGCCAAGGCACCACTCTCACAGTCTCCTCA | 177 |
| 18C7 | Light chain | CAAATTGTTCTCACCCAGTCTCCAGCAATCATGT<br>CTGCATCTCCAGGGGAGAAGGTCACCATGACCT<br>GCAGTGCCAGCTCAAGTATAAGTTACATGCACT<br>GGTACCACCAGAAGCCAGGCACCTCCCCCAAAA<br>GATGGATTTATGACACATCCAAACTGGCTTCTG<br>GAGTCCCTGCTCGCTTCAGTGGCAGTGGGTCTG<br>GGACCTCTTATTCTCTCACAATCAGCAGCATGGA<br>GGCTGAAGATGCTGCCACTTATTACTGCCATCA<br>GCGGAGTAGTTACACGTTCGGAGGGGGGACCAA<br>GCTGGAAATAAAACG | 178 |
| 18D2(2) | Heavy chain | ATGGACAGGCTTACTTCCTCATTCTTGCTACTGA<br>TTGTCCCTGCATATGTCCTGTCCCAGGTTACTCT<br>GAAAGAGTCTGGCCCTGGGATATTGCAGCCCTC<br>CCAGACCCTCAGTCTGACTTGTTCTTTCTCTGGG<br>TTTTCACTGAGCACTTCTAATATGGGTATAGGCT<br>GGATTCGTCAGCCTTCAGGGAAGGGTCTAGAGT<br>GGCTGGCACACATTTGGTGGCATGATGATAAGT<br>ACTATAACCCATCCCTGAAGAGCCGGCTCACAA<br>TCTCCAAGGATATCTCCAACAACCAGGTATTCCT<br>CAAGATCACCAGTGTGGACACTGCAGATACTGC<br>CACGTACTACTGTGCTCAAGTCCCGTTTTACTAC<br>GGAACCTCGTTCGATGTCTGGGGCACAGGGACC<br>ACGGTCACCGTCTCCTCAGCCAAAACGACACCC<br>CCATCTGTCTATCCGCTCGCCCCTGGATCTGCTG<br>CCCAAACTAACTCCATGGTGACCCTGGGATGCC<br>TGGTCAAGGGCTATTTCCCTGAGCCAGTGACAG<br>TGACCTGGAACTCTGGATCCCTGTCCAGCGGTGT<br>GCACACCTTCCCAGCTGTCCTGCAGTCTGACCTC<br>TACACTCTGAGCAGCTCAGTGACTGTCCCCTCCA<br>GCACCTGGCCCAGCGAGACCGTCACCTGCAACG<br>TTGCCCACCCGGCCAGCAGCACCAAGGTGGACA<br>AGACAATTGTGCCCAGGGATTGTGGTTGTAAGC<br>CTTGCATATGTACAGTCCCAGAAGTATCATCTGT<br>CTTCATCTTCCCCCCAAAGCCCAAGGATGTGCTC<br>ACCATTACTCTGACTCCTAAGGTCACGTGTGTTG<br>TGGTAGACATCAGCCAGGATGATCCCGAGGTCA<br>GTTCAGCTGTTTGTAGATGATGTGGAAGTGCAC<br>ACAGCTCAAAACAACCCCCCGAGAGGACATTTC<br>ACAACATTTCCGCTCATCAGTGAATTTCCCATCT<br>GCACAAGACTGCTTAATGGCAAGAGTTAAATGC<br>AGGTCAAAGGGCAGTTTCCTGCCCCATCAAAAA<br>CTTTTCAAAA | 179 |
| 18D2(2) | Light chain | ATGGATTTTCAAGTGCAGATTTTCAGCTTCCTGC<br>TAATCAGTGCCTCAGTCATACTGTCCAGAGGAC<br>AAATTGTTCTCACCCAGTCTCCAGCAATCATGTC<br>TGCATCTCCAGGGGAGACGGTCACCATGACCTG<br>CAGTGCCAGCTCAAGTATAACTTACATGCACTG<br>GTACCAGCAGAAGCCAGGCACCTCCCCCAAAAG<br>ATGGATTTATGACACATCCAAACTGGCTTCTGG<br>AGTCCCTGCTCGCTTCAGTGGCAGTGGGTCTGG<br>GACCTCTTATTCTCTCACAATCAGCAGCATGGAG<br>GCTGAAGATGCTGCCACTTATTACTGCCATCAGC<br>GGAGTAGTTACACGTTCGGAGGGGGGACCAAGC<br>TGGAAATAAAACGGGCTGATGCTGCACCAACTG<br>TATCCATCTTCCCACCATCCAGTGAGCAGTTAAC<br>ATCTGGAGGTGCCTCAGTCGTGTGCTTCTTGAAC | 180 |

TABLE 4 -continued

| Variable domain nucleotide sequences | | | |
|---|---|---|---|
| Antibody ID Number | Variable chain | Sequence | SEQ ID NO |
| | | AACTTCTACCCCAAAGACATCAATGTCAAGTGG<br>AAGATTGATGGCAGTGAACGACAAAATGGCGTC<br>CTGAACAGTTGGACTGATCAGGACAGCAAAGAC<br>AGCACCTACAGCATGAGCAGCACCCTCACGTTG<br>ACCAAGGACGAGTATGAACGACATAACAGCTAT<br>ACCTGTGAGGCCACTCACAAGACATCAACTTCA<br>CCCATTGTCAAGAGCTTCAACAGGAATGAGTGT<br>TAG | |
| 18C7(2) | Heavy chain | ATGGACAGGCTTACTTCCTCATTCCTGTTACTGA<br>TTGTCCCTGCATATGTCCTGTCCCAGGTTACTCT<br>GAAAGAGTCTGGCCCTGGGATATTGCAGCCCTC<br>CCAGACCCTCAGTCTGACTTGTTCTTTCTCTGGG<br>TTTTCACTGAGCACTTTTGGTATGGGTGTAGGCT<br>GGATTCGTCAGCCTTCAGGGAAGGGTCTGGAGT<br>GGCTGGCACACATTTGGTGGGATGATGATAAGT<br>ACTATAACCCAGCCCTGAAGAGTCGGCTCACAA<br>TCTCCAAGGATACCTCCAAAAACCAGGTATTCC<br>TCAAGATCGCCAATGTGGACACTGCAGATACTG<br>CCACATACTACTGTGCTCGAATAGCCTATTACTA<br>CGGTAGCGAGAGGGACTACTGGGGCCAAGGCA<br>CCACTCTCACAGTCTCCTCAGCCAAAACGACAC<br>CCCCATCTGTCTATCCGCTCGCCCCTGGATCTGC<br>TGCCCAAACTAACTCCATGGTGACCCTGGGATG<br>CCTGGTCAAGGGCTATTTCCCTGAGCCAGTGAC<br>AGTGACCTGGAACTCTGGATCCCTGTCCAGCGG<br>TGTGCACACCTTCCCAGCTGTCCTGCAGTCTGAC<br>CTCTACACTCTGAGCAGCTCAGTGACTGTCCCCT<br>CCAGCACCTGGCCCAGCGAGACCGTCACCTGCA<br>ACGTTGCCCACCCGGCCAGCAGCACCAAGGTGG<br>ACAAGAAAATTGTGCCCAGGGATTGTGGTTGTA<br>AGCCTTGCATATGTACAGTCCCAGAAGTATCAT<br>CTGTCTTCATCTTCCCCCCAAAGCCCAAGGATGT<br>GCTCACCATTACTCTGACTCCTAAGGTCACGTGT<br>GTTGTGGTAGACATCAGCAAGGATGATCCCGAG<br>GTCCAGTTCAGCTGGTTTGTAGATGATGTGGAA<br>GTGCACACAGCTCAGACGNCACCCCGGGGAGA<br>GCAGTTTCACAGCACTTTCCGCTCAGTCAGTGAA<br>CTTCCCATCATGCACCANGACTGGGCTCATGGN<br>CAGGAGTTCAANTGCAGGTCACAGTGCAGCTTT<br>CCTGCCCCATCGAGAAACATCTCCNAAACAAGG<br>CGACGAAAGCTCACAGGGTACACATTCCACTCC<br>CNAGAGCAATGCCAGATAAGTCATCTGACTGCT<br>GATACAACTCTTCTGAAAATACTGTGAATGCAT<br>GGATGCCACCACGAAAATCAAACCTCGCCCTTG<br>GACNATGGCTTATTTTACCAGCTAGTCAAAACCT<br>GGGGGGAATTTCCCGTCTGTT | 181 |
| 18C7(2) | Light chain | ATGGTTTTCACACCTCAGATACTTGGACTTATGC<br>TTTTTTGGATTTCAGCCTCCAGATGTGACATTGT<br>GATGACTCAGTCTCCAGCCACCCTGTCTGTGACT<br>CCAGGAGATAGAGTCTCTCTTTCCTGCAGGGCC<br>AGCCAGAGTATTAGCGACTACTTACACTGGTAT<br>CAACAAAAATCACATGAGTCTCCAAGGCTTCTC<br>ATCAAATATGCTTCCCAATCCATCTCTGGGATCC<br>CCTCCAGGTTCAGTGGCAGTGGATCAGGGTCAG<br>ATTTCACTCTCAGTATCAACAGTGTGGAACCTGA<br>AGATGTTGGAGTGTATTACTGTCAAAATGGTCA<br>CAGCTTTCCTCTCACGTTCGGTGCTGGGACCAAG<br>CTGGAAATAAAACGGGCTGATGCTGCACCAACT<br>GTATCCATCTTCCCACCATCCAGTGAGCAGTTAA<br>CATCTGGAGGTGCCTCAGTCGTGTGCTTCTTGAA<br>CAACTTCTACCCCAAAGACATCAATGTCAAGTG<br>GAAGATTGATGGCAGTGAACGACAAAATGGCGT<br>CCTGAACAGTTGGACTGATCAGGACAGCAAAGA<br>CAGCACCTACAGCATGAGCAGCACCCTCACGTT<br>GACCAAGGACGAGTATGAACGACATAACAGCTA<br>TACCTGTGAGGCCACTCACAAGACATCAACTTC<br>ACCCATTGTCAAGAGCTTCAACAGGAATGAGTG<br>TTAG | 182 |

TABLE 4 -continued

Variable domain nucleotide sequences

| Antibody ID Number | Variable chain | Sequence | SEQ ID NO |
|---|---|---|---|
| 10A5-2A12 | Heavy chain | CAGGTGCAGCTGAAGGAGTCAGGACCTGGCCTG GTGGCGCCCTCACAGAGCCTGTCCATCACATGC ACTGTCTCAGGGTTCTCATTAACCAGCTATGGTG TAAGCTGGGTTCGCCAGCCTCCAGGAAAGGGTC TGGAGTGGCTGGGAGTAATATGGGGTGACGGAA GCACAAATTATCATTCATCTCTCATATCCAGACT GAGCATCAGCAAGGATAACTCCAAGAGCCAAGT TTTCTTAAAACTGAACAGTCTGCAAACTGATGA CACAGCCACGTACTACTGTGCCAGAGCCTTTGTT TACTGGGGCCAAGGGACTCTGGTCACTGTCTCT GCA | 183 |
| 10A5-2A12 | Light chain | CAAATTGTTCTCACCCAGTCTCCAGCAATCATGT CTGCATCTCCAGGGGAGAAGGTCACCATGACCT GCAGTGCCAGCTCAAGTGTAAGTTACATACACT GGTACCAGCAGAAGTCAGGCACCTCCCCCAAAA GATGGATTTATGACACATCCAAACTGGCTTCTG GAGTCCCTGCTCGCTTCAGTGGCAGTGGGTCTG GGACCTCTTACTCTCTCACAATCAGCAGCATGG AGGCTGAAGATGCTGCCACTTATTACTGCCAGC AGTGGAGTAGTAACCCACCCATGCTCACGTTCG GTGCTGGGACCAAGCTGGAGCTGAAAC | 184 |
| 8C11-1D10 | Heavy chain | CAGGTGCAGCTGAAGGAGTCAGGACCTGGCCTG GTGGCGCCCTCACAGAGCCTGTCCATCACATGC ACTGTCTCAGGGTTCTCATTAACCAGCTATGGTG TAAGCTGGGTTCGCCAGCCTCCAGGAAAGGGTC TGGAGTGGCTGGGAGTAATATGGGGTGACGGGA GCACAAATTATCATTCAGCTCTCATATCCAGACT GATCATCAGCAAGGATAACTCCAAGAGCCAAGT TTTCTTAAAACTGAACAGTCTGCAAACTGATGA CACAGCCACCTACTACTGTACCAAAGGCTTTAC TTACTGGGGCCAGGGGACTCTGGTCACTGTCTCT GCA | 185 |
| 8C11-1D10 | Light chain | CAAATTGTTCTCACCCAGTCTCCAGCAATCATGT CTGCATCTCCAGGGGAGAAGGTCACCATGACCT GCAGTGCCAGCTCAAGTGTAAGTTACATGCACT GGTACCAGCAGAAGTCAGGCACCTCCCCCAAAA GATGGATTTTTGACACATCCAAACTGGCTTCTGG AGTCCCTGCTCGCTTCAGTGGCAGTGGGTCTGG GACCTCTTACTCTCTCACAATCAGCAGCATGGA GGCTGAAGATGCTGCCACTTATTACTGCCAGCA GTGGAGTAGTAACCTGCTCACGTTCGGTGCTGG GACCAAGCTGGAGCTGAAAC | 186 |
| 2D4-1B4 | Heavy chain | CAGGTGCAGCTGCAGGAGTCAGGACCTGGCCTG GTGGCGCCCTCACAGAGCCTGTCCATCACATGC ACTGTCTCAGGGTTCTCATTAATCAGCTATGGTG TAAACTGGGTTCGCCAGCCTCCAGGAAAGGGTC TGGAGTGGCTGGGAGTGATATGGGGTGACGGGA GCACAAATTATCAGTCAGCTCTCATATCCAGACT GATCATCAGCAAGGATAACTCCAAGAGCCAAGT TTTCTTAAAACTGAACAGTCTGCAAACTGATGA CACAGCCACGTACTACTGTACCAAAGGCTTTGC TTACTGGGGCCAAGGGACTCTGGTCACTGTCTCT GCA | 187 |
| 2D4-1B4 | Light chain | CAAATTGTTCTCACCCAGTCTCCAGCAATCATGT CTGCATCTCCAGGGGAGAAGGTCACCATGACCT GCAGTGCCAGCTCAAGTGTAAGTTACATGCACT GGTTCCAGCAGAAGTCAGGCACCTCCCCCAAAA GATGGATTTATGACACATCCAAACTGGCTTCTG GAGTCCCTGCTCGCTTCAGTGGCAGTGGGTCTG GGACCTCTTACTCTCTCACAATCAGCAGCATGG AGGCTGAAGATGCTGCCACTTATTACTGCCAGC AGTGGAGTAGTAACCTGCTCACGTTCGGTGCTG GGACCAAGCTGGAGCTGAAAC | 188 |
| 7G9-1A8 | Heavy chain | CAGGTGCAGCTGAAGGAGTCAGGACCTGGCCTG GTGGCGCCCTCACAGAACCTGTCCATCACATGC ACTGTCTCAGGGTTCTCATTAACCAGTTATGGTG TAAACTGGGTTCGCCAGCCTCCAGGAAAGGGTC | 189 |

TABLE 4 -continued

Variable domain nucleotide sequences

| Antibody ID Number | Variable chain | Sequence | SEQ ID NO |
|---|---|---|---|
| | | TGGAGTGGCTGGGAGTAATATGGGGTGACGGGA<br>GCACAAATTATCATTCAGCTCTCATTTCCAGACT<br>GATCATCAGCAAGGAAAACTCCAAGAGCCAAGT<br>TTTCTTAAAACTGAACAGTCTGCAAACTAATGA<br>CACAGCCACGTATTACTGTACCAAAGGCTTTGTT<br>TACTGGGGCCAAGGGACTCTGGTCACTGTCTCT<br>GCA | |
| 7G9-1A8 | Light chain | CAAATTGTTCTCACCCAGTCTCCAGCAATCATGT<br>CTGCATCTCCAGGGGAGAAGGTCACCATGACCT<br>GCAGTGCCAGCTCAAGTGTAAGTTACATGCACT<br>GGTACCAGCAGAAGTCAGGCACCTCCCCCAAAA<br>GATGGATTTTTGACACATCCAAACTGGCTTCTGG<br>AGTCCCTGCTCGCTTCAGTGGCAGTGGGTCTGG<br>GACCTCTTACTCTCTCACAATCAGCAGCATGGA<br>GGCTGAAGATGCTGCCACTTATTACTGCCAGCA<br>GTGGAGTAGTAACCTGCTCACGTTCGGTGCTGG<br>GACCAAGCTGGAGCTGAAAC | 186 |
| 1A12-2B2 | Heavy chain | CAGGTGCAGCTGAAGGAGTCAGGACCTGGCCTG<br>GTGGCGCCCTCACAGAGCCTGTCCATCACATGC<br>ACTGTCTCAGGGTTCTCATTAACCAGCTATGGTG<br>TAAGCTGGGTTCGCCAGCCTCCAGGAAAGGGTC<br>TGGAGTGGCTGGGAGTAATATGGGGTGACGGGA<br>GCACAAATTATCATTCAGCTCTCATATCCAGACT<br>GAGCATCAGCAAGGATAACTCCAAGAGCCAAGT<br>TTTCTTAAAACTGAACAGTCTGCAAACTGATGA<br>CACAGCCACGTACTACTGTGCCAAAGGGGGCTA<br>CTTTGACTACTGGGGCCAAGGCACCACTCTCAC<br>AGTCTCCTCA | 190 |
| 1A12-2B2 | Light chain | CAAATTGTTCTCACCCAGTCTCCAGCAGTCATGT<br>CTGCATCTCCAGGGGAGAAGGTCGCCATAACCT<br>GCAGTGCCAGCTCAAGTGTAAGTTACATGCACT<br>GGTTCCAGCAGAAGCCAGGCACTTCTCCCAAAC<br>TCTGGATTTATAGCACATCCAACCTGGCTTCTGG<br>AGTCCCTGCTCGCTTCAGTGGCAGTGGATCTGG<br>GACCTCTTACTCTCTCACAATCAGCCGAATGGA<br>GGCTGAAGATGCTGCCACTTATTACTGCCAGCA<br>AAGGAGTAGTTACCCGTGGACGTTCGGTGGAGG<br>CACCAAGCTGGAAATCAAAC | 191 |
| 7D3-2C10 | Heavy chain | CAGGTTCAGTTGCTGCAGTATGACGCTGAGTTG<br>GTGAAACCTGGGGGGTCAGTGAAGATATCGTGC<br>AAGGCCTCTGGCTACACCTTCACTGACCATGCT<br>ATTCACTGGGTGAAGCAGAAGCCTGAACAGGGC<br>CTGGAATGGATTGGATATTTTTCTCCCGGAAATG<br>ATGATATTAAGTACAGTGAGAAGTTCAAGGGCA<br>AGGCCACACTGACTGCAGACAAGTCCTCCAGCA<br>CTGCCTACATGCAGCTCAACAGCCTGACATCTG<br>AGGATTCTGCAGTGTATTTCTGTAAAAGATCCAT<br>TACTACGCCTTACTGGGGCCAAGGGACTCTGGT<br>CACTGTCTCTGCA | 192 |
| 7D3-2C10 | Light chain | GACATCCAGATGAACCAGTCTCCATCCAGTCTG<br>TCTGCATCCCTTGGAGACACAATTACCATCACTT<br>GCCATGCCAGTCAGAACATTAATGTTTGGTTAA<br>GCTGGTACCAGCAGAAACCAGGAAATATTCCTA<br>AACTATTGATCTATAAGGTTTCCAACTTGCACAC<br>AGGCGTCCCATCAAGGTTTAGTGGCAGTGGATC<br>TGGAACAGGTTTCACATTAACCATCAGCAGCCT<br>GCAGCCTGAAGACATTGCCACTTACTACTGTCA<br>ACAGGATCAAAGTTATCCGTACACGTTCGGAGG<br>GGGGACCAAGCTGAAAAAAA | 193 |
| A5-2G12 | Heavy chain | CAGGTTCAGCTGCAGCAGTCTGACGCTGAGTTG<br>GTGAAACCTGGGGCTTCAGTGAAGATATCCTGC<br>AAGGCCTCTGGCTACACCTTCACTGACCATGCT<br>ATTCACTGGGTGAAGCAGAAGCCTGAACAGGGC<br>CTGGAATGGATTGGATATATTTCTCCCGGAAAT<br>GATGATATTAAGTACAATGAGAAGTTCAAGGGC<br>AAGGCCACACTGACTGCAGACAAATCCTCCAGC | 194 |

TABLE 4 -continued

Variable domain nucleotide sequences

| Antibody ID Number | Variable chain | Sequence | SEQ ID NO |
|---|---|---|---|
| | | ACTGCCTACATGCAGCTCAACAGCCTGACATCT<br>GAGGATTCTGCAGTGTATTTCTGTAAAAGATCC<br>ATTACTACGTCTTACTGGGGCCAAGGGACTCTG<br>GTCACTGTCTCTGCA | |
| A5-2G12 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTATTTATGTTTC<br>CTGGTATCAACAGAAACCAGAGCAGTCTCCTAA<br>ACTGCTGATATACGGGGCATCCAACCGGTACAC<br>TGGGGTCCCCGATCGCTTCACAGGCAGTGGATC<br>TGCAACAGATTTCACTCTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 195 |
| 1A5-2C9 | Heavy chain | CAGGTTCAGTTGCAGCAGTCTGACGCTGAGTTG<br>GTGAAACCTGGGGCTTCAGTGAAGATATCCTGC<br>AAGGCTTCTGGCTACACCTTCACTGACCATGCC<br>ATTCATTGGGTGAAGCAGAAGCCTGAACAGGGC<br>CTGGAATGGATTGGATATGTTTCTCCCGGAAAT<br>GGTGATATTAAGTACAATGAGAAGTTCAAGGGC<br>AAGGCCACACTGACTGCAGACAAATCCTCCAGC<br>ACTGCCTACATGCAGCTCAACAGCCTGACATCG<br>GAGGATTCTGCAGTGTATTTCTGTAAAAGATCTT<br>TAATTGGAGACTATTGGGGCCAAGGCACCACTC<br>TCACAGTCTCCTCA | 196 |
| 1A5-2C9 | Light chain | GACATTGTGATGACCCAGTCTCAAAAATTCATG<br>TCCTCATCAGTAGGAGACAGGGTCACCATCACC<br>TGCAAGGCCAGTCAGAATGTGGGTACTGCTGTA<br>GCCTGGTATCAACAGAAACCAGGACAATCTCCT<br>AAATTTCTGATTTACTCGGCATCCAATCGGTACA<br>CTGGAGTCCCTGATCGCTTCACAGGCAGTGGAT<br>CTGGGACAGATTTCACTCTCACGATCAGCAATA<br>TGCAGTCTGAAGACCTGGCAGATTATTTCTGCCA<br>GCAATATAGCAGCTATCGTCTGACGTTCGGTGG<br>AGGCACCAAGCTGGAAATCAAAC | 197 |
| 4D9-2C11 | Heavy chain | CAGGTTCAGCTGCAGCAGTCTGACGCTGAATTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATCTTTCTCCCGGAAATG<br>ATGATATTAAGTACAGTGAGAAGTTCAAGGACA<br>AGGCCACACTGACTGCAGACAAATCCTCCAGCA<br>CTGCCTACATGCAGCTCAACAGCCTGACATCTG<br>AGGATTCTGCAGTGTATTTCTGTAAAAGATCCAT<br>AGGGGGGGACCACTGGGGCCAAGGCACCACTCT<br>CACAGTCTCCTCA | 198 |
| 4D9-2C11 | Light chain | GACATCCAGATGAACCAGTCTCCATCCAGTCTG<br>TCTGCATCCCTTGGAGACACAATTACCATCACTT<br>GCCATGCCAGTCAGAACATTAATGTTTGGTTAA<br>ACTGGTACCAGCAGAAACCAGGAAATATTCCTA<br>AACTATTGATCTATAAGGCTTCCAACTTGCACAC<br>AGGCGTCCCATCAAGGTTTAGTGGCAGTGGATC<br>TGGAACAGGTTTCACATTAACCATCGGCAGCCT<br>GCAGCCTGAAGACATTGCCACTTACTACTGTCA<br>ACAGGGTCAAAGTTATCCGTTCACGTTCGGAGG<br>GGGGACCAAGCTGGAAATAAAACG | 199 |
| 2F4-1E2 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAACAGAAGCCTGAACAGGGCC<br>TGGAATGGATTGGATATATTTCTCCCGGAAATG<br>GTGATATTAAGTATAATGAGAAGTTCAAGGGCA<br>AGGCCACACTGACTGCAGACAAATCCTCCAGCA<br>CTGCCTACATGCAGCTCAACAGCCTGACATCTG<br>AGGATTCTGCAGTGTATTTCTGTCAAAGACAACT<br>GGGACAAGGCTACTGGGGCCAAGGCACCACTCT<br>CACAGTCTCCTCA | 200 |

TABLE 4 -continued

Variable domain nucleotide sequences

| Antibody ID Number | Variable chain | Sequence | SEQ ID NO |
|---|---|---|---|
| 2F4-1E2 | Light chain | GATGTTGTGATGACCCAAACTCCACTCTCCCTGC<br>CTGTCAGTCTTGGAGATCAAGCCTCCATCTCTTG<br>CAGATCTAGTCAGAGCCTTGTACACAGTTATGG<br>AAACACCTATTTACATTGGTACCTGCAGAAGCC<br>AGGCCAGTCTCCAAAGCTCCTGATTTACAAAGT<br>TTCCAACCGATTTTCTGGGGTCCCAGACAGGTTC<br>AGTGGCAGTGGATCAGGGACAGATTTCACACTC<br>AAGATCAGCAGAGTGGAGGCTGAGGATCTGGG<br>AGTTTATTTCTGCTCTCAAAATACACATGTTCCG<br>TACACGTTCGGAGGGGGGACCAAGCTGGAAATA<br>AAACG | 201 |
| 2F4-1H8 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAACAGAAGCCTGAACAGGGCC<br>TGGAATGGATTGGATATATTTCTCCCGGAAATG<br>GTGATATTAAGTATAATGAGAAGTTCAAGGGCA<br>AGGCCACACTGACTGCAGACAAATCCTCCAGCA<br>CTGCCTACATGCAGCTCAACAGCCTGACATCTG<br>AGGATTCTGCAGTGTATTTCTGTCAAAGACAACT<br>GGGACAAGGCTACTGGGGCCAAGGCACCACTCT<br>CACAGTCTCCTCA | 200 |
| 2F4-1H8 | Light chain | GATGTTGTGATGACCCAAACTCCACTCTCCCTGC<br>CTGTCAGTCTTGGAGATCAAGCCTCCATCTCTTG<br>CAGATCTAGTCAGAGCCTTGTACACAGTTATGG<br>AAACACCTATTTACATTGGTACCTGCAGAAGCC<br>AGGCCAGTCTCCAAAGCTCCTGATTTACAAAGT<br>TTCCAACCGATTTTCTGGGGTCCCAGACAGGTTC<br>AGTGGCAGTGGATCAGGGACAGATTTCACACTC<br>AAGATCAGCAGAGTGGAGGCTGAGGATCTGGG<br>AGTTTATTTCTGCTCTCAAAATACACATGTTCCG<br>TACACGTTCGGAGGGGGGACCAAGCTGGAAATA<br>AAACG | 201 |
| 2C6-2F11 | Heavy chain | CAGGTTCAGCTGCAGCAGTCTGACGCTGAGTTG<br>GGGAAACCTGGGGCTTCAGTGAAGATATCCTGC<br>AAGGCTTCTGGCTACACCTTCAGTGACCATGCTA<br>TTCACTGGGTGAAGCAGAAGCCTGAACAGGGCC<br>TGGAATGGATTGGATATATCTCTCCCGGAAACG<br>ATGATATTAAGTACAATGAGAAGTTCAAGGGCA<br>AGGCCACACTGACTGCAGACAAATCCTCCAGCA<br>CTGCCTACATGCAGCTCAACAGCCTGACATCTG<br>AGGATTCTGCAGTGTATTTCTGTGAAAGATCGAT<br>GATTGGGGTTTACTGGGGCCAAGGGACTCTGGT<br>CACTGTCTCTGCA | 202 |
| 2C6-2F11 | Light chain | GATGTTGTGATGACCCAAACTCCACTCTCCCTGA<br>CTGTCAGTCTTGGCGATCAAGCCTCCATCTCTTG<br>CAGATTTAGTCAGAGCCTTGTACAAAGTAATGG<br>AAATACCTATTTACAGTGGTATCTGCAGAAGCC<br>AGGCCAGTCTCCAAAGCTCCTGATTTACAAAGT<br>CTCCAACCGATTTTGTGGGGTCCCAGACAGGTTC<br>AGTGGCAGTGGATCAGGGACAGATTTCACACTC<br>AAGATCAGCAGAGTGGAGGCTGAGGATCTGGG<br>AGTTTATTTCTGCTCTCAAAGTACACATGCTCCG<br>CTCACGTTCGGTGCTGGGACCAAGCTGGAGCTG<br>AAAC | 203 |
| 2B2-2A7 | Heavy chain | CAGGTTCAGCTGCAGCAGTCTGACGCTGAGTTG<br>GTGAAACCTGGGGCTTCAGTGAAGATATCCTGC<br>AAGACTTCTGGCTACACCTTCACTGACCATGCA<br>ATTCACTGGGTGAAGCAGAAGCCTGAACAGGGC<br>CTGGAATGGATTGGATATATTTCTCCCGGAAAT<br>GGTGATATTAAGTACAATGAGAAGTTCAAGGGC<br>AAGGCCACCCTGACTGCAGACAAATCCTCCAGC<br>ACTGCCTATATGCAGCTCAGCAGCCTGACACCT<br>GAGGATTCTGCAGTGTATTTCTGTAAAATATCTT<br>ACTACGGTATTTGGGGCCAAGGCACCACTCTCA<br>CAGTCTCCTCA | 204 |

TABLE 4 -continued

Variable domain nucleotide sequences

| Antibody ID Number | Variable chain | Sequence | SEQ ID NO |
|---|---|---|---|
| 2B2-2A7 | Light chain | GACATCCAGATGACTCAGTCTCCAGCCTCCCTAT<br>CTGTATCTGTGGGAGAGTCTGTCACCATCACATG<br>TCGACTAAGTGAAGATATTTACAGTAATTTAGC<br>ATGGTTTCAGCAGAGACCGGGAAAATCTCCTCA<br>GCTCCTGGTTTATAAAGCAACAAACTTAGCAGA<br>CGGTGTGCCATCAAGGTTCAGTGGCAGTGGATC<br>AGGCACACAGTATTCCCTCAAGATCAACAGCCT<br>GCAGTCTGAAGATTTTGGGACTTATTACTGTCAA<br>CATTTTTGGGGTACTCCATTCACGTTCGGCTCGG<br>GGACCAAGGTGGAAATAAAAC | 205 |
| 5G2-1B3 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATTTTTCTCCCGGAAATGA<br>TGATATTAAGTATAATGAGAAGTTCAAGGTCAA<br>GGCCACACTGACTGCAGACAAATCCTCCAGCAC<br>TGCCTACATGCAACTCACCAGCCTGACATCTGA<br>AGATTCTGCAGTGTATTTCTGTAAAAGATCTTAC<br>TACGGTGATTGGGGCCAAGGCACCACTCTCACA<br>GTCTCCTCA | 206 |
| 5G2-1B3 | Light chain | GACATCCAGATGACTCAGTCTCCAGCCTCCCTAT<br>CTGTTTCTGTGGGAGAAACTGTCACCATCACATG<br>TCGAGCAAGTGAGAATATTTACAGTCATTTAGC<br>ATGGTATCAACAGAAACAGGGAAAATCTCCTCA<br>ACTCCTGGTCTATGGTGCAACTAACTTAGCAGAT<br>GGTGTGCCATCAAGGTTCAGTGGCAGTGGATCA<br>GGCACACAGTTTTCCCTCAAGATCCACAGCCTG<br>CAGTCTGAAGATTTTGGGAGTTATTACTGTCAAC<br>ATTTTTGGGGTGCTCCATTCACGTTCGGCTCGGG<br>GACAAAGTTGGAAATAAAAC | 207 |
| 7A6-2A2 | Heavy chain | CAAATTCAGCTGCAGCAGTCTGACGCTGAGTTG<br>GTGAAACCTGGGACTTCAGTGAAGATGTCCTGC<br>AAGGCTTCTGGCTACACCTTCACTGACCATGCTA<br>TTCACTGGGTGAAGCAGAAGCCTGAACAGGGCC<br>TGGAATGGATTGGATATTTTTCTCCCGGAAATGA<br>TGATATTAAGTATAATGTGAAGTTCAAGGGCAA<br>GGCCACACTGACTGCAGACAAATCCTCCAGCAC<br>TGCCTACATGCAGCTCAACAGCCTGACATCTGA<br>AGATTCTGCAGTGTATTTCTGTTCGGTGGGATAC<br>GCCCTTGACTACTGGGGCCTAGGCACCACTCTC<br>ACAGTCTCCTCA | 208 |
| 7A6-2A2 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTACTTATGTTT<br>CCTGGTATCAACAGAAACCAGAGCAGTCTCCTA<br>AACTGCTGATATACGGGGCATCCAACCGGTACA<br>CTGGGGTCCCCGATCGCTTCACAGGCAGTGGAT<br>CTGCAACAGATTTCACTCTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 209 |
| 10C9-2G7 | Heavy chain | CAGGTTCAGCTGCAACAGTCTGACGCTGAGTTG<br>GTGAAACCTGGGACTACAGTGAAGATATCCTGC<br>AAGGCTTCTGGCTACACTTTCACTGACCATGCTA<br>TTCACTGGGTGAAGGAGAAGCCTGAACAGGGCC<br>TGGAATGGATCGGATATATTTCTCCCGGAAATG<br>ATGATATTAAGTACAGTGAGAAGTTCAAGGGCA<br>AGGCCACACTGACTGCAGACAAATCCTCCAGCA<br>CTGCTTACATGCAGCTCAACAGCCTGACATCTG<br>ATGATTCTGCAGTGTATTTCTGTAAAAGATCGCT<br>TAGTACGCCTTACTGGGGCCAAGGGACTCTGGT<br>CACTGTCTCTGCA | 210 |
| 10C9-2G7 | Light chain | TTTTTAATACGACTCCCTATAGGGCAAGCAGTG<br>GTATCAATGCAGATTACAAGGGGGAAAGGCATC<br>AGACCAGCATGGGCATCAAGGTGGAATCACAGA<br>CTCTGGTCTTCATATCCATACTGTTTGGGTTATA | 211 |

TABLE 4 -continued

Variable domain nucleotide sequences

| Antibody ID Number | Variable chain | Sequence | SEQ ID NO |
|---|---|---|---|
| | | TGGAGCTGATGGGAACACATTAATGACCCAATC<br>TCCCACATCCATGTACATGTCAGTAGGAGAGAG<br>GGTCACCTTGACTTGCAAGGCCAGTGAGAATGA<br>GATTAATTATGTTTCCTGGTATCAACAGAAACCA<br>GAGCAGTCTCCTAAACTGTTGATATACGGGGCA<br>TCCAACCGGTACTCTGGGGTCCCCGATCGCTTCA<br>CAGGCAGTGGATCTGCAACAGATTTCACTCTGA<br>CCATCAGCAGTGTGCAGGCTGAAGACCTTGCAG<br>ATTATCCCTGTGGAGCAAGGGATTAACTAGCTA<br>TCCGTACACGTTCGGAGGGGGGACCAAGCTGGA<br>AATAAAACGGGC | |
| 1C11-2G9 | Heavy chain | Unknown | |
| 1C11-2G9 | Light chain | GACATTGTGATGACACAGTCTCCATCCTCCCTGA<br>CTGTGACAGCAGGAGAGAAGGTCACTATGAGCT<br>GCAGGTCCAGTCAGAGTCTGTTAAACAGTGGAA<br>ATCAAAAGAACTACTTGACCTGGTACCAGCAGA<br>AACCAGGGCAGCCTCCTAAACTGTTGATCTACT<br>GGGCATCCACTAGGGAATCTGGGGTCCCTGATC<br>GCTTCACAGGCAGTGGATCTGGAACAGATTTCA<br>CTCTCACCATCAGCAGTGTGCAGGCTGAAGACC<br>TGGCAGTTTATTACTGTCAGAATGATTATAGTTA<br>TCCGTACACGTTCGGAGGGGGGACCAAGCTGGA<br>AATAAAACG | 212 |
| 1F6-1B7 (also sequence of 1F6-1C10) | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGATGCAGATGCCTGAACAGGGCC<br>TGGAATGGATTGGATATATTTCTCCCGGAAATG<br>GTGATGTTAAGTACAGTGAGAGGTTCAAGGGCA<br>GGGCCACACTGACTGCAGACAAATCCTCCAGCT<br>CTGCCTACATGCAGCTCAACAGCCTGACATCTG<br>AGGATTCTGCAGTTTATTTCTGTAAAAGATCGCT<br>TAGTACGCCTTACTGGGGCCAAGGGACTCTGGT<br>CACTGTCTCTG | 213 |
| 1F6-1B7 (also sequence of 1F6-1C10) | Light chain | GACATTGTGATGACACAGTCTCCATCCTCCCTGA<br>CTGTGACAGCAGGAGAGAGGGTCACTATGAGCT<br>GCAAGTCCAGTCAGAGTCTGTTAAACAGTGGAA<br>ATCAAAAGAGCTACTTGACCTGGTACCAGCAGA<br>AACCAGGGCAGCCTCCTAAACTGTTGATCTCCT<br>GGGCATCCACTAGGGATTCTGGGGTCCCTGATC<br>GCTTCACAGGCAGTGGATCTGGAACAGATTTCA<br>CTCTCACCATCAGCAGTGTGCAGGCTGAAGACC<br>TGGCAGTTTATTACTGTCAGAGTGATTATAGTTA<br>TCCGTACACGTTCGGAGGGGGGACCAAGCTGGA<br>AATAAAACG | 214 |
| 2G12-2B2 | Heavy chain | CAGGTTCAGCTGCAGCAGTCTGACGNTGAGTTG<br>GTGAAACCGGGGGCTTCAGTGAAGATATCCTGT<br>AAGGCTTCTGGCTACACCTTCACTGACCATGCTA<br>TTCACTGGGTGAAGCAGAAGCCTGAACAGGGCC<br>TGGAATGGATTGGATATTTTTCTCCCGGAAATGA<br>TGATATTAAGTACAATGAGAAGTTTAGGGGCAA<br>GGCCACACTGACTGCAGACAAATCCTCCAGCAC<br>TGCCTACATGCAGCTCAACAGCCTGTCATCTGAT<br>GATTCTGCAGTGTATTTCTGTAAAAGATCGCTTA<br>GTACGCCTTACTGGGGCCAAGGGACTCTGGNCA<br>CTGTCTCTGCA | 215 |
| 2G12-2B2 | Light chain | GACATTGTGATGACACAGTCTCCATCCTCCCTGA<br>CTGTGACAGCAGGAGAGAAAGTCACTATGAGCT<br>GCAAGTCCAGTCAGAGTCTGTTAAACCGTGGAA<br>ATCATAAGAACTACTTGACCTGGTACCGGCAGA<br>AACCAGGGCTGCCTCCTAAACTGTTGATTTACTG<br>GGCATCCACTAGGGAATCTGGGGTCCCTGATCG<br>CTTCACAGGCAGTGGATCTGGAACAGATTTCGC<br>TCTCACCATCAGCAGTGTTCAGGCTGAAGACCT<br>GGCAGTTTATTACTGTCAGAATGATTATACTTAT<br>CCGTACACGTTCGGAGGGGGGACCAAGCTGGAG<br>ATAAAACG | 216 |

TABLE 4 -continued

Variable domain nucleotide sequences

| Antibody ID Number | Variable chain | Sequence | SEQ ID NO |
|---|---|---|---|
| 5E6-2E7 | Heavy chain | CAGGTTCAGCTGCAGCAGTCTGACGCTGAGTTG<br>GTGAAACCTGGGGCTTCAATGAAGATTTCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACAATGAGAAGTTCAAGGTCA<br>AGGCCACACTGACTGCAGACAAATCCTCCAGCA<br>CTGCCTACATGCAGCTCAACAGCCTGACATCTG<br>AGGATTCTGCAGTGTATTTCTGTAAAAGATCGAT<br>TACTACGCCTTACTGGGGCCAAGGGACTCTGGT<br>CACTGTCTCTGCA | 217 |
| 5E6-2E7 | Light chain | GACATTGTGATGACACAGTCTCCATCCTCCCTGA<br>CTGTGACAGCAGGAGAGAAGGTCACTATGAGCT<br>GCAAGTCCAGTCAGAGTCTGTTAAACAGTGGAA<br>AAACAAAGAACTACTTGACGTGGTACCAGCAGA<br>AACCAGGGCAGCCTCCTAAACTGTTGATCTACT<br>GGGCATCCACTAGGGAATCTGGGGTCCCTGATC<br>GCTTCACAGGCAGTGGATCTGGAACAGATTTCA<br>CTCTCACCATCAGCAGTGTGCAGGCTGAAGACC<br>TGGCAGTTTATTACTGTAAGAATGATTATAGTTA<br>TCCGTACACGTTCGGAGGGGGGACCAAGCTGGA<br>AATAAAACG | 218 |
| 9E5-1A8 | Heavy chain | CAGGTTCAGCTGCAGCAGTCTGACGCTGAATTG<br>GTGAAGCCTGGGGCTTCAGTGAAGATATCCTGC<br>AAGACTTCTGGCTACACCTTCACTGACCATGCTA<br>TTCACTGGGTGAAGCAGAAGCCTGAACAGGGCC<br>TGGAATGGATTGGATATATCTCTCCCGGAAATG<br>ATGATATTAAGTACACTGAGAAGTTCAAGGGCA<br>AGGTCACACTGACTGCAGACAAATCCTCCAGCA<br>CTGCCTACATGCAGCTCAACAGCCTGACATCTG<br>AGGATTCTGCAGTCTATTTCTGTAAAAGATCGAT<br>TACTACGCCTTACTGGGGCCAAGGGACTCTGGT<br>CACTGTCTCTGCA | 219 |
| 9E5-1A8 | Light chain | TTTTTATACGCCACTTTCTAATACGCCTCACTAT<br>AGGGCAAGCAGTGGTATCAACGCAGATTACAAA<br>GGGGAAAGGAATCAGACCGACTCGCGCATCAA<br>GATGGAATCACAGACTCTGGTCTTCATATCCAGT<br>ACGCTCGGGGACTATGGAGNGGAACAGTACATT<br>TTAATGACCCAATGTCCCAAAGGCAAGAACATG<br>TCAGTAGGAGAGAGGGTCACTCAGAGTGCAAGG<br>CCAGGAGAAATCAAAACACTTATGTTTCCTGGT<br>ATCAACAGAAACCAGAGCANNCTNTAAAATGN<br>NGATTACGGGGCATCCAACCGGGAATCTGGGGT<br>CNCCGATCGCTTCACAGGCAGTGGATCTGGAAC<br>AGATTTCACTCTCACCATCAGCAGTGTGCAGGCT<br>GAAGACCNGGCAGTNTTCACTGTGGACAGGGNT<br>ACAGTTATCCGTACACGTTCGGAGGGGGGACCA<br>AGCTGAAAAAAACGGGC | 220 |
| 9F11-1F7 | Heavy chain | CAGGTTCAGCTGCAGCAGTCTGACGCTGAGTTG<br>GTGAAACCTGGGGCTTCAATGAAGATTTCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACAATGAGAAGTTCAAGGTCA<br>AGGCCACACTGACTGCAGACAAATCCTCCAGCA<br>CTGCCTACATGCAGCTCAACAGCCTGACATCTG<br>AGGATTCTGCAGTGTATTTCTGTAAAAGATCGAT<br>TACTACGCCTTACTGGGGCCAAGGGACTCTGGT<br>CACTGTCTCTGCA | 217 |
| 9F11-1F7 | Light chain | GACATTGTGATGACACAGTCTCCATCCTCCCTGA<br>CTGTGACAGCAGGAGAGAAGGTCACTATGAGCT<br>GCAAGTCCAGTCAGAGTCTGTTAAACAGTGGAA<br>AAACAAAGAACTACTTGACGTGGTACCAGCAGA<br>AACCAGGGCAGCCTCCTAAACTGTTGATCTACT<br>GGGCATCCACTAGGGAATCTGGGGTCCCTGATC<br>GCTTCACAGGCAGTGGATCTGGAACAGATTTCA | 218 |

TABLE 4 -continued

Variable domain nucleotide sequences

| Antibody ID Number | Variable chain | Sequence | SEQ ID NO |
|---|---|---|---|
| | | CTCTCACCATCAGCAGTGTGCAGGCTGAAGACC<br>TGGCAGTTTATTACTGTAAGAATGATTATAGTTA<br>TCCGTACACGTTCGGAGGGGGGACCAAGCTGGA<br>AATAAAACG | |
| 10F4-2F2 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACGATGAGAAGTTTAAGGGCA<br>AGGCCACACTGACTGCAGACAAATCCTCCTCCA<br>CTGCCTACATGCAGCTCAACAGCCTGACATCTG<br>AAGATTCTGCAGTGTATTTCTGTAAAAGATCGAT<br>TACTACCTCTTACTGGGGCCAAGGGACTCTGGTC<br>ACTGTCTCTGCA | 221 |
| 10F4-2F2 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTACTTATGTTT<br>CCTGGTATCAACAGAAACCAGAGCAGTCTCCTA<br>AACTGCTGATATACGGGGCATCCAACCGGTACA<br>CTGGGGTCCCCGATCGCTTCACAGGCAGTGGAT<br>CTGCAACAGATTTCACTCTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 209 |
| 2B8-2F10 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>ATGATATTAAGTACAATGAGAAGTTCAAGGGCA<br>AGGCCACACTGACTGCAGACAAGTCCTCCAGCA<br>CTGCCTACATGCAGCTCAACAGCCTGACATCTG<br>AGGATTCTGCAGTGTTTTTCTGTAAAAGATCGAT<br>TACTACCTCTTACTGGGGCCAAGGGACTCTGGTC<br>ACTGTCTCTGCA | 222 |
| 2B8-2F10 | Light chain | TTNATAGGACTCAATATAGGGCAAGCAGTGGTA<br>TTAACGCCGAGTACATGGGGAGGGCAAGGGCA<br>GAAAGTCACTTTCAGTGAGGATACACCATCAGC<br>ATGAGGGTCCTTGTTGAGCTCCTGGGGGGGCTG<br>GTGTTNTGCTTTTTAGGTGTGAGATGTGACATCC<br>AGATGAACCAGTCTCCATCCAGTCTGTNTGCATC<br>CTTTGGAGACACAATTACCATCATTTGCCATTCC<br>AGTCAGAACATTAATGTTTGGTTAAGATGGTAC<br>CAGCAGAAACCAGGAAATATTCCTAAAATATTG<br>ATATATAAGGGTTCCAACTTGTACACAGGCGTC<br>CCATCAAGGTTTAGTGGCAGTGGATTTGGAACA<br>GGTTTCACATTAACCATCAGCAGCGTGCAGCGG<br>GAAGACATTGCCACTTACTACTGTCAACAGGAT<br>CAAAGTTATCCGTACACGTTCGGAGGGGGGACC<br>AAGCTGAAATAAAACGGGC | 223 |
| 4G8-1E3 | Heavy chain | CAGGTTCAGCTGCAGCAGTCTGACGCCGAGTTG<br>GTGAAACCTGGGGCTTCAGTGAAGATATCCTGC<br>AAGGCTTCTGGCTACATCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACAATGAGAAGTTCAAGGGCA<br>AGGCCACACTGACTGCAGACAAATCCTCCAGCA<br>CTGCCTACATGCATCTCAACAGCCTGACATCTG<br>AGGATTCTGCAGTGTATTTCTGTAAAAGATCGAT<br>TACTACCTCTTACTGGGGCCAAGGGACTCTGGTC<br>ACTGTCTCTGCA | 224 |
| 4G8-1E3 | Light chain | GACATCCAGATGAACCAGTCCCCATCCAGTCTG<br>TCTGCATCCCTTGGAGACACAATTACCATCACTT<br>GCCATGCCAGTCAGCACATTAATTTTTGGTTAAG<br>CTGGTACCAGCAGAAACCAGGAAATATTCCTAA<br>ACTCTTGATCTATAAGGCTTCCAACTTGCACACA<br>GGCGTCCCATCAAGGTTTAGTGGCAGTGGATCT | 225 |

TABLE 4 -continued

| Variable domain nucleotide sequences | | | |
|---|---|---|---|
| Antibody ID Number | Variable chain | Sequence | SEQ ID NO |
| | | GGAACAGGTTTCACATTAACCATCAGCAGCCTG<br>CTGCCTGAAGACGTTGCCACTTACTACTGTCAAC<br>AGGATCAAAGTTATCCGTATATGTTCGGAGGGG<br>GGACCAAGCTGGAAATAAAACG | |
| 6B11-2E3 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>ATGATATTAAGTACAATGAGAAGTTTAAGGGCA<br>AGGCCACACTGACTGCAGACAAATCCTCCAGCA<br>CTGCCTACATGCTGCTCAACAGCCTGACATCTG<br>AGGATTCTGCAGTGTATTTCTGTAAAAGATCGAT<br>TACTACCTCTTACTGGGGCCAAGGGACTCTGGTC<br>ACTGTCTCTGCA | 226 |
| 6B11-2E3 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTACTTATGTTT<br>CCTGGTATCAACAGAAACCAGAGCAGTCTCCTA<br>AACTGCTGATATACGGGGCATCCAACCGGTACA<br>CTGGGGTCCCCGATCGCTTCACAGGCAGTGGAT<br>CTGCAACAGATTTCACTTTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 227 |
| 7D3-2C10 | Heavy chain | CAGGTTCAGTTGCTGCAGTATGACGCTGAGTTG<br>GTGAAACCTGGGGGGTCAGTGAAGATATCGTGC<br>AAGGCCTCTGGCTACACCTTCACTGACCATGCT<br>ATTCACTGGGTGAAGCAGAAGCCTGAACAGGGC<br>CTGGAATGGATTGGATATTTTTCTCCCGGAAATG<br>ATGATATTAAGTACAGTGAGAAGTTCAAGGGCA<br>AGGCCACACTGACTGCAGACAAGTCCTCCAGCA<br>CTGCCTACATGCAGCTCAACAGCCTGACATCTG<br>AGGATTCTGCAGTGTATTTCTGTAAAAGATCCAT<br>TACTACGCCTTACTGGGGCCAAGGGACTCTGGT<br>CACTGTCTCTGCA | 192 |
| 7D3-2C10 | Light chain | GACATCCAGATGAACCAGTCTCCATCCAGTCTG<br>TCTGCATCCCTTGGAGACACAATTACCATCACTT<br>GCCATGCCAGTCAGAACATTAATGTTTGGTTAA<br>GCTGGTACCAGCAGAAACCAGGAAATATTCCTA<br>AACTATTGATCTATAAGGTTTCCAACTTGCACAC<br>AGGCGTCCCATCAAGGTTTAGTGGCAGTGGATC<br>TGGAACAGGTTTCACATTAACCATCAGCAGCCT<br>GCAGCCTGAAGACATTGCCACTTACTACTGTCA<br>ACAGGATCAAAGTTATCCGTACACGTTCGGAGG<br>GGGGACCAAGCTGAAAAAAA | 193 |
| 7A5-2G12 | Heavy chain | CAGGTTCAGCTGCAGCAGTCTGACGCTGAGTTG<br>GTGAAACCTGGGGCTTCAGTGAAGATATCCTGC<br>AAGGCCTCTGGCTACACCTTCACTGACCATGCT<br>ATTCACTGGGTGAAGCAGAAGCCTGAACAGGGC<br>CTGGAATGGATTGGATATATTTCTCCCGGAAAT<br>GATGATATTAAGTACAATGAGAAGTTCAAGGGC<br>AAGGCCACACTGACTGCAGACAAATCCTCCAGC<br>ACTGCCTACATGCAGCTCAACAGCCTGACATCT<br>GAGGATTCTGCAGTGTATTTCTGTAAAAGATCC<br>ATTACTACGTCTTACTGGGGCCAAGGGACTCTG<br>GTCACTGTCTCTGCA | 194 |
| 7A5-2G12 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTATTTATGTTTC<br>CTGGTATCAACAGAAACCAGAGCAGTCTCCTAA<br>ACTGCTGATATACGGGGCATCCAACCGGTACAC<br>TGGGGTCCCCGATCGCTTCACAGGCAGTGGATC<br>TGCAACAGATTTCACTCTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 195 |

TABLE 4 -continued

Variable domain nucleotide sequences

| Antibody ID Number | Variable chain | Sequence | SEQ ID NO |
|---|---|---|---|
| 1A5-2C9 | Heavy chain | CAGGTTCAGTTGCAGCAGTCTGACGCTGAGTTG<br>GTGAAACCTGGGGCTTCAGTGAAGATATCCTGC<br>AAGGCTTCTGGCTACACCTTCACTGACCATGCC<br>ATTCATTGGGTGAAGCAGAAGCCTGAACAGGGC<br>CTGGAATGGATTGGATATGTTTCTCCCGGAAAT<br>GGTGATATTAAGTACAATGAGAAGTTCAAGGGC<br>AAGGCCACACTGACTGCAGACAAATCCTCCAGC<br>ACTGCCTACATGCAGCTCAACAGCCTGACATCG<br>GAGGATTCTGCAGTGTATTTCTGTAAAAGATCTT<br>TAATTGGAGACTATTGGGGCCAAGGCACCACTC<br>TCACAGTCTCCTCA | 196 |
| 1A5-2C9 | Light chain | GACATTGTGATGACCCAGTCTCAAAAATTCATG<br>TCCTCATCAGTAGGAGACAGGGTCACCATCACC<br>TGCAAGGCCAGTCAGAATGTGGGTACTGCTGTA<br>GCCTGGTATCAACAGAAACCAGGACAATCTCCT<br>AAATTTCTGATTTACTCGGCATCCAATCGGTACA<br>CTGGAGTCCCTGATCGCTTCACAGGCAGTGGAT<br>CTGGGACAGATTTCACTCTCACGATCAGCAATA<br>TGCAGTCTGAAGACCTGGCAGATTATTTCTGCCA<br>GCAATATAGCAGCTATCGTCTGACGTTCGGTGG<br>AGGCACCAAGCTGGAAATCAAAC | 197 |
| 8C2-2D6 | Heavy chain | CAGGTTCAACTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACAATGAGAAGTTCAAGGGTA<br>AGGCCACACTGACTGCAGACACTTCCTCCACCA<br>CTGCCTACATGCAGCTCAACAGCCTGACATCTG<br>AGGATTCTGCAATGTATTTCTGTAAAAGATCCAT<br>TACTACGTCTTACTGGGGCCAAGGGACTCTGGT<br>CACTGTCTCTGCA | 228 |
| 8C2-2D6 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTACTTATGTTT<br>CCTGGTATCAACAGAAACCAGAGCAGTCTCCTA<br>AACTGCTGATATACGGGGCATCCAACCGGTACA<br>CTGGGGTCCCCGATCGCTTCACAGGCAGTGGAT<br>CTGCAACAGATTTCACTCTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 209 |
| 7D4-2A2-2F2 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACATCTTCACTGACCATGCAA<br>TTCACTGGGTGAAGCAGAAGCCTGAACAGGGCC<br>TGGAATGGATTGGATATATTTCTCCCGGAAATG<br>GTGATATTAAGTACATTGAGAAGTTCAGGGGCA<br>AGGCCACACTGACTGCAGACAAATCCTCCAGCA<br>CTGCCTACATGCAGCTCAACAGCCTGACATCTG<br>AGGATTCTGCAGTGTATTTCTGTAAAAGATCGCT<br>TAGTACGCCTTACTGGGGCCAAGGGACTCTGGT<br>CACTGTCTCTGCA | 229 |
| 7D4-2A2-2F2 | Light chain | AACATTTTAATGACCCAATCTCCCAAATCCATGT<br>CCATGTCAGTAGGAGAGAGGGTCACCTTGACCT<br>GCAAGGCCAGTGAGAATGTGGTTAATTATGTTT<br>CCTGGTATCAACAGAAACCAGAGCAGTCTCCTA<br>AACTGCTGATATTCGGGGCATCCAACCGGTACT<br>CTGGGGTCCCCGATCGCTTCACAGGCAGTGGAT<br>CTGCAACAGATTTCACTCTGACCATCAGCAGTGT<br>GCAGGCTGAAGACCTTGCAGATTATCACTGTGG<br>AAGCAAGTGGATTACTAGCTATCCGTACACGTT<br>CGGAGGGGGGACCAAGCTGGAAATAAAACG | 230 |
| 7D4-1H12-2B3 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACATCTTCACTGACCATGCAA<br>TTCACTGGGTGAAGCAGAAGCCTGAACAGGGCC<br>TGGAATGGATTGGATATATTTCTCCCGGAAATG | 229 |

TABLE 4 -continued

| Variable domain nucleotide sequences | | | |
|---|---|---|---|
| Antibody ID Number | Variable chain | Sequence | SEQ ID NO |
| | | GTGATATTAAGTACATTGAGAAGTTCAGGGGCA<br>AGGCCACACTGACTGCAGACAAATCCTCCAGCA<br>CTGCCTACATGCAGCTCAACAGCCTGACATCTG<br>AGGATTCTGCAGTGTATTTCTGTAAAAGATCGCT<br>TAGTACGCCTTACTGGGGCCAAGGGACTCTGGT<br>CACTGTCTCTGCA | |
| 7D4-1H12-2B3 | Light chain | AACATTTTAATGACCCAATCTCCCAAATCCATGT<br>CCATGTCAGTAGGAGAGAGGGTCACCTTGACCT<br>GCAAGGCCAGTGAGAATGTGGTTAATTATGTTT<br>CCTGGTATCAACAGAAACCAGAGCAGTCTCCTA<br>AACTGCTGATATACGGGGCATCCAACCGGTACT<br>CTGGGGTCCCCGATCGCTTCACAGGCAGTGGAT<br>CTGCAACAGATTTCACTCTGACCATCAGCAGTGT<br>GCAGGCTGAAGACCTTGCAGATTATCACTGTGG<br>AGCAAGGGTTACTAGCTATCCGTACACGTTCGG<br>AGGGGGGACCAAGCTGGAAATAAAACG | 231 |
| 2C2-2C5 | Heavy chain | CAGGTTCAGCTGCAGCAGTCTGACGCTGAGTTG<br>GTGAAACCTGGGACTTCAGTGAAGATATCCTGC<br>AGGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACAATGAGAAGTTCAAGGGCA<br>AGGCCACACTGACTGCAGACAAATCCTCCAGCA<br>CTGCCTACATGCAGCTCAACAGCCTGACATCTG<br>ACGATTCTGCAGTGTATTTCTGTAAAAGATCCAT<br>TACTACGCCTTACTGGGGCCAAGGCACCACTCT<br>CACAGTCTCCTCA | 232 |
| 2C2-2C5 | Light chain | AGTTTTGTGATGACCCAGACTCCCAAATTCCTGC<br>TTGTGTCAGCAGGAGACAGGGTTACCATAACCT<br>GCAAGGCCAGTCAGAGTGTGAATAATAATGTAG<br>CTTGGTACCAACAGAAGCCAGGGCAGTCTCCTA<br>AACAGCTGATATACTATGCATCCAATCGCTACA<br>CTGGAGTCCCTGATCGCTTCACTGGCAGTGGAT<br>ATGGGACGGATTTCACTTTCACCATCTACACTGT<br>GCAGGCTGAAGACCTGGCAGTTTATTTCTGTCA<br>GCAGGGTTATAGCTCTCCGTGGACGTTCGGTGG<br>AGGCACCAAGCTGAAA | 233 |
| 10F4-2A9 | Heavy chain | CAGGTTCAGCTGCAGCAGTCTGACGCTGAGTTG<br>GTGAAACCTGGGGCTTCAGTGAAGATATCCTGC<br>AAGGCTTCTGGCTACACCTTCACTGACCATGCTA<br>TTCACTGGGTGAAGCAGAAGCCTGAACAGGGCC<br>TGGAATGGATTGGATATATTTCTCCCGGAAATG<br>GTGATATTAAGTACGATGAGAAGTTTAAGGGCA<br>AGGCCACACTGACTGCAGACAAATCCTCCTCCA<br>CTGCCTACATGCAGCTCAACAGCCTGACATCTG<br>AAGATTCTGCAGTGTATTTCTGTAAAAGATCGAT<br>TACTACCTCTTACTGGGGCCAAGGGACTCTGGTC<br>ACTGTCTCTGCA | 221 |
| 10F4-2A9 | Light chain | AACATTGTAATGACCCAATCTCCCAAATCCATGT<br>CCATGTCAGTAGGAGAGAGGGTCACCTTGACCT<br>GCAAGGCCAGTGAGAATGTGGTTACTTATGTTT<br>CCTGGTATCAACAGAAACCAGAGCAGTCTCCTA<br>AACTGCTGATATACGGGGCATCCAACCGGTACA<br>CTGGGGTCCCCGATCGCTTCACAGGCAGTGGAT<br>CTGCAACAGATTTCACTCTGACCATCAGCAGTGT<br>GCAGGCTGAAGACCTTGCAGATTATCACTGTGG<br>ACAGGGTTACAGCTATCCGTACACGTTCGGAGG<br>GGGGACCAAGCTGGAAATAAAACG | 209 |

In some cases, antibodies or antigen binding fragments of the invention may comprise the IgG2a heavy chain and/or kappa light chain constant domain sequences listed in Table 5. In some cases, antibodies or fragments thereof may comprise an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the constant domain sequences listed in Table 5. In some cases, antibodies or fragments thereof of the invention may comprise an amino acid sequence comprising one or more fragments of any of the sequences listed in Table 5.

TABLE 5

Constant domain sequences

| Domain | Sequence | SEQ ID NO |
|---|---|---|
| IgG2a heavy chain constant domain | AKTTAPSVYPLAPVCGDTTGSSVTLGCLVKGYFPE PVTLTWNSGSLSSGVHTFPAVLQSDLYTLSSSVTV TSSTWPSQSITCNVAHPASSTKVDKKIEPRGPTIK PCPPCKCPAPNLLGGPSVFIFPPKIKDVLMISLSP IVTCVVVDVSEDDPDVQISWFVNNVEVHTAQTQTH REDYNSTLRVVSALPIQHQDWMSGKEFKCKVNNKD LPAPIERTISKPKGSVRAPQVYVLPPPEEEMTKKQ VTLTCMVTDFMPEDIYVEWTNNGKTELNYKNTEPV LDSDGSYFMYSKLRVEKKNWVERNSYSCSVVHEGL HNHHTTKSFSRTPGK | 234 |
| kappa light chain constant domain | RADAAPTVSIFPPSSEQLTSGGASVVCFLNNFYPK DINVKWKIDGSERQNGVLNSWTDQDSKDSTYSMSS TLTLTKDEYERHNSYTCEATHKTSTSPIVKSFNRN EC | 235 |

In some cases, antibodies may comprise the heavy chain sequence of

QVQLQQSDAELVKPGASVKISCKASGYTFTDHAIHWVKQKPEQGLDWIGYISPGNG

DIKYNEKFKDKVTLTADKSSSTACMHLNSLTSEDSAVYFCKRSLLALDYWGQGTTL

TVSSAKTTAPSVYPLAPVCGDTTGSSVTLGCLVKGYFPEPVTLTWNSGSLSSGVHTFP

AVLQSDLYTLSSSVTVTSSTWPSQSITCNVAHPASSTKVDKKIEPRGPTIKPCPPCKCP

APNLLGGPSVFIFPPKIKDVLMISLSPIVTCVVVDVSEDDPDVQISWFVNNVEVHTAQ

TQTHREDYNSTLRVVSALPIQHQDWMSGKEFKCKVNNKDLPAPIERTISKPKGSVRA

PQVYVLPPPEEEMTKKQVTLTCMVTDFMPEDIYVEWTNNGKTELNYKNTEPVLDSD

GSYFMYSKLRVEKKNWVERNSYSCSVVHEGLHNHHTTKSFSRTPGK(SEQ ID NO.

236) which may been coded by the nucleotide sequence

ATGGAGACCGACACCCTGCTGCTCTGGGTGCTGCTGCTCTGGGTGCCCGGCTCCA

CCGGACAGGTTCAGCTGCAGCAGTCTGACGCTGAGTTGGTGAAACCTGGGGCTTC

AGTGAAGATATCCTGCAAGGCTTCTGGCTACACCTTCACTGACCATGCTATTCAC

TGGGTGAAGCAAAAGCCTGAACAGGGCCTGGACTGGATTGGATATATTTCTCCC

GGAAATGGTGATATTAAGTACAATGAGAAGTTCAAGGACAAGGTCACACTGACT

GCAGACAAATCCTCCAGCACTGCCTGCATGCACCTCAACAGCCTGACATCTGAGG

ATTCTGCAGTGTATTTCTGCAAAAGATCCCTACTAGCTCTTGACTACTGGGGCCA

AGGCACCACTCTCACAGTCTCCTCAGCTAAAACAACAGCCCCATCGGTCTATCCA

CTGGCCCCTGTGTGTGGAGATACAACTGGCTCCTCGGTGACTCTAGGATGCCTGG

TCAAGGGTTATTTCCCTGAGCCAGTGACCTTGACCTGGAACTCTGGTTCCCTGTCC

AGTGGTGTGCACACCTTCCCAGCTGTCCTGCAGTCTGACCTCTACACCCTCAGCT

CAAGCGTGACTGTAACCAGCTCGACCTGGCCCAGCCAGTCCATCACCTGCAATGT

GGCCCACCCGGCAAGCAGCACCAAGGTGGACAAGAAAATTGAGCCCAGAGGGC

CCACAATCAAGCCCTGTCCTCCATGCAAATGCCCAGCACCTAACCTCTTGGGTGG

ACCATCCGTCTTCATCTTCCCTCCAAAGATCAAGGATGTACTCATGATCTCCCTGA

GCCCCATAGTCACATGTGTAGTCGTTGATGTGAGCGAGGATGACCCAGATGTCCA

GATCAGCTGGTTTGTGAACAACGTGGAAGTGCACACTGCTCAGACACAGACGCA

TAGAGAGGATTACAACAGTACTCTCCGGGTTGTCAGTGCCCTCCCCATCCAGCAC

CAGGACTGGATGAGTGGCAAGGAGTTCAAATGCAAGGTCAACAACAAAGACCTC

CCAGCGCCCATCGAGAGAACCATCTCAAAACCCAAAGGGTCAGTAAGAGCTCCA

-continued

```
CAGGTATATGTCTTGCCTCCACCAGAAGAGGAGATGACTAAGAAACAGGTCACT
CTGACCTGCATGGTCACAGACTTCATGCCTGAAGACATTTACGTGGAGTGGACCA
ACAACGGGAAAACAGAGCTAAACTACAAGAACACTGAACCAGTCCTGGACTCTG
ATGGTTCTTACTTCATGTACAGCAAGCTGAGAGTGGAGAAGAAGAACTGGGTGG
AGAGAAATAGCTACTCCTGTTCAGTGGTCCACGAGGGTCTGCACAATCACCACAC
GACTAAGAGCTTCTCCCGGACTCCGGGTAAATAG (SEQ ID NO: 237) or an
optimized version thereof. In some cases, antibodies of the invention
may comprise the light chain amino acid sequences of
DIVMTQSHKFMSTSVGDRVSITCKASQDVGTNIAWYQQKPGRSPKVLIYSASTRHTG
VPDRFTGSGSGTDFTLTISNVQSEDLTDYFCQQYSSFPLTFGVGTKLELKRADAAPTV
SIFPPSSEQLTSGGASVVCFLNNFYPKDINVKWKIDGSERQNGVLNSWTDQDSKDST
YSMSSTLTLTKDEYERHNSYTCEATHKTSTSPIVKSFNRNEC (SEQ ID NO: 238),
which may be encoded by the nucleotide sequence
ATGGAGACCGACACCCTGCTGCTCTGGGTGCTGCTGCTCTGGGTGCCCGGCTCCA
CCGGAGACATTGTGATGACCCAGTCTCACAAATTCATGTCCACATCAGTAGGAGA
CAGGGTCAGCATCACCTGCAAGGCCAGTCAGGATGTGGGCACTAATATAGCCTG
GTATCAACAGAAACCAGGCCGATCTCCTAAAGTACTGATTTACTCGGCATCCACC
CGGCACACTGGAGTCCCTGATCGCTTCACAGGCAGTGGATCTGGGACAGATTTCA
CTCTCACCATTAGCAATGTGCAGTCTGAAGACTTGACAGATTATTTCTGTCAGCA
ATATAGCAGCTTTCCTCTCACGTTCGGTGTTGGGACCAAGCTGGAGCTGAAACGG
GCAGATGCTGCACCAACTGTATCCATCTTCCCACCATCCAGTGAGCAGTTAACAT
CTGGAGGTGCCTCAGTCGTGTGCTTCTTGAACAACTTCTACCCCAAAGACATCAA
TGTCAAGTGGAAGATTGATGGCAGTGAACGACAAAATGGCGTCCTGAACAGTTG
GACTGATCAGGACAGCAAAGACAGCACCTACAGCATGAGCAGCACCCTCACGTT
GACCAAGGACGAGTATGAACGACATAACAGCTATACCTGTGAGGCCACTCACAA
GACATCAACTTCACCCATTGTCAAGAGCTTCAACAGGAATGAGTGTTGA (SEQ ID NO: 239)
```

or an optimized version thereof. In some cases, antibodies or fragments thereof may comprise an amino acid sequence with from about 50% to about 99.9% sequence identity (e.g., from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the amino acid sequences of SEQ ID NOs: 236 and/or 227. In some cases, antibodies or fragments thereof of the invention may comprise an amino acid sequence comprising one or more fragments of any of the sequences of SEQ ID NOs: 236 and/or 238. In some cases, antibodies or fragments thereof may be encoded by a nucleotide sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the nucleotide sequences of SEQ ID NOs: 237 and/or 239.

IgG Synthesis

IgG antibodies (e.g. IgG1, IgG2, IgG3 or IgG4) comprising one or more variable domain and/or CDR amino acid sequences presented herein (or fragment or variants thereof) may be synthesized for further testing and/or product development. Such antibodies may be produced by insertion of one or more segments of cDNA encoding desired amino acid sequences into expression vectors suited for IgG production. Expression vectors may comprise mammalian expression vectors suitable for IgG expression in mammalian cells. Mammalian expression of IgGs may be carried out to ensure that antibodies produced comprise modifications (e.g. glycosylation) characteristic of mammalian proteins and/or to ensure that antibody preparations lack endotoxin and/or other contaminants that may be present in protein preparations from bacterial expression systems.

Cancer-Related Targets

In some embodiments, targets of the present invention are cancer-related antigens or epitopes. As used herein, the term "cancer-related" is used to describe entities that may be in some way associated with cancer, cancerous cells and/or cancerous tissues. Many cancer-related antigens or epitopes comprising glycans have been identified that are expressed in correlation with tumor cells (Heimburg-Molinaro, J. et al., Cancer vaccines and carbohydrate epitopes. Vaccine. 2011 Nov. 8; 29(48):8802-26). These are referred to herein as "tumor-associated carbohydrate antigens" or "TACAs." TACAs include, but are not limited to mucin-related antigens [including, but not limited to Tn, Sialyl Tn (STn) and Thomsen-Friedenreich antigen], blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids comprising sialic acid], ganglioside-related antigens [including, but not limited to gangliosides GD2, GD3, GM2, fucosyl GM1 and Neu5GcGM3] and polysialic acid-related antigens. Many of such antigens are described in International Patent Application No. PCT/US2011/021387, the contents of which are herein incorporated by reference in their entirety.

In some embodiments, TACA targets of the present invention include Lewis blood group antigens. Lewis blood group antigens comprise a fucose residue linked to GlcNAc by an α1-3 linkage or an α1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, TACA targets of the present invention comprise Le$^Y$. Le$^Y$ (also known as CD174) is made up of Galβ1,4GlcNAC comprising α1,2- as well as α1,3-linked fucose residues yielding the Fucα(1,2)Galβ(1,4)Fucα(1,3) GlcNAc epitope. It is synthesized from the H antigen by α1,3 fucosyltransferases which attach the α1,3 fucose to the GlcNAc residue of the parent chain. Le$^Y$ may be expressed in a variety of cancers including, but not limited to ovarian, breast, prostate, colon, lung, and epithelial. Due to its low expression level in normal tissues and elevated expression level in many cancers, the Le$^Y$ antigen is an attractive target for therapeutic antibodies.

In some embodiments, TACA targets of the present invention comprise Le$^X$. Le$^X$ comprises the epitope Galβ1-4 (Fucα1-3)GlcNAcβ-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, TACA targets of the present invention comprise SLe$^A$ and/or SLe$^X$. SLe$^A$ and SLe$^X$ comprise the structures [Neu5Acα2-3Galβ1-3(Fucα1-4)GlcNAcβ-R] and [Neu5Acα2-3Galβ1-4(Fucα1-3)GlcNAcβ-R] respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets comprise Neu5Gc (referred to herein as GcSLe$^A$ and GcSLe$^X$, respectively).

In some cases, cancer-related targets of the invention may include mucins. Ishida et al demonstrate that interaction of MUC2 with dendritic cells (with anti-tumor activity) leads to dendritic cell apoptosis (Ishida, A. et al., 2008. Proteomics. 8: 3342-9, the contents of which are herein incorporated by reference in their entirety). In some aspects, the present invention provided anti-mucin antibodies to prevent dendritic cell apoptosis and support anti-tumor activity.

In some embodiments, TACA targets of the present invention comprise glycolipids and/or epitopes present on glycolipids, including, but not limited to glycosphingolipids. Glycosphingolipids comprise the lipid ceramide linked to a glycan by the ceramide hydroxyl group. On the cell membrane, glycosphingolipids form clusters referred to as "lipid rafts".

In some embodiments, TACA targets of the present invention comprise Globo H. Globo H is a cancer-related glycosphingolipid first identified in breast cancer cells. The glycan portion of Globo H comprises Fucα(1-2)Galβ(1-3) GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, cancer-related glycosphingolipid targets of the present invention include gangliosides. Gangliosides are glycosphingolipids comprising sialic acid. According to ganglioside nomenclature, G is used as an abbreviation for ganglioside. This abbreviation is followed by the letters M, D or T referring to the number of sialic acid residues attached (1, 2 or 3 respectively). Finally the numbers 1, 2 or 3 are used to refer to the order of the distance each migrates when analyzed by thin layer chromatography (wherein 3 travels the greatest distance, followed by 2 and then 1). Gangliosides are known to be involved in cancer-related growth and metastasis and are expressed on the cell surface of tumor cells. Gangliosides expressed on tumor cells include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. GD3 associated with some tumor cells may comprise 9-O-acetylated sialic acid residues (Mukherjee, K. et al., 2008. J Cell Biochem. 105: 724-34 and Mukherjee, K. et al., 2009. Biol Chem. 390: 325-35, the contents of each of which are herein incorporated by reference in their entirety). In some cases, antibodies of the invention are selective for 9-O-acetylated sialic acid residues. Some antibodies may be specific for 9-O-acetylated GD3s. Such antibodies may be used to target tumor cells expressing 9-O-acetylated GD3. In some embodiments of the present invention, glycan interacting antibodies are directed toward GM2. In some embodiments, GM2-directed antibodies are used to modulate cell to cell contact. In some embodiments, ganglioside targets of the present invention comprise Neu5Gc. In some embodiments, such targets may include a GM3 variant comprising Neu5Gc (referred to herein as GcGM3). The glycan component of GcGM3 is Neu5Gcα2-3Galβ1-4Glc. GcGM3 is a known component of tumor cells (Casadesus, A. V. et al., 2013. Glycoconj J. 30(7):687-99, the contents of which are herein incorporated by reference in their entirety).

In some embodiments, tumor-associated carbohydrate antigens of the present invention comprise Neu5Gc.

Immunogenic Hosts

In some embodiments, glycan-interacting antibodies of the present invention may be developed through the use of non-human animals as hosts for immunization, referred to herein as "immunogenic hosts". In some embodiments, immunogenic hosts are mammals. In some embodiments, immunogenic hosts are transgenic knockout mice. Antigens comprising target sites and/or epitope targets of glycan-interacting antibodies may be used to contact immunogenic hosts in order to stimulate an immune response and produce antibodies in the immunogenic host that specifically bind the target sites and/or epitope targets present on the antigens introduced.

According to some methods of the present invention, the development of anti-STn antibodies may comprise immunizing mice that have had the Cmah gene disrupted. Such mutations may result in more human-like physiology in that Neu5Gc, the immunogenic, non-human form of sialic acid, is no longer produced in such mice. Also provided is a $Cmah^{-/-}$ myeloma cell for producing a hybridoma that is free of Neu5Gc expression, for production of a GcSTn monoclonal antibody either by reducing the amount of recoverable anti-GcSTn or the hybridoma will begin to die due to antibody binding back to the hybridoma. Other genes can be knocked out in the background of $Cmah^{-/-}$ myeloma cells. For example, the alpha1,3-galactosyltransferase gene, which encodes an enzyme critical for the formation of an epitope highly-immunogenic to humans (Chung, C. H. et al., Cetuximab-induced anaphylaxis and IgE specific for galactose-alpha-1,3-galactose. N Engl J Med. 2008 Mar. 13; 358(11):1109-17), can be knocked out in the background of $Cmah^{-/-}$ myeloma cells.

According to other methods of the present invention, wild type mice may be used for immunization. Such methods may sometimes be favorable for the production of antibodies that interact with AcSTn or pan-STn epitopes. In some cases, immune responses in wild type mice may be more robust.

Antibodies produced through immunization may be isolated from serum of the immunogenic hosts. Antibody producing cells from the immunogenic hosts may also be used to generate cell lines that produce the desired antibody. In some embodiments, screening for antibodies and/or antibody producing cells from the immunogenic host may be carried out through the use of enzyme-linked immunosorbent assays (ELISAs) and/or glycan arrays.

Adjuvants

Immunization of immunogenic hosts with antigens described herein may comprise the use of one or more adjuvants. Adjuvants may be used to elicit a higher immune response in such immunogenic hosts. As such, adjuvants used according to the present invention may be selected based on their ability to affect antibody titers.

In some embodiments, water-in-oil emulsions may be useful as adjuvants. Water-in-oil emulsions may act by forming mobile antigen depots, facilitating slow antigen release and enhancing antigen presentation to immune components. Freund's adjuvant may be used as complete Freund's adjuvant (CFA), which comprises mycobacterial particles that have been dried and inactivated, or as incomplete Freund's adjuvant (IFA), lacking such particles. Other water-in-oil-based adjuvants may include EMULSIGEN® (MVP Technologies, Omaha, Nebr.). EMULSIGEN® comprises micron sized oil droplets that are free from animal-based components. It may be used alone or in combination with other adjuvants, including, but not limited to aluminum hydroxide and CARBIGEN™ (MVP Technologies, Omaha, Nebr.).

In some embodiments, TITERMAX® adjuvant may be used. TITERMAX® is another water-in-oil emulsion comprising squalene as well as sorbitan monooleate 80 (as an emulsifier) and other components. In some cases, TITERMAX® may provide higher immune responses, but with decreased toxicity toward immunogenic hosts.

Immunostimmulatory oligonucleotides may also be used as adjuvants. Such adjuvants may include CpG oligodeoxynucleotide (ODN). CpG ODNs are recognized by Toll-like receptor 9 (TLR9) leading to strong immunostimulatory effects. Type C CpG ODNs induce strong IFN-α production from plasmacytoid dendritic cell (pDC) and B cell stimulation as well as IFN-γ production from T-helper ($T_H$) cells. CpG ODN adjuvant has been shown to significantly enhance pneumococcal polysaccharide (19F and type 6B)-specific IgG2a and IgG3 in mice. CpG ODN also enhanced antibody responses to the protein carrier CRM197, particularly CRM197-specific IgG2a and IgG3 (Chu et al., Infection Immunity 2000, vol 68(3):1450-6). Additionally, immunization of aged mice with pneumococcal capsular polysaccharide serotype 14 (PPS14) combined with a CpG-ODN restored IgG anti-PPS14 responses to young adult levels (Sen et al., Infection Immunity, 2006, 74(3):2177-86). CpG ODNs used according to the present invention may include class A, B or C ODNs. In some embodiments, ODNs may include any of those available commercially, such as ODN-1585, ODN-1668, ODN-1826, ODN-2006, ODN-2007, ODN-2216, ODN-2336, ODN-2395 and/or ODN-M362, each of which may be purchased, for example, from InvivoGen, (San Diego, Calif.). In some cases, ODN-2395 may be used. ODN-2395 is a class C CpG ODN that specifically stimulated human as well as mouse TLR9. These ODNs comprise phosphorothioate backbones and CpG palindromic motifs.

In some embodiments, immune stimulating complexes (ISCOMs) may be used as adjuvants. ISCOMs are spherical open cage-like structures (typically 40 nm in diameter) that are spontaneously formed when mixing together cholesterol, phospholipids and Quillaia saponins under a specific stoichiometry. ISCOM technology is proven for a huge variety of antigens from large glycoproteins such as gp340 from Epstein-Barr virus (a 340 kDa antigen consisting of 80% carbohydrates) down to carrier-conjugated synthetic peptides and small haptens such as biotin. Some ISCOMs are capable of generating a balanced immune response with both $T_{H1}$ and $T_{H2}$ characteristics. Immune response to ISCOMs is initiated in draining lymph nodes, but is efficiently relocated to the spleen, which makes it particularly suitable for generating monoclonal antibodies as well. In some embodiments, the ISCOM adjuvant AbISCO-100 (Isconova, Uppsala, Sweden) may be used. AbISCO-100 is a saponin-based adjuvant specifically developed for use in immunogenic hosts, such as mice, that may be sensitive to other saponins.

According to embodiments of the present invention, adjuvant components of immunization solutions may be varied in order to achieve desired results. Such results may include modulating the overall level of immune response and/or level of toxicity in immunogenic hosts.

Antibody Sequence and Structural Analysis and Optimization

In some embodiments, antibodies of the present invention may be subjected to sequence analysis and/or structural analysis wherein they are analyzed for characteristics that may affect affinity, specificity, protein folding, stability, manufacturing, expression, and/or immunogenicity (i.e., immune reactions in subjects being treated with such antibodies). Such analysis may include comparisons between antibodies binding to the same or similar epitopes.

Antibodies sequences of antibodies binding to the same epitope may be analyzed for variation in light and/or heavy chain sequences. Such analysis may include germline sequences and/or CDR sequences. Information obtained from such analysis may be used to identify (and optionally to modify, delete, replace or repair) conserved amino acid residues; conserved segments of amino acids; amino acid positions with conserved side chain characteristics; conserved CDR lengths; and other features conserved among antibodies binding to the same epitope. This information may be used to design variants or to inform antibody optimization procedures to improve antibody affinity, specificity, protein folding, stability, manufacturing, expression and/or immunogenicity.

Sequence analysis may include aligning two or more antibodies that bind to the same or similar epitopes to identify similarities. Such analysis may compare the sequence and/or length of antibody regions (e.g., CDRs, variable domains, germline segments). Amino acid insertions, amino acid deletions, and substitutions may be identified and assessed. Sequence differences may be compared against antibody affinity and/or specificity.

In some cases, sequence analyses are conducted to identify (and optionally to modify, delete, replace or repair) one or more of unpaired cysteines or irregular disulfides; glycosylation sites (e.g., N-linked NXS/T sites); acid cleavage sites, amino acid oxidation sites, conformity with mouse germline sequences; asparagine deamidation sites; aspartate isomerization sites; N-terminal pyroglutamate formation sites; and aggregation-prone patches in CDRs.

In some cases, the present invention provides sequence analysis-informed variants of antibodies presented herein. As used herein, the term "sequence analysis-informed variant" refers to an antibody variant that has been modified based on one or more conclusions derived from antibody sequence analysis. In some cases, antibodies of the invention may be modified to produce antibody variants comprising modifications to one or more of antibody affinity, specificity, protein folding, stability, manufacturing, expression and/or immunogenicity.

Some sequence analysis-informed variants comprise one or more CDR length modification. CDR length modified antibodies may comprise one or more added or deleted amino acids in one or more CDRs relative to an original antibody sequence. In some cases, sequence analysis-informed variants may comprise a substitution of one or more CDRs with one or more CDRs derived from another antibody (e.g., an antibody binding to the same or similar epitope). In some cases, sequence analysis-informed variants may comprise a substitution of a heavy or light chain variable domain from another antibody (e.g., an antibody binding to the same or similar epitope). Sequence analysis-informed variants may comprise modifications to one or more germline genes that the antibody is expressed from. Such modifications may include point mutations, regional mutations, insertional mutations or deletional mutations. In some case, germline gene modifications are carried out to move CDRs from one known germline gene to another. Sequence analysis-informed variants may include other variants described herein, including, but not limited to scFvs, monobodies, diabodies, intrabodies, CARs, antibody mimetics, etc.

In some embodiments, sequence and/or structural analysis may be used to inform the construction of antibody fragment display libraries (including, but not limited to scFv libraries, phage display libraries, and yeast display libraries). In one example, sequence alignment may be carried out to align two or more antibodies with a common antigen or epitope and amino acid residues may be identified that are conserved among the aligned antibodies or that are variable among the aligned antibodies. In such cases, antibody fragment display libraries may be constructed such that variability among library members is primarily limited to the variable amino acids identified in the sequence analysis. In some cases, such libraries may be used to identify variants with altered affinity and/or specificity for a target antigen (e.g., STn) or a specific epitope of the target antigen (e.g., the epitopes recognized by Group 1, 2, 3 and 4 antibodies as described in Example 1, hereinbelow).

In some embodiments, antibodies of the invention may be modified to remove, replace or otherwise eliminate one or more unpaired cysteine residues. In some cases, unpaired cysteine residues may be reactive and in some cases may affect antibody affinity and/or specificity. Accordingly, some antibodies of the invention have been modified to eliminate unpaired cysteine residues. In some cases, such variants may have modified epitope specificity and/or affinity. In some cases, modification of unpaired cysteine residues may alter antibody folding. In some cases, these variants comprise a substitution or deletion of one or more cysteine residues. In some cases, these variants comprise one or more additional amino acid residues (including, but not limited to, the addition of one or more cysteine residues) to prevent or reduce undesired effects from unpaired cysteine residues. In some cases, cysteine residues are replaced with an amino acid having a hydrophobic side chain (e.g., tyrosine, alanine, valine, isoleucine, leucine, methionine, phenylalanine or tryptophan).

Antibody Testing and Characterization

Antibodies described herein may be tested and/or characterized using a variety of methods. Such methods may be used to determine a variety of characteristics that may include, but are not limited to, antibody affinity; specificity; and activity (e.g., activation or inhibition of cellular signaling pathways or other cellular or biological activities).

Cell-Based Assays

In some embodiments, antibodies of the present invention may be tested or characterized through the use of one or more cell-based assays. Such cell-based assays may be carried out in vitro with cells in culture. In some cases, cell-based assays may be carried out in vivo. Examples of cell-based in vivo assays include tumor models in which tumor cells are injected or otherwise introduced into a host.

In some cases, cells used in cell-based assays may express one or more target glycans recognized by one or more antibodies of the invention. Such glycans may be naturally expressed by such cells or, alternatively, cells may be induced to express one or more glycans desired for purposes of a particular assay. Induced expression may be through one or more treatments that upregulate expression of glycosylated proteins or enzymes that regulate glycosylation. In some embodiments, induced expression may include transfection, transduction, or other form of introduction of one or more genes or transcripts for the endogenous expression of one or more glycosylated proteins or enzymes involved in regulation of glycosylation.

In some cases, cell-based assays used herein may include the use of cancer cells. Many cancer cell lines are available for experiments to test antibodies of the invention. Such cells may express target glycan or may be induced to express target glycans. Additionally, cancer cell lines may be used to test antibodies of the invention, where the cancer cell lines are representative of cancer stem cells. Cancer stem cell (CSC) cell lines may be isolated or differentiated from cancer cells grown in culture (e.g., through sorting based on markers specific for cancer stem cells).

In some embodiments, ovarian cancer cell lines may be used. Such cell lines may include, but are not limited to SKOV3, OVCAR3, OV90 and A2870 cell lines. In some cases, CSC cells may be isolated from these cell lines by isolating cells expressing CD44 and/or CD133 cell markers.

OVCAR3 cells were first established using malignant ascites obtained from a patient suffering from progressive ovarian adenocarcinoma (Hamilton, T. C. et al., 1983. Cancer Res. 43: 5379-89). Cancer stem cell populations may be isolated from OVCAR3 cell cultures through selection based on specific cell surface markers such as CD44 (involved in cell adhesion and migration), CD133 and CD117 (Liang, D. et al., 2012. BMC Cancer. 12: 201, the contents of which are herein incorporated by reference in their entirety). OV90 cells are epithelial ovarian cancer cells that were similarly derived from human ascites (see U.S. Pat. No. 5,710,038). OV-90 cells may also express CD44 when activated (Meunier, L. et al., 2010. Transl Oncol. 3(4): 230-8).

In some embodiments, cell lines derived from gastric cancers may be used. Such cell lines may include, but are not limited to SNU-16 cells (see description in Park J. G. et al., 1990. Cancer Res. 50: 2773-80, the contents of which are herein incorporated by reference in their entirety). SNU-16 cells express STn naturally, but at low levels.

Glycan Arrays

In some embodiments, glycan-interacting antibodies of the present invention may be developed through the use of glycan arrays. As used herein, the term "glycan array" refers to a tool used to identify agents that interact with any of a number of different glycans linked to the array substrate. In some embodiments, glycan arrays comprise a number of chemically-synthesized glycans, referred to herein as "glycan probes". In some embodiments, glycan arrays comprise at least 2, at least 5, at least 10, at least 20, at least 30, at least 40, at least 50, at least 60, at least 70, at least 80, at least 90, at least 100, at least 150, at least 350, at least 1000 or at least 1500 glycan probes. In some embodiments, glycan arrays may be customized to present a desired set of glycan probes. In some embodiments, glycan probes may be attached to the array substrate by a linker molecule. Such linkers may comprise molecules including, but not limited to —$O(CH_2)_2CH_2)NH_2$ and $O(CH_2)_3NHCOCH_2(OCH_2CH_2)_6NH_2$.

In some embodiments, a glycan array has more than 70 chemically-synthesized glycans, most of which are presented as Neu5Ac and Neu5Gc-containing glycan pairs. Some examples of glycan probes may include: Neu5Ac-α-2-6-GalNAc (AcSTn); Neu5Gc-α-2-6-GalNAc (GcSTn); Neu5,9Ac2-α-2,6-GalNAc; Neu9Ac5Gc-α-2,6-GalNAc, and GalNAc (Tn). The antibody binding specificity to AcSTn vs. GcSTn can be determined using the array or other methods of determining specificity known in the art. In addition, the binding profile of antibodies to O-acetylated STn can be determined. The loss of O-acetylation on STn is relevant to cancer as cancer-associated expression correlates with increased STn recognition by antibodies (Ogata, S. et al., Tumor-associated sialylated antigens are constitutively expressed in normal human colonic mucosa. Cancer Res. 1995 May 1; 55(9):1869-74). In some cases, glycan arrays may be used to determine recognition of STn vs. Tn.

Antibody Fragment Display Library Screening Techniques

In some embodiments, antibodies of the present invention may be produced and/or optimized using high throughput methods of discovery. Such methods may include any of the display techniques (e.g. display library screening techniques) disclosed in International Patent Application No. WO2014074532, the contents of which are herein incorporated by reference in their entirety. In some embodiments, synthetic antibodies may be designed, selected or optimized by screening target antigens using display technologies (e.g. phage display technologies). Phage display libraries may comprise millions to billions of phage particles, each expressing unique antibody fragments on their viral coats. Such libraries may provide richly diverse resources that may be used to select potentially hundreds of antibody fragments with diverse levels of affinity for one or more antigens of interest (McCafferty, et al., 1990. Nature. 348:552-4; Edwards, B. M. et al., 2003. JMB. 334: 103-18; Schofield, D. et al., 2007. Genome Biol. 8, R254 and Pershad, K. et al., 2010. Protein Engineering Design and Selection. 23:279-88; the contents of each of which are herein incorporated by reference in their entirety). Often, the antibody fragments present in such libraries comprise scFv antibody fragments, comprising a fusion protein of $V_H$ and $V_L$ antibody domains joined by a flexible linker. In some cases, scFvs may contain the same sequence with the exception of unique sequences encoding variable loops of the complementarity determining regions (CDRs). In some cases, scFvs are expressed as fusion proteins, linked to viral coat proteins (e.g. the N-terminus of the viral pIII coat protein). $V_L$ chains may be expressed separately for assembly with $V_H$ chains in the periplasm prior to complex incorporation into viral coats. Precipitated library members may be sequenced from the bound phage to obtain cDNA encoding desired scFvs. Such sequences may be directly incorporated into antibody sequences for recombinant antibody production, or mutated and utilized for further optimization through in vitro affinity maturation.

Development of Cytotoxic Antibodies

In some embodiments, antibodies of the present invention may be capable of inducing antibody-dependent cell-mediated cytotoxicity (ADCC) and/or antibody-dependent cell phagocytosis (ADCP). ADCC is an immune mechanism whereby cells are lysed as a result of immune cell attack. Such immune cells may include CD56+ cells, CD3-natural killer (NK) cells, monocytes and neutrophils (Strohl, W. R. Therapeutic Antibody Engineering. Woodhead Publishing, Philadelphia Pa. 2012. Ch. 8, p 186, the contents of which are herein incorporated by reference in their entirety).

In some cases, antibodies of the present invention may be engineered to comprise a given isotype depending on whether or not ADCC or ADCP is desired upon antibody binding. Such antibodies, for example, may be engineered according to any of the methods disclosed by Alderson, K. L. et al., J Biomed Biotechnol. 2011. 2011:379123). In the case of mouse antibodies, different isotypes of antibodies are more effective at promoting ADCC. IgG2a, for example, is more effective at inducing ADCC than is IgG2b. Some antibodies of the present invention, comprising mouse IgG2b antibodies may be reengineered to comprise IgG2a antibodies. Such reengineered antibodies may be more effective at inducing ADCC upon binding cell-associated antigens.

In some embodiments, genes encoding variable regions of antibodies developed according to methods of the present invention may be cloned into mammalian expression vectors encoding human Fc regions. Such Fc regions may comprise Fc regions from human IgG1κ. IgG1κ Fc regions may comprise amino acid mutations known to enhance Fc-receptor binding and antibody-dependent cell-mediated cytotoxicity (ADCC).

In some embodiments, antibodies of the invention may be developed for antibody-drug conjugate (ADC) therapeutic applications. ADCs are antibodies in which one or more cargo (e.g. therapeutic agents or cytotoxic agents) are attached [e.g. directly or via linker (e.g. a cleavable linker or a non-cleavable linker)]. ADCs are useful for delivery of such therapeutic agents or cytotoxic agents to one or more target cells or tissues (Panowski, S. et al., 2014. mAbs 6:1, 34-45). In some cases, ADCs may be designed to bind to a surface antigen on a targeted cell. Upon binding, the entire antibody-antigen complex may be internalized and directed to a cellular lysosome. ADCs may then be degraded, releasing the bound cargo. Where the cargo is a cytotoxic agent, the target cell will be killed or otherwise disabled. Cytotoxic agents may include, but are not limited to cytoskeletal inhibitors [e.g. tubulin polymerization inhibitors such as maytansines or auristatins (e.g. monomethyl auristatin E [MMAE] and monomethyl auristatin F [MMAF])] and DNA damaging agents (e.g. DNA polymerization inhibitors such as calcheamicins and duocarmycins).

In some embodiments, antibodies of the invention may be tested for their ability to promote cell death when developed as ADCs. Cell viability assays may be performed in the presence and absence of secondary antibody-drug conjugates. Antibodies with potent cell growth inhibition may then be used to design direct antibody-drug conjugates (ADCs). The use of such secondary antibody-drug conjugates in cell-based cytotoxic assays may allow for quick pre-screening of many ADC candidates. Based on such assays, an unconjugated antibody candidate is directly added to cells in the presence of a secondary antibody that is conjugated to one or more cytotoxic agents (referred to herein as a 2° ADC). Internalization of the antibody/2° ADC complex into cells that express a high density of the targeted antigen can achieve a dose-dependent drug release within the cells, causing a cytotoxic effect to kill the cells (e.g., tumor cells), while cells expressing a low density of the targeted antigen are not affected (e.g., normal cells).

ADCs of the invention may be designed to target cancer cells. Such ADCs may comprise antibodies directed to one or more tumor-associated carbohydrate antigen (TACA). In some cases, ADCs of the invention comprise anti-STn antibodies.

Development of Chimeric Antigen Receptors

In some embodiments, antibody sequences of the invention may be used to develop a chimeric antigen receptor (CAR). CARs are transmembrane receptors expressed on immune cells that facilitate recognition and killing of target cells (e.g. tumor cells). CARs typically comprise three basic parts. These include an ectodomain (also known as the recognition domain), a transmembrane domain and an intracellular (signaling) domain. Ectodomains facilitate binding to cellular antigens on target cells, while intracellular domains typically comprise cell signaling functions to promote the killing of bound target cells. Further, they may have an extracellular domain with one or more antibody variable domains described herein or fragments thereof. CARs of the invention also include a transmembrane domain and cytoplasmic tail. CARs may be designed to include one or more segments of an antibody, antibody variable domain and/or antibody CDR, such that when such CARs are expressed on immune effector cells, the immune effector cells bind and clear any cells that are recognized by the antibody portions of the CARs.

Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

CARs engineered to target tumors may have specificity for one or more tumor associated carbohydrate antigens (TACAs). In some embodiments, ectodomains of these CARs may comprise one or more antibody variable domains or a fragment thereof. In some embodiments, CARs are expressed in T cells, and may be referred to as "CAR-engineered T cells" or "CAR-Ts". CAR-Ts may be engineered with CAR ectodomains having one or more antibody variable domains.

Structural Features of Chimeric Antigen Receptors

With gene-transfer technology, T cells can be engineered to stably express antibodies on their surface, conferring a desired antigen specificity. Chimeric antigen receptors (CARs) combine an antigen-recognition domain of a specific antibody with an intracellular domain of the CD3-zeta chain or FcγRI protein having T cell activating properties into a single chimeric fusion protein. CAR technology provides MHC-unrestricted recognition of target cells by T cells. Removal of the MHC restriction of T cells facilitates the use of these molecules in any patient, and also, in both $CD8^+$ and $CD4^+$ T cells, usually restricted to MHC class I or II epitopes, respectively. The use of Ab-binding regions allows T cells to respond to epitopes formed not only by protein, but also carbohydrate and lipid. This chimeric receptor approach is especially suited to immunotherapy of cancer, being able to bypass many of the mechanisms by which tumors avoid immunorecognition, such as MHC down-regulation, lack of expression of costimulatory molecules, CTL resistance, and induction of T cell suppression, and where the use of both $CD8^+$ CTL and $CD4^+$ T cells are best combined for optimum antitumor efficacy. This approach has been demonstrated to be applicable to a wide range of tumor antigens, in addition to viruses such as HIV (Finney, et al., J. Immunology, 2004, 172:104-113).

Although chimeric antigen receptors can trigger T-cell activation in a manner similar to that of endogenous T-cell receptors, in practice, the clinical application of CAR technology has been impeded by inadequate in vivo expansion of chimeric antigen receptor T cells. For example, first generation CARs included as their signaling domain the cytoplasmic region of the CD3 or Fc receptor γ chain. These first generation CARs were tested in phase I clinical studies in patients with ovarian cancer, renal cancer, lymphoma, and neuroblastoma, and were found to induce modest responses, effectively redirecting T cell cytotoxicity but failing to enable T cell proliferation and survival upon repeated antigen exposure. The prototypes for second generation CARs involved receptors encompassing both CD28 and CD3, and second generation CARs have been tested for treatment of B cell malignancies and other cancers (Sadelain, et al., (2009) Current Opinion in Immunology, 21(2):215-223). Thus, CARs have rapidly expanded into a diverse array of receptors with different functional properties.

More recently, it was discovered that CAR-mediated T-cell responses can be enhanced with the addition of a costimulatory domain. In preclinical models, the inclusion of the CD137 (4-1BB) signaling domain was found to significantly increase antitumor activity and in vivo persistence of chimeric antigen receptors as compared with inclusion of the CD3-zeta chain alone (Porter, et al., N. Engl. J. Med. 2011, 365:725-733).

Thus, in some embodiments of the present disclosure, antibody sequences of the invention may be used to develop a chimeric antigen receptor (CAR). In some embodiments, CARs are transmembrane receptors expressed on immune cells that facilitate recognition and killing of target cells (e.g. tumor cells).

In many cancers, tumor-specific antigens for targeting have not been defined, but in B-cell neoplasms, CD19 is an attractive target. Expression of CD19 is restricted to normal and malignant B cells and B-cell precursors. A pilot clinical trial of treatment with autologous T cells expressing an anti-CD19 chimeric antigen receptor (CART19) was performed in patients with advanced, p53-deficient chronic lymphoid leukemia (CLL). The generation of a CD19-specific immune response in bone marrow was demonstrated by temporal release of cytokines and ablation of leukemia cells that coincided with peak infiltration of chimeric antigen receptor T cells. (Porter, et al., N. Engl. J. Med. 2011, 365:725-733).

Further structural features of CARs may include any of those disclosed in several PCT Publications assigned to City of Hope and having the common inventor Michael Jensen. For example, PCT Publication WO 00/23573 describes genetically engineered, CD20-specific redirected T cells expressing a cell surface protein having an extracellular domain comprising a receptor specific for CD20, an intracellular signaling domain, and a transmembrane domain. Use of such cells for cellular immunotherapy of $CD20^+$ malignancies and for abrogating any untoward B cell function. In one embodiment, the cell surface protein is a single chain FvFc:ζ receptor where Fv designates the VH and VL chains of a single chain monoclonal antibody to CD20 linked by peptide, Fc represents a hinge-CH2-CH3 region of a human IgG1, and ζ represents the intracellular signaling domain of the zeta chain of human CD3. A method of making a redirected T cell expressing a chimeric T cell receptor by electroporation using naked DNA encoding the receptor. Similarly, PCT Publication WO 02/077029 describes genetically engineered, CD19-specific redirected immune cells expressing a cell surface protein having an extracellular domain comprising a receptor which is specific for CD19, an intracellular signaling domain, and a transmembrane domain. Use of such cells for cellular immunotherapy of $CD19^+$ malignancies and for abrogating any untoward B cell function. In one embodiment, the immune cell is a T cell and the cell surface protein is a single chain svFvFc:ζ receptor where scFv designates the VH and VL chains of a single chain monoclonal antibody to CD19, Fc represents at least part of a constant region of an IgG1, and zeta represents the intracellular signaling domain of the T cell antigen receptor complex zeta chain (zeta chain of human CD3). The extracellular domain scFvFc and the intracellular domain zeta are linked by a transmembrane domain such as the transmembrane domain of CD4. A method of making a redirected T cell expressing a chimeric T cell receptor by electroporation using naked DNA encoding the receptor. These chimeric antigen receptors have the ability, when expressed in T cells, to redirect antigen recognition based on the monoclonal antibody's specificity. The design of scFvFc: receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen positive tumors. City of Hope PCT Publications WO 02/088334, WO 2007/059298 and WO 2010/065818 describe "zetakines" comprised of an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those specific cells expressing a receptor for which the soluble receptor ligand is specific.

Additional features of CARs may include any of those disclosed in two PCT Publications assigned to University of Texas and having a common inventor Lawrence Cooper. PCT Publication No. WO 2009/091826 describes compositions comprising a human CD19-specific chimeric T cell receptor (or chimeric antigen receptor, CAR) polypeptide (designated hCD19CAR) comprising an intracellular signaling domain, a transmembrane domain and an extracellular domain, the extracellular domain comprising a human CD 19 binding region. In another aspect, the CD 19 binding region is an F(ab')2, Fab', Fab, Fv or scFv. The intracellular domain may comprise an intracellular signaling domain of human CD3 and may further comprise human CD28 intracellular segment. In certain aspects the transmembrane domain is a CD28 transmembrane domain. PCT Publication No. WO 2013/074916 describes methods and compositions for immunotherapy employing $CAR^+$ T cells genetically modified to eliminate expression of T cell receptor and/or HLA. In particular embodiments, the T cell receptor-negative and/or HLA-negative T cells are generated using zinc finger nucleases, for example. The $CAR^+$ T cells from allogeneic healthy donors can be administered to any patient without causing graft versus host disease (GVHD), acting as universal reagents for off-the-shelf treatment of medical conditions such as cancer, autoimmunity, and infection.

PCT Publication WO 2011/041093 assigned to the U.S. Department of Health and Human Services describes anti-vascular endothelial growth factor receptor-2 chimeric antigen receptors comprising an antigen binding domain of a KDR-1121 or DC101 antibody, an extracellular hinge domain, a T cell receptor transmembrane domain, and an intracellular T cell receptor signaling domain, and their use in the treatment of cancer.

PCT Publications WO 2012/079000 and WO 2013/040557, the contents of each of which are herein incorporated by reference in their entirety, are assigned to University of Pennsylvania and share the common inventor Carl H. June; these publications describe CARs comprising an antigen binding domain, a transmembrane domain, a costimulatory signaling region, and a CD3 zeta signaling domain, and methods for generating RNA Chimeric Antigen Receptor (CAR) transfected T cells, respectively.

PCT Publication WO2013/126712, also assigned to University of Pennsylvania and sharing the common inventor Carl H. June, describes compositions and methods for generating a persisting population of T cells exhibiting prolonged exponential expansion in culture that is ligand independent and independent of the addition of exogenous cytokines or feeder cells, which are useful for the treatment of cancer. In some embodiments, the antigen binding domain is an anti-cMet binding domain. In some embodiments, the antigen binding domain is an anti-mesothelin binding domain. In some embodiments, the antigen binding domain is an anti-CD 19 binding domain. The hinge domain is IgG4, the transmembrane domain is a CD28 transmembrane domain. In some embodiments, the costimulatory signaling region is a CD28 signaling region. Also provided is a vector comprising a nucleic acid sequence encoding a chimeric antigen receptor (CAR), and the CAR comprising an antigen binding domain, a hinge domain, a transmembrane domain, a costimulatory signaling region, and a CD3 zeta signaling domain.

PCT Publication WO 2014/039513 assigned to University of Pennsylvania describes compositions and methods for inhibiting one or more diacylglycerol kinase (DGK) isoform in a cell in order to enhance the cytolytic activity of the cell. The cells may be used in adoptive T cell transfer in which, the cell is modified to express a chimeric antigen receptor (CAR). Inhibition of DGK in T cells used in adoptive T cell transfer increases cytolytic activity of the T cells and thus may be used in the treatment of a variety of conditions, including cancer, infection, and immune disorders.

PCT Publication WO 2014/055771 assigned to University of Pennsylvania describes compositions and methods for treating ovarian cancer. Specifically, the invention relates to administering a genetically modified T cell having alpha-folate receptor (FR-alpha) binding domain and CD27 costimulatory domain to treat ovarian cancer. In one embodiment, the FR-alpha binding domain is said to be fully human, thereby preventing a host immune response.

In some embodiments, CARs of the invention may be engineered to target tumors. Such CARs may have specificity for one or more TACAs. In some case, ectodomains of these CARs may comprise one or more antibody variable domain presented herein or a fragment thereof. In some embodiments, CARs of the invention are expressed in T cells, referred to herein as "CAR-engineered T cells" or "CAR-Ts". CAR-Ts may be engineered with CAR ectodomains having one or more antibody variable domain presented herein.

Multispecific Antibodies

In some embodiments, antibodies of the present invention may bind more than one epitope. As used herein, the terms "multibody" or "multispecific antibody" refer to an antibody wherein two or more variable regions bind to different epitopes. The epitopes may be on the same or different targets. In certain embodiments, a multi-specific antibody is a "bispecific antibody," which recognizes two different epitopes on the same or different antigens.

Bispecific Antibodies

Bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. One common application for this technology is in cancer immunotherapy, where BsMAbs are engineered to simultaneously bind to a cytotoxic cell (using a receptor like CD3) and a target like a tumor cell to be destroyed.

Bispecific antibodies may include any of those described in Riethmuller, G., 2012. Cancer Immunity 12:12-18; Marvin, J. S. et al., 2005. Acta Pharmacologica Sinica. 26(6): 649-58; and Schaefer, W. et al., 2011. PNAS. 108(27): 11187-92, the contents of each of which are herein incorporated by reference in their entirety.

New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

Of the two paratopes that form the tops of the variable domains of a bispecific antibody, one can be directed against a target antigen and the other against a T-lymphocyte antigen like CD3. In the case of trifunctional antibodies, the Fc region may additionally binds to a cell that expresses Fc receptors, like a macrophage, a natural killer (NK) cell or a dendritic cell. In sum, the targeted cell is connected to one or two cells of the immune system, which subsequently destroy it.

Other types of bispecific antibodies have been designed to overcome certain problems, such as short half-life, immunogenicity and side-effects caused by cytokine liberation. They include chemically linked Fabs, consisting only of the Fab regions, and various types of bivalent and trivalent single-chain variable fragments (scFvs), fusion proteins mimicking the variable domains of two antibodies. The furthest developed of these newer formats are the bi-specific T-cell engagers (BiTEs) and mAb2's, antibodies engineered to contain an Fcab antigen-binding fragment instead of the Fc constant region.

A bispecific, single-chain antibody Fv fragment (Bs-scFv) was successfully used to kill cancer cells. Some human cancers are caused by functional defects in p53 that are restored by gene therapy with wild-type p53. Weisbart, et al., describe the construction and expression of a bispecific single-chain antibody that penetrates living colon cancer cells, binds intracellular p53, and targets and restores its wild type function (Weisbart, et al., Int. J. Oncol. 2004 October; 25(4):1113-8; and Weisbart, et al., Int. J. Oncol. 2004 December; 25(6):1867-73). In these studies, a bispecific, single-chain antibody Fv fragment (Bs-scFv) was constructed from (i) a single-chain Fv fragment of mAb 3E10 that penetrates living cells and localizes in the nucleus, and (ii) a single-chain Fv fragment of a non-penetrating antibody, mAb PAb421 that binds the C-terminal of p53. PAb421 binding restores wild-type functions of some p53 mutants, including those of SW480 human colon cancer cells. The Bs-scFv penetrated SW480 cells and was cytotoxic, suggesting an ability to restore activity to mutant p53. COS-7 cells (monkey kidney cells with wild-type p53) served as a control since they are unresponsive to PAb421 due to the presence of SV40 large T antigen that inhibits binding of PAb421 to p53. Bs-scFv penetrated COS-7 cells but was not cytotoxic, thereby eliminating non-specific toxicity of Bs-scFv unrelated to binding p53. Fv fragments alone were not cytotoxic, indicating that killing was due to transduction of p53. A single mutation in CDR1 of PAb421 VH eliminated binding of the Bs-scFv to p53 and abrogated cytotoxicity for SW480 cells without altering cellular penetration, further supporting the requirement of PAb421 binding to p53 for cytotoxicity (Weisbart, et al., Int. J. Oncol. 2004 October; 25(4):1113-8; and Weisbart, et al., Int. J. Oncol. 2004 December; 25(6):1867-73).

In some embodiments, antibodies of the present invention may be diabodies. Diabodies are functional bispecific single-chain antibodies (bscAb). These bivalent antigen-binding molecules are composed of non-covalent dimers of scFvs, and can be produced in mammalian cells using recombinant methods. (See, e.g., Mack et al, Proc. Natl. Acad. Sci., 92: 7021-7025, 1995). Few diabodies have entered clinical development. An iodine-123-labeled diabody version of the anti-CEA chimeric antibody cT84.66 has been evaluated for pre-surgical immunoscintigraphic detection of colorectal cancer in a study sponsored by the Beckman Research Institute of the City of Hope (Clinicaltrials.gov NCT00647153) (Nelson, A. L., MAbs. 2010. January-February; 2(1):77-83).

Using molecular genetics, two scFvs can be engineered in tandem into a single polypeptide, separated by a linker domain, called a "tandem scFv" (tascFv). TascFvs have been found to be poorly soluble and require refolding when produced in bacteria, or they may be manufactured in mammalian cell culture systems, which avoids refolding requirements but may result in poor yields. Construction of a tascFv with genes for two different scFvs yields a "bispecific single-chain variable fragments" (bis-scFvs). Only two tascFvs have been developed clinically by commercial firms; both are bispecific agents in active early phase development by Micromet for oncologic indications, and are described as "Bispecific T-cell Engagers (BiTE)." Blinatumomab is an anti-CD19/anti-CD3 bispecific tascFv that potentiates T-cell responses to B-cell non-Hodgkin lymphoma in Phase 2. MT110 is an anti-EP-CAM/anti-CD3 bispecific tascFv that potentiates T-cell responses to solid tumors in Phase 1. Bispecific, tetravalent "TandAbs" are also being researched by Aimed (Nelson, A. L., MAbs. 2010. January-February; 2(1):77-83).

Also included are maxibodies (bivalent scFv fused to the amino terminus of the Fc (CH2-CH3 domains) of IgG.

Bispecific T-cell-engager (BiTE) antibodies are designed to transiently engage cytotoxic T-cells for lysis of selected target cells. The clinical activity of BiTE antibodies corroborates findings that ex vivo expanded, autologous T-cells derived from tumor tissue, or transfected with specific T-cell receptors, have shown therapeutic potential in the treatment of solid tumors. While these personalized approaches prove that T-cells alone can have considerable therapeutic activity, even in late-stage cancer, they are cumbersome to perform on a broad basis. This is different for cytotoxic T-lymphocyte antigen 4 (CTLA-4) antibodies, which facilitate generation of tumor-specific T-cell clones, and also for bi- and tri-specific antibodies that directly engage a large proportion of patients' T-cells for cancer cell lysis. The potential of global T-cell engagement for human cancer therapy by T-cell-engaging antibodies is under active investigation (Baeuerle P A, et al., Current Opinion in Molecular Therapeutics. 2009, 11(1):22-30).

Third generation molecules include "miniaturized" antibodies. Among the best examples of mAb miniaturization are the small modular immunopharmaceuticals (SMIPs) from Trubion Pharmaceuticals. These molecules, which can be monovalent or bivalent, are recombinant single-chain molecules containing one $V_L$, one $V_H$ antigen-binding domain, and one or two constant "effector" domains, all connected by linker domains. Presumably, such a molecule might offer the advantages of increased tissue or tumor penetration claimed by fragments while retaining the immune effector functions conferred by constant domains. At least three "miniaturized" SMIPs have entered clinical development. TRU-015, an anti-CD20 SMIP developed in collaboration with Wyeth, is the most advanced project, having progressed to Phase 2 for rheumatoid arthritis (RA). Earlier attempts in systemic lupus erythematosus (SLE) and B cell lymphomas were ultimately discontinued. Trubion and Facet Biotechnology are collaborating in the development of TRU-016, an anti-CD37 SMIP, for the treatment of CLL and other lymphoid neoplasias, a project that has reached Phase 2. Wyeth has licensed the anti-CD20 SMIP SBI-087 for the treatment of autoimmune diseases, including RA, SLE and possibly multiple sclerosis, although these projects remain in the earliest stages of clinical testing. (Nelson, A. L., MAbs. 2010. January-February; 2(1):77-83).

Genmab is researching application of their "Unibody" technology, in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo. This configuration may minimize the risk of immune activation or oncogenic growth, as IgG4 interacts poorly with FcRs and monovalent unibodies fail to promote intracellular signaling complex formation. These contentions are, however, largely supported by laboratory, rather than clinical, evidence. Biotecnol is also developing a "miniaturized" mAb, CAB051, which is a "compacted" 100 kDa anti-HER2 antibody in preclinical research (Nelson, A. L., MAbs. 2010. January-February; 2(1):77-83).

Recombinant therapeutics composed of single antigen-binding domains have also been developed, although they currently account for only 4% of the clinical pipeline. These molecules are extremely small, with molecular weights approximately one-tenth of those observed for full-sized mAbs. Arana and Domantis engineer molecules composed of antigen-binding domains of human immunoglobulin light or heavy chains, although only Arana has a candidate in clinical testing, ART-621, an anti-TNFa molecule in Phase 2 study for the treatment of psoriasis and rheumatoid arthritis. Ablynx produces "nanobodies" derived from the antigen-binding variable heavy chain regions ($V_{HH}$s) of heavy chain antibodies found in camels and llamas, which lack light chains. Two Ablynx anti-von Willebrand Factor nanobodies have advanced to clinical development, including ALX-0081, in Phase 2 development as an intravenous therapy to prevent thrombosis in patients undergoing percutaneous coronary intervention for acute coronary syndrome, and ALX-0681, a Phase 1 molecule for subcutaneous administration intended for both patients with acute coronary syndrome and thrombotic thrombocytopenic purpura (Nelson, A. L., MAbs. 2010. January-February; 2(1):77-83).

Development of Multispecific Antibodies

In some embodiments, antibody sequences of the invention may be used to develop multispecific antibodies (e.g., bispecific, tri specific, or of greater multi specificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tutt, A. et al., Trispecific F(ab)3 derivatives that use cooperative signaling via the TCR/CD3 complex and CD2 to activate and redirect resting cytotoxic T cells. J. Immunol. 1991 Jul. 1; 147(1): 60-9; U.S. Pat. Nos. 4,474,893; 4,714,681; 4,925,648; 5,573,920; 5,601,819; and Kostelny, S. A. et al., Formation of a bispecific antibody by the use of leucine zippers. J. Immunol. 1992 Mar. 1; 148(5):1547-53); U.S. Pat. No. 5,932,448.

Disclosed and claimed in PCT Publication WO2014144573 to Memorial Sloan-Kettering Cancer Center are multimerization technologies for making dimeric multispecific binding agents (e.g., fusion proteins comprising antibody components) with improved properties over multispecific binding agents without the capability of dimerization.

Disclosed and claimed in PCT Publication WO2014144357 to Merck Patent GMBH are tetravalent bispecific antibodies (TetBiAbs), and methods of making and methods of using TetBiAbs for diagnostics and for the treatment of cancer or immune disorders. TetBiAbs feature a second pair of Fab fragments with a second antigen specificity attached to the C-terminus of an antibody, thus providing a molecule that is bivalent for each of the two antigen specificities. The tetravalent antibody is produced by genetic engineering methods, by linking an antibody heavy chain covalently to a Fab light chain, which associates with its cognate, co-expressed Fab heavy chain.

Disclosed and claimed in PCT Publication WO2014028560 to IBC Pharmaceuticals, Inc. are T cell redirecting bispecific antibodies (bsAb), with at least one binding site for a T-cell antigen and at least one binding site for an antigen on a diseased cell or pathogen, for treatment of disease. Preferably, this bsAb is an anti-CD3×anti-CD19 bispecific antibody, although antibodies against other T-cell antigens and/or disease-associated antigens may be used. The complex is capable of targeting effector T cells to induce T-cell-mediated cytotoxicity of cells associated with a disease, such as cancer, autoimmune disease or infectious disease. The cytotoxic immune response is enhanced by co-administration of interferon-based agents that comprise interferon-α, interferon-bgr; interferon-λ1, interferon-λ2 or interferon-λ3.

Disclosed and claimed in PCT Publication WO2013092001 to Synimmune GMBH is a bispecific antibody molecule, as well as a method for producing the same, its use and a nucleic acid molecule encoding the bispecific antibody molecule. In particular is provided an antibody molecule that is capable of mediating target cell restricted activation of immune cells.

Disclosed and claimed in PCT Publication WO2012007167 is a multispecific modular antibody specifically binding to at least a glycoepitope and a receptor of the erbB class on the surface of a tumor cell, thereby crosslinking the glycoepitope and the receptor, which antibody has apoptotic activity effecting cytolysis independent of NK cells.

Disclosed and claimed in PCT Publications WO2012048332 and WO2013055404 are meditopes, meditope-binding antibodies, meditope delivery systems, as well as a monoclonal antibody framework binding interface for meditopes, and methods for their use. Specifically, two antibody binding peptides, C-QFDLSTRRLK-C ("cQFD"; sequence identification number 1 therein; SEQ ID NO: 240 herein) and C-QYNLSSRALK-C ("cQYN"; sequence identification number 2 therein; SEQ ID NO: 241 herein) were shown to have novel mAb binding properties. Also called "meditopes," cQFD and cQYN were shown to bind to a region of the Fab framework of the anti-EGFR mAb cetuximab and not to bind the complementarity determining regions (CDRs) that bind antigen. The binding region on the Fab framework is distinct from other framework-binding antigens, such as the superantigens Staphylococcal protein A (SpA) (Graille et al., 2000) and Peptostreptococcus magnus protein L (PpL) (Graille et al., 2001). Accordingly, one embodiment disclosed is a framework binding interface comprising a framework region of a unique murine-human antibody or functional fragment thereof that binds a cyclic meditope.

Exemplary patents and patent publications of interest are: U.S. Pat. Nos. 5,585,089; 5,693,761; and 5,693,762, all filed Jun. 7, 1995 and U.S. Pat. No. 6,180,370, all assigned to Protein Design Labs, Inc., describe methods for producing, and compositions of, humanized immunoglobulins having one or more complementarity determining regions (CDR's) and possible additional amino acids from a donor immunoglobulin and a framework region from an accepting human immunoglobulin. Each humanized immunoglobulin chain is said to usually comprise, in addition to the CDR's, amino acids from the donor immunoglobulin framework that are, e.g., capable of interacting with the CDRs to effect binding affinity, such as one or more amino acids which are immediately adjacent to a CDR in the donor immunoglobulin or those within about 3 Å as predicted by molecular modeling. The heavy and light chains may each be designed by using any one or all of various position criteria. When combined into an intact antibody, the humanized immunoglobulins of the present invention is said to be substantially non-immunogenic in humans and retain substantially the same affinity as the donor immunoglobulin to the antigen, such as a protein or other compound containing an epitope.

U.S. Pat. No. 5,951,983, assigned to Universite Catholique De Louvain and Bio Transplant, Inc., describes a humanized antibody against T-lymphocytes. Framework regions from a human V kappa gene designated as HUM5400 (EMBL accession X55400) and from the human antibody clone Amu 5-3 (GenBank accession number U00562) are set forth therein.

U.S. Pat. No. 5,091,513, to Creative Biomolecules, Inc., describes a family of synthetic proteins having affinity for a preselected antigen. The proteins are characterized by one or more sequences of amino acids constituting a region which behaves as a biosynthetic antibody binding site (BABS). The sites comprise 1) non-covalently associated or disulfide bonded synthetic $V_H$ and $V_L$ dimers, 2) $V_H$-$V_L$ or $V_L$-$V_H$ single chains wherein the $V_H$ and $V_L$ are attached by a polypeptide linker, or 3) individuals $V_H$ or $V_L$ domains. The binding domains comprise linked CDR and FR regions, which may be derived from separate immunoglobulins. The proteins may also include other polypeptide sequences which function, e.g., as an enzyme, toxin, binding site, or site of attachment to an immobilization media or radioactive atom. Methods are disclosed for producing the proteins, for designing BABS having any specificity that can be elicited by in vivo generation of antibody, and for producing analogs thereof.

U.S. Pat. No. 8,399,625, to ESBATech, an Alcon Biomedical Research Unit, LLC, describes antibody acceptor frameworks and methods for grafting non-human antibodies, e.g., rabbit antibodies, using a particularly well suited antibody acceptor framework.

Intrabodies

In some embodiments, antibodies of the present invention may be intrabodies. Intrabodies are a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. In some embodiments, methods described herein include intrabody-based therapies. In some such embodiments, variable domain sequences and/or CDR sequences disclosed herein are incorporated into one or more constructs for intrabody-based therapy. For example, intrabodies may target one or more glycated intracellular proteins or may modulate the interaction between one or more glycated intracellular proteins and an alternative protein.

More than two decades ago, intracellular antibodies against intracellular targets were first described (Biocca, Neuberger and Cattaneo EMBO J. 9: 101-108, 1990). The intracellular expression of intrabodies in different compartments of mammalian cells allows blocking or modulation of the function of endogenous molecules (Biocca, et al., EMBO J. 9: 101-108, 1990; Colby et al., Proc. Natl. Acad. Sci. U.S.A. 101: 17616-21, 2004). Intrabodies can alter protein folding, protein-protein, protein-DNA, protein-RNA interactions and protein modification. They can induce a phenotypic knockout and work as neutralizing agents by direct binding to the target antigen, by diverting its intracellular traffic or by inhibiting its association with binding partners. They have been largely employed as research tools and are emerging as therapeutic molecules for the treatment of human diseases as viral pathologies, cancer and misfolding diseases. The fast growing bio-market of recombinant antibodies provides intrabodies with enhanced binding specificity, stability and solubility, together with lower immunogenicity, for their use in therapy (Biocca, abstract in Antibody Expression and Production Cell Engineering Volume 7, 2011, pp. 179-195).

In some embodiments, intrabodies have advantages over interfering RNA (iRNA); for example, iRNA has been shown to exert multiple non-specific effects, whereas intrabodies have been shown to have high specificity and affinity of to target antigens. Furthermore, as proteins, intrabodies possess a much longer active half-life than iRNA. Thus, when the active half-life of the intracellular target molecule is long, gene silencing through iRNA may be slow to yield an effect, whereas the effects of intrabody expression can be almost instantaneous. Lastly, it is possible to design intrabodies to block certain binding interactions of a particular target molecule, while sparing others.

Development of Intrabodies

Intrabodies are often single chain variable fragments (scFvs) expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies may be produced using methods known in the art, such as those disclosed and reviewed in: (Marasco et al., 1993 Proc. Natl. Acad. Sci. USA, 90: 7889-7893; Chen et al., 1994, Hum. Gene Ther. 5:595-601; Chen et al., 1994, Proc. Natl. Acad. Sci. USA, 91:5932-5936; Maciejewski et al., 1995, Nature Med., 1: 667-673; Marasco, 1995, Immunotech, 1: 1-19; Mhashilkar, et al., 1995, EMBO J. 14: 1542-51; Chen et al., 1996, Hum. Gene Therap., 7: 1515-1525; Marasco, Gene Ther 4:11-15, 1997; Rondon and Marasco, 1997, Annu. Rev. Microbiol. 51:257-283; Cohen, et al., 1998, Oncogene 17:2445-56; Proba et al., 1998, J. Mol. Biol. 275:245-253; Cohen et al., 1998, Oncogene 17:2445-2456; Hassanzadeh, et al., 1998, FEBS Lett. 437:81-6; Richardson et al., 1998, Gene Ther. 5:635-44; Ohage and Steipe, 1999, J Mol. Biol. 291:1119-1128; Ohage et al., 1999, J. Mol. Biol. 291:1129-1134; Wirtz and Steipe, 1999, Protein Sci. 8:2245-2250; Zhu et al., 1999, J. Immunol. Methods 231:207-222; Arafat et al., 2000, Cancer Gene Ther 7:1250-6; der Maur et al., 2002, 1 Biol. Chem. 277:45075-85; Mhashilkar et al., 2002, Gene Ther. 9:307-19; and Wheeler et al., 2003, FASEB J. 17: 1733-5; and references cited therein). In particular, a CCRS intrabody has been produced by Steinberger et al., 2000, Proc. Natl. Acad. Sci. USA 97:805-810). See generally Marasco, W A, 1998, "Intrabodies: Basic Research and Clinical Gene Therapy Applications" Springer:New York; and for a review of scFvs, see Pluckthun in "The Pharmacology of Monoclonal Antibodies," 1994, vol. 113, Rosenburg and Moore eds. Springer-Verlag, New York, pp. 269-315.

In some embodiments, antibody sequences are used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form a single chain antibody comprising the variable domains of the heavy and light chain joined by a flexible linker polypeptide. Intrabodies typically lack disulfide bonds and are capable of modulating the expression or activity of target genes through their specific binding activity. Single chain antibodies can also be expressed as a single chain variable region fragment joined to the light chain constant region.

As is known in the art, an intrabody can be engineered into recombinant polynucleotide vectors to encode subcellular trafficking signals at its N or C terminus to allow expression at high concentrations in the sub-cellular compartments where a target protein is located. For example, intrabodies targeted to the endoplasmic reticulum (ER) are engineered to incorporate a leader peptide and, optionally, a C-terminal ER retention signal, such as the KDEL (SEQ ID NO: 242) amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

There are certain technical challenges with intrabody expression. In particular, protein conformational folding and structural stability of the newly-synthesized intrabody within the cell is affected by reducing conditions of the intracellular environment. In human clinical therapy, there are safety concerns surrounding the application of transfected recombinant DNA, which is used to achieve intrabody expression within the cell. Of particular concern are the various viral-based vectors commonly-used in genetic manipulation. Thus, one approach to circumvent these problems is to fuse protein transduction domains (PTD) to scFv antibodies, to create a 'cell-permeable' antibody or 'Transbody.' Transbodies are cell-permeable antibodies in which a protein transduction domain (PTD) is fused with single chain variable fragment (scFv) antibodies (Heng and Cao, 2005, Med Hypotheses. 64:1105-8).

Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

In one embodiment, intrabodies are used to capture a target in the nucleus, thereby preventing its activity within the nucleus. Nuclear targeting signals are engineered into such intrabodies in order to achieve the desired targeting.

Such intrabodies are designed to bind specifically to a particular target domain. In another embodiment, cytosolic intrabodies that specifically bind to a target protein are used to prevent the target from gaining access to the nucleus, thereby preventing it from exerting any biological activity within the nucleus (e.g., preventing the target from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

Protein transduction domains (PTDs) are short peptide sequences that enable proteins to translocate across the cell membrane and be internalized within the cytosol, through atypical secretory and internalization pathways. There are a number of distinct advantages that a 'Transbody' would possess over conventional intrabodies expressed within the cell. For a start, 'correct' conformational folding and disulfide bond formation can take place prior to introduction into the target cell. More importantly, the use of cell-permeable antibodies or 'Transbodies' would avoid the overwhelming safety and ethical concerns surrounding the direct application of recombinant DNA technology in human clinical therapy, which is required for intrabody expression within the cell. Transbodies' introduced into the cell would possess only a limited active half-life, without resulting in any permanent genetic alteration. This would allay any safety concerns with regards to their application in human clinical therapy (Heng and Cao 2005, Med Hypotheses. 64:1105-8).

Intrabodies are promising therapeutic agents for the treatment of misfolding diseases, including Alzheimer's, Parkinson's, Huntington's and prion diseases, because of their virtually infinite ability to specifically recognize the different conformations of a protein, including pathological isoforms, and because they can be targeted to the potential sites of aggregation (both intra- and extracellular sites). These molecules can work as neutralizing agents against amyloidogenic proteins by preventing their aggregation, and/or as molecular shunters of intracellular traffic by rerouting the protein from its potential aggregation site (Cardinale, and Biocca, Curr. Mol. Med. 2008, 8:2-11).

Exemplary Patent Publications describing intracellular antibodies or intrabodies are set forth hereinbelow, each of which is incorporated by reference in its entirety.

PCT Publication WO03014960 and U.S. Pat. No. 7,608,453 granted to Cattaneo, et al., describe an intracellular antibody capture technology method of identifying at least one consensus sequence for an intracellular antibody (ICS) comprising the steps of: creating a database comprising sequences of validated intracellular antibodies (VIDA database) and aligning the sequences of validated intracellular antibodies according to Kabat; determining the frequency with which a particular amino acid occurs in each of the positions of the aligned antibodies; selecting a frequency threshold value (LP or consensus threshold) in the range from 70% to 100%; identifying the positions of the alignment at which the frequency of a particular amino acid is greater than or equal to the LP value; and identifying the most frequent amino acid, in the position of said alignment.

PCT Publications WO0054057; WO03077945; WO2004046185; WO2004046186; WO2004046187; WO2004046188; WO2004046189; US Patent Application Publications US2005272107; US2005276800; US2005288492; US2010143939; granted U.S. Pat. Nos. 7,569,390 and 7,897,347 and granted European Patents EP1560853; and EP1166121 all assigned to the Medical Research Council and including inventors Cattaneo, et al., describe intracellular intracellular single domain immunoglobulins, and a method for determining the ability of a immunoglobulin single domain to bind to a target in an intracellular environment, as well as methods for generating intracellular antibodies.

PCT Publication WO0235237; US Patent Application Publication 2003235850 and granted European Patent EP1328814 naming Catteneo as an inventor and assigned to S.I.S.S.A. Scuola Internazionale Superiore describe a method for the in vivo identification of epitopes of an intracellular antigen.

PCT Publication WO2004046192 and European Patent EP1565558 assigned to Lay Line Genomics SPA and naming Catteneo as an inventor describe a method for isolating intracellular antibodies that disrupt and neutralize an interaction between a protein ligand x and a protein ligand y inside a cell. Also disclosed are a method to identify a protein ligand x able to bind to a known y ligand using intracellular antibodies able to the interaction between x and y; and a method for the isolation of a set of antibody fragments against a significant proportion of the protein-protein interactions of a given cell (interactome) or against the protein interactions that constitute an intracellular pathway or network.

US Patent Application Publication 2006034834 and PCT Publication WO9914353 entitled "Intrabody-mediated control of immune reactions" and assigned to Dana Farber Cancer Institute Inc. name inventors Marasco and Mhashilkar are directed to methods of altering the regulation of the immune system, e.g., by selectively targeting individual or classes of immunomodulatory receptor molecules (IRMs) on cells comprising transducing the cells with an intracellularly expressed antibody, or intrabody, against the IRMs. In a preferred embodiment the intrabody comprises a single chain antibody against an IRM, e.g, MHC-1 molecules.

PCT Publication WO2013033420 assigned to Dana Farber Cancer Institute Inc. and Whitehead Biomedical Institute, and naming inventors Bradner, Rahl and Young describes methods and compositions useful for inhibiting interaction between a bromodomain protein and an immunoglobulin (Ig) regulatory element and downregulating expression of an oncogene translocated with an Ig locus, as well as for treating a cancer (e.g., hematological malignancy) characterized by increased expression of an oncogene which is translocated with an Ig locus. Intrabodies are generally described.

PCT Publication WO02086096 and US Patent Application Publication 2003104402 entitled "Methods of producing or identifying intrabodies in eukaryotic cells," assigned to University of Rochester Medical Center and naming inventors Zauderer, Wei and Smith describe a high efficiency method of expressing intracellular immunoglobulin molecules and intracellular immunoglobulin libraries in eukaryotic cells using a trimolecular recombination method. Further provided are methods of selecting and screening for intracellular immunoglobulin molecules and fragments thereof, and kits for producing, screening and selecting intracellular immunoglobulin molecules, as well as the intracellular immunoglobulin molecules and fragments produced using these methods.

PCT Publication WO2013023251 assigned to Affinity Biosciences PTY LTD and naming inventors Beasley, Niven and Kiefel describes polypeptides, such as antibody molecules and polynucleotides encoding such polypeptides, and libraries thereof, wherein the expressed polypeptides that demonstrate high stability and solubility. In particular, polypeptides comprising paired VL and VH domains that demonstrate soluble expression and folding in a reducing or intracellular environment are described, wherein a human scFv library was screened, resulting in the isolation of soluble scFv genes that have identical framework regions to the human germline sequence as well as remarkable thermostability and tolerance of CDR3 grafting onto the scFv scaffold.

European Patent Application EP2314622 and PCT Publications WO03008451 and WO03097697 assigned to Esbatech AG and University of Zuerich and naming inventors Ewert, Huber, Honneger and Pluckthun describe the modification of human variable domains and provide compositions useful as frameworks for the creation of very stable and soluble single-chain Fv antibody fragments. These frameworks have been selected for intracellular performance and are thus ideally suited for the creation of scFv antibody fragments or scFv antibody libraries for applications where stability and solubility are limiting factors for the performance of antibody fragments, such as in the reducing environment of a cell. Such frameworks can also be used to identify highly conserved residues and consensus sequences which demonstrate enhanced solubility and stability.

PCT Publication WO02067849 and US Patent Application Publication 2004047891 entitled "Systems devices and methods for intrabody targeted delivery and reloading of therapeutic agents" describe systems, devices and methods for intrabody targeted delivery of molecules. More particularly, some embodiments relate to a reloadable drug delivery system, which enables targeted delivery of therapeutic agents to a tissue region of a subject, in a localized and timely manner.

PCT Publication WO2005063817 and U.S. Pat. No. 7,884,054 assigned to Amgen Inc. and naming inventors Zhou, Shen and Martin describe methods for identifying functional antibodies, including intrabodies. In particular, a homodimeric intrabody is described, wherein each polypeptide chain of the homodimer comprises an Fc region, an scFv, and an intracellular localization sequence. The intracellular localization sequence may cause the intrabody to be localized to the ER or the Golgi. Optionally, each polypeptide chain comprises not more than one scFv.

PCT Publication WO2013138795 by Vogan, et al. and assigned to Permeon Biologics Inc. describes cell penetrating compositions for delivery of intracellular antibodies and antibody-like moieties and methods for delivering them (referred to herein as "AAM moieties" or "an AAM moiety") into a cell. Without being bound by theory, the present disclosure is based, at least in part, on the discovery that an AAM moiety can be delivered into a cell by complexing the AAM moiety with a cell penetrating polypeptide having surface positive charge (referred to herein as a "Surf+ Penetrating Polypeptide"). Examples of some applications of intraphilin technology are also provided PCT Publication WO2010004432 assigned to the Pasteur Institute describes immunoglobulins from camelidae (camels, dromedaries, llamas and alpacas), about 50% of which are antibodies devoid of light chain. These heavy-chain antibodies interact with the antigen by the virtue of only one single variable domain, referred to as VHH(s), VHH domain(s) or VHH antibody(ies). Despite the absence of light chain, these homodimeric antibodies exhibit a broad antigen-binding repertoire by enlarging their hypervariable regions, and can act as a transbody and/or intrabody in vitro as well as in vivo, when the VHH domain is directed against an intracellular target.

PCT Publication WO2014106639 describes a method for identifying a cellular target involved in a cell phenotype by identifying an intrabody that can modify a cell phenotype and identifying a direct or indirect cellular target of the intrabody. In particular, intrabodies 3H2-1, 3H2-VH and 5H4 are capable of inhibiting the degranulation reaction in mast cells triggered by an allergic stimulus; furthermore, intrabodies 3H2-1 and 5H4 directly or indirectly targeted a protein of the ABCF1 family and C120RF4 family, respectively. These ABCF1 and C120RF4 inhibitors are said to be useful in therapy, in particular for treating allergic and/or inflammatory conditions.

PCT Publication WO0140276 assigned to Urogenesis Inc. generally describes the possibility of inhibition of STEAP (Six Transmembrane Epithelial Antigen of the Prostate) proteins using intracellular antibodies (intrabodies).

PCT Publication WO02086505 assigned to University of Manchester and US Patent Application Publication US2004115740 naming inventors Simon and Benton describe a method for the intracellular analysis of a target molecule, wherein intrabodies are said to be preferred. In one embodiment, a vector (designated pScFv-ECFP) capable of expressing an anti-MUC1 intrabody coupled to CFP is described.

PCT Publication WO03095641 and WO0143778 assigned to Gene Therapy Systems Inc. describe compositions and methods for intracellular protein delivery, and intrabodies are generally described.

PCT Publication WO03086276 assigned to Selective Genetics Inc. describes a platform technology for the treatment of intracellular infections. Compositions and methods described therein include non-target specific vectors that target infectable cells via linked ligands that bind and internalize through cell surface receptors/moieties associated with infection. The vectors comprise exogenous nucleic acid sequences that are expressed upon internalization into a target cell. Vector associated ligands and nucleic acid molecules may be altered to target different infectious agents. In addition, the invention provides methods of identifying epitopes and ligands capable of directing internalization of a vector and capable of blocking viral entry.

PCT Publication WO03062415 assigned to Erasmus University describes a transgenic organism comprising a polynucleotide construct encoding an intracellular antibody which disrupts the catalysis of the production of the xenoantigen galactose alpha 1,3 galactose and/or a polynucleotide construct which encodes an intracellular antibody which binds specifically to a retrovirus protein, such as a PERV particle protein. Cells, tissues and organs of the transgenic organism may be used in xenotransplantation.

PCT Publication WO2004099775 entitled "Means for detecting protein conformation and applications thereof" describes the use of scFv fragments as conformation-specific antibodies for specifically detecting a conformational protein state, said to have applications as sensors for following in livings cells, upon intracellular expression, the behavior of endogenous proteins.

PCT Publication WO2008070363 assigned to Imclone Systems Inc. describes a single domain intrabody that binds to an intracellular protein or to an intracellular domain of an intracellular protein, such as Etk, the endothelial and epithelial tyrosine kinase, which is a member of the Tec family of non-receptor tyrosine kinases. Also provided is a method of inhibiting an intracellular enzyme, and treating a tumor in a patient by administering the intrabody or a nucleic acid expressing the intrabody.

PCT Publication WO2009018438 assigned to Cornell Research Foundation Inc. describes a method of identifying a protein that binds to a target molecule and has intracellular functionality, by providing a construct comprising a DNA molecule encoding the protein which binds to the target molecule, with the DNA molecule being coupled to a stall sequence. A host cell is transformed with the construct and then cultured under conditions effective to form, within the host cell, a complex of the protein whose translation has been stalled, the mRNA encoding the protein, and ribosomes. The protein in the complex is in a properly folded, active form and the complex is recovered from the cell. This method can be carried out with a cell-free extract preparation containing ribosomes instead of a host cell. The present invention also relates to a construct which includes a DNA molecule encoding a protein that binds to a target molecule and an SecM stalling sequence coupled to the DNA molecule. The DNA molecule and the SecM stalling sequence are coupled with sufficient distance between them to permit expression of their encoded protein, within the cell, in a properly folded, active form. The use of intrabodies is generally described.

PCT Publication WO2014030780 assigned to Mogam Biotech Research Institute describes a method named Tat-associated protein engineering (TAPE), for screening a target protein having higher solubility and excellent thermostability, in particular, an immunoglobulin variable domain (VH or VL) derived from human germ cells, by preparing a gene construct where the target protein and an antibiotic-resistant protein are linked to a Tat signal sequence, and then expressing this within E. coli. Also disclosed are human or engineered VH and VL domain antibodies and human or engineered VH and VL domain antibody scaffolds having solubility and excellent thermostability, which are screened by the TAPE method. Also provided is a library including random CDR sequences in the human or engineered VH or VL domain antibody scaffold screened by the TAPE method, a preparing method thereof, a VH or VL domain antibody having binding ability to the target protein screened by using the library, and a pharmaceutical composition including the domain antibody.

European Patent Application EP2422811 describes an antibody that binds to an intracellular epitope; such intrabodies comprise at least a portion of an antibody that is capable of specifically binding an antigen and preferably does not contain operable sequences coding for its secretion and thus remains within the cell. In one embodiment, the intrabody comprises a scFv. The scFv polypeptide further comprises a polypeptide linker between the VH and VL domains which enables the scFv to form the desired structure for antigen binding. Also described is a specific embodiment in which the intrabody binds to the cytoplasmic domain of an Eph receptor and prevents its signaling (e.g., autophosphorylation). In another specific embodiment, an intrabody binds to the cytoplasmic domain of a B-type Ephrin (e.g., EphrinB1, EphrinB2 or EphrinB3).

PCT Publication WO2011003896 and European Patent Application EP2275442 describe intracellular functional PCNA-Chromobodies made using nucleic acid molecule encoding a polypeptide specifically binding to proliferating cell nuclear antigen (PCNA). Examples of such polypeptides comprising conservative substitutions of one or more amino acids in one or two framework regions are represented by SEQ ID NOs: 16 and 18 disclosed therein, including the framework region of the polypeptide. In the examples, the framework regions as well as the CDR regions involved in the binding of PCNA have been determined.

European Patent Application EP2703485 describes a method for selecting plasma cells or plasmablasts, as well as for producing target antigen specific antibodies, and novel monoclonal antibodies. In one embodiment, cells expressing intracellular immunoglobulin were identified.

Proteins and Variants

Glycan-interacting antibodies of the present invention may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multimolecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences of the glycan-interacting antibodies of the invention may comprise naturally occurring amino acids and as such may be considered to be proteins, peptides, polypeptides, or fragments thereof.

Alternatively, the glycan-interacting antibodies may comprise both naturally and non-naturally occurring amino acids.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least about 70% homology to a native sequence, and preferably, they will be at least about 80%, more preferably at least about 90% homologous to a native sequence. "Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species. "Analogs" is meant to include polypeptide variants which differ by one or more amino acid alterations, e.g., substitutions, additions or deletions of amino acid residues that still maintain the properties of the parent polypeptide.

The present invention contemplates several types of glycan-interacting antibodies which are amino acid based including variants and derivatives. These include substitutional, insertional, deletion and covalent variants and derivatives. As such, included within the scope of this invention are glycan-interacting antibody molecules containing substitutions, insertions and/or additions, deletions and covalently modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

Covalent derivatives specifically include fusion molecules in which proteins of the invention are covalently bonded to a non-proteinaceous polymer. The non-proteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol. The proteins may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

"Features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and comprises four or more amino acid residues. Oliva et al. have identified at least 5 classes of protein loops (J. Mol Biol 266 (4): 814-830; 1997).

As used herein when referring to proteins the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+1−0.5 being 3 or 4).

As used herein when referring to proteins the term "domain" refers to a motif of a polypeptide having one or more identifiable structural or functional characteristics or properties (e.g., binding capacity, serving as a site for protein-protein interactions.

As used herein when referring to proteins the term "half-domain" means portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Isotopic Variations

The glycan-interacting antibodies of the present invention may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. The glycan-interacting antibodies may be deuterated in order to change a physical property of the compound, such as stability, or to allow the compounds to be used in diagnostic and experimental applications.

Conjugates and Combinations

It is contemplated by the present invention that the glycan-interacting antibodies of the present invention may be complexed, conjugated or combined with one or more homologous or heterologous molecules. As used herein, "homologous molecule" means a molecule which is similar in at least one of structure or function relative to a starting molecule while a "heterologous molecule" is one that differs in at least one of structure or function relative to a starting molecule. Structural homologs are therefore molecules which are substantially structurally similar. They can be identical. Functional homologs are molecules which are substantially functionally similar. They can be identical.

Glycan-interacting antibodies of the invention may comprise conjugates. Such conjugates of the invention may include a naturally occurring substance or ligand, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

The conjugates can also include targeting groups, e.g., a cell or tissue targeting agent or group, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In still other embodiments, glycan-interacting antibodies are covalently conjugated to a cell penetrating polypeptide. The cell-penetrating peptide may also include a signal sequence. The conjugates of the invention can be designed to have increased stability; increased cell transfection; and/or altered biodistribution (e.g., targeted to specific tissues or cell types).

Conjugating moieties may be added to glycan-interacting antibodies such that they allow labeling or flagging targets for clearance. Such tagging/flagging molecules include, but are not limited to ubiquitin, fluorescent molecules, human influenza hemagglutinin (HA), c-myc [a 10 amino acid segment of the human protooncogene myc with sequence EQKLISEEDL (SEQ ID NO: 243)], histidine (His), flag [a short peptide of sequence DYKDDDDK (SEQ ID NO: 244)], glutathione S-transferase (GST), V5 (a paramyxovirus of simian virus 5 epitope), biotin, avidin, streptavidin, horse radish peroxidase (HRP) and digoxigenin.

In some embodiments, glycan-interacting antibodies may be combined with one another or other molecule in the treatment of a disease or condition.

Nucleic Acids

The present invention embraces nucleic acid molecules. In some embodiments, nucleic acids encode antibodies of the invention (including, but not limited to antibodies, antibody fragments, intrabodies and chimeric receptor antigens). Such nucleic acid molecules include, without limitation, DNA molecules, RNA molecules, polynucleotides, oligonucleotides, mRNA molecules, vectors, plasmids and other constructs. As used herein, the term "construct" refers to any recombinant nucleic acid molecule including, but not limited to plasmids, cosmids, autonomously replicating polynucleotide molecules or linear or circular single-stranded or double-stranded DNA or RNA polynucleotide molecules. The present invention also embraces cells programmed or generated to express nucleic acid molecules encoding glycan-interacting antibodies. Such cells may be generated through the use of transfection, electroporation, viral delivery and the like. Viruses engineered with constructs of the invention may include, but are not limited to lentiviruses, adenoviruses, adeno-associated viruses and phages. In some cases, nucleic acids of the invention include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety.

II. Methods and Uses

Therapeutics

Cancer-Related Applications

Aberrant glycosylation is a hallmark of cancer cell transformation. Multiple aberrant glycosylation forms have been described in human cancers, identifying specific tumor-associated carbohydrate antigens (TACAs) as a class of cell surface molecules suitable for specific tumor targeting (Cheever, M. A. et al., Clin Cancer Res. 2009 Sep. 1; 15(17):5323-37). TACA antigen expression has been found in epithelial cancers including, but not limited to, breast, colon, lung, bladder, cervical, ovarian, stomach, prostate, and liver. TACA antigen expression has been found in embryonal cancers including, but not limited to, yolk sac tumors and seminomas. In addition, TACA antigen expression has been found in many melanomas, carcinomas, and leukemias of various tissues (Heimburg-Molinaro et al., Vaccine. 2011 Nov. 8: 29(48):8802-8826). Antibodies of the present invention that target one or more TACA are referred to herein as "anti-TACA antibodies."

MUC1 is a key cell surface glycoprotein that is normally extensively glycosylated but is underglycosylated in tumor cells. Sparse glycosylation of MUC1 leads to exposure of immunogenic antigens. These may be along the MUC1 core peptide sequence or along core carbohydrate residues. These TACAs include, but are not limited to N-acetylgalactosamine (Tn), sialyl(α2,6)N-acetylgalactosamine (STn) and galactose(β1-3)N-acetylgalactosamine (also known as Thomsen-Friedenreich antigen or TF). It has been estimated that about 80% of all carcinomas express Tn among the core carbohydrates of MUC1 with STn being strongly expressed on human carcinoma cells and linked to cancer progression and metastasis. With few exceptions, Tn and STn are not expressed in normal healthy tissues. Sialic acid forms a prominent epitope on STn. The invention takes advantage of the fact that aberrant Neu5Gc-STn (GcSTn) glycan expression appears to be highly specific to various carcinomas.

In the case of MUC1, Neu5Gc incorporation into STn yields a tumor-specific target, a site that is an attractive target for antibody-based therapies to treat tumor tissue. In some embodiments of the present invention, glycan-interacting antibodies target MUC1 expressing cancer cells comprising Neu5Gc. To date, Neu5Gc has been detected in glycoconjugates from a number of human cancer tissues including, but not limited to colon cancer, retinoblastoma tissue, melanoma, breast cancer and yolk sac tumor tissue. In some embodiments of the present invention, methods are contemplated for glycan-interacting antibody treatment of these forms of cancer as well as other forms of cancer, not specifically listed here, characterized by the presence of cancer cells comprising Neu5Gc.

Additional antigens comprising glycans have been identified that are expressed in correlation with cancer (Heimburg-Molinaro, J. et al., Cancer vaccines and carbohydrate epitopes. Vaccine. 2011 Nov. 8; 29(48):8802-26). These tumor-associated carbohydrate antigens include, but are not limited to blood group Lewis related antigens [including, but not limited to Lewis$^{Y}$ (Le$^{Y}$), Lewis$^{X}$ (Le$^{X}$), Sialyl Lewis$^{X}$ (SLe$^{X}$) and Sialyl Lewis$^{A}$ (SLe$^{A}$)], glycosphingolipid-related antigens [including, but not limited to Globo H, stage-specific embryonic antigen-3 (SSEA-3) and glycosphingolipids comprising sialic acid], ganglioside-related antigens [including, but not limited to gangliosides GD2, GD3, GM2, fucosyl GM1 and Neu5GcGM3] and polysialic acid-related antigens.

In some embodiments, therapeutics of the present invention may be directed toward Lewis blood group antigens. Lewis blood group antigens comprise a fucose residue linked to GlcNAc by an α1-3 linkage or an α1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, therapeutics of the present invention may be directed toward Le$^{Y}$. Le$^{Y}$ (also known as CD174) is made up of Galβ1,4GlcNAC comprising α1,2- as well as α1,3-linked fucose residues yielding the Fucα(1,2)Galβ1,4)Fucα(1,3)GlcNAc epitope. It is synthesized from the H antigen by α1,3 fucosyltransferases which attach the α1,3 fucose to the GlcNAc residue of the parent chain. Le$^{Y}$ may be expressed in a variety of cancers including, but not limited to ovarian, breast, prostate, colon, lung, and epithelial. Due to its low expression level in normal tissues and elevated expression level in many cancers, the Le$^{Y}$ antigen is an attractive target for therapeutic antibodies.

In some embodiments, therapeutics of the present invention may be directed toward Le$^{X}$. Le$^{X}$ comprises the epitope Galβ1-4(Fucα1-3)GlcNAcβ-R. It is also known as CD15 and stage-specific embryonic antigen-1 (SSEA-1). This antigen was first recognized as being immunoreactive with sera taken from a mouse subjected to immunization with F9 teratocarcinoma cells. Le$^{X}$ was also found to correlate with embryonic development at specific stages. It is also expressed in a variety of tissues both in the presence and absence of cancer, but can also be found in breast and ovarian cancers where it is only expressed by cancerous cells.

In some embodiments, therapeutics of the present invention may be directed toward SLe$^{A}$ and/or SLe$^{X}$. SLe$^{A}$ and SLe$^{X}$ comprise the structures [Neu5Aca2-3Galβ1-3(Fucα1-4)GlcNAcβ-R] and [Neu5Acα2-3Galβ1-4(Fucα1-3)GlcNAcβ-R] respectively. Their expression is upregulated in cancer cells. The presence of these antigens in serum correlates with malignancy and poor prognosis. SLe$^{X}$ is mostly found as a mucin terminal epitope. It is expressed in a number of different cancers including breast, ovarian, melanoma, colon, liver, lung and prostate. In some embodiments of the present invention, SLe$^{A}$ and SLe$^{X}$ targets comprise Neu5Gc (referred to herein as GcSLe$^{A}$ and GcSLe$^{X}$, respectively).

In some embodiments, therapeutics of the present invention may be directed toward glycolipids and/or epitopes present on glycolipids, including, but not limited to glycosphingolipids. Glycosphingolipids comprise the lipid ceramide linked to a glycan by the ceramide hydroxyl group. On the cell membrane, glycosphingolipids form clusters referred to as "lipid rafts".

In some embodiments, therapeutics of the present invention may be directed toward Globo H. Globo H is a cancer-related glycosphingolipid first identified in breast cancer cells. The glycan portion of Globo H comprises Fucα(1-2)Galβ(1-3)GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, therapeutics of the present invention may be directed toward gangliosides. Gangliosides are glycosphingolipids comprising sialic acid. According to ganglioside nomenclature, G is used as an abbreviation for ganglioside. This abbreviation is followed by the letters M, D or T referring to the number of sialic acid residues attached (1, 2 or 3 respectively). Finally the numbers 1, 2 or 3 are used to refer to the order of the distance each migrates when analyzed by thin layer chromatography (wherein 3 travels the greatest distance, followed by 2 and then 1). Gangliosides are known to be involved in cancer-related growth and metastasis and are expressed on the cell surface of tumor cells. Gangliosides expressed on tumor cells include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. In some embodiments of the present invention, glycan interacting antibodies are directed toward GM2. In some embodiments, GM2-directed antibodies are used to modulate cell to cell contact. In some embodiments, ganglioside targets of the present invention comprise Neu5Gc. In some embodiments, such targets may include a GM3 variant comprising Neu5Gc (referred to herein as GcGM3). The glycan component of GcGM3 is Neu5Gcα2-3Galβ1-4Glc. GcGM3 is a known component of tumor cells.

In some embodiments, TACAs targeted by anti-TACA antibodies of the present invention may include, but are not limited to any of those listed in US Publication Nos. US2013/0236486A1, US2013/0108624A1, US2010/0178292A1, US2010/0104572A1, US2012/0039984A1, US2009/0196916A1, and US2009/0041836A1, the contents of each of which are herein incorporated by reference in their entirety.

In some embodiments, the present invention provides methods of treating cancer that include the administration of anti-glycan antibodies taught herein or the administration of compositions of such antibodies (e.g., compositions of anti-glycan antibodies having at least one excipient).

STn in Cancer

The immune system has multiple mechanisms for promoting anti-tumor cell immune activity including both innate and adaptive immune activity. As used herein, the term "anti-tumor cell immune activity" refers to any activity of the immune system that kills or prevents growth and/or proliferation of tumor cells. In some cases, anti-tumor immune activity includes recognition and tumor cell killing by natural killer (NK) cells and phagocytosis by macrophages. Adaptive anti-tumor immune responses include tumor antigen uptake and presentation by antigen presenting cells (APCs,) such as dendritic cells (DCs,) leading to modulation of T cell anti-tumor activity and/or expansion of B cells with secretion of tumor-specific antibodies. The binding of tumor-specific antibodies to tumors can lead to antibody-dependent cellular cytotoxicity (ADCC) and complement-dependent cytotoxicity (CDC) mechanisms of tumor cell death.

As used herein, the term "immune-resistant tumor cell" refers to a tumor cell that reduces or evades anti-tumor cell immune activity. Some studies indicate that the expression of STn (a known TACA) on tumor cell surfaces or secreted into the tumor cell microenvironment can promote tumor cell evasion of anti-tumor immune activity. As used herein, the term "tumor cell microenvironment" refers to any area adjacent to or surrounding a tumor cell. Such areas include, but are not limited to areas between tumor cells, between tumor and non-tumor cells, surrounding fluids and surrounding components of the extracellular matrix.

Sialylated mucins comprising STn were demonstrated by Ogata et al to reduce NK cell targeting of tumor cells (Ogata, S. et al., 1992. Canc. Res. 52:4741-6, the contents of which are herein incorporated by reference in their entirety). This study found that the presence of ovine, bovine and porcine submaxillary mucin (OSM, BSM and PSM, respectively) led to nearly one hundred percent inhibition of cytotoxicity (see Table 2 of Ogata et al). Further studies by Jandus et al, demonstrate that some tumor cells can evade NK destruction due to the expression of sialoglycan ligands that can interact with NK cell siglec receptors, leading to NK inhibition (Jandus, C. et al., 2014, JCI. pii: 65899, the contents of which are herein incorporated by reference in their entirety).

Studies by Toda et al., demonstrate that STn may bind CD22 receptors on B cells, leading to decreased signal transduction and reduced B cell activation (Toda, M. et al., 2008. Biochem Biophys Res Commun. 372(1):45-50, the contents of which are herein incorporated by reference in their entirety). Dendritic cells (DCs) can affect adaptive immune activity by modulating T cell activity. Studies by Carrascal et al found that STn expression by bladder cancer cells induced tolerance in DCs, reducing their ability to induce anti-tumor cell immune activity in T cells (Carrascal, M A et al., 2014. Mol Oncol. pii: S1574-7891(14)00047-7, the contents of which are herein incorporated by reference in their entirety). These studies revealed that DCs coming into contact with STn-positive bladder cancer cells displayed a tolorigenic expression profile with low expression of CD80, CD86, IL-12 and TNF-α. Further, DCs were found to modulate regulatory T cells such that the T cells had low expression of IFNy and high expression of FoxP3. Other studies by van Vliet and others, indicate that DC surface expression of macrophage galactose-type lectin (MGL) can lead to targeting of those cells to tumor tissues (van Vliet, S J., 2007. Amsterdam: Vrije Universiteit. p 1-232 and van Vliet, S J. et al., 2008. J Immunol. 181(5):3148-55, Nollau, P. et al., 2013. J Histochem Cytochem. 61(3):199-205, the contents of each of which are herein incorporated by reference in their entirety). DCs arriving at tissues due to MGL interactions may influence T helper (Th) cells in one of three ways. DCs can induce T cell tolerance, T cell immune activity or downregulation of effector T cells. MGL has been shown to bind to both AcSTn and GcSTn and the affinity has been analyzed in depth (Mortezai, N. et al., 2013. Glycobiology. 23(7):844-52, the contents of which are herein incorporated by reference in their entirety). Interestingly, MUC1 expression on tumors has been shown to lead to T cell tolerance, protecting tumor cells from immune eradication.

In some embodiments, glycan-interacting antibodies (including, but not limited to anti-STn antibodies) of the present invention may be used to treat subjects comprising one or more tumor cells expressing one or more TACAs. In some cases, glycan-interacting antibodies (including, but not limited to anti-STn antibodies) of the invention may be used to increase anti-tumor cell immune activity toward tumor cells expressing STn. Such antibodies may increase the adaptive immune response and/or the innate immune response toward immune-resistant tumor cells. Some glycan-interacting antibodies may be used to increase NK anti-tumor cell activity. Such glycan-interacting antibodies may, in some cases, block the interaction between glycan receptors expressed on NK cells and STn glycans on cancer cells or in surrounding tissues.

In some embodiments, glycan-interacting antibodies (including, but not limited to anti-STn antibodies) of the invention may be used to increase B cell anti-tumor cell activity. Such antibodies may reduce the interaction between CD22 receptors on B cells and STn glycans on cancer cells or in surrounding tissues. A study by Sjoberg et al. demonstrates that 9-O-acetylation of α2,6-linked sialic acids on glycoproteins also reduced interaction between B cell CD22 receptors and such glycoproteins (Sjoberg, E. R. et al. 1994. JCB. 126(2): 549-562). Another study by Shi et al. reveals that higher levels of 9-O-acetylated sialic acid residues on murine erythroleukemia cells makes these cells more susceptible to complement-mediated lysis (Shi, W-X. et al., 1996. J of Biol Chem. 271(49): 31526-32, the contents of which are herein incorporated by reference in their entirety). In some embodiments, anti-STn antibodies of the invention are capable of selectively binding non-9-O-acetylated STn, reducing overall STn binding, but reducing tumor cell growth and/or proliferation (e.g., through increased B cell anti-tumor activity and increased complement-mediated tumor cell destruction). In some embodiments, glycan-interacting antibodies (including, but not limited to anti-STn antibodies) of the invention may be used to increase DC anti-tumor activity. Such antibodies may be used to reduce DC tolerance to tumor cells. Reduced DC tolerance may comprise increasing DC expression of CD80, CD86, IL-12 and/or TNF-α. In some cases, DC anti-tumor cell activity may comprise promotion of T cell anti-tumor cell activity. Such antibodies may prevent binding between DC MGL and glycans expressed on or around cancer cells.

A study by Ibrahim et al. suggests that high levels of anti-STn antibodies along with endocrine therapy may increase overall survival and time to progression (TTP) in women with metastatic breast cancer (Ibrahim, N. K. et al., 2013. 4(7): 577-584, the contents of which are herein incorporated by reference in their entirety). In this study, anti-STn antibody levels were elevated after vaccination with STn linked to keyhole-limpet Hemocyanin (KLH). In some embodiments, anti-STn antibodies of the invention may be used in combination with endocrine therapy (e.g. tamoxifen and/or an aromatase inhibitor).

In some embodiments, glycan-interacting antibodies of the invention may be used to reduce or eliminate cancerous cells and/or cells expressing STn. Such cells include cells that may be part of a tumor.

In some embodiments, the present invention provides methods of reducing tumor volumes by administering anti-glycan antibodies of the invention to subjects with one or more tumors. Reduction in tumor volumes may be determined by comparing tumor volumes in a subject before and after treatment, or by comparing tumor volumes between anti-glycan antibody-treated and control treated subjects.

In some embodiments, anti-glycan antibodies of the invention may be administered to achieve a desired percent reduction in tumor volume in a subject. This may assessed by determining the volume of one or more tumors (e.g., through the use of calipers or imaging techniques like CT scan) in a subject before and after treatment with an anti-glycan antibody and then calculating the percent reduction in tumor volume from the two values. In some embodiments, tumor volume in subjects treated with anti-glycan antibodies may be reduced by from about 0.1% to about 2%, from about 1% to about 5%, from about 3% to about 12%, from about 10% to about 30%, from about 20% to about 50%, from about 40% to about 60%, from about 50% to about 75%, from about 60% to about 85%, or from about 80% to about 99%. In some embodiments, tumor volume in subjects treated with anti-glycan antibodies may be reduced by at least 1%, by at least 5%, by at least 10%, by at least 20%, by at least 40%, by at least 50%, by at least 60%, by at least 80%, by at least 85%, by at least 90%, by at least 95%, by at least 98%, by at least 99%, or by 100%.

In some embodiments, anti-glycan antibodies of the invention may be administered to achieve a desired percent tumor growth inhibition (% T/C). % T/C is calculated by determining tumor volumes in treated subjects and comparing them to tumor volumes in non-treated or placebo-treated subjects. In some embodiments, the present invention provides methods of reducing tumor volume in a subject by administering an anti-glycan antibody, wherein the % T/C is from about 0.1% to about 1%, from about 0.5% to about 5%, from about 2% to about 20%, from about 3% to about 16%, from about 10% to about 30%, from about 20% to about 60%, or from about 40% to about 80%. In some embodiments the % T/C is at least 80%. In other embodiments the % T/C is less than 0.1%.

Cancer Stem Cells as Therapy Targets

Cancer stem cells or CSCs (also called tumor initiating cells) are a subset of cells within a heterogeneous tumor population that drive the initiation, growth, dissemination, and recurrence of primary and metastatic tumors (Karsten and Goletz, SpringerPlus, 2013, 2, 301), which can occur in varying proportions of the total population depending on tumor type. CSCs are distinguished from terminally differentiated cells by their capacity to self-renew and give rise to non-CSC, differentiated progeny (Gupta et al., Nature medicine, 2009, 15, 1010-1012). These properties are akin to those of normal stem cells. Such distinctions between normal stem cells and CSCs have important implications for therapy.

An increasing number of cell-surface biomarkers have been identified that purport to differentiate CSCs from their non-CSC counterparts (Medema et al., Nature cell biology, 2013, 15, 338-344; Zoller, Cancer, 2011, 11, 254-267). Although many of these derive from studies of mouse tumors and human cell lines, several have been validated using primary human tumor samples. One of these, the membrane-spanning CD44 glycoprotein, or hyaluronan receptor, which is a well-known constituent of a variety of tumor types, has also more recently found acceptance as a bona fide CSC marker in human cancers, and in fact is the one most frequently observed (Lobo et al., 2007, 23, 675-699).

CD44 exists in several variant isoforms generated by alternative splicing events occurring among the 20 exons and 19 introns of the full-length CD44 gene (Williams et al, Experimental biology and medicine, 2013, 238, 324-338). Growing experimental evidence points to the supporting role of CD44 and its variants in contributing to the innate metastatic and drug resistant phenotype of CSCs (Negi et al., Journal of drug targeting, 2012, 20, 561-573), in part due to modulation of intracellular signal transduction pathways (Williams et al, Experimental biology and medicine, 2013, 238, 324-338). Additionally, patients with triple negative breast cancer, along with several other cancer types, that display high levels of CD44 cells are known to have a poor prognosis and higher mortality (Negi et al., Journal of drug targeting, 2012, 20, 561-573). These observations support the notion that targeting CD44 offers a means of treating cancer through inhibition or elimination of CSCs, in addition to mature cancer cells. Indeed, numerous approaches to targeting CD44 have been attempted experimentally with varying degrees of success. These comprise a wide range of technologies that include the use of conjugated and unconjugated antibodies, nano-carrier drug systems, and hyaluronan-conjugated drugs (Negi et al., Journal of drug targeting, 2012, 20, 561-573). In several instances, however, toxic effects were observed in in vivo studies; these untoward side effects may be attributable to the widespread occurrence of CD44 and variants on the membranes of most vertebrate cells (Naor et al., Seminars in cancer biology, 2008, 18, 260-267), in addition to its presence on the surface of the targeted CSCs and mature tumor cells. Targeting CD44 protein, which is a constituent of normal human stem cells (Williams et al, Experimental biology and medicine, 2013, 238, 324-338), can also harm normal stem cell function (Leth-Larsen et al., Molecular medicine, 2012, 18, 1109-1121). Although a large body of research points to the desirability of targeting CD44 protein on CSCs, as well as on mature tumor cells, the intrinsic problem with this approach remains the present difficulty in designing inhibitors that will spare normal tissue as well as normal stem cells.

Another well-known tumor antigen with implications to CSC biology is the epithelial mucin MUC1, a membrane tethered glycoprotein that is differentially expressed at high levels on the majority of adenocarcinomas but at low levels or not at all on normal epithelial cells. MUC1 has recently been identified as a CSC biomarker on a variety of neoplasias including breast (Engelmann et al., Cancer research, 2008, 68, 2419-2426), and pancreatic cancers, where its expression is correlated with high metastasis and poor prognosis. As a constituent of CSCs, MUC1 has been shown to function in cell adhesion, proliferation, survival, and signaling (Engelmann et al., Cancer research, 2008, 68, 2419-2426) and may also be co-expressed with CD44 (Leth-Larsen et al., Molecular medicine, 2012, 18, 1109-1121). Immunotherapeutic approaches for targeting MUC1 in cancer are being pursued using vaccines as well as other approaches, but primarily in the context of mature cancer cell therapy (Julien et al., Biomolecules, 2012, 2, 435-466; Acres et al., Expert review of vaccines, 2005, 4, 493-502).

Cancer stem cells have been hypothesized to be generated through the epithelial-to-mesenchymal (EMT) transition (Gupta et al., Nature medicine, 2009, 15, 1010-1012), and/or reversely the mesenchymal-to-epithelial (MET) transition that occurs at the site of metastasis (Leth-Larsen et al., Molecular medicine, 2012, 18, 1109-1121) (also called CSCs plasticity where non-CSCs can give rise to CSCs). This discovery further underscores the need to eliminate both CSCs and non-CSCs in a tumor population.

Recent studies with enriched CSC populations has revealed that these cells, unlike the bulk of the tumor, are relatively quiescent and are preferentially resistant to many types of current therapies, including chemotherapy and radiation (Leth-Larsen et al., Molecular medicine, 2012, 18, 1109-1121). Thus current therapeutic strategies target non-CSC components of the tumor, leaving CSCs largely unaffected only to re-emerge after appropriate cues to reform recurrent primary tumors at the initial site or to disseminate to distant sites, colonize, and create metastatic disease, the major cause of cancer mortality.

Current understanding of the properties of cancer stem cells clearly emphasized the need not only to target the bulk of cells present in tumors, as is current practice, but also the CSC compartment in order to potentially effect complete cures.

As discussed above, strategies that have been developed based on tumor (including CSCs) associated biomarkers face a challenge that most cancer biomarkers are also present in normal cells including normal stem cells. A therapy that targets a protein biomarker to eliminate CSCs, may also target normal stem cells, causing elimination of normal cells.

Tumor-Specific Glycans in CSCs

Aberrant forms of glycosylation, including appearance of the Thomsen-nouveau (Tn) antigen (GalNAc-O-Ser/Thr), have been described in numerous human cancers, identifying glycans as an entirely novel class of tumor-associated carbohydrate antigens suitable for specific tumor targeting (Rabu et al., Future oncology, 2012, 8, 943-960). The formation of the sialyl derivative of Tn (STn) is mediated by the sialyl transferase ST6GalNAc-I which adds sialic acid in an α2,6 linkage to the Tn antigen. The sialylation of STn prevents further sugar additions, thus truncating further glycan extensions (Schultz et al., Cancer metastasis reviews, 2012, 31, 501-518).

While the presence of STn in normal adult human tissues is rare, STn occurs in various human cancers, including ovarian, bladder, breast, cervical, colon, and lung cancer, among others (Ferreira et al., Molecular oncology, 2013, 7, 719-731; Kinney et al., Cancer, 1997, 80, 2240-2249). Further, the presence of STn in tumors is associated with metastatic disease, poor prognosis, and reduced overall survival (Ferreira et al., Molecular oncology, 2013, 7, 719-731; Kinney et al., Cancer, 1997, 80, 2240-2249); therefore, STn is considered a highly attractive target for cancer detection and therapy. There are two distinct forms of sialic acid—Neu5Ac and Neu5Gc—located at the terminal position of STn. The Neu5Ac-sialylated form is predominant in humans since humans cannot synthesize Neu5Gc due to an inactive CMP-Neu5Ac hydroxylase (CMAH) gene. However, consumption of Neu5Gc-rich foods leads to foreign Neu5Gc incorporation into human cells, especially in carcinomas. Previous studies have shown that solid tumors take up and express the Neu5Gc form of sialic acid (Inoue et al., Glycobiology, 2010, 20, 752-762; Malykh et al., Biochimie, 2001, 83, 623-634; Padler-Karavani et al., Cancer research, 2011, 71, 3352-3363). mAbs that bind to both glyco-isoforms of STn that are potential cancer targets: Neu5Ac-STn (AcSTn) and Neu5Gc-STn (GcSTn) (i.e., designated as pan-STn antibodies).

STn accumulation is associated with specific somatic mutations observed repeatedly in solid tumors and with the inactivation of the gene that encodes the molecular chaperone Cosmc, which is required for the formation of active T-synthase (Ju et al., Nature, 2005, 437, 125). T-synthase competes with ST6GalNAc-I for the GalNAc substrate and therefore when inactivated by mutation results in elevated STn synthesis. Additionally, STn accumulation can also result from increased expression of ST6GalNAc-I, which is often observed (Brockhausen et al., Biological chemistry, 2001, 382, 219-232; Ikehara et al., Glycobiology, 1999, 9, 1213-1224). De novo expression of STn can modulate carcinoma cells, change the malignant phenotype, and lead to more aggressive cell behaviors (Pinho et al., Cancer letters, 2007, 249, 157-170). As such, STn is not only an interesting cancer biomarker and therapeutic target, but interfering with STn function offers the intriguing potential to have significant functional, anti-metastatic therapeutic benefits.

Although it is well-known that glycosylation of cellular glycoproteins is altered in cancer, it appears that aberrant glycosylation is selective with respect to both the glycoprotein and glycan in question. In fact, in human tumor CSCs only CD44 and MUC1 are major carriers of the STn antigen (Cazet et al., Breast cancer research: BCR, 2010, 12,204; Julien et al., Glycobiology, 2006, 16, 54-64), immediately suggesting a selective approach for targeting not only mature tumor cells but also CSCs. Whereas MUC1 is a normal surface constituent of some epithelial cells where it serves a barrier function. Tumor-associated MUC1 is characterized by hypoglycosylation and increased sialylation on CSCs in the same fashion as observed in mature cancer cells, with STn appearing as a specific marker for both CSCs and mature tumor cells (Curry et al., Journal of surgical oncology, 2013, 107, 713-722). The aberrant oligosaccharide profile of MUC1 gives rise to the expression of neomarkers such as sialyl-$Le^a$ (used in the CA19-9 test), sialyl-$Le^x$, and sialyl-Tn (TAG-72), as well as the cryptic epitopes such as Tn in cancer cells (e.g., CSCs). In addition, because of underglycosylation, the peptide core of the mucin becomes exposed such that epitopes within the core (not accessible within normal tissue-derived MUC1) may serve as potential antigens.

Clinical approaches targeting STn have thus far consisted solely of STn vaccines. The most advanced clinical candidate is Theratope, a therapeutic vaccine consisting of STn coupled to keyhole limpet hemocyanin. In in vivo mouse studies Theratope immunization induced a potent antibody response that was shown to mediate a delay in the growth of injected STn-expressing mammary carcinoma cells (Julien et al., British journal of cancer, 2009, 100, 1746-1751). However, Theratope failed to meet its primary endpoint in a phase III clinical trial in metastatic breast cancer. A leading hypothesis for why the Theratope trial missed its primary endpoint is that the patient population was not evaluated for STn expression prior to enrollment. Since STn expression in breast cancer is highly heterogeneous between patients, ranging from 25%-80% depending on the study and detection method, lack of ability to correlate STn expression with response may have masked any benefit from Theratope. Importantly, a subset of patients receiving hormonal therapy showed a significant 7.5 month increase in median overall survival when treated with Theratope compared to hormone therapy alone (Ibrahim et al., Journal of clinical oncology: official journal of the American Society of Clinical Oncology, 2004, 22, 2547; and Miles et al., The oncologist, 2011, 16, 1092-1100), validating the therapeutic potential of targeting STn in particular patient populations. Additionally, since the immune response often varies considerably between vaccinated patients, vaccine approaches lack the ability to control or modulate antibody titer, resulting in wide ranges of therapeutic antibody exposure among patients. Nonetheless, Theratope was well tolerated with minimal toxicity, demonstrating the safety of targeting STn for cancer therapy.

The growing understanding of the molecular basis of STn expression in cancer cells strongly suggests that cells that express STn on any cell surface protein will also express STn on many (if not all) other O-glycosylated cell surface proteins, rendering it an excellent widely-distributed cancer-associated therapeutic target. Thus, STn positive cancer cell populations may be enriched for CSCs. In addition, recent data demonstrate that abrogation of STn expression renders cancers less aggressive with significant reductions in metastatic behavior (Gill et al., Proceedings of the National Academy of Sciences of the United States of America 2013, 110, E3152-3161).

Anti-STn Antibodies Targeting CSCs as Cancer Treatment

Several anti-STn antibodies have been described in the field, but some demonstrate low specificity towards the STn antigen or sialylated isoforms. For example, the commercial B72.3 anti-STn antibody has been shown to bind not only to STn but also to the Tn antigen (Bapat, S. A. (2010) Human ovarian cancer stem cells. Reproduction 140, 33-41). The availability of monoclonal antibodies (mAbs) targeting STn, engineered to induce antibody-dependent cellular cytotoxicity (ADCC) and/or complement-dependent cytotoxicity (CDC), or conjugated with a cytotoxic payload [e.g. antibody drug conjugate (ADC)], offers the potential of a significant therapeutic benefit for cancer patients with STn-expressing tumors. In addition, such antibodies would also allow for the development of a companion diagnostic to pre-select patients most likely to respond to therapy.

STn is often present on one or more of CSC surface antigens, and together they serve to promote the sternness and chemoresistance properties associated with CSCs. Thus, anti-STn antibodies offer a CSC-associated cancer targeting agent with the potential not only to directly kill CSCs via direct engagement and/or ADCC, but also offer a unique opportunity to bind to a wide array of cell-surface proteins and interfere with their associated functions essential for CSC viability, self-renewal, and replication.

As discuss herein, the rationale and advantages of targeting STn on CSCs may include: (1) many tumor-specific truncated glycoproteins carry STn in cancer; (2) STn is a unique glycan target expressed preferentially on CD44, MUC1, and potentially other important cell-surface markers, on both CSCs and mature tumor cells, irrespective of proliferation status, allowing for targeting of both of these tumor components by a single therapeutic agent; (3) STn is also a component of CA-125, a biomarker of ovarian cancer and others; (4) STn is a component of the ovarian CSC marker CD44. Therefore, the use of pan-STn murine mAbs, targeting an epitope that encompasses both the Neu5Ac and Neu5Gc forms of sialic acid linked to Tn, will bind to and kill or impair the function of CSCs and, by virtue of the common epitope, non-CSC tumor cells.

In some embodiments, the present invention provides new anti-pan STn mAb(s) for specific elimination of human CSCs as well as mature tumor cells. In one aspect of the present invention, the anti-STn antibody will target the validated STn glycan itself—not a particular glycopeptide or carrier protein, which should offer the broad potential of binding to CD44, MUC1, or other STn-glycosylated markers on both CSC and non-CSC tumor populations.

Given the exceptional specificity in targeting tumor-associated STn, the present invention may spare normal tissues, including normal adult stem cells, thereby allowing for an excellent therapeutic window.

In accordance with the present invention, provided herein is a unique immunotherapeutic solution aimed at eradicating human neoplasias by eliminating both CSCs and mature cancer cells contained within the tumor compartment. The present invention provides therapies and methods specifically targeting tumors, which now include targeting CSCs, and hence expanding the therapeutic window by targeting associated tumor-specific carbohydrate moieties of these potential targets. The elimination is specifically conferred through targeting tumor associated cell-surface sialylated Tn antigen (STn) structures that are uniquely present in cancer tissue, including cancer stem cells Ovarian CSCs Ovarian cancer is the leading gynecological cancer effecting women in the U.S. During 2013. It is estimated that 22,240 women will be diagnosed with and 14,030 will die of this disease, making it the fifth leading cause of female-related cancer deaths and the most lethal gynecologic malignancy in the U.S. (Siegel et al., Cancer statistics, 2013. CA: a cancer journal for clinicians 63, 11-30). This high mortality can be ascribed to non-symptomatic onset, late-stage initial diagnosis, aggressiveness of this type of cancer, and a general lack of therapeutically targetable genetic changes. The current standard of care is tumor debulking followed by taxane and platinum based chemotherapy. While this initial treatment results in ~70% of patients achieving an initial complete clinical response, a majority of these patients will unfortunately relapse with chemoresistant disease (Foster et al., Cancer letters, 2013, 338, 147-157; and McCann et al., PloS one, 2011, 6, e28077). In part, recurrent disease has been attributable, as with other cancer types, to the presence of CSCs within the total tumor population. Indeed, ovarian CSCs have been identified and shown to be resistant to chemo- and radiotherapy (Burgos-Ojeda et al., Cancer letters, 2012, 322, 1-7). Thus, again as the case with other forms of cancer, eliminating CSCs along with mature cells in the tumor population offers the best hope to manage recurrent disease and ideally effect cures.

In some embodiments of the present invention, ovarian CSCs may be targeted for ovarian cancer treatment. Although CD133 is the most widely studied of putative ovarian CSC markers, it is recognized that CD44, a known carrier of STn as discussed above, is associated with ovarian cancer and is included in the set of markers that identify ovarian CSCs (Zhang et al., Cancer research, 2008, 68, 4311-4320; Foster et al., Cancer letters, 2013, 338, 147-157; and Zoller, Cancer, 2011, 11, 254-267). Further, STn is expressed on the well-known ovarian cancer biomarker CA-125 (MUC16), as well as on MUC1, where the levels of these STn-associated mucins in serum have been used recently as further differentiators of cancerous versus benign ovarian disease. Elevated serum levels of STn occur in ~50% of ovarian cancer patients and correlate with a lower 5-year survival rate (Kobayashi et al., Journal of clinical oncology: official journal of the American Society of Clinical Oncology, 1991, 9, 983-987; Kobayashi et al., Journal of clinical oncology: official journal of the American Society of Clinical Oncology, 1992, 10, 95-101; and Chen et al., Journal of proteome research, 2013, 12, 1408-1418). Finally, Vathipadiekal et al. in a study of differential gene expression between human primary ovarian carcinoma CSCs and non-CSC populations found that the expression of STn-generating sialyl transferase ST6GalNAc-I did not differ among cells from the two compartments.

In some embodiments, the present invention provides antibodies for targeting CSCs to prevent control or cure cancer related to CSCs. Such antibodies may include anti-STn antibodies, including, but not limited to any of those described (or derived from any of those described) in international application number PCT/US14/60079, the contents of which are herein incorporated by reference in their entirety. Further anti-STn antibodies may include antibody 3F1 (SBH Sciences, Natick, Mass.) or derivatives thereof, including recombinant antibodies with CDRs from 3F1 and/or humanized derivatives.

Combined Cancer Therapies

In some embodiments, compounds and compositions of the invention may be combined with one or more additional forms of cancer treatment. In some cases, such additional forms may include chemotherapeutic treatments.

As used herein, the term, "chemotherapy" refers to a form of treatment using chemical substances. Such chemical substances are referred to herein as "chemotherapeutic agents." In the treatment of cancer, chemotherapeutic agents may comprise one or more anticancer drugs. In some embodiments, chemotherapeutic agents that may be used according to methods of the present invention or in combination with compounds or compositions of the invention may include, but are not limited to capecitabine, gemcitabine, ABRAXANE® (paclitaxel protein-bound particles for injectable suspension), docetaxel, fluorouracil (5-FU), oxaliplatin, cisplatin, carboplatin, irinotecan, topotecan, paclitaxel, leucovorin, doxorubicin, and combinations thereof.

Immune-Related Targets

In some embodiments, glycan-interacting antibodies of the invention may be immunomodulatory antibodies. As used herein, an immunomodulatory antibody is an antibody that enhances or suppresses one or more immune function or pathway.

Many bacterial glycans are known to comprise sialic acid. In some cases, such glycans allow bacteria to evade the innate immune system of hosts, including, but not limited to humans. In one example, bacterial glycans inhibit alternate complement pathway activation through factor H recognition. In another example, bacterial glycans mask underlying residues that may be antigenic. Some bacterial glycans participate in cell signaling events through activation of inhibitory sialic acid binding Ig-like lectins (Siglecs) that dampen the immune response to entities comprising certain sialylated moieties (Chen, X. et al., Advances in the biology and chemistry of sialic acids. ACS Chem Biol. 2010 Feb. 19; 5(2):163-76). In some embodiments, glycan-interacting antibodies of the present invention may be used to treat immune complications related to bacterial glycans.

Due to the foreign nature of Neu5Gc as described herein, some Neu5Gc glycans are immunogenic resulting in immune related destruction of cells and other entities where these glycans may be expressed. Such autoimmune destruction may be pathogenic. In some embodiments, glycan-interacting antibodies may be used to treat patients suffering from autoimmune disorders related to Neu5Gc glycans.

In some embodiments, immunomodulatory antibodies of the invention may be used to promote or suppress T cell-mediated immunity. Such antibodies may interact with one or more glycans present on T cells, T cell-related proteins and/or on one or more other cell types that interact with T cells. Immunomodulatory antibodies that enhance T cell mediated immunity may be used to stimulate T cell mediated targeting of cancer cells.

In some tumors, infiltration by tumor-associated macrophages (TAMs) may lead to immunosuppression promoting tumor cell viability and growth. This is thought to be due to immunosuppressive cell signaling that occurs through interactions between myeloid C-type lectin receptors (CLRs) present on TAMs and tumor-associated mucins (Allavena, P. et al., Clin Dev Immunol. 2010; 2010:547179). In some embodiments, binding of immunomodulatory antibodies of the invention to one or more tumor-associated mucin or TACA prevents immunosuppressive cell signaling in TAMs.

Anti-Viral Applications

In some embodiments, glycan-interacting antibodies of the invention may target viruses. Viral coat proteins and viral envelopes often comprise glycans, referred to herein as viral surface glycans. Such glycans may be targets of glycan-interacting antibodies. In some embodiments, viral surface glycans comprise sialyl-STn. In a further embodiment, viral surface glycans comprise GcSTn. Viruses that may be targeted by glycan-interacting antibodies include, but are not limited to HIV, influenza, rhinovirus, varicella-zoster, rotavirus, herpes (e.g. types 1 and 2), hepatitis (e.g. types A, B, C, D and E), yellow fever and human papillomavirus.

Other Therapeutic Applications

In some embodiments, glycan-interacting antibodies of the invention may act to alter or control proteolytic events. In some embodiments, glycan-interacting antibodies of the present invention may be internalized into cells prior to binding to targets.

Veterinary Applications

It is contemplated that glycan-interacting antibodies of the invention will find utility in the area of veterinary care including the care and treatment of non-human vertebrates. As described herein, the term "non-human vertebrate" includes all vertebrates with the exception of Homo sapiens, including wild and domesticated species such as companion animals and livestock. Non-human vertebrates include mammals, such as alpaca, banteng, bison, camel, cat, cattle, deer, dog, donkey, gayal, goat, guinea pig, horse, llama, mule, pig, rabbit, reindeer, sheep water buffalo, and yak. Livestock includes domesticated animals raised in an agricultural setting to produce materials such as food, labor, and derived products such as fiber and chemicals. Generally, livestock includes all mammals, avians and fish having potential agricultural significance. In particular, four-legged slaughter animals include steers, heifers, cows, calves, bulls, cattle, swine and sheep.

Bioprocessing

In some embodiments of the invention are methods for producing biological products in host cells by contacting the cells with one or more glycan-interacting antibody (such as an antibody or fusion protein) capable of modulating gene expression, or altering levels and/or types of glycans produced wherein such modulation or alteration enhances production of biological products. According to the present invention, bioprocessing methods may be improved by using one or more of the glycan-interacting antibodies of the present invention. They may also be improved by supplementing, replacing or adding one or more glycan-interacting antibodies.

Diagnostics

In some embodiments, compounds and compositions of the invention may be used as diagnostics. In some cases, antibodies of the invention may be used to identify, label or stain cells, tissues, organs, etc. expressing target antigens. In further embodiments, antibodies of the invention may be used to identify STn present in tissue sections (i.e., histological tissue sections), including tissue known or suspected of having cancerous cells. Such methods of using antibodies of the invention may in some cases be used to identify cancerous cells or tumors in tissue sections. Tissue sections may be from any tissue or organ including, but not limited to breast, colon, pancreatic, ovarian, brain, liver, kidney, spleen, lung, skin, stomach, intestine, esophagus, or bone.

III. Pharmaceutical Compositions

The pharmaceutical compositions described herein can be characterized by one or more of bioavailability, therapeutic window and/or volume of distribution.

Bioavailability

Glycan-interacting antibodies, when formulated into a composition with a delivery/formulation agent or vehicle as described herein, can exhibit an increase in bioavailability as compared to a composition lacking a delivery agent as described herein. As used herein, the term "bioavailability" refers to the systemic availability of a given amount of glycan-interacting antibodies administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a glycan-interacting antibody, measured as AUC, $C_{max}$, or $C_{min}$ in a mammal is greater, when co-administered with a delivery agent as described herein, than when such co-administration does not take place. In some embodiments, the bioavailability of the glycan-interacting antibody can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

Glycan-interacting antibodies, when formulated into a composition with a delivery agent as described herein, can exhibit an increase in the therapeutic window of the administered glycan-interacting antibody composition as compared to the therapeutic window of the administered glycan-interacting antibody composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the glycan-interacting antibody when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

Glycan-interacting antibodies, when formulated into a composition with a delivery agent as described herein, can exhibit an improved volume of distribution (Vdist), e.g., reduced or targeted, relative to a composition lacking a delivery agent as described herein. The volume of distribution (Vdist) relates the amount of the drug in the body to the concentration of the drug in the blood or plasma. As used herein, the term "volume of distribution" refers to the fluid volume that would be required to contain the total amount of the drug in the body at the same concentration as in the blood or plasma: Vdist equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, Vdist can be used to determine a loading dose to achieve a steady state concentration. In some embodiments, the volume of distribution of the glycan-interacting antibody when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

In some embodiments, glycan-interacting antibodies comprise compositions and/or complexes in combination with one or more pharmaceutically acceptable excipients. Pharmaceutical compositions may optionally comprise one or more additional active substances, e.g. therapeutically and/or prophylactically active substances. General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

In some embodiments, compositions are administered to humans, human patients or subjects. For the purposes of the present disclosure, the phrase "active ingredient" generally refers to glycan-interacting antibodies to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, or at least 80% (w/w) active ingredient. In one embodiment, active ingredients are antibodies directed toward cancer cells.

Formulation

Glycan-interacting antibodies of the invention can be formulated using one or more excipients to: (1) increase stability; (2) increase cell permeability; (3) permit the sustained or delayed release (e.g., from a formulation of the glycan-interacting antibody); and/or (4) alter the biodistribution (e.g., target the glycan-interacting antibody to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present invention can include, without limitation, liposomes, lipid nanoparticles, polymers, lipoplexes, core-shell nanoparticles, peptides, proteins, cells transfected with the glycan-interacting antibodies (e.g., for transplantation into a subject) and combinations thereof.

Excipients

As used herein, the term "excipient" refers to any substance combined with a compound and/or composition of the invention before use. In some embodiments, excipients are inactive and used primarily as a carrier, diluent or vehicle for a compound and/or composition of the present invention. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference).

The use of a conventional excipient medium is contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), micro-crystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC®F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL 115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

In some embodiments, anti-glycan antibodies of the invention are formulated with an excipient that includes citrate and/or NaCl. Such composition may include from about 1 mM to about 10 mM, from about 2 mM to about 20 mM, from about 5 mM to about 50 mM, from about 10 mM to about 100 mM, from about 50 mM to about 200 mM, or from about 100 mM to about 1,000 mM citrate. Further compositions may include from about 1 mM to about 10 mM, from about 5 mM to about 20 mM, from about 15 mM to about 50 mM, from about 30 mM to about 60 mM, from about 50 mM to about 200 mM, from about 100 mM to about 300 mM, or from about 250 mM to about 1000 mM NaCl.

Vehicles

Liposomes, Lipoplexes and Lipid Nanoparticles

Glycan-interacting antibodies of the present invention may be formulated using one or more liposomes, lipoplexes, or lipid nanoparticles. In one embodiment, pharmaceutical compositions comprising glycan-interacting antibodies further comprise liposomes. Liposomes are artificially-prepared vesicles which may primarily comprise one or more lipid bilayers and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment such formulations may also be constructed or compositions altered such that they passively or actively are directed to different cell types in vivo.

Formulations can also be selectively targeted through expression of different ligands on their surface as exemplified by, but not limited by, folate, transferrin, N-acetylgalactosamine (GalNAc), and antibody targeted approaches.

Liposomes, lipoplexes, or lipid nanoparticles may be used to improve the efficacy of glycan-interacting antibody function as these formulations may be able to increase cell transfection with glycan-interacting antibodies. The liposomes, lipoplexes, or lipid nanoparticles may also be used to increase the stability of glycan-interacting antibodies.

Liposomes that are specifically formulated for antibody cargo are prepared according to techniques known in the art, such as described by Eppstein et al. (Eppstein, D. A. et al., Biological activity of liposome-encapsulated murine interferon gamma is mediated by a cell membrane receptor. Proc Natl Acad Sci USA. 1985 June; 82(11):3688-92); Hwang et al. (Hwang, K. J. et al., Hepatic uptake and degradation of unilamellar sphingomyelin/cholesterol liposomes: a kinetic study. Proc Natl Acad Sci USA. 1980 July; 77(7):4030-4); U.S. Pat. No. 4,485,045 and U.S. Pat. No. 4,544,545. Production of liposomes with sustained circulation time is also described in U.S. Pat. No. 5,013,556.

Liposomes comprising glycan-interacting antibodies of the present invention may be generated using reverse phase evaporation utilizing lipids such as phosphatidylcholine, cholesterol as well as phosphatidylethanolamine that has been polyethylene glycol-derivatized. Filters with defined pore size are used to extrude liposomes of the desired diameter. In another embodiment, glycan-interacting antibodies of the present invention can be conjugated to the external surface of liposomes by disulfide interchange reaction as is described by Martin et al. (Martin, F. J. et al., Irreversible coupling of immunoglobulin fragments to preformed vesicles. An improved method for liposome targeting. J Biol Chem. 1982 Jan. 10; 257(1):286-8).

Polymers and Nanoparticles

Glycan-interacting antibodies of the invention can be formulated using natural and/or synthetic polymers. Non-limiting examples of polymers which may be used for delivery include, but are not limited to DMRI/DOPE, poloxamer, chitosan, cyclodextrin, and poly(lactic-co-glycolic acid) (PLGA) polymers. These may be biodegradable.

The polymer formulation can permit the sustained or delayed release of glycan-interacting antibodies (e.g., following intramuscular or subcutaneous injection). The altered release profile for glycan-interacting antibodies can result in, for example, release of the glycan-interacting antibodies over an extended period of time. The polymer formulation may also be used to increase the stability of glycan-interacting antibodies.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; herein incorporated by reference in its entirety).

Glycan-interacting antibodies of the invention can also be formulated as nanoparticles using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so delivery of glycan-interacting antibodies may be enhanced. For glycan-interacting antibodies, systems based on poly(2-(methacryloyloxy)ethyl phosphorylcholine)-block-(2-(diisopropylamino)ethyl methacrylate), (PMPC-PDPA), a pH sensitive diblock copolymer that self-assembles to form nanometer-sized vesicles, also known as polymersomes, at physiological pH may be used. These polymersomes have been shown to successfully deliver relatively high antibody payloads within live cells. (Massignani, et al, Cellular delivery of antibodies: effective targeted subcellular imaging and new therapeutic tool. Nature Proceedings, May, 2010).

In one embodiment, a PEG-charge-conversional polymer (Pitella et al., Biomaterials. 2011 32:3106-3114) may be used to form a nanoparticle to deliver glycan-interacting antibodies of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle.

In one embodiment, matrices of poly(ethylene-co-vinyl acetate), are used to deliver glycan-interacting antibodies of the invention. Such matrices are described in Nature Biotechnology 10, 1446-1449 (1992).

Antibody Formulations

Glycan-interacting antibodies of the invention may be formulated for intravenous administration or extravascular administration (Daugherty, et al., Formulation and delivery issues for monoclonal antibody therapeutics. Adv Drug Deliv Rev. 2006 Aug. 7; 58(5-6):686-706, US patent publication number 2011/0135570, all of which are incorporated herein in their entirety). Extravascular administration routes may include, but are not limited to subcutaneous administration, intraperitoneal administration, intracerebral administration, intraocular administration, intralesional administration, topical administration and intramuscular administration.

Antibody structures may be modified to improve their effectiveness as therapeutics. Improvements may include, but are not limited to improved thermodynamic stability, reduced Fc receptor binding properties and improved folding efficiency. Modifications may include, but are not limited to amino acid substitutions, glycosylation, palmitoylation and protein conjugation.

Glycan-interacting antibodies may be formulated with antioxidants to reduce antibody oxidation. Glycan-interacting antibodies may also be formulated with additives to reduce protein aggregation. Such additives may include, but are not limited to albumin, amino acids, sugars, urea, guanidinium chloride, polyalcohols, polymers (such as polyethylene glycol and dextrans), surfactants (including, but not limited to polysorbate 20 and polysorbate 80) or even other antibodies.

Glycan-interacting antibodies of the present invention may be formulated to reduce the impact of water on antibody structure and function. Antibody preparations in such formulations may be may be lyophilized. Formulations subject to lyophilization may include carbohydrates or polyol compounds to protect and stabilize antibody structure. Such compounds include, but are not limited to sucrose, trehalose and mannitol.

Glycan-interacting antibodies of the present invention may be formulated with polymers. In one embodiment, polymer formulations may contain hydrophobic polymers. Such polymers may be microspheres formulated with polylactide-co-glycolide through a solid-in-oil-in-water encapsulation method. Microspheres comprising ethylene-vinyl acetate copolymer are also contemplated for antibody delivery and may be used to extend the time course of antibody release at the site of delivery. In another embodiment, polymers may be aqueous gels. Such gels may, for example, comprise carboxymethylcellulose. Aqueous gels may also comprise hyaluronic acid hydrogel. Antibodies may be covalently linked to such gels through a hydrazone linkage that allows for sustained delivery in tissues, including but not limited to the tissues of the central nervous system.

Peptide and Protein Formulations

Glycan-interacting antibodies of the invention may be formulated with peptides and/or proteins. In one embodiment, peptides such as, but not limited to, cell penetrating peptides and proteins and peptides that enable intracellular delivery may be used to deliver pharmaceutical formulations. A non-limiting example of a cell penetrating peptide which may be used with the pharmaceutical formulations of the present invention includes a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3):310-8 (2001); Langel, Cell-Penetrating Peptides: Processes and Applications (CRC Press, Boca Raton Fla., 2002); El-Andaloussi et al., Curr. Pharm. Des. 11(28):3597-611 (2003); and Deshayes et al., Cell. Mol. Life Sci. 62(16):1839-49 (2005), all of which are incorporated herein by reference). The compositions can also be formulated to include a cell penetrating agent, e.g., liposomes, which enhance delivery of the compositions to the intracellular space. Glycan-interacting antibodies of the invention may be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106:6111-6116; Sawyer, Chem Biol Drug Des. 2009 73:3-6; Verdine and Hilinski, Methods Enzymol. 2012; 503:3-33; all of which are herein incorporated by reference in their entirety).

In one embodiment, the cell-penetrating polypeptide may comprise a first domain and a second domain. The first domain may comprise a supercharged polypeptide. The second domain may comprise a protein-binding partner. As used herein, "protein-binding partner" includes, but are not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where glycan-interacting antibodies may be introduced.

In formulations of the present invention, peptides or proteins may be incorporated to increase cell transfection by glycan-interacting antibodies or alter the biodistribution of glycan-interacting antibodies (e.g., by targeting specific tissues or cell types).

Cell Formulations

Cell-based formulations of glycan-interacting antibody compositions of the invention may be used to ensure cell transfection (e.g., in the cellular carrier) or alter the biodistribution of the compositions (e.g., by targeting the cell carrier to specific tissues or cell types).

Cell Transfer Methods

A variety of methods are known in the art and are suitable for introduction of nucleic acids or proteins, such as glycan-interacting antibodies, into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The technique of sonoporation, or cellular sonication, is the use of sound (e.g., ultrasonic frequencies) for modifying the permeability of the cell plasma membrane. Sonoporation methods are known to those in the art and are used to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; all herein incorporated by reference in their entirety). Sonoporation methods are known in the art and are also taught for example as it relates to bacteria in US Patent Publication 20100196983 and as it relates to other cell types in, for example, US Patent Publication 20100009424, each of which are incorporated herein by reference in their entirety.

Electroporation techniques are also well known in the art and are used to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). In one embodiment, glycan-interacting antibodies may be delivered by electroporation.

Administration and Delivery

The compositions of the present invention may be administered by any of the standard methods or routes known in the art.

Glycan-interacting antibodies of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Non-limiting routes of administration for glycan-interacting antibodies of the present invention are described below.

Parenteral and Injectable Administration

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Rectal and Vaginal Administration

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Oral Administration

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Topical or Transdermal Administration

As described herein, compositions containing glycan-interacting antibodies of the invention may be formulated for administration topically. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compositions will depend on the route of nucleic acid delivery. Three routes are commonly considered to deliver glycan-interacting antibodies to the skin: (i) topical application (e.g. for local/regional treatment and/or cosmetic applications); (ii) intradermal injection (e.g. for local/regional treatment and/or cosmetic applications); and (iii) systemic delivery (e.g. for treatment of dermatologic diseases that affect both cutaneous and extracutaneous regions). Glycan-interacting antibodies can be delivered to the skin by several different approaches known in the art.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or glycan-interacting antibodies described herein to allow a user to perform multiple treatments of a subject(s).

In one embodiment, the invention provides for compositions comprising glycan-interacting antibodies to be delivered in more than one injection.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required.

Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

Depot Administration

As described herein, in some embodiments, compositions of the present invention are formulated in depots for extended release. Generally, a specific organ or tissue (a "target tissue") is targeted for administration.

In some aspects of the invention, glycan-interacting antibodies are spatially retained within or proximal to a target tissue. Provided are methods of providing compositions to one or more target tissue of a mammalian subject by contacting the one or more target tissue (comprising one or more target cells) with compositions under conditions such that the compositions, in particular glycan-interacting antibody component(s) of the compositions, are substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the level of glycan-interacting antibodies present in the compositions entering the target tissues and/or cells. For example, at least 1, 5, 10, 20, 30, 40, 50, 60, 70, 80, 85, 90, 95, 96, 97, 98, 99, 99.9, 99.99 or greater than 99.99% of glycan-interacting antibodies administered to the subject are present intracellularly at a period of time following administration. For example, intramuscular injection to a mammalian subject is performed using an aqueous composition comprising one or more glycan-interacting antibody and a transfection reagent, and retention of the composition is determined by measuring the level of glycan-interacting antibodies present in the muscle cells.

Certain aspects of the invention are directed to methods of providing compositions to target tissues of mammalian subjects, by contacting the target tissues (containing one or more target cells) with compositions under conditions such that the compositions are substantially retained in the target tissue. Compositions contain an effective amount of glycan-interacting antibodies such that the effect of interest is produced in at least one target cell. Compositions generally contain cell penetration agents and a pharmaceutically acceptable carrier, although "naked" glycan-interacting antibodies (such as glycan-interacting antibodies without cell penetration agents or other agents) are also contemplated.

In some embodiments, compositions include a plurality of different glycan-interacting antibodies, where one or more than one of the glycan-interacting antibodies targets a glycan of interest. Optionally, compositions also contain cell penetration agents to assist in the intracellular delivery of compositions. A determination is made of the composition dose required to target glycans of interest in a substantial percentage of cells contained within a predetermined volume of the target tissue (generally, without targeting glycans in tissue adjacent to the predetermined volume, or distally to target tissues). Subsequent to this determination, the determined dose may be introduced directly into the tissue of the mammalian subject.

In one embodiment, the invention provides for glycan-interacting antibodies to be delivered in more than one injection or by split dose injections.

Pulmonary Administration

Pharmaceutical compositions may be prepared, packaged, and/or sold in formulations suitable for pulmonary administration via the buccal cavity. Such formulations may comprise dry particles further comprising active ingredients and having a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

Ophthalmic or Otic Administration

A pharmaceutical composition may be prepared, packaged, and/or sold in a formulation suitable for ophthalmic or otic administration. Such formulations may, for example, be in the form of eye or ear drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Subretinal inserts may also be used as a form of administration.

Payload Administration

Glycan-interacting antibodies described herein may be used in a number of different scenarios in which delivery of a substance (the "payload") to a biological target is desired, for example delivery of detectable substances for detection of the target, or delivery of a therapeutic or diagnostic agent. Detection methods can include, but are not limited to, both imaging in vitro and in vivo imaging methods, e.g., immunohistochemistry, bioluminescence imaging (BLI), Magnetic Resonance Imaging (MM), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

Glycan-interacting antibodies can be designed to include both a linker and a payload in any useful orientation. For example, a linker having two ends is used to attach one end to the payload and the other end to the glycan-interacting antibody. The glycan-interacting antibodies of the invention can include more than one payload as well as a cleavable linker. In another example, a drug that may be attached to glycan-interacting antibodies via a linker and may be fluorescently labeled can be used to track the drug in vivo, e.g. intracellularly.

Other examples include, but are not limited to, the use of glycan-interacting antibodies in reversible drug delivery into cells.

Glycan-interacting antibodies described herein can be used in intracellular targeting of a payload, e.g., detectable or therapeutic agents, to specific organelles. In addition, glycan-interacting antibodies described herein may be used to deliver therapeutic agents to cells or tissues, e.g., in living animals. For example, glycan-interacting antibodies described herein may be used to deliver chemotherapeutic agents to kill cancer cells. Glycan-interacting antibodies attached to therapeutic agents through linkers can facilitate member permeation allowing the therapeutic agent to travel into a cell to reach an intracellular target.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, TAXOL™, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, TAXOL™ and maytansinoids). In the case of anti-STn antibodies of the present invention, tumor killing may be boosted by the conjugation of a toxin to such anti-STn antibodies.

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}F$, $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, $^{3}H$, or $^{99m}Tc$ (e.g., as pertechnetate (technetate (VII), $TcO_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine (1:1) (IR144); 5-chloro-2-[2-[3-[(5-chloro-3-ethyl-2(3H)-benzothiazolylidene)ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosanilin; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable precursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

Combinations

Glycan-interacting antibodies may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, and/or imaging compositions in combination with agents that may improve their bioavailability, reduce and/or modify their metabolism, inhibit their excretion, and/or modify their distribution within the body.

Dosage

The present disclosure encompasses delivery of glycan-interacting antibodies for any of therapeutic, pharmaceutical, diagnostic or imaging by any appropriate route taking into consideration likely advances in the sciences of drug delivery. Delivery may be naked or formulated.

Naked Delivery

Glycan-interacting antibodies of the present invention may be delivered to cells, tissues, organs or organisms in naked form. As used herein in, the term "naked" refers to glycan-interacting antibodies delivered free from agents or modifications which promote transfection or permeability. Naked glycan-interacting antibodies may be delivered to cells, tissues, organs and/or organisms using routes of administration known in the art and described herein. Naked delivery may include formulation in a simple buffer such as saline or PBS.

Formulated Delivery

Glycan-interacting antibodies of the present invention may be formulated, using methods described herein. Formulations may comprise glycan-interacting antibodies which may be modified and/or unmodified. Formulations may further include, but are not limited to, cell penetration agents, pharmaceutically acceptable carriers, delivery agents, bioerodible or biocompatible polymers, solvents, and sustained-release delivery depots. Formulated glycan-interacting antibodies may be delivered to cells using routes of administration known in the art and described herein.

Compositions may also be formulated for direct delivery to organs or tissues in any of several ways in the art including, but not limited to, direct soaking or bathing, via a catheter, by gels, powder, ointments, creams, gels, lotions, and/or drops, by using substrates such as fabric or biodegradable materials coated or impregnated with compositions, and the like.

Dosing

The present invention provides methods comprising administering one or more glycan-interacting antibodies in accordance with the invention to a subject in need thereof. Nucleic acids encoding glycan-interacting antibodies, proteins or complexes comprising glycan-interacting antibodies, or pharmaceutical, imaging, diagnostic, or prophylactic compositions thereof, may be administered to a subject using any amount and any route of administration effective for preventing, treating, diagnosing, or imaging a disease, disorder, and/or condition. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, glycan-interacting antibodies may be administered in split-dose regimens. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in a 24 hr period. It may be administered as a single unit dose. In one embodiment, glycan-interacting antibodies of the present invention are administered to a subject in split doses. Glycan-interacting antibodies may be formulated in buffer only or in a formulation described herein. Pharmaceutical compositions comprising glycan-interacting antibodies as described herein may be formulated into a dosage form described herein, such as a topical, intranasal, intratracheal, or injectable (e.g., intravenous, intraocular, intravitreal, intramuscular, intracardiac, intraperitoneal or subcutaneous). General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

IV. Kits and Devices

Kits

Any of the compositions described herein may be comprised in a kit. In a non-limiting example, reagents for generating glycan-interacting antibodies, including antigen molecules are included in a kit. The kit may further include reagents or instructions for creating or synthesizing glycan-interacting antibodies. It may also include one or more buffers. Other kits of the invention may include components for making glycan-interacting antibody protein or nucleic acid arrays or libraries and thus, may include, for example, a solid support.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. The kits may also comprise a second container means for containing a sterile, pharmaceutically acceptable buffer and/or other diluent. However, various combinations of components may be comprised in a vial. The kits of the present invention also will typically include a means for containing the glycan-interacting antibodies, e.g., proteins, nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried powder. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least 1000 micrograms or at most 10 g of dried dye are provided in kits of the invention. The dye may then be resuspended in any suitable solvent, such as DMSO.

A kit may include instructions for employing the kit components as well the use of any other reagent not included in the kit. Instructions may include variations that can be implemented.

Devices

Any of the compositions described herein may be combined with, coated onto or embedded in a device. Devices include, but are not limited to, dental implants, stents, bone replacements, artificial joints, valves, pacemakers or other implantable therapeutic devices.

V. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Glycan Array Analysis

Optimized glycan arrays are utilized to test antibody affinity and specificity for multiple glycans in a single experiment. Glycan arrays used herein include arrays that comprise 71 chemically synthesized and well-defined glycans, most of which comprise Neu5Ac and Neu5Gc glycan pairs. Array slides are obtained commercially (Arraylt Corp, Sunnyvale, Calif.) and include the glycans listed in the following Table.

TABLE 6

| Array glycans | |
|---|---|
| Glycan ID No. | Glycan |
| 1 | Neu5,9Ac2α2,3Galβ1,4GlcNAcβO(CH2)2CH2NH2 |
| 2 | Neu5Gc9Acα2,3Galβ1,4GlcNAcβO(CH2)2CH2NH2 |
| 3 | Neu5,9Ac2α2,6Galβ1,4GlcNAcβO(CH2)2CH2NH2 |
| 4 | Neu5Gc9Acα2,6Galβ1,4GlcNAcβO(CH2)2CH2NH2 |
| 5 | Neu5Acα2,6GalNAcαO(CH2)2CH2NH2 |
| 6 | Neu5Gcα2,6GalNAcαO(CH2)2CH2NH2 |
| 7 | Neu5,9Ac2α2,3Galβ1,3GlcNAcβO(CH2)2CH2NH2 |
| 8 | Neu5Gc9Acα2,3Galβ1,3GlcNAcβO(CH2)2CH2NH2 |
| 9 | Neu5,9Ac2α2,3Galβ1,3GalNAcαO(CH2)2CH2NH2 |
| 10 | Neu5Gc9Acα2,3Galβ1,3GalNAcαO(CH2)2CH2NH2 |
| 11 | Neu5Acα2,3Galβ1,4GlcNAcβO(CH2)2CH2NH2 |
| 12 | Neu5Gcα2,3Galβ1,4GlcNAcβO(CH2)2CH2NH2 |

TABLE 6-continued

| Array glycans | |
|---|---|
| Glycan ID No. | Glycan |
| 13 | Neu5Acα2,3Galβ1,3GlcNAcβO(CH2)2CH2NH2 |
| 14 | Neu5Gcα2,3Galβ1,3GlcNAcβO(CH2)2CH2NH2 |
| 15 | Neu5Acα2,3Galβ1,3GalNAcαO(CH2)2CH2NH2 |
| 16 | Neu5Gcα2,3Galβ1,3GalNAcαO(CH2)2CH2NH2 |
| 17 | Neu5Acα2,6Galβ1,4GlcNAcβO(CH2)2CH2NH2 |
| 18 | Neu5Gcα2,6Galβ1,4GlcNAcβO(CH2)2CH2NH2 |
| 19 | Neu5Acα2,6Galβ1,4GlcβO(CH2)2CH2NH2 |
| 20 | Neu5Gcα2,6Galβ1,4GlcβO(CH2)2CH2NH2 |
| 21 | Neu5Acα2,3Galβ1,4GlcβO(CH2)2CH2NH2 |
| 22 | Neu5Gcα2,3Galβ1,4GlcβO(CH2)2CH2NH2 |
| 23 | Neu5,9Ac2α2,6GalNAcαO(CH2)2CH2NH2 |
| 24 | Neu5Gc9Acα2,6GalNAcαO(CH2)2CH2NH2 |
| 25 | Neu5Acα2,3GalβO(CH2)2CH2NH2 |
| 26 | Neu5Gcα2,3GalβO(CH2)2CH2NH2 |
| 27 | Neu5Acα2,6GalβO(CH2)2CH2NH2 |
| 28 | Neu5Gcα2,6GalβO(CH2)2CH2NH2 |
| 29 | Neu5,9Ac2α2,3GalβO(CH2)2CH2NH2 |
| 30 | Neu5Gc9Acα2,3GalβO(CH2)2CH2NH2 |
| 31 | Neu5,9Ac2α2,6GalβO(CH2)2CH2NH2 |
| 32 | Neu5Gc9Acα2,6GalβO(CH2)2CH2NH2 |
| 33 | Neu5Acα2,3Galβ1,3GalNAcβO(CH2)2CH2NH2 |
| 34 | Neu5Gcα2,3Galβ1,3GalNAcβO(CH2)2CH2NH2 |
| 35 | Neu5,9Ac2α2,3Galβ1,3GalNAcβO(CH2)2CH2NH2 |
| 36 | Neu5Gc9Acα2,3Galβ1,3GalNAcβO(CH2)2CH2NH2 |
| 37 | Neu5,9Ac2α2,6Galβ1,4GlcβO(CH2)2CH2NH2 |
| 38 | Neu5Gc9Acα2,6Galβ1,4GlcβO(CH2)2CH2NH2 |
| 39 | Neu5,9Ac2α2,3Galβ1,4GlcβO(CH2)2CH2NH2 |
| 40 | Neu5Gc9Acα2,3Galβ1,4GlcβO(CH2)2CH2NH2 |
| 41 | Neu5Acα2,8Neu5Acα2,3Galβ1,4GlcβO(CH2)2CH2NH2 |
| 42 | Neu5Acα2,8Neu5Acα2,8Neu5Acα2,3Galβ1,4GlcβO(CH2)2CH2NH2 |
| 43 | Galβ1,4GlcβO(CH2)2CH2NH2 |
| 45 | Galβ1,4GlcNAcβO(CH2)2CH2NH2 |
| 47 | GalNAcαO(CH2)2CH2NH2 |
| 51 | Galβ1,3GalNAcβO(CH2)2CH2NH2 |
| 52 | Galβ1,3GlcNAcαO(CH2)2CH2NH2 |
| 53 | Galβ1,3GlcNAcβO(CH2)2CH2NH2 |
| 54 | Galβ1,4GlcNAc6SβO(CH2)2CH2NH2 |
| 55 | Neu5Acα2,3Galβ1,4(Fucα1,3)GlcNAcβO(CH2)2CH2NH2 |
| 56 | Neu5Gcα2,3Galβ1,4(Fucα1,3)GlcNAcβO(CH2)2CH2NH2 |
| 57 | Neu5Acα2,3Galβ1,4(Fucα1,3)GlcNAc6SβO(CH2)2CH2NH2 |
| 58 | Neu5Gcα2,3Galβ1,4(Fucα1,3)GlcNAc6SβO(CH2)2CH2NH2 |
| 59 | Galβ1,3GlcNAcβ1,3Galβ1,4GlcβO(CH2)2CH2NH2 |
| 60 | Neu5Acα2,3Galβ1,3GlcNAcβ1,3Galβ1,4GlcβO(CH2)2CH2NH2 |
| 61 | Neu5Gcα2,3Galβ1,3GlcNAcβ1,3Galβ1,4GlcβO(CH2)2CH2NH2 |
| 62 | Neu5Acα2,3Galβ1,4GlcNAc6SβO(CH2)2CH2NH2 |
| 63 | Neu5Gcα2,3Galβ1,4GlcNAc6SβO(CH2)2CH2NH2 |
| 64 | Neu5Acα2,8Neu5Acα2,3Galβ1,4GlcβO(CH2)3NHCOCH2(OCH2CH2)6NH2 |
| 65 | Neu5Acα2,8Neu5Acα2,8Neu5Acα2,3Galβ1,4GlcβO(CH2)3NHCOCH2(OCH2CH2)6NH2 |
| 66 | Neu5Acα2,6(Neu5Acα2,3)Galβ1,4GlcβO(CH2)2CH2NH2 |
| 67 | Neu5Acα2,6(Neu5Gcα2,3)Galβ1,4GlcβO(CH2)2CH2NH2 |
| 68 | Neu5Acα2,6(KDNα2,3)Galβ1,4GlcβO(CH2)2CH2NH2 |
| 69 | Neu5Gcα2,8Neu5Acα2,3Galβ1,4GlcβO(CH2)2CH2NH2 |
| 70 | KDNα2,8Neu5Acα2,3Galβ1,4GlcβO(CH2)2CH2NH2 |
| 71 | Neu5Acα2,8Kdnα2,6Galβ1,4GlcβO(CH2)2CH2NH2 |
| 72 | Neu5Acα2,8Neu5Gcα2,3Galβ1,4GlcβO(CH2)2CH2NH2 |
| 73 | Neu5Acα2,8Neu5Gcα2,6Galβ1,4GlcβO(CH2)2CH2NH2 |
| 74 | KDNα2,8Neu5Gcα2,3Galβ1,4GlcβO(CH2)2CH2NH2 |
| 75 | Neu5Gcα2,8Neu5Gcα2,3Galβ1,4GlcβO(CH2)2CH2NH2 |
| 76 | Neu5Acα2,8Neu5Acα2,6Galβ1,4GlcβO(CH2)2CH2NH2 |

300 ml of epoxy blocking buffer is prepared by combining 15 ml of 2 M Tris buffer (pH 8) with 0.9 ml of 16.6 M ethanolamine and 284.1 ml of distilled water. The solution is brought to a final pH of 9.0 with HCl. The solution is filtered using a 0.2 nitrocellulose membrane. The epoxy buffer solution as well as 1 L of distilled water are pre-warmed to 50° C. Glass slides are arranged in a slide holder and quickly submerged in a staining tub with the warmed epoxy blocking buffer. Slides are incubated in the epoxy blocking buffer for 1 hour at 50° C. with periodic shaking to deactivate epoxy binding sites. Next, slides are rinsed and blocked with PBS with 1% OVA at 25° C. for one hour. Serum samples with polyclonal antibodies (1:1000) or purified monoclonal antibodies (1 ug/mL), are diluted in PBS with 1% OVA and added to the glycan array for one hour at 25° C. After extensive washing, binding of antibodies are detected by incubating glycan microarray slides with Cy3-conjugated anti-mouse IgG (Jackson Immunoresearch, West Grove, Pa.) for one hour. Slides are then washed extensively, dried and scanned with a Genepix 4000B scanner (Laser at 100%; gain at 350; 10 μm pixels). Raw data from scanned images are extracted using the Genepix software and analysis of raw data is carried out. Antibodies are considered to be highly specific for AcSTn and GcSTn if they demonstrate binding to both molecules, but not to Tn or any other glycans on the array.

Based on array analysis, antibodies are classified according to array glycan binding profile. Antibodies are classified as "Group 1" antibodies, capable of binding AcSTn and GcSTn, if they bind to glycans 5, 6, 23 and 24. Such antibodies are referred to as Pan-STn antibodies due to their ability to associate with a wider range of STn structures and the portion of STn indicated by the large oval in FIG. 1A. Antibodies are classified as "Group 2" antibodies, capable of binding STn as well as some related structures that include an O-linkage to serine or threonine, if they bind to glycans 5, 6, 23, 24, 27 and 31. These antibodies are thought to associate with the portion of STn indicated by the large oval in FIG. 1B. Some Group 2 antibodies preferably bind to structures with AcSTn over structures with GcSTn. Antibodies are classified as "Group 3" antibodies (capable of binding STn, but may also bind a broader set of related structures) if they bind glycans 5, 6, 23, 24, 17, 3, 19, 37, 27 and 31. Unlike Group 2 antibodies, Group 3 antibodies do not require that such structures have an O-linkage to serine or threonine. Group 3 antibodies are thought to associate with the portion of STn indicated by the large oval in FIG. 1C. Finally, antibodies are "Group 4" antibodies, capable of binding to both AcSTn and GcSTn as well as the unsialylated Tn antigen (therefore having broader specificity) if they bind to glycans 5, 6, 23, 24 and 47. Group 4 antibodies are thought to associate with the portion of STn indicated by the large oval in FIG. 1D.

Example 2. Flow Cytometry-Based Analysis of Antibody Binding

Flow cytometry-based analysis is carried out to elucidate the dose-response curve for binding of antibodies to cell surface antigens. For these analyses, various cell lines are employed.

MDA-MB-231 cells are human breast cancer cells. They are grown in Earle's Minimum Essential Medium supplemented with 10% fetal calf serum (FCS), 100 μg/ml penicillin, 100 UI/ml streptomycin and 45 μg/ml gentamycin. MCF-7 cells are also human breast cancer cells and are grown under the same conditions as MDA-MB-231 cells. Stably transfected versions of MDA-MB-231 and MCF-7 cells (clone TAH3.P10 for MDA-MB-231 cells and clone A12.1 for MCF-7 cells) that over express GalNAc α2,6-sialyltransferase (ST6GalNAc 1,) are also cultured under the same conditions with the exception of an added 1 mg/ml of G418 to support cells expressing the transgene. ST6GalNAc 1 is an enzyme capable of sialylating GalNAc. As a result of over expression, transfected cells express high levels of Neu5Ac-STn (see Julien, S. et al., Glycoconjugate journal. 2001. 18, 883-93; the contents of which are herein incorporated by reference in their entirety).

E3 cells are murine breast cancer cells. They are cultured in Dulbecco's E4 medium with 10% FCS. Stably transfected versions of E3 cells expressing high levels of Neu5Gc-STn (E3-STn) are cultured with 600 μg/ml of G418 and 200 μg/ml hygromycin. During growth and maintenance of experimental cells, trypsin is not used for cell passaging.

OV90 and OVCAR3 cells are also used. These are human ovarian cancer cell lines, described previously.

SNU-16 cells are also used. These are gastric cancer cell lines that express low levels of STn.

For analysis, cells are harvested using StemPro Accutase (Life Technologies, Carlsbad, Calif.) and washed with PBS comprising 5% FBS before pelleting by light centrifugation. Cell numbers and viability are determined by trypan blue dye exclusion analysis and cell concentrations are adjusted to $5\times10^6$ cells/ml in PBS with 5% FBS. 50 μl of cells are added to each well of an assay plate. Cells are combined with 50 μl solutions of antibody being analyzed or control antibodies and incubated for 1 hour at 4° C. Cells are washed and pelleted twice with PBS with 5% FBS before being treated with 100 μl of PBS with 5% FBS comprising a 1:1,500 dilution of anti-mouse IgG (Southern Biotech, Birmingham, Ala.,) conjugated to allophycocyanin (APC). Cells are incubated for 30 min at 4° C. before washing and resuspending in 200 μl of propidium iodide (PI) diluted 1:1000 in PBS with 5% FBS. Treated cells are then subjected to flow cytometry analysis and 10,000 events are acquired for each sample.

Example 3. Immunization with Alternative Antigens and Adjuvants

An immunization study was carried out to develop antibodies against STn. 40 C57BL/6 or Balb/C wild type mice (females, 6-8 weeks old) were acclimated for at least 3 days and given access to standard diet (2920X.10, Global 18% Protein Rodent Diet, Harlan, San Diego, Calif.) and acidified water (pH 2.7-3.0) ad libitum throughout the study period. Mice were divided into 4 groups of 10 mice each (a total of 8 groups). Mice were immunized according to the study design shown in the following Table, using either PSM (including digested PSM) and/or OSM at a dose of 10 μg mixed with adjuvants. Adjuvants included either Freund's adjuvant (complete or incomplete) or enhanced adjuvants comprising AbiSCO-100 (12 μg) and ODN-2395 (50 μg).

TABLE 7

Study Design

| Group | Strain | Immunogen and Adjuvant |
|---|---|---|
| 1 | C57B1/6 or Balb/C | PSM (10 μg) + AbiSCO-100(12 μg) + ODN-2395 (50 μg) |
| 2 | C57B1/6 or Balb/C | PSM (10 μg) or OSM + AbiSCO-100(12 μg) + ODN-2395 (50 μg) |
| 3 | C57B1/6 or Balb/C | Digested PSM (10 μg) + AbiSCO-100(12 μg) + ODN-2395 (50 μg) |
| 4 | C57B1/6 or Balb/C | OSM (10 μg) + AbiSCO-100(12 μg) + ODN-2395 (50 μg) |

Mice were randomized for placement into individual treatment groups based on body weight and sex. Vaccinations were given by subcutaneous (SC) injections around armpits and inguinal regions (50 μl per site, 4 sites for a total of 200 μl per mouse). Each mouse received 4 immunizations on days 0, 14, 28 and 42 by subcutaneous injection during the study period. Each mouse was immunized with 10 μg PSM, digested PSM or OSM antigen which was mixed with 12 μg of AbiSCO-100 and 50 μg of ODN-2395. After the 4th subcutaneously injection, each mouse was immunized with 10 μg PSM, digested PSM or OSM only intraperitoneally (IP) on day 63, 64 or 70 as the final immunization for each mouse, depending on which animal or group was selected. The detailed immunization schedule is presented in the following Table.

Additionally, body weight and health observations for each mouse were determined twice per week. Blood was collected from all animals prior to the immunization at each immunization date expect for the last boost (i.e. the 5th immunization by IP) during the study period. The last blood sample was collected on day 51.

During each blood collection, approximately 0.2 ml of whole blood was collected by facial vein bleed and placed into serum separator tubes. Tubes were then kept at room temperature for at least 30 minutes to allow clotting. Serum was then divided into aliquots of equal volume and stored at −80° C. until analysis.

TABLE 8

Immunization schedule

| | Schedule (days) | | | | |
|---|---|---|---|---|---|
| Group | 1st (day 0) | 2nd (day 14) | 3rd (day28) | 4th (day 42) | 5th (day 63 or 64 or 70) |
| 1 | SC, with PSM + adjuvant | SC, with PSM + adjuvant | SC, with PSM + adjuvant | SC, with PSM + adjuvant | IP; selected animals; PSM, Digested PSM or OSM only (no adjuvant) |
| 2 | SC, with PSM + adjuvant | SC, with OSM + adjuvant | SC, with PSM + adjuvant | SC, with OSM + adjuvant | |
| 3 | SC, with Digested PSM + adjuvant | SC, with Digested PSM + adjuvant | SC, with Digested PSM + adjuvant | SC, with Digested PSM + adjuvant | |
| 4 | SC, with OSM + adjuvant | SC, with OSM + adjuvant | SC, with OSM + adjuvant | SC, with OSM + adjuvant | |

Anti-STn serum titer was determined using a murine anti-STn bovine submaxillary mucin (BSM) ELISA (with or without periodate treatment) together with serum profiles observed by glycan microarray. 96-well plates were coated with 1 μg/well of BSM and incubated overnight at 4° C. O-acetylation of BSM antigen was removed by treating wells with 0.1 M sodium hydroxide. Specific binding to STn was determined by treatment of wells with sodium periodate. Periodate treatment destroys the C6 side chain of sialic acid; therefore antibodies raised against STn should not bind to periodate-treated wells. Wells were blocked with PBS 1% ovalbumin (OVA). Serum samples to be assayed were serially diluted in PBS 1% OVA. A commercially available mouse anti-STn monoclonal antibody, 3F1 (SBH Sciences, Natick, Mass.) was used as a positive control. This antibody was also serially diluted in PBS with 1% OVA. A pool of serum from naive wild type mice was used for the preparation of negative control samples. Detection of anti-STn antibodies present in serum was determined using an HRP-conjugated polyclonal goat anti-mouse IgG antibody (Jackson Immunoresearch, West Grove, Pa.). The reaction was stopped by addition of sulfuric acid (1.6 M). Optical densities were measured at 490 nm using a Spectramax microplate reader (Molecular Devices, Sunnyvale, Calif.). The serum titer was obtained by comparison of OD values with a cutoff value calculated as two standard deviations above the mean of optical density values of the negative control. Sample tests were considered positive if the mean optical density value was greater than the cutoff value.

Mice with high anti-STn antibody titers were selected for hybridoma fusions. Resulting hybridomas were screened by BSM ELISA (with or without periodate treatment to indicate antibodies capable of differentiating between 9-O-acetylated STn variants) as described above. Selected hybridomas were subcloned and subclones were further characterized by ELISA and flow cytometry analysis (using MDA-MB-231 cells expressing STn, as described previously, or using OV90 cells) to identify whether the antibodies produced by such cells are capable of binding epitope Group 1, 2, 3 or 4 (see FIG. 1). Characterization data obtained for select antibodies is presented in the following Table. In the Table, NB indicates that weak or no binding was observed and ND indicates that a value was not determined.

TABLE 9

Anti-STn antibody subclone ELISA and flow cytometry characterization

| | | BSM ELISA | | Flow Cytometry (MDA-MB-231 STn+) | | | Flow Cytometry (OV90) | | |
|---|---|---|---|---|---|---|---|---|---|
| Clone | Isotype | $EC_{50}$ (nM) | Hill Slope | $EC_{50}$ (nM) | Hill Slope | High Value | $EC_{50}$ (nM) | Hill Slope | High Value |
| 4D9-2D4 | IgG1, k | NB | ND | 10.8 | ND | ND | ND | ND | ND |
| 1A5-2C9 | IgG3, k | NB | ND | NB | ND | ND | ND | ND | ND |
| 8C2-2D6 | IgG2a, k | 0.4 | 1.1 | 2.8 | 0.9 | 653 | 2.8 | 0.8 | 1237 |
| 7D3-2C10 | IgG1, k | 0.3 | 0.9 | 0.6 | 1.1 | 211 | 0.422 | 0.91 | 1021 |
| 2C6-2F11 | IgG1, k | 0.1 | 1.7 | 0.7 | 1.2 | 268 | 11.56 | 0.35 | 604 |
| 2B2-2A7 | IgG1, k | NB | ND | 0.3 | ND | ND | ND | ND | ND |
| 5G2-1B3 | IgG1, k | 0.4 | 2.7 | 0.2 | 1.3 | 376 | 1.68 | 0.79 | 570 |
| 7A5-2G12 | IgG3, k | 0.5 | 1.3 | 0.5 | 1.3 | 223 | 3.0 | 7.0 | 446 |
| 6B11-2E3 | IgG3, k | 0.3 | 0.5 | 0.2 | 1.5 | 229 | 0.266 | 0.89 | 359 |
| 1C11-2G9 | IgG2a, k | NB | ND | 3.3 | ND | ND | ND | ND | ND |
| 2G12-2B2 | IgG2a, k | 0.1 | 0.6 | 0.3 | 1.3 | 489 | 0.43 | 0.63 | 960 |
| 9E5-1A8 | IgG3, k | NB | ND | 3.1 | ND | ND | ND | ND | ND |
| 10C9-2G7 | IgG1, k | NB | ND | 2.3 | ND | ND | ND | ND | ND |
| 2F4- | IgG3, | 4.2 | 9.6 | 0.36 | 1.26 | 144 | 4.35 | 0.53 | 88 |

TABLE 9-continued

Anti-STn antibody subclone ELISA and flow cytometry characterization

| | | BSM ELISA | | Flow Cytometry (MDA-MB-231 STn+) | | | Flow Cytometry (OV90) | | |
|---|---|---|---|---|---|---|---|---|---|
| Clone | Isotype | $EC_{50}$ (nM) | Hill Slope | $EC_{50}$ (nM) | Hill Slope | High Value | $EC_{50}$ (nM) | Hill Slope | High Value |
| 1E2 | k | | | | | | | | |
| 2F4-1H8 | IgG3, k | NB | ND | 1.4 | ND | ND | ND | ND | ND |
| 2B8-2F10 | IgG3, k | 3.5 | ND | 5.2 | ND | ND | ND | ND | ND |
| 5E6-2E7 | IgG3, k | 5.8 | 1.1 | 1.8 | 1.0 | 126 | 1.9 | 0.8 | 259 |
| 9F11-1F7 | IgG3, k | 4.6 | 1.0 | 0.8 | 0.9 | 124 | 1.98 | 0.89 | 265 |
| IF6-1C10 | IgG3, k | 0.3 | 1.2 | 1.0 | 0.6 | 167 | 0.5 | 13.0 | 347 |
| 4D9-2C11 | IgG1, k | NB | ND | 2.7 | ND | ND | ND | ND | ND |
| 7D4-2A2-2F2 | IgG2a, k | 0.7 | ND | 14.1 | ND | ND | ND | ND | ND |
| 7D4-1H12-2B3 | IgG2a, k | 1.2 | 0.9 | 0.7 | 1.0 | 619 | 0.54 | 1.13 | 912 |
| 4G8-1E3 | IgG2a, k | 1.0 | 1.3 | 0.8 | 0.8 | 153 | 1.0 | 1.1 | 221 |
| 2C2-2C5 | IgG3, k | 1.1 | 2.0 | 1.0 | 1.1 | 141 | 1.08 | 1.05 | 342 |
| 10F4-2A9 | IgG3, k | 5.1 | ND | 1.9 | ND | ND | ND | ND | ND |

Results of glycan array characterization are presented in the following Table. The highest level of signal obtained for each antibody during glycan array analysis is indicated as is the resulting group and specificity determination based on the glycans that each antibody associated with and the intensity of the signal obtained for each glycan. Group determination was made according to the method of Example 1. Specificity determinations also factor in intensity of association with Ac versus Gc structures.

TABLE 10

Anti-STn glycan array characterization data

| | Glycan Array | | |
|---|---|---|---|
| Clone | Highest Signal | Group | Specificity |
| 4D9-2D4 | 700 | 1 | Pan-STn |
| 1A5-2C9 | 5800 | 1 | Pan-STn |
| 8C2-2D6 | 16000 | 1 | Pan-STn |
| 7D3-2C10 | 4000 | 1 | Gc-STn |
| 2C6-2F11 | 1200 | 1 | Pan-STn |
| 2B2-2A7 | 13400 | 4 | Pan-STn and Tn |
| 5G2-1B3 | 14000 | 4 | Pan-STn and Tn |
| 7A5-2G12 | 35000 | 1 | Pan-STn |
| 6B11-2E3 | 25000 | 1 | Pan-STn |
| 1C11-2G9 | 700 | 1 | Gc-STn |
| 2G12-2B2 | 25000 | 1 | Pan-STn |
| 9E5-1A8 | 500 | ND | ND |
| 10C9-2G7 | 6000 | 1 | Pan-STn |
| 2F4-1E2 | 25000 | 4 | Pan-STn and Tn |
| 2F4-1H8 | 1900 | 4 | Pan-STn and Tn |
| 2B8-2F10 | 2000 | 1 | Gc-STn |
| 5E6-2E7 | 14000 | 1 | Pan-STn |
| 9F11-1F7 | 16000 | 1 | Gc-STn |

TABLE 10-continued

Anti-STn glycan array characterization data

| | Glycan Array | | |
|---|---|---|---|
| Clone | Highest Signal | Group | Specificity |
| 1F6-1B7 | 7200 | 1 | Pan-STn |
| IF6-1C10 | 35000 | 1 | Pan-STn |
| 4D9-2C11 | 1400 | 1 | Pan-STn |
| 7D4-2A2-2F2 | 5100 | 1 | Pan-STn |
| 7D4-1H12-2B3 | 25000 | 1 | Pan-STn |
| 4G8-1E3 | 35000 | 1 | Pan-STn |
| 2C2-2C5 | 25000 | 1 | Pan-STn |
| 10F4-2A9 | 2400 | 1 | Gc-STn |

Subclones expressing antibodies capable of binding STn were subjected to amino acid and nucleotide sequence analysis (see the following Example).

Example 4. Variable Domain Pairs

Sequenced clones yielded variable domain pairs with the amino acid sequences presented in the following Table. "ND" indicates that the sequence was not determined.

TABLE 11

Variable domain pairs

| Clone ID Number | VH, SEQ ID NO | VL, SEQ ID NO |
|---|---|---|
| 7D3-2C10 | 15 | 16 |
| A5-2G12 | 17 | 18 |
| 1A5-2C9 | 19 | 20 |
| 4D9-2C11 | 21 | 22 |

TABLE 11-continued

| Variable domain pairs | | |
|---|---|---|
| Clone ID Number | VH, SEQ ID NO | VL, SEQ ID NO |
| 2F4-1E2 | 23 | 24 |
| 2F4-1H8 | 23 | 24 |
| 2C6-2F11 | 25 | 26 |
| 2B2-2A7 | 27 | 28 |
| 5G2-1B3 | 29 | 30 |
| 7A6-2A2 | 31 | 32 |
| 10C9-2G7 | 33 | ND |
| 1F6-1B7 (also referred to as 1F6-1C10) | 35 | 36 |
| 2G12-2B2 | 37 | 38 |
| 5E6-2E7 | 39 | 40 |
| 9F11-1F7 | 39 | 40 |
| 9E5-1A8 | 41 | |
| 10F4-2A9 | 42 | 32 |

TABLE 11-continued

| Variable domain pairs | | |
|---|---|---|
| Clone ID Number | VH, SEQ ID NO | VL, SEQ ID NO |
| 10F4-2F2 | 42 | 32 |
| 2B8-2F10 | 43 | |
| 4G8-1E3 | 44 | 45 |
| 6B11-2E3 | 46 | 32 |
| 8C2-2D6 | 47 | 32 |
| 7D4-1H12-2B3 | 48 | 50 |
| 7D4-2A2-2F2 | 48 | 49 |
| 2C2-2C5 | 51 | 52 |
| 1C11-2G9 | ND | 34 |

CDRs for each variable domain were determined and are presented in the following Table. Each row presents a set of six CDRs identified for each clone.

TABLE 12

| CDR sequences | | | | | | | | | | | | | |
|---|---|---|---|---|---|---|---|---|---|---|---|---|---|
| Clone ID | CDR-H1 | SEQ ID NO | CDR-H2 | SEQ ID NO | CDR-H3 | SEQ ID NO | CDR-L1 | SEQ ID NO | CDR-L2 | SEQ ID NO | CDR-L3 | SEQ ID NO |
| 7A6-2A2 | GYTF TDHA IHWV | 81 | FSPG NDDI KY | 84 | SVGY ALDY | 90 | ENVV TY | 100 | GASN RYT | 115 | GQGY SYPY T | 127 |
| 2B2-2A7 | GYTF TDHA IHWV | 81 | ISPGN GDIK Y | 85 | KISY YGI | 91 | EDIYS N | 101 | KATN LAD | 116 | QHFW GTPF T | 128 |
| 5G2-1B3 | GYTF TDHA IHWV | 81 | FSPG NDDI KY | 84 | KRSY YGD | 92 | ENIYS H | 102 | GATN LAD | 117 | QHFW GAPF T | 129 |
| 4D9-2C11 | GYTF TDHA IHWV | 81 | LSPG NDDI KY | 86 | KRSIG GDH | 93 | QNIN VW | 103 | KASN LHT | 118 | QQGQ SYPFT | 130 |
| 2F4-1E2 | GYTF TDHA IHWV | 81 | ISPGN GDIK Y | 85 | QRQL GQGY | 94 | QSLV HSYG NTY | 104 | KVSN RFS | 119 | SQNT HVPY T | 131 |
| 2F4-1H8 | GYTF TDHA IHWV | 81 | ISPGN GDIK Y | 85 | QRQL GQGY | 94 | QSLV HSYG NTY | 104 | KVSN RFS | 119 | SQNT HVPY T | 131 |
| 1A5-2C9 | GYTF TDHA IHWV | 81 | VSPG NGDI KY | 87 | KRSLI GDY | 95 | QNVG TA | 105 | SASN RYT | 120 | QQYS SYRL T | 132 |
| 1F6-1B7 | GYTF TDHA IHWV | 81 | ISPGN GDVK Y | 88 | KRSL STPY | 96 | QSLL NSGN QKSY | 106 | WAST RDS | 121 | QSDY SYPY T | 133 |
| 2C2-2C5 | GYTF TDHA IHWV | 81 | ISPGN GDIK Y | 85 | KRSIT TPY | 97 | QSVN NN | 107 | YASN RYT | 122 | QQGY SSPW T | 134 |
| 2G12-2B2 | GYTF TDHA IHWV | 81 | FSPG NDDI KY | 84 | KRSL STPY | 96 | QSLL NRGN HKNY | 108 | WAST RES | 123 | QNDY TYPY T | 135 |
| 2C6-2F11 | GYTF SDHA IHWV | 82 | ISPGN DDIK Y | 89 | ERSM IGVY | 98 | QSLV QSNG NTY | 109 | KVSN RFC | 124 | SQST HAPL T | 136 |
| 7D4-2A2-2F2 | GYIFT DHAI HWV | 83 | ISPGN GDIK Y | 85 | KRSL STPY | 96 | ENVV NY | 110 | GASN RYS | 125 | GSKW ITSYP YT | 137 |

TABLE 12 -continued

| CDR sequences | | | | | | | | | | | | |
|---|---|---|---|---|---|---|---|---|---|---|---|---|
| Clone ID | CDR-H1 | SEQ ID NO | CDR-H2 | SEQ ID NO | CDR-H3 | SEQ ID NO | CDR-L1 | SEQ ID NO | CDR-L2 | SEQ ID NO | CDR-L3 | SEQ ID NO |
| 7D4-1H12-2B3 | GYIFT DHAI HWV | 83 | ISPGN GDIK Y | 85 | KRSL STPY | 96 | ENVV NY | 110 | GASN RYS | 125 | GARV TSYP YT | 138 |
| 7D3-2C10 | GYTF TDHA IHWV | 81 | FSPG NDDI KY | 84 | KRSIT TPY | 97 | QNIN VW | 103 | KVSN LHT | 126 | QQDQ SYPY T | 139 |
| 8C2-2D6 | GYTF TDHA IHWV | 81 | ISPGN GDIK Y | 85 | KRSIT TSY | 99 | ENVV TY | 100 | GASN RYT | 115 | GQGY SYPY T | 127 |
| 5E6-2E7 | GYTF TDHA IHWV | 81 | ISPGN GDIK Y | 85 | KRSIT TPY | 97 | QSLL NSGK TKNY | 111 | WAST RES | 123 | KNDY SYPY T | 140 |
| 9F11-1F7 | GYTF TDHA IHWV | 81 | ISPGN GDIK Y | 85 | KRSIT TPY | 97 | QSLL NSGK TKNY | 111 | WAST RES | 123 | KNDY SYPY T | 140 |
| 4G8-1E3 | GYIFT DHAI HWV | 83 | ISPGN GDIK Y | 85 | KRSIT TSY | 99 | QHIN FW | 112 | KASN LHT | 118 | QQDQ SYPY M | 141 |
| 10F4-2F2 | GYTF TDHA IHWV | 81 | ISPGN GDIK Y | 85 | KRSIT TSY | 99 | ENVV TY | 100 | GASN RYT | 115 | GQGY SYPY T | 127 |
| 10F4-2A9 | GYTF TDHA IHWV | 81 | ISPGN GDIK Y | 85 | KRSIT TSY | 99 | ENVV TY | 100 | GASN RYT | 115 | GQGY SYPY T | 127 |
| 6B11-2E3 | GYTF TDHA IHWV | 81 | ISPGN DDIK Y | 89 | KRSIT TSY | 99 | ENVV TY | 100 | GASN RYT | 115 | GQGY SYPY T | 127 |
| 7A5-2G12 | GYTF TDHA IHWV | 81 | ISPGN DDIK Y | 89 | KRSIT TSY | 99 | ENVV W | 113 | GASN RYT | 115 | GQGY SYPY T | 127 |

Example 5. Flow Cytometry Analysis of Antibody Internalization

Flow cytometry analysis is carried out in order to quantify the extent of antibody internalization. For analysis, stably transfected variants of MDA-MB-231 cells (clone TAH3.P10) that express high levels of cell surface-bound Neu5Ac-STn are harvested using 10 mM EDTA and washed with PBS comprising 1% BSA before pelleting by light centrifugation. Cell numbers and viability are determined by trypan blue dye exclusion analysis and cell concentrations are adjusted to $5\times10^6$ cells/ml in PBS with 1% BSA. 50 μl of cells are added to each well of an assay plate. Cells are combined with 50 μl solutions of antibody or fluorescently-labeled antibody and incubated for 1 hour at 4° C. Following this incubation period, cells are washed with PBS to remove unbound antibody and aliquots are removed for incubation for various times (15, 30, 60 minutes) at 37° C. to allow bound antibody to internalize at a physiologically relevant temperature. After each incubation, cell surface-bound antibody is removed by treating cells with acidic medium (150 mM NaCl, pH=2.5) Cells treated with unlabeled antibody are washed with PBS and fixed with paraformaldehyde fixation buffer (PFA) containing 3% paraformaldehyde and 2% sucrose in PBS for 15 minutes at room temperature. These cells are rinsed again in PBS and treated with blocking buffer made up of PBS with 1% bovine serum albumin (BSA). Cells are incubated for 30 min at room temperature, rinsed in PBS and treated with secondary antibody (allophycocyanin-labeled goat-anti-mouse IgG) for 2 hours at room temperature. All cells are then washed with PBS and subjected to flow cytometry analysis wherein 10,000 events are recorded for each sample. Residual fluorescent signal in acid-treated samples is further quenched via treatment with trypan blue dye.

Example 6. Evaluation of Antibody Internalization Through Cell Viability Assay Cell viability assays are performed to screen anti-STn antibodies of the present invention in the presence and absence of secondary antibody-drug conjugates (2° ADCs). The purpose of the screen is to identify the ability of each anti-STn antibody to inhibit cell growth. Antibodies with potent cell growth inhibition are used to design direct antibody-drug conjugates (ADCs). Using such secondary antibody-drug conjugates (2° ADCs) in cell-based cytotoxic assays can quickly pre-screen many ADC candidates against tumor cells. Based on the assay, a naked antibody candidate is directly added to cells in the presence of a 2° ADC. Internalization of the mAb/2° ADC complex into cells that express a high density of the targeted antigen can achieve a dose-dependent drug release within the cells, causing a cytotoxic effect to kill the cells (e.g., tumor cells), while cells expressing a low density of the targeted antigen are not affected (e.g., normal cells).

To perform cell viability assays, cell lines described in the present application (MDA-MB-231 parental, MDA-MB-231-STn+, and OV-90) are prepared and cultured for the assays. The cell culture is optimized for cell density by plating different densities of cells (e.g., 2,000, 4,000 and 7,500 per well) on a 96-well plate and observing the cell growth for 96 hours. The plating condition in which cells reach around 90% confluence at the end of the 96 hours is identified and the optimal cell number is then used in the final viability assay.

Antibodies are tested in one or more cell lines in the presence and absence of a 2° ADC such as Fab aMFc-CL-MMAF. Duplicate or triplicate cell plates for each cell line are used for testing each antibody candidate.

For cell viability assays, data points are collected for each antibody candidate with duplicates for each data point. Each antibody candidate is diluted in serial concentrations from 0.3 pM to 20 nM. A constant amount of Fab αMFc-CL-MMAF (40 nM) is used in the viability assay.

Alternatively, data points are collected for each antibody candidate with triplicates for each data point. Each antibody candidate is diluted in serial concentrations from 1 pM to 20 nM. A constant amount of Fab αMFc-CL-MMAF (40 nM) is used in the viability assay.

Cell viabilities are measured by Cell-Titer Glo luminescence based assays.

Example 7. Demonstration of In Vivo Tumor Killing Ability

In vivo tumor killing ability is demonstrated with mouse and/or human tumor cell lines. Tumor cell lines expressing STn targets are transferred into mice and the ability of the antibody candidates to kill the resulting tumors is determined.

Mouse cell lines used in vivo in tumor killing assays include the mouse colon adenocarcinoma cell line, MC38, derived from C57BL/6 mice and stably transfected with ST6 (alpha-N-acetyl-neuraminyl-2,3-beta-galactosyl-1,3)-N-acetylgalactosaminide alpha-2,6-sialyltransferase 1 (ST6GalNac1). These cells are fed with sialic acid (Neu5Ac and/or Neu5Gc, depending on target) before their use in in vivo tumor killing assays using syngeneic $Cmah^{-/-}$ mice.

Alternatively, for in vivo tumor killing assays human breast cancer cell lines (T47-D, MCF-7 or MDA-MB-231) induced to express a high level of STn are transferred into immune-deficient FOXN1−/− (nude) cells, non-obese diabetic (NOD) cells, or severe immunodeficiency (SCID) mice.

In vivo ADCC is induced by passive transfer of human peripheral blood mononuclear cells (PBMCs) or purified natural killer (NK) cells. In cases where candidate antibodies bind unspecifically to wild-type mouse tissue, immunedeficient mice are bred into the Cmah−/− background.

Example 8. Phage Library Construction and Selection

RNA is prepared from spleens harvested from mice with a strong immune response to immunization. Mouse variable (V) regions are PCR amplified and assembled into scFv expression constructs. ScFv sequences are cloned into phagemid display vectors allowing for scFv display on the surface of M13 phage particles. The resulting library is transformed into E. coli (TG1). Bulk transformations of E. coli are grown and phage are prepared by phage rescue. In the first round of selection, phage from the culture medium are purified by PEG precipitation.

Candidate scFvs are selected using both negative and positive selection methods. For negative selection, the library is incubated with "destroyed" STn-negative mucin (e.g. chemically treated PSM). For positive selection, the library is incubated with GcSTn mucin (e.g. PSM and/or de-O-acetylated BSM), AcSTn mucin (e.g. OSM and/or de-O-acetylated BSM) or BSM (and/or de-O-acetylated BSM) and a synthetic glycan (Neu5Gc and/or Neu5Ac) in the presence of a Neu5Ac or Neu5Gc (depending on the desired target).

After 3-4 rounds of selection with reducing antigen concentrations, 1000 clones are analyzed by ELISA for binding to STn (e.g. Neu5Ac and/or Neu5Gc) using synthetic and natural glycan targets. Lead phage/scFv candidates are tested in a secondary flow cytometry-based cellular assay for binding to GcSTn and/or AcSTn using Jurkat cells with or without "induction" of GcSTn or AcSTn. Up to 20 selected scFv candidates of interest are subjected to further analysis.

Lead scFv candidates are selected for conversion to IgG. Variable regions from each scFv are cloned into mammalian expression vectors between an upstream CMV promoter and a downstream immunoglobulin constant region. Heavy chain vector includes murine IgG1 and κ constant regions. Vectors are transiently transfected into HEK293/EBNA cells. Antibody samples are purified and characterized by binding to positive and negative glycan epitopes. Samples of up to 0.5 mg of each whole IgG are further analyzed.

Example 9. Antibody-Dependent Cell-Mediated Cytotoxicity Optimization

Genes encoding the variable regions of a selected IgG are cloned into mammalian expression vectors encoding human Fc regions (huIgG1κ) containing amino acid mutations known to enhance Fc-receptor binding and antibody-dependent cell-mediated cytotoxicity (ADCC). Vectors are transiently transfected into HEK293/EBNA cells. After 2-7 days, IgG expression is quantified and samples of antibody are purified on protein A columns. Antibodies are then tested in ADCC assays. Neu5Gc and Neu5Ac-expressing Jurkat cell lines are used as the target cells and human peripheral blood mononuclear cells (PBMC) are used as a source of effector cells. Target cells are titrated using maximum cell lysis to determine the optimum cell density for use in multiwall plate format assay. ADCC-mutated antibody together with the non-mutated IgG are pre-incubated with target cells, effector cells are then added at varying target: effector cell ratios, and cultures are incubated at 37° C. Percentage viability is determined using Calcein-AM dye (BD Biosciences, San Jose, Calif.) release. Samples of up to 0.5 mg of ADCC-mutated IgG are subjected to further analysis.

Example 10. Production of Lead Antibody from Semi-Stable HEK Cell Line

Variable regions from IgG are cloned into mammalian expression vectors between an upstream CMV promoter and a downstream immunoglobulin constant region. Heavy chain vector includes murine IgG1 and κ constant regions. Vectors are transiently transfected into HEK293/EBNA cells and antibody titers are assessed at 72 hours. Transiently transfected HEK293/EBNA cells are selected with hygromycin to establish a semi-stable expression system. Semi-stable cells are expanded to 10 liters. Antibodies are purified from the culture supernatant by Protein A, dialyzed into PBS and the resulting preparation is analyzed for (1) aggregates by analytical size exclusion chromatography (SEC), (2) endotoxin levels by Limulus amebocyte lysate (LAL) testing (expressed as EU/mg), and (3) binding to antigen in the primary assay.

Example 11. Additional Assays for Screening scFv Candidates for Target Affinity

ScFv candidates are subjected to additional screening methods for STn (pan-STn, AcSTn and/or GcSTn) affinity using a variety of proposed targets.

Synthetic Glycan Target Screening

As used herein, the term "target screening" refers to the use of a target substance to identify binding partners for that substance. Synthetic glycan target screening is carried out using desired STn target antigens bound to poly(acrylic acid) (PAA) with a biotin tag. Undesired STn target antigens as well as Tn bound to PAA with a biotin tag are used as negative controls. Cells associated with candidate scFvs are isolated through precipitation with avidin-associated entities.

Natural Glycan Target Screening on Live Cells

Target screening using live cells is carried out using Jurkat cells fed with sialic acid (Neu5Gc and/or Neu5Ac, depending on the desired antibody target) or Jurkat cells fed with an alternative form of sialic acid (Neu5Gc and/or Neu5Ac, depending on the desired antibody target) as a negative control. Target screening using live cells is also carried out using MCF-7 or MDA-MB-231 cells fed with sialic acid (Neu5Gc and/or Neu5Ac, depending on the desired antibody target or whether being used for negative control screening) and stable transfection. Flow cytometry is used in either case to isolate cells associated with scFv candidates.

Natural Glycan Target Screening on Tissue (Ex Vivo)

Target screening using ex vivo tissue is carried out using biopsy tissue samples. Binding of scFv candidates with ex vivo tissue is analyzed using standard immunohistochemical methods. Single tissue sections as well as tissue microarray sections are used. Samples are treated with or without sialidase and/or periodate in control experiments.

Example 12. Antibody Humanization

Fully humanized heavy and light chains are designed with CDRs presented herein. Protein models of the variable regions are generated using existing antibody structures as templates. Segments of starting heavy and light chain variable region amino acid sequences are compared with human sequences for possible inclusion in the fully humanized sequences. Series of humanized heavy and light chain variable regions are designed entirely from segments of human variable region sequences with the objective that T cell epitopes be avoided. Variant human sequence segments with significant incidence of potential T cell epitopes as determined by in silico technologies are discarded.

Humanized heavy and light chain variable region genes are constructed from overlapping oligonucleotides assembled into full length genes using the ligase chain reaction (LCR). LCR products are amplified and suitable restriction sites are added for cloning into expression vectors. PCR products are cloned into intermediate vectors and confirmed by sequencing.

For construction of expression plasmids encoding fully humanized antibodies with human constant regions, DNA sequences for each variable region are inserted into mammalian expression vectors between an upstream cytomegalovirus immediate/early promoter/enhancer (CMV IE) plus the immunoglobulin signal sequence and a downstream immunoglobulin constant region gene. DNA samples are prepared for transfection into mammalian cells.

For generation of cell lines and selection of lead fully humanized antibodies, heavy and light chain plasmid DNA pairs are transfected into mammalian cells (NS0). Cell lines producing humanized antibodies are expanded and antibody samples are purified. Antibodies are tested in primary and secondary binding assays to determine leading antibody candidates. The 3 leading candidates are used for further analysis.

Example 13. Immunogenicity Testing

Lead antibodies are subjected to EpiScreen (Antitope, Paradise Valley, Ariz.) whole antibody human T cell assays using a minimum of 20 blood samples from healthy volunteer donors. Immunogenicity of lead antibodies is compared with control chimeric antibodies with starting antibody variable regions and matched human constant regions. Data are benchmarked against EpiScreen whole protein data for clinical-stage biologics.

Example 14. Cell Line Development

Cell lines are developed with the ability to yield high levels of antibody with no non-human glycosylation due to knock down of the CMAH gene. Cell lines are glycoengineered to increase ADCC. These cell lines have the ability to perform in small and large scale production.

Example 15. Antibody-Dependent Inhibition of STn-Positive Tumor Cell Immune Tolerance Anti-STn antibodies of the present invention are provided and used to contact tumor cells and tissues comprising STn glycans. Immune-dependent targeting of STn-tumor cells is increased.

Example 16. Treatment of Immune Tolerant Tumors Using Anti-STn Antibodies

A subject with STn glycans expressed on and around tumor cells is treated with an anti-STn antibody of the present invention. Immune tolerance of subject tumor cells is decreased.

Example 17. Generation of S3F Antibodies

S3F IgG2a antibodies were generated through the combination of 3F1 IgG1 variable domains (SBH Biosciences, Natick, Mass.) with antibody constant domain regions from IgG2 antibodies. The heavy and light chain variable domains of 3F1 were sequenced and constructs were generated encoding 3F1 variable domains upstream of IgG2 expression vectors, plasmid H1206 (LakePharma, Belmont, Calif.) for antibody heavy chains and plasmid L1206 (LakePharma, Belmont, Calif.) for antibody light chains. Related sequences are presented in the following Table.

TABLE 13

Sequences utilized in S3F IgG2 antibody generation

| Description | SEQ ID NO |
|---|---|
| 3F1 VH domain | 53 |
| 3F1 VL domain | 54 |
| IgG2a heavy chain constant domain | 234 |
| kappa light chain constant domain | 235 |
| S3F full length heavy chain | 236 |
| S3F full length light chain | 238 |
| S3F full length heavy chain nucleotide sequence | 237 |
| S3F full length light chain nucleotide sequence | 239 |

Plasmids encoding S3F full heavy chain amino acid sequences and plasmids encoding S3F full light chain amino acid sequences were transfected into Chinese hamster ovary-K1 (CHO-K1) cells for the generation of stable cell lines expressing S3F IgG2a antibodies. The cells were cultured in a humidified 5% CO2 incubator at 37° C. in chemically defined media (CD-CHO, Invitrogen, Carlsbad, Calif.) supplemented with L-glutamine.

Approximately 80 million suspension CHO cells, growing in log phase, were transfected by electroporation (MaxCyte) with 80 μg of total plasmid encoding the full length heavy and light chains of S3F. Twenty four hours later, the transfected cells were placed under selection for stable integration of the antibody genes. During the selection process the cells were spun down and resuspended in fresh selection media every 2-3 days until the pool recovered its growth rate and viability. Cells were monitored for growth, titer, and stable integration of the antibody expression constructs. The doubling rate was 20 hours.

Two small scale production scale-ups were performed using the stably transfected cells. The cells were scaled up for production in OptiCHO CD Growth Medium (Invitrogen). The product was produced at a titer of approximately 12 mg per liter. The doubling rate was 20 hours. The conditioned media supernatant harvested from the transient transfection production run was clarified by centrifuge spinning. The protein was run over a Protein A column and eluted using two different buffer formulations (Citrate Buffer and HEPES buffer). Filtration using a 0.2 μm membrane filter was performed. Size exclusion chromatography (SEC) was performed for both formulations (see the following Table).

TABLE 14

SEC data

| Buffer | Results |
|---|---|
| 20 mM Citrate (pH 5.5) + 150 mM NaCl | Purity 91.4%, aggregates 3.4% |
| 200 mM HEPES (pH 7) ± 0.2% acetate | Purity 96.2%, aggregates 3.8% |

Stable cell lines were cultured for large scale production and 10 L of culture was produced. The conditioned media harvested from the stable cell pool production run was clarified by centrifugation and 0.2 μm membrane filtration. The antibody was purified using Protein A affinity chromatography, then sterilized and cleared of particulates by passing through a 0.2 μm membrane filter. After low endotoxin purification and filtration, concentration was set to 5 mg/mL and 120 mg of antibody S3F was recovered.

Example 18. Characterization of Carcinoma Cancer Stem Cell Lines and CSC Sub-Fractions by Expression Levels of STn Antigens Using Anti-STn Antibodies In order to test the viability of the present unique immunotherapeutic approach to the eradication of CSCs, human ovarian carcinoma cell lines and their associated CSC subfractions are employed as the target cell population.

To identify appropriate ovarian carcinoma cell lines and CSC subfractions from these identified cell lines, for further in vitro analysis of anti-STn antibody efficacy, different human ovarian cancer cell lines including SKOV3, OVCAR3, OVCAR4, OV90 and A2870 are analyzed for the expression of Ovarian CSC biomarkers: CD44 and CD133, by flow cytometry. CD44 and/or CD133 positive/expressed ovarian CSC subfractions are then further tested for the co-expression levels of cell-surface STn antigen using specific anti-STn antibodies, for example, anti-STn antibodies S3F and recombinant 18D2 pan anti-STn IgG2a mAb [R18D2; IgG2a version of 18D2 (which is an IgG2b) described in international publication No. WO2015/054600, the contents of which are herein incorporated by reference in their entirety]. CSC subfractions that show strong anti-STn staining are purified by cell sorting and subject to further test for stem cell attributes. Selected CSC subfractions are tested for "stem-like" characteristics by performing serial colony-forming transplantation assays. Then STn+ subfractions that demonstrate superior colony-forming ability are identified for efficacy experiments. In addition to colony formation assays, cell cycle and chemoresistance are also analyzed.

To verify this, CSC fractions are isolated from ovarian cancer cell lines based on surface markers (CD44, CD133) known to enrich for CSCs in ovarian cancer. Five different ovarian cancer cell lines (SKOV3, OV90, OVCAR3, OVCAR4, and A2870) are utilized. Only OV90, OVCAR4, and OVCAR3 harbor subfractions of CD133-expressing and/or CD44-expressing cells that display some aspect of stem-like properties. These ovarian cancer cell lines are subjected to flow cytometric analysis (via Aria) using the FlowJo software and sorting via multiple strategies.

To characterize the expression of STn on CSC subfractions expressing CD44 and/or CD133, flow cytometry of the parental cell lines is used along with fluorophore-conjugated antibodies to CD44 and CD133 (Miltenyl Biotech, Cambridge, Mass.) to prepare subfractions expressing one or both of these markers as well as a fraction in which neither of these markers is expressed. Subsequently fluorophore-conjugated mAb S3F is used to determine the levels of STn labeling of these subfractions using standard procedures. Several concentrations of conjugated S3F are tested along with time-course experiments to establish optimal cell binding conditions. Appropriate fluorophore-conjugated, isotype matched antibodies are used as controls to establish background staining. Labeled cells are resuspended in PBS buffer and subjected to flow cytometric analysis using a BD FACSAria instrument and FlowJo 7.6.5 software (Treestar, Ashland, Oreg.).

Consequently, these analyses are used to characterize the CD44/133 defined subfractions of ovarian CSCs in terms of co-expression of STn.

In addition, the same cell lines described above are subjected to FACS sort based on STn+ and STn− cell fractions, followed by a second sort based on expression of CD44 and CD133. These eight subfractions are seeded in a colony-forming assay. It is well accepted that stem-like cells are thought to replicate infrequently, only giving rise to a limited number of daughter cells that eventually give rise to the bulk of the tumor cell population. This property has been widely exploited to identify and track stem cells. Colonies are allowed to form for 3-4 weeks and then counted under a microscope after overnight staining with 1 mg/ml nitroblue tetrazolium chloride in PBS. Colony forming efficiency is calculated by dividing the number of colonies by the total number of cells plated and then multiplying by 100.

The in vitro serial transplantation methodology is carried out as described by Padler-Karavani et al (Padler-Karavani et al., Cancer research, 2011, 71, 3352-3363; and Friel et al., Cell cycle, 2008, 7, 242-249). Culture plates containing Noble agar underlayers are used to seed sorted cell subfractions at a seeding density of $1\times10^4$ into Noble agar overlayers. Cultures are incubated in a humidified 5% $CO_2$ environment at 37° C. After about 4 weeks in culture, cells are counted under a microscope after overnight staining with 1 mg/ml nitroblue tetrazolium chloride in PBS and replated as above. Serial transplantation in vitro continues for several passages (depending on characteristics of the individual cell lines). The CD44+ and/or CD133+ cells that co-express STn display an enhanced colony-forming advantage over the CD44−/CD133−/STn−, CD44+/CD133−/STn−, CD44+/CD133+/STn−, CD44−/CD133+/STn−, and CD44−/CD133−/STn+ cell subfractions.

Further cell lines are analyzed for their potential for STn synthesis using PCR to measure the expression of the sole enzyme known to be responsible for its biosynthesis, namely the sialyltransferase ST6GalNAc I. RNA is isolated from frozen, sorted subfractions as initially cultured and cDNA prepared by standard methods prior to quantitative PCR. A set of housekeeping genes (e.g. PUM1, RPLP0, ACTB) are first tested to determine which is more appropriate (i.e., to determine which are the most homogenously expressed across the cell subfractions) to use as an internal reference. Expression of ST6GalNAc I is then measured using a set of PCR probes validated for their efficiency in the method. Each subfraction is further compared with positive controls, including ST6GalNAc I cDNA inserted into bacterial plasmids, and total RNA from breast cancer cells stably transfected with ST6GalNAc I cDNA as described (Julien et al., Glycoconjugate journal, 2001, 18, 883-893). Based on levels of ST6GalNac I mRNA, culture conditions are manipulated to ensure that cell-surface STn is expressed and studies are carried out for further analysis.

Studies are used to define the levels of STn expression in the various CSC subfractions as determined by flow cytometric analysis of three CD44/CD133 positive ovarian carcinoma CSCs. Further, serial transplantation colony-forming assays are carried out to compare the characteristic stem cell-like properties of the CSC subfractions from these three lines. On the basis of STn expression levels and STn+ subfraction colony-forming ability, two of the three ovarian cell lines are chosen for in vitro and in vivo functional assays.

Example 19. Determining the Anti-CSC Activity of Murine Anti-STn mAbs In Vitro The proliferative ability of STn+ subfractions and the anti-CSC activity of anti-STn mAbs (e.g. S3F) are tested in vitro. A series of in vitro experiments are performed to assess the effects of mAb treatment on stem cell proliferation and ADC-induced killing of CSC subfractions and parent cell lines. In appropriate assays, anti-STn mAbs are combined with standard-of-care chemotherapy agents (e.g., carboplatin, paclitaxel).

In order to optimize subsequent assays used to determine the effect of the anti-STn antibody S3F on the CSC subfractions, proliferation assays are performed essentially as described (Friel et al., Cell cycle, 2008, 7, 242-249). The eight sorted CSC subfraction combinations possible from each of the two selected ovarian carcinoma cell lines plus cells from the two parental lines are seeded in triplicate (dilutions beginning at $5\times10^3$ cells/well) in 24-well culture plates. Viable cells, as determined by trypan blue exclusion, are counted using a hemocytometer and or plate reader via MTT assay on days 1, 3, 5, 7, 8, and 9, or longer if necessary. Student's t-test is used to compare groups and comparisons with a p value of $\leq0.05$ are considered significant. Based on the results, sub-objective protocols are devised in order to perform cytotoxicity assays.

Cytotoxicity assays are performed to assess sensitivity of the eight STn+ and STn− sorted subfractions from each cell line as well as the parental lines to S3F mAb alone, S3F+paclitaxel+carboplatin or the combination of chemotherapeutic agents alone. S3F (along with an irrelevant, isotype-matched antibody as control) is tested at several dilutions beginning at 0.1 μM. The chemotherapeutic agents are used at 0.1, 1.0, 10, and 100 nM. Appropriate vehicle control groups are also included and assays are performed essentially as described previously (Friel et al., Cell cycle, 2008, 7, 242-249). Sorted CSC subfractions are seeded in triplicate at cell numbers determined in cell proliferation assays into 24-well culture plates and allowed to reach 50% confluence. Cells are then starved for 24 hours after which inhibitory agents are added. Cell viability is determined as above on days 2, 4, and 5, or longer if necessary. Student's t-test is used to compare groups and comparisons with a p value of $\leq0.05$ are considered significant.

The proliferative ability of all possible combinations of CSC marker-defined subfractions (CD44, CD133, and STn), as well as the parental cell lines, is measured and used to establish protocols to assess the effect of the anti-STn antibody (+/− standard chemotherapy) on these cells. Stem cell marker positive cells have a reduced proliferative capacity when compared to parental lines and those subfractions that are negative for CSC antigens. The anti-CSC effect of ADC-formatted S3F (+/− standard chemotherapy) and its mechanism(s) of action are determined.

Example 20. Determining the Anti-CSC Activity of Murine Anti-STn In Vivo

To determine whether murine STn antibodies possess anti-tumor activity in vivo as the result of targeting CSCs, in vivo toxicology and pharmacology experiments are performed in mice. The growth conditions of CSC subfractions in NOD/SCID mice is established and analyzed. Anti-STn antibodies are administered to mice as conjugates with chemotherapy and treated mice are tested for toxicity efficacy through mouse observations and weights.

An equivalent amount of serially-diluted positive or negative subfraction cells (i.e., $1\times10^5$, $1\times10^4$, and $1\times10^3$/mouse; 2-8 mice/group) are injected subcutaneously (s.c.) into NOD/SCID mice, to compare their potential generate tumors. Following injection of tumor cells, the mice are monitored daily for evidence of tumor formation and general health. For treatment, tumors may be generated in mice from up to four sources: 1) primary ovarian tumors; 2) xenograft tumors previously established in NOD/SCID mice; 3) cryopreserved xenograft tumor tissue; or 4) human ovarian cancer cell lines or isolated cell line subfractions based on CD133/STn expression. For each tumor type, once a sufficient number of mice have tumors ranging from 200-300 $mm^3$ in volume, the mice are randomized into 4 groups (n=8-14 mice/group) such that the mean group tumor volumes are essentially equivalent. The first group receives a single isotype antibody control, IgG-MMAE (1-5 mg/kg), in 200 μl of vehicle administered intraperitoneally (i.p.) once weekly; the second group receives i.p. S3F-MMAE (1-5 mg/kg), in 200 μl of vehicle administered intraperitoneally (i.p.) once weekly; the third group will receive, by i.p. injection, SIA101-MMAE (1-5 mg/kg), in 200 μl of vehicle administered intraperitoneally (i.p.) once weekly, and the fourth group receives vehicle i.p. weekly.

Tumors are then measured twice weekly with calipers [tumor volume=(Lmm×Wmm×Lmm)/2]. Mice, at the same time, are observed frequently and weighed twice weekly to assess potential toxic effects. Mice with excessive tumor burden or in a moribund state are euthanized Non-parametric Wilcoxon rank sum test for unpaired samples is used to compare tumor volumes among the different arms.

S3F-MMAE is capable of delaying the growth of or eradicating CSC tumors and combination with standard chemotherapy agents used for ovarian cancer increases the efficacy of the mAb.

Example 21. In Vitro Testing of ADC Antibodies

S3F, 8C2-2D6, 2G12-2B2, 4G8-1E3 and 5G2-1B3 antibodies were conjugated with maleimidocaproyl-valine-citrulline-p-aminobenzyloxycarbonyl-monomethyl auristatin E (MC-vc-PAB-MMAE). Conjugation was carried out by first reducing the antibody interchain disulfide bonds with TCEP and then linking the maleimide moiety of the drug to reduced cysteines. Conjugated antibodies were desalted on Sephadex G50 columns to remove residual unreactive toxins and then dialyzed in 30 mM HEPES pH 7.7 with 150 mM NaCl. Drug-antibody ratio (DAR) was determined for each conjugated antibody using the ratio of UV absorbance values at 248 and 280 nm ($A_{248}$ and $A_{280}$, respectively; see the following Table).

TABLE 15

MMAE conjugated antibodies

| Antibody | Ratio of $A_{248}/A_{280}$ | Drug:Antibody Ratio |
|---|---|---|
| S3F | 0.73 | 4.6 |
| 8C2-2D6 | 0.75 | 4.8 |
| 2G12-2B2 | 0.73 | 4.6 |
| 4G8-1E3 | 0.73 | 4.5 |
| 5G2-1B3 | 0.62 | 3 |

Antibody preparations were analyzed by size exclusion chromatography to confirm the presence of pure monomers.

Conjugated antibodies were then tested for their ability to kill cells expressing STn. Cultures of MDA-MB-231 cells, with or without STn surface expression. MDA STn negative cells were grown in EMEM supplemented with 10% FBS, 1× Pen/Strep and 45 ug/mL gentamycin. MDA STn positive cells were grown in the same media except with the addition of 1 mg/mL G418 for antibiotic selection. Cells were seeded separately (4,000 cells/well STn negative or 2,000/well STn positive) in 96 well plates using proper media described above. Cells were grown overnight. After 16-20 hours, cells were treated with a serial dilution of test antibodies in triplicate (50 nM to 0.012 nM, 1:4 serial dilution in media) for 72 hours. After treatment, no significant decrease in STn-negative cell viability was observed by CELLTITER-GLO® luminescent cell viability assay, while decreases in cell viability were observed with all conjugated antibodies (with the exception of non-STn-specific control conjugated antibody) in STn-positive cell cultures (see the following Table).

TABLE 16

IC50 values for MMAE conjugated antibodies tested on STn+ MDA cells

| Antibody | IC50 |
|---|---|
| S3F | 0.51 |
| 8C2-2D6 | 2.44 |
| 2G12-2B2 | 1.19 |
| 4G8-1E3 | 1.80 |
| 5G2-1B3 | 11.13 |
| Control | 0.0 |

Of the conjugated antibodies tested, S3F antibody had lowest inhibitory concentration (IC50). Antibodies 2G12-2B2, 4G8-1E3 and 8C2-2D6 all had single digit nanomolar IC50s. Antibody 5G2-1B3 was the least effective with an IC50 value over 10. This may have been due to a lower DAR and different IgG isotype (5G2-1B3 is IgG1, whereas others are IgG2a). Isotype control conjugated antibody showed no effect.

Example 22. ADC In Vitro Assay with OVCAR3 and SNU-16 Cell Lines

The experiment performed above was repeated using OVCAR3 cells (shown to express moderate levels of STn) or SNU-16 cells (shown to express low levels of STn). Cells were seeded (10,000 cells/well) in 96-well assay plates using RPMI media with 10% FBS with 0.01% bovine insulin and 1× Pen/Strep. Cells were incubated in standard cell culture conditions overnight before treatment with test antibodies (with or without MMAE drug conjugates) or irrelevant control antibody. Cells were treated with a serial dilution of test antibodies in triplicate (50 nM to 0.012 nM, 1:4 serial dilution in media)

Four days later, cell viability was measured by CELL TITER-GLO® luminescent cell viability assay. As in the previous assay, unconjugated antibodies had no effect on cell viability; however, conjugated anti-STn decreased cell viability with increasing doses (see following Table).

TABLE 17

IC50 values for antibodies tested

| Antibody | OVCAR3 cells (IC50, nM) | SNU-16 cells (IC50, nM) |
|---|---|---|
| S3F | 0.75 | 6.3 |
| 8C2-2D6 | 14.45 | 31.8 |
| 2G12-2B2 | 6.82 | 24.5 |
| 4G8-1E3 | 9.09 | 28.7 |
| 5G2-1B3 | 11.3 | 96.3 |

Of the antibodies tested in OVCAR3 cells, conjugated S3F had the lowest IC50, while all other antibodies tested had IC50 values greater than 5. 8C2-2D6 and 5G2-1B3 had IC50s above 10 nM, while antibody 2G12-2B2 and 4G8-1E3 had more desirable IC50s in the single nanomolar range. Isotype control conjugated antibody showed no effect.

Similar results were observed in SNU-16 cells, with conjugated S3F demonstrating the greatest effect. 2G12-2B2, 8C2-2D6 and 5G2-1B3 also demonstrated strong ability to kill SNU-16 cells.

Example 23. OVCAR3 Binding Affinity

Antibodies S3F, 8C2-2D6, 4G8-1E3 and 2G12-2B2 were tested for binding to OVCAR3 cells using flow cytometry analysis. For analysis, OVCAR3 cells were grown and harvested using StemPro Accutase (Life Technologies, Carlsbad, Calif.) and washed with PBS comprising 5% FBS before pelleting by light centrifugation. Cell numbers and viability were determined by trypan blue dye exclusion analysis and cell concentrations were adjusted to $5\times10^6$ cells/ml in PBS with 5% FBS. 50 μl of cells were added to each well of an assay plate. Cells were then combined with 50 μl solutions of the antibodies being analyzed or control antibodies and incubated for 1 hour at 4° C. Cells were next washed and pelleted twice with PBS with 5% FBS before being treated with 100 μl of PBS with 5% FBS comprising a 1:1,500 dilution of anti-mouse IgG (Southern Biotech, Birmingham, Ala.,) conjugated to allophycocyanin (APC). Cells were then incubated for 30 min at 4° C. before washing and resuspending in 200 μl of propidium iodide (PI) diluted 1:1000 in PBS with 5% FBS. Finally, treated cells were subjected to flow cytometry analysis.

Mean of APC fluorescence intensity was plotted against the log of the antibody concentration to yield a curve used for EC50 calculation. EC50 values obtained for each antibody are presented in the following Table.

TABLE 18

Effective concentration for OVCAR3 binding

| Antibody | EC50 |
|---|---|
| S3F | 0.92 |
| 8C2-2D6 | 3.13 |
| 2G12-2B2 | 0.80 |
| 4G8-1E3 | 1.66 |

All antibodies were effective binders with single digit nanomolar EC50 values.

Example 24. Antibody Testing by Immunohistochemistry

S3F, 2C2-2C5, 5E6-2E7, 9F11-1F7, 5G2-1B3, 4G8-IE3 and 8C2-2D6 were tested for their ability to detect STn in frozen tissue sections, fixed tissue sections, and in cancer tissue microarrays. 2429-2B2-3B9 (as described in U.S. publication No. US2014/0178365, the contents of which are herein incorporated by reference in their entirety) was also tested. Further, antibody B72.3 (Thermo Fisher Scientific, Waltham, Mass.) was used as a positive control (except in testing of frozen tissue).

Frozen tissue samples were derived from human pancreatic carcinoma (Hu14 Neo-1) and staining was examined in tumor cells, endothelium, spindloid cells, and duct epithelium. Formalin-fixed paraffin embedded (FFPE) tissue samples were derived from human pancreatic carcinoma (Hu3 PA Neo-1) and staining was examined in tumor cells, stroma, and lumen.

Antibodies being tested were used to treat tissue sections and then detected using peroxidase-labeled secondary detection reagents. Tissue sections were observed and evaluated for intensity of specific reactivity, frequency of cells displaying specific reactivity, and subcellular localization of specific reactivity.

Staining observations are presented in the following Tables.

TABLE 19

Abbreviation key for staining observations

| Intensity of specific reactivity | Frequency of cells displaying specific reactivity | Subcellular localization of specific reactivity (when applicable) |
|---|---|---|
| 0—Negative | N—Negative, no reactivity | M—Membrane |
| 1—Weak | VR—Very rare, <5% of cells of that cell type | C—Cytoplasm |
| 2—Mild | R—Rare, 5-25% of cells of that cell type | M > C—Membrane staining with lesser amounts of cytoplasmic |
| 3—Moderate | O—Occasional, 26-50% of cells of that cell type | C > M—Cytoplasmic staining with lesser amounts of membrane |
| 4—Strong | F—Frequent, 51-75% of cells of that cell type | |
| 5—Intense | VF—Very frequent, 76-100% of cells of that cell type | |

TABLE 20

FFPE tissue evaluation

| | | Specific Reactivity (Intensity/Frequency) | | |
|---|---|---|---|---|
| Antibody | Concentration | Hu3 PA Neo-1 (pancreatic carcinoma, tumor cells, cytoplasm > membrane) | Stroma (extracellular matrix) | Lumen contents |
| Assay Control | 0 μg/mL | 0/N | 0/N | 0/N |
| 2C2-2C5 | 10 μg/mL | 3-5/R | 1-2/VR | 3-5/VR |
| | 1 μg/mL | 3-5/VR | 1-2/VR | 3-5/VR |
| 5E6-2E7 | 10 μg/mL | 1-3/VR | 0/N | 1-3/VR |
| | 1 μg/mL | 1-2/VR | 0/N | 0/N |
| 9F11-1F7 | 10 μg/mL | 3-5/VR | 1/VR | 1-2/VR |
| | 1 μg/mL | 1-3VR | 1/VR | 1-2/VR |
| 5G2-1B3 | 10 μg/mL | 2-4/R | 1-2/VR | 3-5/VF |
| | 1 μg/mL | 1-2/VR | 0/N | 1-3/F |
| 4G8-IE3 | 10 μg/mL | 3-5/O | 3-5/VR | 4-5/VF |
| | 1 μg/mL | 3-5/R | 3-5/VR | 4-5/R |
| 8C2-2D6 | 10 μg/mL | 3-5/O | 3-5/VR | 4-5/VF |
| | 1 μg/mL | 3-5/O | 3-5/VR | 4-5/VF |
| 2G12-2B2 | 10 μg/mL | 3-5/O | 3-5/VR | 4-5/VF |
| | 1 μg/mL | 3-5/R | 3-5/VR | 4-5/R |
| S3F | 10 μg/mL | 3-5/O | 3-5/VR | 4-5/VF |
| | 1 μg/mL | 3-5/O | 3-5/VR | 4-5/VF |
| 2429-2B2-3B9 | 10 μg/mL | 3-5/VR | 1/VR | 1-3/VR |
| | 1 μg/mL | 1-3VR | 1/VR | 1-3/VR |

Antibody S3F and 8C2-2D6 demonstrated the strongest staining results. 4G8-IE3 and 2G12-2B2 also had strong staining results when higher concentrations were used (10 μg/ml over 1 μg/ml).

TABLE 21

| Frozen tissue evaluation | | | | | |
|---|---|---|---|---|---|
| | | Specific Reactivity (Intensity/Frequency) | | | |
| Antibody | Concentration | Hu14 PA Neo-1 (pancreatic carcinoma, tumor cells, cytoplasm> membrane) | Endothelium (membrane, cytoplasm) | Spindloid cells, tumor cell stroma (cytoplasm> membrane) | Duct epithelium (apical membrane, cytoplasm) |
| 2C2-2C5 | 10 μg/mL | 3-5/O | 0/N | 0/N | 0/N |
| | 1 μg/mL | 3-5/O | 0/N | 0/N | 0/N |
| | Assay Control | 0/N | 0/N | 0/N | 0/N |
| 5E6-2E7 | 10 μg/mL | 3-5/R | 0/N | 0/N | 0/N |
| | 1 μg/mL | 3-5/VR | 0/N | 0/N | 0/N |
| | Assay Control | 0/N | 0/N | 0/N | 0/N |
| 9F11-1F7 | 10 μg/mL | 3-5/R | 0/N | 0/N | 0/N |
| | 1 μg/mL | 3-5/R | 0/N | 0/N | 0/N |
| | Assay Control | 0/N | 0/N | 0/N | 0/N |
| 5G2-1B3 | 10 μg/mL | 3-5/O | 0/N | 0/N | 0/N |
| | 1 μg/mL | 3-5/O | 0/N | 0/N | 0/N |
| | Assay Control | 0/N | 0/N | 0/N | 0/N |
| 4G8-IE3 | 10 μg/mL | 3-5/F | 0/N | 1-2/VR | 0/N |
| | 1 μg/mL | 3-5/O | 0/N | 1-2/VR | 0/N |
| | Assay Control | 0/N | 0/N | 0/N | 0/N |
| 8C2-2D6 | 10 μg/mL | 3-5/F | 1-2/VR | 1-2/R | 0/N |
| | 1 μg/mL | 3-5/F | 0/N | 1-2/VR | 0/N |
| | Assay Control | 0/N | 0/N | 0/N | 0/N |
| 2G12-2B2 | 10 μg/mL | 3-5/F | 0/N | 1-2/R | 0/N |
| | 1 μg/mL | 3-5/F | 0/N | 1-2/VR | 0/N |
| | Assay Control | 0/N | 0/N | 0/N | 0/N |
| S3F | 10 μg/mL | 4-5/F | 2-3/F | 1-2/O | 1-2 |
| | 1 μg/mL | 4-5/F | 1-2/F | 1-2/O | 1/VR |
| | Assay Control | 0/N | 0/N | 0/N | 0/N |
| 2429-2B2-3B9 | 10 μg/mL | 3-5/O | 0/N | 2-3/VR | 0/N |
| | 1 μg/mL | 2-3/VR | 0/N | 0/N | 0/N |
| | Assay Control | 0/N | 0/N | 0/N | 0/N |

In frozen tissue samples, 2C2-2C5, 4G8-IE3, 2G12-2B2 and S3F yielded the most intense and frequent staining in tumor cells. Little staining was observed with any antibodies in endothelium, stroma or ducts in the tissue samples tested.

Cancer tissue microarray studies examined antibody staining in cancerous ovary, lung, pancreas and urinary bladder tissues. 4G8-1E3 and 8C2-2D6 demonstrated the best overall reactivity with multiple tumor types and had limited reactivity with normal tissues. 5G2-1B3 and 5E6-2E7 had good reactivity with pancreatic carcinoma with low reactivity with normal tissues. 5E6-2E7 had some reactivity with pancreatic adenocarcinoma, transitional cell carcinoma in urinary bladder, and ovarian adenocarcinoma with fairly low reactivity with normal tissues. 2G12-2B2 had good reactivity with ovarian carcinoma, lung carcinoma and relatively low reactivity with endothelial tissues.

S3F demonstrated strong carcinoma staining, but also exhibited moderate staining of endothelial cells. This endothelial staining was not observed with 2G12-2B2. These results suggest that antibody S3F may recognize broader STn epitopes, possibly due to the presence of unpaired cysteines and/or a longer CDR-H3 region.

Example 25. Antibody Sequence Analysis

Variable domain sequences for antibodies generated according to the immunization study described herein were analyzed for sequence similarities as well as for characteristics that may impact antibody function, expression, stability or immunogenicity.

Sequence analysis identified CDR regions presented in the following Table. The analysis further revealed that antibodies generated according to the study demonstrated far more variability in the light chain variable domains as compared to the heavy chain variable domains. Additionally, it was determined that heavy chain variable domains of the study antibodies originated from one germline gene, muIGHV1S53, a germline gene that is shared with anti-STn antibodies known in the art: antibody 3F1 (SBH Sciences, Natick, Mass.), antibody B72.3 (see Colcher, D. et al., 1981. PNAS. 78(5): 3199-203), and antibody CC49 (see Muraro, R. et al., 1988. Cancer Res. 48: 4588-96). A comparative view of heavy chain CDR sequences based on the analysis is presented in the following Table.

TABLE 22

| CDR sequence heavy chain comparison | | | | | | |
|---|---|---|---|---|---|---|
| Clone ID | CDR-H1 | SEQ ID NO | CDR-H2 | SEQ ID NO | CDR-H3 | SEQ ID NO |
| 8C2-2D6 | GYTFTDHAIH | 143 | YISPGNGDI KYNEKFKG | 145 | SITTSY | 152 |
| 4G8-1E3 | GYIFTDHAIH | 144 | YISPGNGDI KYNEKFKG | 145 | SITTSY | 152 |
| 2G12-2B2 | GYTFTDHAIH | 143 | YFSPGNDDI KYNEKFRG | 146 | SLSTPY | 153 |
| 5G2-1B3 | GYTFTDHAIH | 143 | YFSPGNDDI KYNEKFKV | 147 | SYYGD | 154 |
| 5E6-2E7 | GYTFTDHAIH | 143 | YISPGNGDI KYNEKFKV | 148 | SITTPY | 155 |
| 2C2-2C5 | GYTFTDHAIH | 143 | YISPGNGDI KYNEKFKG | 145 | SITTPY | 155 |

TABLE 22-continued

CDR sequence heavy chain comparison

| Clone ID | CDR-H1 | SEQ ID NO | CDR-H2 | SEQ ID NO | CDR-H3 | SEQ ID NO |
|---|---|---|---|---|---|---|
| 3F1 | GYTFTDHAIH | 143 | YISPGNGDI KYNEKFKD | 149 | SLLALD Y | 156 |
| CC49 | GYTFTDHAIH | 143 | YFSPGNDDF KYNEKFKG | 150 | SLNMAY | 157 |
| B72.3 | GYTFTDHAIH | 143 | YISPGNDDI KYNEKFKG | 151 | SYYGH | 158 |
| Consensus | GYTFTDHAIH | 143 | YISPGNGDI KYNEKFKG | 145 | SITTSY | 152 |

CDR-H3 sequences varied by plus or minus one amino acid relative to the median length.

Interestingly, target-specific light chains had the same is CDR-L2 and CDR-L3 sequence lengths. Two classes of CDR-L1 sequences were found to persist [long (2G12-2B2, 5E6-2E7 and CC49) and short (8C2-2D6, 4G8-1E3, 5G2-1B3, 2C2-2C5, 3F1 and B72.3)], potentially presenting unified topology in each class. A comparison of light chain CDR sequences is presented in the following Table.

TABLE 23

CDR sequence light chain comparison

| Clone ID | CDR-L1 | SEQ ID NO | CDR-L2 | SEQ ID NO | CDR-L3 | SEQ ID NO |
|---|---|---|---|---|---|---|
| 8C2-2D6 | KASENVVTYVS | 159 | GASNRYT | 115 | GQGYSYPYT | 127 |
| 4G8-1E3 | HASQHINFWLS | 160 | KASNLHT | 118 | QQDQSYPYM | 141 |
| 2G12-2B2 | KSSQSLLNRGN HKNYLT | 161 | WASTRES | 123 | QNDYTYPYT | 135 |
| 5G2-1B3 | RASENIYSHLA | 162 | GATNLAD | 117 | QHFWGAPFT | 129 |
| 5E6-2E7 | KSSQSLLNSGK TKNYLT | 163 | WASTRES | 123 | KNDYSYPYT | 140 |
| 2C2-2C5 | KASQSVNNNVA | 164 | YASNRYT | 122 | QQGYSSPWT | 134 |
| 3F1 | KASQDVGTNIA | 165 | SASTRHT | 168 | QQYSSFPLT | 171 |
| CC49 | KSSQSLLYSGN QKNYLA | 166 | WASARES | 169 | QQYYSYPLT | 172 |
| B72.3 | RASENIYSNLA | 167 | AATNLAD | 170 | QHFWGTPYT | 173 |

Taken together, the sequence analysis suggests distinct patterns of CDR-H3 diversity that correspond with specific light chain germline pairings. Three groups were identified based on these pairings. Group A includes antibodies 8C2-2D6, 4G8-1E3 and S3F. These antibodies have similar CDR-H3 sequences, with the exception of S3F, which is distinct from all other antibodies in terms of CDR-H3 length (having an extra amino acid, creating a longer loop). Group A antibodies also have light chain CDRs with similarities, especially in CDR residue lengths.

Group B includes antibodies 2G12-2B2 and CC49. Among the similarities in heavy chain sequences, these antibodies have conserved F and D residues in the CDR-H2 and a conserved L residue in the CDR-H3. Additionally, Group B antibodies have highly similar light chain sequences.

Group C antibodies include 5G2-1B3 and B72.3. Among the similarities between their heavy chain sequences, these antibodies have conserved D residues in their CDR-H2 sequences as well as a YYG motif in their CDR-H3 sequences. Group C antibodies also have highly similar light chain sequences.

The limited number of groups identified highlights the relatively rare sequence specificity necessary for anti-STn binding. Antibody grouping facilitates the identification of relevant intra-group sequence-based contributions to epitope binding. Notably, within Group A, S3F uniquely contains an extended CDR-H3 loop that may contribute to a novel binding profile. Interestingly, immunohistochemistry data indicates that S3F may bind to a broader range of targets, including undesired binding to endothelial cells.

Example 26. Antibody Variants

Variable domain sequences for antibodies generated according to the immunization study described herein were analyzed for sequence characteristics that may impact antibody function, expression, stability and/or immunogenicity.

Many of the antibodies generated in the study had CDR-H2 sequences containing NG residue pairs, making them susceptible to asparagine deamidation, with possible conversion to glutamate and pyroglutamate in a 3:1 ratio over time. These sequences may be subjected to mutagenesis to convert NG residue pairs to SG or QG pairs to prevent deamidation at these sites. Alternatively, these antibodies may be formulated to reduce deamidation.

Antibodies 2B2-2A7 and 5G2-1B3 had aspartate isomerization sites (identified by DG amino acid residue pairs) in their light chain variable domains. Aspartic acid at these sites can convert into glutamate and pyroglutamate in a 3:1 ratio over time. These sequences may be subjected to mutagenesis to convert DG residue pairs to SG or QG to prevent isomerization at these sites. Alternatively, these antibodies may be formulated to reduce isomerization.

Many of the antibodies have heavy chains with N-terminal glutamine residues. These sequences may be subjected to mutagenesis to convert N-terminal glutamine residues to glutamate residues.

Sequence analysis for aggregation-prone patches revealed an HFW segment in the CDR-L3 of 5G2-1B3, which carries some risk of increasing antibody aggregation. Aggregation stability studies may be carried out with variants of this motif to identify less aggregation-prone antibodies.

Example 27. Cancer Cell Binding Comparison

Antibodies S3F, 8C2-2D6, 4G8-1E3 and 2G12-2B2 were tested for binding to OVCAR3 cells and SNU-16 cells using flow cytometry analysis. For analysis, cells were grown and harvested using StemPro Accutase (Life Technologies, Carlsbad, Calif.) and washed with PBS comprising 5% FBS before pelleting by light centrifugation. Cell numbers and viability were determined by trypan blue dye exclusion analysis and cell concentrations were adjusted to $5\times10^6$ cells/ml in PBS with 5% FBS. 50 μl of cells were added to each well of an assay plate. Cells were then combined with 50 μl solutions of the antibodies being analyzed or control antibodies and incubated for 1 hour at 4° C. Cells were next washed and pelleted twice with PBS with 5% FBS before being treated with 100 μl of PBS with 5% FBS comprising a 1:1,500 dilution of anti-mouse IgG (Southern Biotech, Birmingham, Ala.,) conjugated to allophycocyanin (APC). Cells were then incubated for 30 min at 4° C. before washing and resuspending in 200 μl of propidium iodide (PI) diluted 1:1000 in PBS with 5% FBS. Finally, treated cells were subjected to flow cytometry analysis.

Figure 2A:
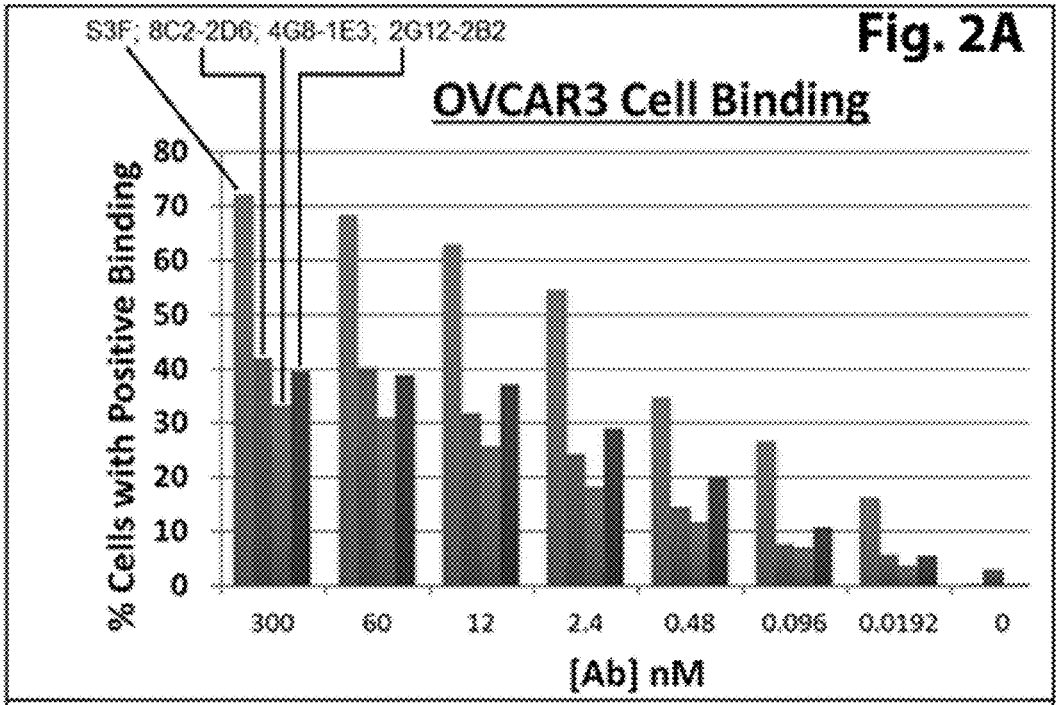
FIGS. 2A and 2B are bar graphs presenting antibody binding data.
Figure 2B:
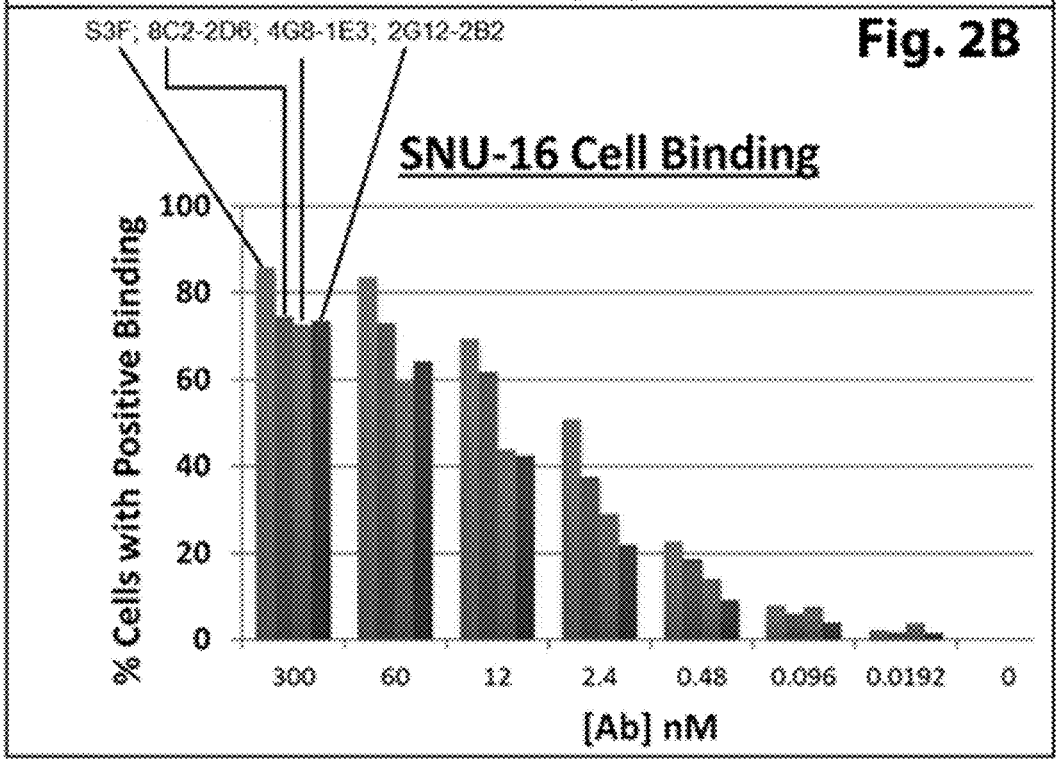

The percentage of cells with positive binding was plotted against the log of the antibody concentration for each cell type (see FIGS. 2A and 2B). S3F antibody demonstrated binding to a significantly higher number of cells as compared to other STn antibodies in all of the concentrations tested suggesting either (1) a broader epitope or (2) more promiscuous binding against certain cell types.

Next, mean APC fluorescence intensity values were plotted against the log of the antibody concentration to determine the concentration of antibody needed to observe half maximal binding efficiency (EC50). Data are presented in the following Table.

TABLE 24

EC50 values for antibody binding to OVCAR3 and SNU-16 cells

| Antibody | EC50 for OVCAR3 binding (nM) | EC50 for SNU-16 binding (nM) |
|---|---|---|
| S3F | 0.9 | 63.9 |
| 8C2-2D6 | 3.1 | 6.3 |
| 2G12-2B2 | 0.8 | 8.9 |
| 4G8-1E3 | 1.7 | 32.7 |

The data overall indicated that SNU-16 cells express less STn. Interestingly, Group A antibodies (S3F and 4G8-1E3) demonstrated much weaker binding to SNU-16 cells.

Example 28. Expanded Antibody Sequence Analysis and Variant Development

Antibody sequence analysis according to Example 25 is carried out to compare additional antibodies targeting STn. Results are used to identify additional sequence-based trends and heavy and light chain pairing patterns. These trends are used to inform affinity maturation strategies to create antibody fragment display libraries based on directed mutations to improve binding characteristics.

Example 29. STn/CD3 Bispecific Antibodies

Bispecific antibodies are produced that bind to both STn and CD3. Such antibodies are used to bind STn-presenting cancer cells and bring them into contact with CD3-expressing cytotoxic cells.

Example 30. Xenograft Model Studies

Xenograft model studies are carried out to test ADC antibodies in vivo. Tumors are induced in mice through injection of MDA-MB-231 STn+ cells, SNU-16 cells, COLO-205 cells or OVAR3 cells. Mice are then treated with MMAE-conjugated S3F, 4G8-1E3, 2G12-2B2, irrelevant control antibodies or naked (non-conjugated) 4G8-1E3 or 2G12-2B2 antibody controls. Mice are monitored for changes in weight and tumor volume.

Example 31. Tumor Reduction in Xenograft Model Studies

Xenograft tumor model studies were carried out to test the ability of ADC antibodies to reduce tumor volume in vivo. MMAE-conjugated S3F, 4G8-1E3, and 2G12-2B2 were tested along with vehicle-only control, isotype control antibodies [(MMAE-conjugated non-specific mouse IgG (MOPC173, Biolegend, San Diego, Calif.)], and naked (non-conjugated) antibody controls (mixture of non-conjugated 4G8-1E3 and 2G12-2B2 antibody). A subcutaneous xenograft model was utilized where a MATRIGEL® (Corning Life Science, Corning, N.Y.) suspension of human breast cancer MDA-MB-231 cells STn+ cells ($5\times10^6$ cells) were injected into the right flank of severe immunodeficiency (SCID) mice to generate tumors of from about 175 $mm^3$ to about 225 $mm^3$.

Figure 3:
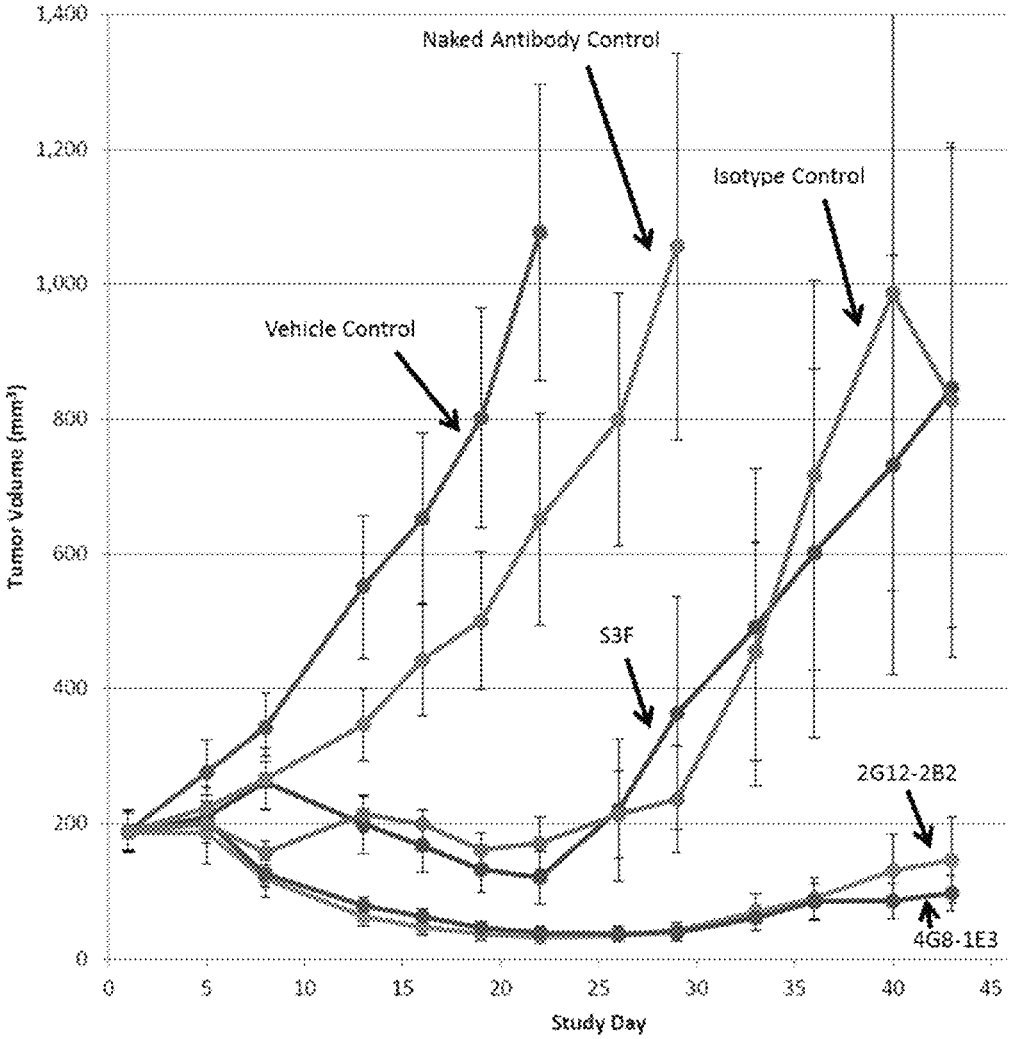
FIG. 3 is a line graph showing changes in tumor volume over time in response to antibody drug conjugate treatment in mouse xenograft studies.

Mice with essentially equivalent group mean tumor sizes were placed into 6 groups (10 mice per group) receiving the following treatments: (1) Group 1—vehicle control only; (2) Group 2—MMAE-conjugated S3F; (3) Group 3—MMAE-conjugated 2G12-2B2; (4) Group 4—MMAE-conjugated 4G8-1E3; (5) Group 5—MMAE-conjugated isotype control antibody; and (6) Group 6—naked antibody control. Groups receiving antibodies were administered 2.5 mg/kg antibody in 20 mM citrate, pH 5.5+150 mM NaCl by intraperitoneal injection, one time per week for three weeks. Group 1 received vehicle-only treatments (20 mM citrate, pH 5.5+150 mM NaCl). Tumor volumes and body weights were measured twice weekly. Tumor volumes were plotted over time and reduced tumor volumes in ADC antibody-treated groups were observed in comparison to vehicle and naked antibody control groups (see FIG. 3).

Percent tumor growth inhibition (% T/C) was calculated by dividing the mean tumor volume at day 22 in treated mice by the mean tumor volume in Group 1 mice at day 22 and multiplying the resulting value by 100. Statistical significance between groups was determined using a Student's t-test. Naked antibody showed some efficacy in mean tumor volume reduction compared to vehicle only, but had weak percent tumor growth inhibition overall (about 60%). Groups 2 and 5 trended in a similar manner with high and intermediate activity by percent tumor growth inhibition, (11.2% and 15.9%, respectively). Groups 3 and 4 showed the most robust percent tumor growth inhibition (3.0% and 3.6%, respectively). Toxicology analysis was also conducted in study mice consisting of body weight observations and organ/tissue pathological examination. Results demonstrated no gross defects in mouse health or behavior between treatment groups. Percent changes in body weight were similar among treatment groups.

SEQUENCE LISTING

```
<160> NUMBER OF SEQ ID NOS: 244

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 1

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Ser Thr Ser
20 25 30

Asn Met Gly Ile Gly Trp Ile Arg Gln Pro Ser Gly Lys Gly Leu Glu
35 40 45

Trp Leu Ala His Ile Trp Trp His Asp Asp Lys Tyr Tyr Asn Pro Ser
50 55 60

Leu Lys Ser Arg Leu Thr Ile Ser Lys Asp Ile Ser Asn Asn Gln Val
65 70 75 80

Phe Leu Lys Ile Thr Ser Val Asp Thr Ala Asp Thr Ala Thr Tyr Tyr
85 90 95

Cys Ala Gln Val Pro Phe Tyr Tyr Gly Thr Ser Phe Asp Val Trp Gly
100 105 110

Thr Gly Thr Thr Val Thr Val Ser Ser
115 120

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

Asp Ile Val Met Thr Gln Ser Pro Ala Thr Leu Ser Val Thr Pro Gly
1 5 10 15

Asp Arg Val Ser Leu Ser Cys Arg Ala Ser Gln Ser Ile Ser Asp Tyr
20 25 30

Leu His Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Gly Ser Asp Phe Thr Leu Ser Ile Asn Ser Val Glu Pro
65 70 75 80

Glu Asp Val Gly Val Tyr Tyr Cys Gln Asn Gly His Ser Phe Pro Leu
85 90 95

Thr Phe Gly Ala Gly Thr Lys Leu Glu Leu Lys
100 105

<210> SEQ ID NO 3
<211> LENGTH: 105
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

Gln Ile Val Leu Thr Gln Ser Pro Ala Ile Met Ser Ala Ser Pro Gly
1 5 10 15

Glu Thr Val Thr Met Thr Cys Ser Ala Ser Ser Ser Ile Thr Tyr Met
20 25 30

His Trp Tyr Gln Gln Lys Pro Gly Thr Ser Pro Lys Arg Trp Ile Tyr
35 40 45

```
Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg
            100                 105


<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Ala Tyr Tyr Tyr Gly Ser Glu Arg Asp Tyr Trp Gly
            100                 105                 110

Gln Gly Thr Thr Leu Thr Val Ser Ser
        115                 120


<210> SEQ ID NO 5
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr His Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg
            100                 105
```

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 6

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Arg Ala Phe Val Tyr Trp Gly Gln Gly Thr Leu Val Thr Val Ser Ala
            100                 105                 110
```

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Ile
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Met
                85                  90                  95

Leu Thr Phe Gly Ala Gly Thr Lys Leu Glu Leu Lys
            100                 105
```

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Gln Val Gln Leu Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ile Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Thr
                85                  90                  95

Lys Gly Phe Thr Tyr Trp Gly Gln Gly Thr Leu Val Thr Val Ser Ala
            100                 105                 110


<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Phe
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Leu Leu Thr
                85                  90                  95

Phe Gly Ala Gly Thr Lys Leu Glu Leu Lys
            100                 105


<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
            20                  25                  30

Gly Val Asn Trp Val Arg Gln Pro Pro Gly Lys Gly Leu Glu Trp Leu
        35                  40                  45

Gly Val Ile Trp Gly Asp Gly Ser Thr Asn Tyr Gln Ser Ala Leu Ile
    50                  55                  60

Ser Arg Leu Ile Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Thr
                85                  90                  95
```

```
Lys Gly Phe Ala Tyr Trp Gly Gln Gly Thr Leu Val Thr Val Ser Ala
            100                 105                 110


<210> SEQ ID NO 11
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Phe Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Leu Leu Thr
                85                  90                  95

Phe Gly Ala Gly Thr Lys Leu Glu Leu Lys
            100                 105


<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Lys Glu Ser Gly Pro Gly Leu Val Ala Pro Ser Gln
1               5                   10                  15

Asn Leu Ser Ile Thr Cys Thr Val Ser Gly Phe Ser Leu Thr Ser Tyr
            20                  25                  30

Gly Val Asn Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ile Ile Ser Lys Glu Asn Ser Lys Ser Gln Val Phe Leu
65                  70                  75                  80

Lys Leu Asn Ser Leu Gln Thr Asn Asp Thr Ala Thr Tyr Tyr Cys Thr
                85                  90                  95

Lys Gly Phe Val Tyr Trp Gly Gln Gly Thr Leu Val Thr Val Ser Ala
            100                 105                 110


<210> SEQ ID NO 13
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Lys Glu Ser Gly Pro Gly Leu Val Ala Pro Ser Gln
```

```
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Phe Asp Tyr Trp Gly Gln Gly Thr Thr Leu Thr Val
            100                 105                 110

Ser Ser


<210> SEQ ID NO 14
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ile Val Leu Thr Gln Ser Pro Ala Val Met Ser Ala Ser Pro Gly
1               5                   10                  15

Glu Lys Val Ala Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gly Gly Thr Lys Leu Glu Ile Lys
            100                 105


<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Leu Gln Tyr Asp Ala Glu Leu Val Lys Pro Gly Gly
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Phe Ser Pro Gly Asn Asp Asp Ile Lys Tyr Ser Glu Lys Phe
    50                  55                  60

Lys Gly Lys Ala Thr Leu Thr Ala Asp Lys Ser Ser Ser Thr Ala Tyr
65                  70                  75                  80
```

```
Met Gln Leu Asn Ser Leu Thr Ser Glu Asp Ser Ala Val Tyr Phe Cys
                85                  90                  95

Lys Arg Ser Ile Thr Thr Pro Tyr Trp Gly Gln Gly Thr Leu Val Thr
            100                 105                 110

Val Ser Ala
        115


<210> SEQ ID NO 16
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Val Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Asp Gln Ser Tyr Pro Tyr
                85                  90                  95

Thr Phe Gly Gly Gly Thr Lys Leu Lys Lys
            100                 105


<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Ile Thr Thr Ser Tyr Trp Gly Gln Gly Thr Leu Val Thr
            100                 105                 110

Val Ser Ala
        115


<210> SEQ ID NO 18
```

<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Asn Ile Val Met Thr Gln Ser Pro Lys Ser Met Ser Met Ser Val Gly
1 5 10 15

Glu Arg Val Thr Leu Thr Cys Lys Ala Ser Glu Asn Val Val Ile Tyr
20 25 30

Val Ser Trp Tyr Gln Gln Lys Pro Glu Gln Ser Pro Lys Leu Leu Ile
35 40 45

Tyr Gly Ala Ser Asn Arg Tyr Thr Gly Val Pro Asp Arg Phe Thr Gly
50 55 60

Ser Gly Ser Ala Thr Asp Phe Thr Leu Thr Ile Ser Ser Val Gln Ala
65 70 75 80

Glu Asp Leu Ala Asp Tyr His Cys Gly Gln Gly Tyr Ser Tyr Pro Tyr
85 90 95

Thr Phe Gly Gly Gly Thr Lys Leu Glu Ile Lys Arg
100 105

<210> SEQ ID NO 19
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 19

Gln Val Gln Leu Gln Gln Ser Asp Ala Glu Leu Val Lys Pro Gly Ala
1 5 10 15

Ser Val Lys Ile Ser Cys Lys Ala Ser Gly Tyr Thr Phe Thr Asp His
20 25 30

Ala Ile His Trp Val Lys Gln Lys Pro Glu Gln Gly Leu Glu Trp Ile
35 40 45

Gly Tyr Val Ser Pro Gly Asn Gly Asp Ile Lys Tyr Asn Glu Lys Phe
50 55 60

Lys Gly Lys Ala Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Lys Arg Ser Leu Ile Gly Asp Tyr Trp Gly Gln Gly Thr Thr Leu Thr
100 105 110

Val Ser Ser
115

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

Asp Ile Val Met Thr Gln Ser Gln Lys Phe Met Ser Ser Ser Val Gly
1 5 10 15

```
Asp Arg Val Thr Ile Thr Cys Lys Ala Ser Gln Asn Val Gly Thr Ala
            20                  25                  30

Val Ala Trp Tyr Gln Gln Lys Pro Gly Gln Ser Pro Lys Phe Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Arg Leu
                85                  90                  95

Thr Phe Gly Gly Gly Thr Lys Leu Glu Ile Lys
            100                 105


<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Leu Ser Pro Gly Asn Asp Asp Ile Lys Tyr Ser Glu Lys Phe
    50                  55                  60

Lys Asp Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Ile Gly Gly Asp His Trp Gly Gln Gly Thr Thr Leu Thr
            100                 105                 110

Val Ser Ser
        115


<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Asn Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Gly Ser Leu Gln Pro
65                  70                  75                  80
```

```
Glu Asp Ile Ala Thr Tyr Tyr Cys Gln Gln Gly Gln Ser Tyr Pro Phe
                85                  90                  95

Thr Phe Gly Gly Gly Thr Lys Leu Glu Ile Lys Arg
            100                 105


<210> SEQ ID NO 23
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Gln Arg Gln Leu Gly Gln Gly Tyr Trp Gly Gln Gly Thr Thr Leu Thr
            100                 105                 110

Val Ser Ser
        115


<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Tyr Thr Phe Gly Gly Gly Thr Lys Leu Glu Ile Lys
            100                 105                 110

Arg


<210> SEQ ID NO 25
<211> LENGTH: 115
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 25

Gln Val Gln Leu Gln Gln Ser Asp Ala Glu Leu Gly Lys Pro Gly Ala
1 5 10 15

Ser Val Lys Ile Ser Cys Lys Ala Ser Gly Tyr Thr Phe Ser Asp His
20 25 30

Ala Ile His Trp Val Lys Gln Lys Pro Glu Gln Gly Leu Glu Trp Ile
35 40 45

Gly Tyr Ile Ser Pro Gly Asn Asp Asp Ile Lys Tyr Asn Glu Lys Phe
50 55 60

Lys Gly Lys Ala Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Glu Arg Ser Met Ile Gly Val Tyr Trp Gly Gln Gly Thr Leu Val Thr
100 105 110

Val Ser Ala
115

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Asp Val Val Met Thr Gln Thr Pro Leu Ser Leu Thr Val Ser Leu Gly
1 5 10 15

Asp Gln Ala Ser Ile Ser Cys Arg Phe Ser Gln Ser Leu Val Gln Ser
20 25 30

Asn Gly Asn Thr Tyr Leu Gln Trp Tyr Leu Gln Lys Pro Gly Gln Ser
35 40 45

Pro Lys Leu Leu Ile Tyr Lys Val Ser Asn Arg Phe Cys Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Ala Pro Leu Thr Phe Gly Ala Gly Thr Lys Leu Glu Leu Lys
100 105 110

<210> SEQ ID NO 27
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

Gln Val Gln Leu Gln Gln Ser Asp Ala Glu Leu Val Lys Pro Gly Ala
1 5 10 15

Ser Val Lys Ile Ser Cys Lys Thr Ser Gly Tyr Thr Phe Thr Asp His
20 25 30

```
Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Pro Glu Asp Ser Ala Val Tyr Phe Cys
                85                  90                  95

Lys Ile Ser Tyr Tyr Gly Ile Trp Gly Gln Gly Thr Thr Leu Thr Val
            100                 105                 110

Ser Ser


<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ala Ser Leu Ser Val Ser Val Gly
1               5                   10                  15

Glu Ser Val Thr Ile Thr Cys Arg Leu Ser Glu Asp Ile Tyr Ser Asn
            20                  25                  30

Leu Ala Trp Phe Gln Gln Arg Pro Gly Lys Ser Pro Gln Leu Leu Val
        35                  40                  45

Tyr Lys Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Phe
                85                  90                  95

Thr Phe Gly Ser Gly Thr Lys Val Glu Ile Lys
            100                 105


<210> SEQ ID NO 29
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Phe Ser Pro Gly Asn Asp Asp Ile Lys Tyr Asn Glu Lys Phe
    50                  55                  60

Lys Val Lys Ala Thr Leu Thr Ala Asp Lys Ser Ser Ser Thr Ala Tyr
65                  70                  75                  80

Met Gln Leu Thr Ser Leu Thr Ser Glu Asp Ser Ala Val Tyr Phe Cys
                85                  90                  95
```

```
Lys Arg Ser Tyr Tyr Gly Asp Trp Gly Gln Gly Thr Thr Leu Thr Val
            100                 105                 110

Ser Ser


<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser His
            20                  25                  30

Leu Ala Trp Tyr Gln Gln Lys Gln Gly Lys Ser Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Thr Gln Phe Ser Leu Lys Ile His Ser Leu Gln Ser
65                  70                  75                  80

Glu Asp Phe Gly Ser Tyr Tyr Cys Gln His Phe Trp Gly Ala Pro Phe
                85                  90                  95

Thr Phe Gly Ser Gly Thr Lys Leu Glu Ile Lys
            100                 105


<210> SEQ ID NO 31
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Ile Gln Leu Gln Gln Ser Asp Ala Glu Leu Val Lys Pro Gly Thr
1               5                   10                  15

Ser Val Lys Met Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Phe Ser Pro Gly Asn Asp Asp Ile Lys Tyr Asn Val Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ser Val Gly Tyr Ala Leu Asp Tyr Trp Gly Leu Gly Thr Thr Leu Thr
            100                 105                 110

Val Ser Ser
        115


<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 32

Asn Ile Val Met Thr Gln Ser Pro Lys Ser Met Ser Met Ser Val Gly
1 5 10 15

Glu Arg Val Thr Leu Thr Cys Lys Ala Ser Glu Asn Val Val Thr Tyr
20 25 30

Val Ser Trp Tyr Gln Gln Lys Pro Glu Gln Ser Pro Lys Leu Leu Ile
35 40 45

Tyr Gly Ala Ser Asn Arg Tyr Thr Gly Val Pro Asp Arg Phe Thr Gly
50 55 60

Ser Gly Ser Ala Thr Asp Phe Thr Leu Thr Ile Ser Ser Val Gln Ala
65 70 75 80

Glu Asp Leu Ala Asp Tyr His Cys Gly Gln Gly Tyr Ser Tyr Pro Tyr
85 90 95

Thr Phe Gly Gly Gly Thr Lys Leu Glu Ile Lys Arg
100 105

<210> SEQ ID NO 33
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Gln Val Gln Leu Gln Gln Ser Asp Ala Glu Leu Val Lys Pro Gly Thr
1 5 10 15

Thr Val Lys Ile Ser Cys Lys Ala Ser Gly Tyr Thr Phe Thr Asp His
20 25 30

Ala Ile His Trp Val Lys Glu Lys Pro Glu Gln Gly Leu Glu Trp Ile
35 40 45

Gly Tyr Ile Ser Pro Gly Asn Asp Asp Ile Lys Tyr Ser Glu Lys Phe
50 55 60

Lys Gly Lys Ala Thr Leu Thr Ala Asp Lys Ser Ser Ser Thr Ala Tyr
65 70 75 80

Met Gln Leu Asn Ser Leu Thr Ser Asp Asp Ser Ala Val Tyr Phe Cys
85 90 95

Lys Arg Ser Leu Ser Thr Pro Tyr Trp Gly Gln Gly Thr Leu Val Thr
100 105 110

Val Ser Ala
115

<210> SEQ ID NO 34
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Asp Ile Val Met Thr Gln Ser Pro Ser Ser Leu Thr Val Thr Ala Gly
1 5 10 15

Glu Lys Val Thr Met Ser Cys Arg Ser Ser Gln Ser Leu Leu Asn Ser
20 25 30

Gly Asn Gln Lys Asn Tyr Leu Thr Trp Tyr Gln Gln Lys Pro Gly Gln
35 40 45

```
Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys Arg


<210> SEQ ID NO 35
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Met Gln Met Pro Glu Gln Gly Leu Glu Trp Ile
        35                  40                  45

Gly Tyr Ile Ser Pro Gly Asn Gly Asp Val Lys Tyr Ser Glu Arg Phe
    50                  55                  60

Lys Gly Arg Ala Thr Leu Thr Ala Asp Lys Ser Ser Ser Ser Ala Tyr
65                  70                  75                  80

Met Gln Leu Asn Ser Leu Thr Ser Glu Asp Ser Ala Val Tyr Phe Cys
                85                  90                  95

Lys Arg Ser Leu Ser Thr Pro Tyr Trp Gly Gln Gly Thr Leu Val Thr
            100                 105                 110

Val Ser


<210> SEQ ID NO 36
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Met Thr Gln Ser Pro Ser Ser Leu Thr Val Thr Ala Gly
1               5                   10                  15

Glu Arg Val Thr Met Ser Cys Lys Ser Ser Gln Ser Leu Leu Asn Ser
            20                  25                  30

Gly Asn Gln Lys Ser Tyr Leu Thr Trp Tyr Gln Gln Lys Pro Gly Gln
        35                  40                  45

Pro Pro Lys Leu Leu Ile Ser Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Ser
                85                  90                  95

Asp Tyr Ser Tyr Pro Tyr Thr Phe Gly Gly Gly Thr Lys Leu Glu Ile
```

```
            100                 105                 110

Lys Arg


<210> SEQ ID NO 37
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid or not present
<220> FEATURE:
<221> NAME/KEY: MOD_RES
<222> LOCATION: (111)..(111)
<223> OTHER INFORMATION: Any amino acid or not present

<400> SEQUENCE: 37

Gln Val Gln Leu Gln Gln Ser Asp Xaa Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Phe Ser Pro Gly Asn Asp Asp Ile Lys Tyr Asn Glu Lys Phe
    50                  55                  60

Arg Gly Lys Ala Thr Leu Thr Ala Asp Lys Ser Ser Ser Thr Ala Tyr
65                  70                  75                  80

Met Gln Leu Asn Ser Leu Ser Ser Asp Asp Ser Ala Val Tyr Phe Cys
                85                  90                  95

Lys Arg Ser Leu Ser Thr Pro Tyr Trp Gly Gln Gly Thr Leu Xaa Thr
            100                 105                 110

Val Ser Ala
        115


<210> SEQ ID NO 38
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Arg
            20                  25                  30

Gly Asn His Lys Asn Tyr Leu Thr Trp Tyr Arg Gln Lys Pro Gly Leu
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Tyr Thr Phe Gly Gly Gly Thr Lys Leu Glu Ile
            100                 105                 110
```

Lys Arg

<210> SEQ ID NO 39
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Gln Val Gln Leu Gln Gln Ser Asp Ala Glu Leu Val Lys Pro Gly Ala
1 5 10 15

Ser Met Lys Ile Ser Cys Lys Ala Ser Gly Tyr Thr Phe Thr Asp His
20 25 30

Ala Ile His Trp Val Lys Gln Lys Pro Glu Gln Gly Leu Glu Trp Ile
35 40 45

Gly Tyr Ile Ser Pro Gly Asn Gly Asp Ile Lys Tyr Asn Glu Lys Phe
50 55 60

Lys Val Lys Ala Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Lys Arg Ser Ile Thr Thr Pro Tyr Trp Gly Gln Gly Thr Leu Val Thr
100 105 110

Val Ser Ala
115

<210> SEQ ID NO 40
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Ser
20 25 30

Gly Lys Thr Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Ala Glu Asp Leu Ala Val Tyr Tyr Cys Lys Asn
85 90 95

Asp Tyr Ser Tyr Pro Tyr Thr Phe Gly Gly Gly Thr Lys Leu Glu Ile
100 105 110

Lys Arg

<210> SEQ ID NO 41
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Gln Val Gln Leu Gln Gln Ser Asp Ala Glu Leu Val Lys Pro Gly Ala
1 5 10 15

Ser Val Lys Ile Ser Cys Lys Thr Ser Gly Tyr Thr Phe Thr Asp His
20 25 30

Ala Ile His Trp Val Lys Gln Lys Pro Glu Gln Gly Leu Glu Trp Ile
35 40 45

Gly Tyr Ile Ser Pro Gly Asn Asp Asp Ile Lys Tyr Thr Glu Lys Phe
50 55 60

Lys Gly Lys Val Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Lys Arg Ser Ile Thr Thr Pro Tyr Trp Gly Gln Gly Thr Leu Val Thr
100 105 110

Val Ser Ala
115

<210> SEQ ID NO 42
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Gln Val Gln Leu Gln Gln Ser Asp Ala Glu Leu Val Lys Pro Gly Ala
1 5 10 15

Ser Val Lys Ile Ser Cys Lys Ala Ser Gly Tyr Thr Phe Thr Asp His
20 25 30

Ala Ile His Trp Val Lys Gln Lys Pro Glu Gln Gly Leu Glu Trp Ile
35 40 45

Gly Tyr Ile Ser Pro Gly Asn Gly Asp Ile Lys Tyr Asp Glu Lys Phe
50 55 60

Lys Gly Lys Ala Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Lys Arg Ser Ile Thr Thr Ser Tyr Trp Gly Gln Gly Thr Leu Val Thr
100 105 110

Val Ser Ala
115

<210> SEQ ID NO 43
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Gln Val Gln Leu Gln Gln Ser Asp Ala Glu Leu Val Lys Pro Gly Ala
1 5 10 15

Ser Val Lys Ile Ser Cys Lys Ala Ser Gly Tyr Thr Phe Thr Asp His
20 25 30

```
Ala Ile His Trp Val Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Phe Phe Cys
                85                  90                  95

Lys Arg Ser Ile Thr Thr Ser Tyr Trp Gly Gln Gly Thr Leu Val Thr
            100                 105                 110

Val Ser Ala
        115


<210> SEQ ID NO 44
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Ile Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met His Leu Asn Ser Leu Thr Ser Glu Asp Ser Ala Val Tyr Phe Cys
                85                  90                  95

Lys Arg Ser Ile Thr Thr Ser Tyr Trp Gly Gln Gly Thr Leu Val Thr
            100                 105                 110

Val Ser Ala
        115


<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln His Ile Asn Phe Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Leu Pro
65                  70                  75                  80
```

```
Glu Asp Val Ala Thr Tyr Tyr Cys Gln Gln Asp Gln Ser Tyr Pro Tyr
                85                  90                  95

Met Phe Gly Gly Gly Thr Lys Leu Glu Ile Lys Arg
            100                 105


<210> SEQ ID NO 46
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Leu Leu Asn Ser Leu Thr Ser Glu Asp Ser Ala Val Tyr Phe Cys
                85                  90                  95

Lys Arg Ser Ile Thr Thr Ser Tyr Trp Gly Gln Gly Thr Leu Val Thr
            100                 105                 110

Val Ser Ala
        115


<210> SEQ ID NO 47
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Gly Lys Ala Thr Leu Thr Ala Asp Thr Ser Ser Thr Thr Ala Tyr
65                  70                  75                  80

Met Gln Leu Asn Ser Leu Thr Ser Glu Asp Ser Ala Met Tyr Phe Cys
                85                  90                  95

Lys Arg Ser Ile Thr Thr Ser Tyr Trp Gly Gln Gly Thr Leu Val Thr
            100                 105                 110

Val Ser Ala
        115


<210> SEQ ID NO 48
<211> LENGTH: 115
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Gln Val Gln Leu Gln Gln Ser Asp Ala Glu Leu Val Lys Pro Gly Ala
1 5 10 15

Ser Val Lys Ile Ser Cys Lys Ala Ser Gly Tyr Ile Phe Thr Asp His
20 25 30

Ala Ile His Trp Val Lys Gln Lys Pro Glu Gln Gly Leu Glu Trp Ile
35 40 45

Gly Tyr Ile Ser Pro Gly Asn Gly Asp Ile Lys Tyr Ile Glu Lys Phe
50 55 60

Arg Gly Lys Ala Thr Leu Thr Ala Asp Lys Ser Ser Ser Thr Ala Tyr
65 70 75 80

Met Gln Leu Asn Ser Leu Thr Ser Glu Asp Ser Ala Val Tyr Phe Cys
85 90 95

Lys Arg Ser Leu Ser Thr Pro Tyr Trp Gly Gln Gly Thr Leu Val Thr
100 105 110

Val Ser Ala
115

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Asn Ile Leu Met Thr Gln Ser Pro Lys Ser Met Ser Met Ser Val Gly
1 5 10 15

Glu Arg Val Thr Leu Thr Cys Lys Ala Ser Glu Asn Val Val Asn Tyr
20 25 30

Val Ser Trp Tyr Gln Gln Lys Pro Glu Gln Ser Pro Lys Leu Leu Ile
35 40 45

Phe Gly Ala Ser Asn Arg Tyr Ser Gly Val Pro Asp Arg Phe Thr Gly
50 55 60

Ser Gly Ser Ala Thr Asp Phe Thr Leu Thr Ile Ser Ser Val Gln Ala
65 70 75 80

Glu Asp Leu Ala Asp Tyr His Cys Gly Ser Lys Trp Ile Thr Ser Tyr
85 90 95

Pro Tyr Thr Phe Gly Gly Gly Thr Lys Leu Glu Ile Lys Arg
100 105 110

<210> SEQ ID NO 50
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Asn Ile Leu Met Thr Gln Ser Pro Lys Ser Met Ser Met Ser Val Gly
1 5 10 15

Glu Arg Val Thr Leu Thr Cys Lys Ala Ser Glu Asn Val Val Asn Tyr

```
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Ser Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Ala Arg Val Thr Ser Tyr Pro
                85                  90                  95

Tyr Thr Phe Gly Gly Gly Thr Lys Leu Glu Ile Lys Arg
            100                 105


<210> SEQ ID NO 51
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Gln Gln Ser Asp Ala Glu Leu Val Lys Pro Gly Thr
1               5                   10                  15

Ser Val Lys Ile Ser Cys Arg Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Asp Asp Ser Ala Val Tyr Phe Cys
                85                  90                  95

Lys Arg Ser Ile Thr Thr Pro Tyr Trp Gly Gln Gly Thr Thr Leu Thr
            100                 105                 110

Val Ser Ser
        115


<210> SEQ ID NO 52
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asn
            20                  25                  30

Val Ala Trp Tyr Gln Gln Lys Pro Gly Gln Ser Pro Lys Gln Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Tyr Thr Val Gln Ala
65                  70                  75                  80

Glu Asp Leu Ala Val Tyr Phe Cys Gln Gln Gly Tyr Ser Ser Pro Trp
```

```
                85                  90                  95

Thr Phe Gly Gly Gly Thr Lys Leu Lys
            100                 105


<210> SEQ ID NO 53
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Asp Trp Ile
        35                  40                  45

Gly Tyr Ile Ser Pro Gly Asn Gly Asp Ile Lys Tyr Asn Glu Lys Phe
    50                  55                  60

Lys Asp Lys Val Thr Leu Thr Ala Asp Lys Ser Ser Ser Thr Ala Cys
65                  70                  75                  80

Met His Leu Asn Ser Leu Thr Ser Glu Asp Ser Ala Val Tyr Phe Cys
                85                  90                  95

Lys Arg Ser Leu Leu Ala Leu Asp Tyr Trp Gly Gln Gly Thr Thr Leu
            100                 105                 110

Thr Val Ser Ser
        115


<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Asn
            20                  25                  30

Ile Ala Trp Tyr Gln Gln Lys Pro Gly Arg Ser Pro Lys Val Leu Ile
        35                  40                  45

Tyr Ser Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Ser Phe Pro Leu
                85                  90                  95

Thr Phe Gly Val Gly Thr Lys Leu Glu Leu Lys
            100                 105


<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 55

Gly Phe Ser Leu Ser Thr Ser Asn Met Gly
1 5 10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Gly Phe Ser Leu Ser Thr Phe Gly Met Gly
1 5 10

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Phe Ser Leu Thr Ser Tyr Gly
1 5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Gly Phe Ser Leu Ile Ser Tyr Gly
1 5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Ile Trp Trp His Asp Asp Lys
1 5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Ile Trp Trp Asp Asp Asp Lys
1 5

<210> SEQ ID NO 61

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Ile Trp Gly Asp Gly Ser Thr
1 5

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Ala Gln Val Pro Phe Tyr Tyr Gly Thr Ser Phe Asp Val
1 5 10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Ala Arg Ile Ala Tyr Tyr Tyr Gly Ser Glu Arg Asp Tyr
1 5 10

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Ala Arg Ala Phe Val Tyr
1 5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Thr Lys Gly Phe Thr Tyr
1 5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Thr Lys Gly Phe Ala Tyr
1 5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Thr Lys Gly Phe Val Tyr
1 5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Ala Lys Gly Gly Tyr Phe Asp Tyr
1 5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ser Ser Ile Ser Tyr
1 5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Ser Ser Val Ser Tyr
1 5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Gln Ser Ile Ser Asp Tyr
1 5

<210> SEQ ID NO 72
<211> LENGTH: 5
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 72

Ser Ser Ile Thr Tyr
1 5

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Asp Thr Ser
1

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Ser Thr Ser
1

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Tyr Ala Ser
1

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

His Gln Arg Ser Ser Tyr Thr
1 5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Gln Gln Trp Ser Ser Asn Pro Pro Met Leu Thr
1 5 10

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Gln Gln Trp Ser Ser Asn Leu Leu Thr
1 5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Gln Gln Arg Ser Ser Tyr Pro Trp Thr
1 5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Gln Asn Gly His Ser Phe Pro Leu Thr
1 5

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Gly Tyr Thr Phe Thr Asp His Ala Ile His Trp Val
1 5 10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gly Tyr Thr Phe Ser Asp His Ala Ile His Trp Val
1 5 10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gly Tyr Ile Phe Thr Asp His Ala Ile His Trp Val
1 5 10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Phe Ser Pro Gly Asn Asp Asp Ile Lys Tyr
1 5 10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Ile Ser Pro Gly Asn Gly Asp Ile Lys Tyr
1 5 10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Leu Ser Pro Gly Asn Asp Asp Ile Lys Tyr
1 5 10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Val Ser Pro Gly Asn Gly Asp Ile Lys Tyr
1 5 10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Ile Ser Pro Gly Asn Gly Asp Val Lys Tyr
1 5 10

<210> SEQ ID NO 89
<211> LENGTH: 10
<212> TYPE: PRT
<213> ORGANISM: Artificial Sequence <220> FEATURE:
<223> OTHER INFORMATION: Description of Artificial Sequence: Synthetic
peptide

<400> SEQUENCE: 89

Ile Ser Pro Gly Asn Asp Asp Ile Lys Tyr
1 5 10

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Ser Val Gly Tyr Ala Leu Asp Tyr
1 5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Lys Ile Ser Tyr Tyr Gly Ile
1 5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Lys Arg Ser Tyr Tyr Gly Asp
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Lys Arg Ser Ile Gly Gly Asp His
1 5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Gln Arg Gln Leu Gly Gln Gly Tyr
1 5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Lys Arg Ser Leu Ile Gly Asp Tyr
1 5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Lys Arg Ser Leu Ser Thr Pro Tyr
1 5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Lys Arg Ser Ile Thr Thr Pro Tyr
1 5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Glu Arg Ser Met Ile Gly Val Tyr
1 5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Lys Arg Ser Ile Thr Thr Ser Tyr
1 5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Glu Asn Val Val Thr Tyr
1 5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Glu Asp Ile Tyr Ser Asn
1 5

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Glu Asn Ile Tyr Ser His
1 5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Gln Asn Ile Asn Val Trp
1 5

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Gln Ser Leu Val His Ser Tyr Gly Asn Thr Tyr
1 5 10

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Gln Asn Val Gly Thr Ala
1 5

<210> SEQ ID NO 106
<211> LENGTH: 12
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 106

Gln Ser Leu Leu Asn Ser Gly Asn Gln Lys Ser Tyr
1 5 10

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Gln Ser Val Asn Asn Asn
1 5

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Gln Ser Leu Leu Asn Arg Gly Asn His Lys Asn Tyr
1 5 10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Gln Ser Leu Val Gln Ser Asn Gly Asn Thr Tyr
1 5 10

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Glu Asn Val Val Asn Tyr
1 5

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Gln Ser Leu Leu Asn Ser Gly Lys Thr Lys Asn Tyr
1 5 10

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Gln His Ile Asn Phe Trp
1 5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Glu Asn Val Val Ile Tyr
1 5

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Gln Ser Leu Leu Asn Ser Gly Asn Gln Lys Asn Tyr
1 5 10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Gly Ala Ser Asn Arg Tyr Thr
1 5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Lys Ala Thr Asn Leu Ala Asp
1 5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Gly Ala Thr Asn Leu Ala Asp
1 5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Lys Ala Ser Asn Leu His Thr
1 5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Lys Val Ser Asn Arg Phe Ser
1 5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Ser Ala Ser Asn Arg Tyr Thr
1 5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Trp Ala Ser Thr Arg Asp Ser
1 5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Tyr Ala Ser Asn Arg Tyr Thr
1 5

<210> SEQ ID NO 123
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Trp Ala Ser Thr Arg Glu Ser
1 5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Lys Val Ser Asn Arg Phe Cys
1 5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Gly Ala Ser Asn Arg Tyr Ser
1 5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Lys Val Ser Asn Leu His Thr
1 5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Gly Gln Gly Tyr Ser Tyr Pro Tyr Thr
1 5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Gln His Phe Trp Gly Thr Pro Phe Thr 1 5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Gln His Phe Trp Gly Ala Pro Phe Thr
1 5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Gln Gln Gly Gln Ser Tyr Pro Phe Thr
1 5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Ser Gln Asn Thr His Val Pro Tyr Thr
1 5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Gln Gln Tyr Ser Ser Tyr Arg Leu Thr
1 5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Gln Ser Asp Tyr Ser Tyr Pro Tyr Thr
1 5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Gln Gln Gly Tyr Ser Ser Pro Trp Thr
1 5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Gln Asn Asp Tyr Thr Tyr Pro Tyr Thr
1 5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Ser Gln Ser Thr His Ala Pro Leu Thr
1 5

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Gly Ser Lys Trp Ile Thr Ser Tyr Pro Tyr Thr
1 5 10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Gly Ala Arg Val Thr Ser Tyr Pro Tyr Thr
1 5 10

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Gln Gln Asp Gln Ser Tyr Pro Tyr Thr
1 5

<210> SEQ ID NO 140

<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Lys Asn Asp Tyr Ser Tyr Pro Tyr Thr
1 5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Gln Gln Asp Gln Ser Tyr Pro Tyr Met
1 5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Gln Asn Asp Tyr Ser Tyr Pro Tyr Thr
1 5

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Gly Tyr Thr Phe Thr Asp His Ala Ile His
1 5 10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Gly Tyr Ile Phe Thr Asp His Ala Ile His
1 5 10

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Tyr Ile Ser Pro Gly Asn Gly Asp Ile Lys Tyr Asn Glu Lys Phe Lys
1 5 10 15

Gly

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 146

Tyr Phe Ser Pro Gly Asn Asp Asp Ile Lys Tyr Asn Glu Lys Phe Arg
1 5 10 15

Gly

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Tyr Phe Ser Pro Gly Asn Asp Asp Ile Lys Tyr Asn Glu Lys Phe Lys
1 5 10 15

Val

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Tyr Ile Ser Pro Gly Asn Gly Asp Ile Lys Tyr Asn Glu Lys Phe Lys
1 5 10 15

Val

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Tyr Ile Ser Pro Gly Asn Gly Asp Ile Lys Tyr Asn Glu Lys Phe Lys
1 5 10 15

Asp

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Tyr Phe Ser Pro Gly Asn Asp Asp Phe Lys Tyr Asn Glu Lys Phe Lys
1 5 10 15

Gly

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Tyr Ile Ser Pro Gly Asn Asp Asp Ile Lys Tyr Asn Glu Lys Phe Lys
1 5 10 15

Gly

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Ser Ile Thr Thr Ser Tyr
1 5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Ser Leu Ser Thr Pro Tyr
1 5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Ser Tyr Tyr Gly Asp
1 5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Ser Ile Thr Thr Pro Tyr
1 5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Ser Leu Leu Ala Leu Asp Tyr
1 5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Ser Leu Asn Met Ala Tyr
1 5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Ser Tyr Tyr Gly His
1 5

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Lys Ala Ser Glu Asn Val Val Thr Tyr Val Ser
1 5 10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

His Ala Ser Gln His Ile Asn Phe Trp Leu Ser
1 5 10

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Lys Ser Ser Gln Ser Leu Leu Asn Arg Gly Asn His Lys Asn Tyr Leu
1 5 10 15

Thr

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Arg Ala Ser Glu Asn Ile Tyr Ser His Leu Ala
1 5 10

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 163

Lys Ser Ser Gln Ser Leu Leu Asn Ser Gly Lys Thr Lys Asn Tyr Leu
1 5 10 15

Thr

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 164

Lys Ala Ser Gln Ser Val Asn Asn Asn Val Ala
1 5 10

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Lys Ala Ser Gln Asp Val Gly Thr Asn Ile Ala
1 5 10

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Lys Ser Ser Gln Ser Leu Leu Tyr Ser Gly Asn Gln Lys Asn Tyr Leu
1 5 10 15

Ala

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Arg Ala Ser Glu Asn Ile Tyr Ser Asn Leu Ala
1 5 10

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Ser Ala Ser Thr Arg His Thr
1 5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Trp Ala Ser Ala Arg Glu Ser
1 5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 170

Ala Ala Thr Asn Leu Ala Asp
1 5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

Gln Gln Tyr Ser Ser Phe Pro Leu Thr
1 5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Gln Gln Tyr Tyr Ser Tyr Pro Leu Thr
1 5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Gln His Phe Trp Gly Thr Pro Tyr Thr
1 5

<210> SEQ ID NO 174
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 174 caggttactc tgaaagagtc tggccctggg atattgcagc cctcccagac cctcagtctg 60 acttgttctt tctctgggtt ttcactgagc acttctaata tgggtatagg ctggattcgt 120 cagccttcag ggaagggtct agagtggctg gcacacattt ggtggcatga tgataagtac 180 tataacccat ccctgaagag ccggctcaca atctccaagg atatctccaa caaccaggta 240 ttcctcaaga tcaccagtgt ggacactgca gatactgcca cgtactactg tgctcaagtc 300 ccgttttact acggaacctc gttcgatgtc tggggcacag ggaccacggt caccgtctcc 360 tca 363

<210> SEQ ID NO 175
<211> LENGTH: 322
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 175 gacattgtga tgactcagtc tccagccacc ctgtctgtga ctccaggaga tagagtctct 60 ctttcctgca gggccagcca gagtattagc gactacttac actggtatca acaaaaatca 120 catgagtctc caaggcttct catcaaatat gcttcccaat ccatctctgg gatcccctcc 180 aggttcagtg gcagtggatc agggtcagat ttcactctca gtatcaacag tgtggaacct 240 gaagatgttg gagtgtatta ctgtcaaaat ggtcacagct ttcctctcac gttcggtgct 300 gggaccaagc tggagctgaa ac 322

<210> SEQ ID NO 176
<211> LENGTH: 314
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 176 caaattgttc tcacccagtc tccagcaatc atgtctgcat ctccagggga gacggtcacc 60 atgacctgca gtgccagctc aagtataact tacatgcact ggtaccagca gaagccaggc 120 acctccccca aaagatggat ttatgacaca tccaaactgg cttctggagt ccctgctcgc 180 ttcagtggca gtgggtctgg gacctcttat tctctcacaa tcagcagcat ggaggctgaa 240 gatgctgcca cttattactg ccatcagcgg agtagttaca cgttcggagg ggggaccaag 300 ctggaaataa aacg 314

<210> SEQ ID NO 177
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 177 caggttactc tgaaagagtc tggccctggg atattgcagc cctcccagac cctcagtctg 60 acttgttctt tctctgggtt ttcactgagc acttttggta tgggtgtagg ctggattcgt 120 cagccttcag ggaagggtct ggagtggctg gcacacattt ggtgggatga tgataagtac 180 tataacccag ccctgaagag tcggctcaca atctccaagg atacctccaa aaaccaggta 240 ttcctcaaga tcgccaatgt ggacactgca gatactgcca catactactg tgctcgaata 300 gcctattact acggtagcga gagggactac tggggccaag gcaccactct cacagtctcc 360 tca 363

<210> SEQ ID NO 178
<211> LENGTH: 314
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 178 caaattgttc tcacccagtc tccagcaatc atgtctgcat ctccagggga gaaggtcacc 60 atgacctgca gtgccagctc aagtataagt tacatgcact ggtaccacca gaagccaggc 120 acctccccca aaagatggat ttatgacaca tccaaactgg cttctggagt ccctgctcgc 180 ttcagtggca gtgggtctgg gacctcttat tctctcacaa tcagcagcat ggaggctgaa 240 gatgctgcca cttattactg ccatcagcgg agtagttaca cgttcggagg ggggaccaag 300 ctggaaataa aacg 314

<210> SEQ ID NO 179
<211> LENGTH: 1047
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 179 atggacaggc ttacttcctc attcttgcta ctgattgtcc ctgcatatgt cctgtcccag 60 gttactctga aagagtctgg ccctgggata ttgcagccct cccagaccct cagtctgact 120 tgttctttct ctgggttttc actgagcact tctaatatgg gtataggctg gattcgtcag 180 ccttcaggga agggtctaga gtggctggca cacatttggt ggcatgatga taagtactat 240

```
aacccatccc tgaagagccg gctcacaatc tccaaggata tctccaacaa ccaggtattc    300

ctcaagatca ccagtgtgga cactgcagat actgccacgt actactgtgc tcaagtcccg    360

ttttactacg gaacctcgtt cgatgtctgg ggcacaggga ccacggtcac cgtctcctca    420

gccaaaacga cacccccatc tgtctatccg ctcgcccctg gatctgctgc ccaaactaac    480

tccatggtga ccctgggatg cctggtcaag ggctatttcc ctgagccagt gacagtgacc    540

tggaactctg gatccctgtc cagcggtgtg cacaccttcc cagctgtcct gcagtctgac    600

ctctacactc tgagcagctc agtgactgtc ccctccagca cctggcccag cgagaccgtc    660

acctgcaacg ttgcccaccc ggccagcagc accaaggtgg acaagacaat tgtgcccagg    720

gattgtggtt gtaagccttg catatgtaca gtcccagaag tatcatctgt cttcatcttc    780

cccccaaagc ccaaggatgt gctcaccatt actctgactc ctaaggtcac gtgtgttgtg    840

gtagacatca gccaggatga tcccgaggtc agttcagctg tttgtagatg atgtggaagt    900

gcacacagct caaaacaacc ccccgagagg acatttcaca acatttccgc tcatcagtga    960

atttcccatc tgcacaagac tgcttaatgg caagagttaa atgcaggtca aagggcagtt   1020

tcctgcccca tcaaaaactt ttcaaaa                                       1047
```

<210> SEQ ID NO 180
<211> LENGTH: 702
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 180

```
atggattttc aagtgcagat tttcagcttc ctgctaatca gtgcctcagt catactgtcc     60

agaggacaaa ttgttctcac ccagtctcca gcaatcatgt ctgcatctcc aggggagacg    120

gtcaccatga cctgcagtgc cagctcaagt ataacttaca tgcactggta ccagcagaag    180

ccaggcacct cccccaaaag atggatttat gacacatcca aactggcttc tggagtccct    240

gctcgcttca gtggcagtgg gtctgggacc tcttattctc tcacaatcag cagcatggag    300

gctgaagatg ctgccactta ttactgccat cagcggagta gttacacgtt cggagggggg    360

accaagctgg aaataaaacg ggctgatgct gcaccaactg tatccatctt cccaccatcc    420

agtgagcagt taacatctgg aggtgcctca gtcgtgtgct tcttgaacaa cttctacccc    480

aaagacatca atgtcaagtg gaagattgat ggcagtgaac gacaaaatgg cgtcctgaac    540

agttggactg atcaggacag caaagacagc acctacagca tgagcagcac cctcacgttg    600

accaaggacg agtatgaacg acataacagc tatacctgtg aggccactca caagacatca    660

acttcaccca ttgtcaagag cttcaacagg aatgagtgtt ag                       702
```

<210> SEQ ID NO 181
<211> LENGTH: 1252
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (919)..(919)
<223> OTHER INFORMATION: a, c, g, t or not present
<220> FEATURE:
<221> NAME/KEY: modified_base
<222> LOCATION: (984)..(984)
<223> OTHER INFORMATION: a, c, g, t or not present <220> FEATURE:
<221> NAME/KEY: modified_base
<222> LOCATION: (999)..(999)
<223> OTHER INFORMATION: a, c, g, t or not present
<220> FEATURE:
<221> NAME/KEY: modified_base
<222> LOCATION: (1011)..(1011)
<223> OTHER INFORMATION: a, c, g, t or not present
<220> FEATURE:
<221> NAME/KEY: modified_base
<222> LOCATION: (1057)..(1057)
<223> OTHER INFORMATION: a, c, g, t or not present
<220> FEATURE:
<221> NAME/KEY: modified_base
<222> LOCATION: (1100)..(1100)
<223> OTHER INFORMATION: a, c, g, t or not present
<220> FEATURE:
<221> NAME/KEY: modified_base
<222> LOCATION: (1201)..(1201)
<223> OTHER INFORMATION: a, c, g, t or not present

<400> SEQUENCE: 181 atggacaggc ttacttcctc attcctgtta ctgattgtcc ctgcatatgt cctgtcccag 60 gttactctga aagagtctgg ccctgggata ttgcagccct cccagaccct cagtctgact 120 tgttctttct ctgggttttc actgagcact tttggtatgg gtgtaggctg gattcgtcag 180 ccttcaggga agggtctgga gtggctggca cacatttggt gggatgatga taagtactat 240 aacccagccc tgaagagtcg gctcacaatc tccaaggata cctccaaaaa ccaggtattc 300 ctcaagatcg ccaatgtgga cactgcagat actgccacat actactgtgc tcgaatagcc 360 tattactacg gtagcgagag ggactactgg ggccaaggca ccactctcac agtctcctca 420 gccaaaacga cacccccatc tgtctatccg ctcgcccctg gatctgctgc ccaaactaac 480 tccatggtga ccctgggatg cctggtcaag ggctatttcc ctgagccagt gacagtgacc 540 tggaactctg gatccctgtc cagcggtgtg cacaccttcc cagctgtcct gcagtctgac 600 ctctacactc tgagcagctc agtgactgtc ccctccagca cctggcccag cgagaccgtc 660 acctgcaacg ttgcccaccc ggccagcagc accaaggtgg acaagaaaat tgtgcccagg 720 gattgtggtt gtaagccttg catatgtaca gtcccagaag tatcatctgt cttcatcttc 780 cccccaaagc ccaaggatgt gctcaccatt actctgactc ctaaggtcac gtgtgttgtg 840 gtagacatca gcaaggatga tcccgaggtc cagttcagct ggtttgtaga tgatgtggaa 900 gtgcacacag ctcagacgnc accccgggga gagcagtttc acagcacttt ccgctcagtc 960 agtgaacttc ccatcatgca ccangactgg gctcatggnc aggagttcaa ntgcaggtca 1020 cagtgcagct ttcctgcccc atcgagaaac atctccnaaa caaggcgacg aaagctcaca 1080 gggtacacat tccactcccn agagcaatgc cagataagtc atctgactgc tgatacaact 1140 cttctgaaaa tactgtgaat gcatggatgc caccacgaaa atcaaacctc gcccttggac 1200 natggcttat tttaccagct agtcaaaacc tgggggggaat ttcccgtctg tt 1252

<210> SEQ ID NO 182
<211> LENGTH: 705
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 182 atggttttca cacctcagat acttggactt atgctttttt ggatttcagc ctccagatgt 60 gacattgtga tgactcagtc tccagccacc ctgtctgtga ctccaggaga tagagtctct 120 ctttcctgca gggccagcca gagtattagc gactacttac actggtatca acaaaaatca 180 catgagtctc caaggcttct catcaaatat gcttcccaat ccatctctgg gatcccctcc 240 aggttcagtg gcagtggatc agggtcagat ttcactctca gtatcaacag tgtggaacct 300 gaagatgttg gagtgtatta ctgtcaaaat ggtcacagct ttcctctcac gttcggtgct 360 gggaccaagc tggaaataaa acgggctgat gctgcaccaa ctgtatccat cttcccacca 420 tccagtgagc agttaacatc tggaggtgcc tcagtcgtgt gcttcttgaa caacttctac 480 cccaaagaca tcaatgtcaa gtggaagatt gatggcagtg aacgacaaaa tggcgtcctg 540 aacagttgga ctgatcagga cagcaaagac agcacctaca gcatgagcag caccctcacg 600 ttgaccaagg acgagtatga acgacataac agctatacct gtgaggccac tcacaagaca 660 tcaacttcac ccattgtcaa gagcttcaac aggaatgagt gttag 705

<210> SEQ ID NO 183
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 183 caggtgcagc tgaaggagtc aggacctggc ctggtggcgc cctcacagag cctgtccatc 60 acatgcactg tctcagggtt ctcattaacc agctatggtg taagctgggt tcgccagcct 120 ccaggaaagg gtctggagtg gctgggagta atatggggtg acggaagcac aaattatcat 180 tcatctctca tatccagact gagcatcagc aaggataact ccaagagcca agttttctta 240 aaactgaaca gtctgcaaac tgatgacaca gccacgtact actgtgccag agcctttgtt 300 tactggggcc aagggactct ggtcactgtc tctgca 336

<210> SEQ ID NO 184
<211> LENGTH: 325
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 184 caaattgttc tcacccagtc tccagcaatc atgtctgcat ctccagggga gaaggtcacc 60 atgacctgca gtgccagctc aagtgtaagt tacatacact ggtaccagca gaagtcaggc 120 acctccccca aaagatggat ttatgacaca tccaaactgg cttctggagt ccctgctcgc 180 ttcagtggca gtgggtctgg gacctcttac tctctcacaa tcagcagcat ggaggctgaa 240 gatgctgcca cttattactg ccagcagtgg agtagtaacc cacccatgct cacgttcggt 300 gctgggacca agctggagct gaaac 325

<210> SEQ ID NO 185
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 185 caggtgcagc tgaaggagtc aggacctggc ctggtggcgc cctcacagag cctgtccatc 60 acatgcactg tctcagggtt ctcattaacc agctatggtg taagctgggt tcgccagcct 120 ccaggaaagg gtctggagtg gctgggagta atatggggtg acgggagcac aaattatcat 180 tcagctctca tatccagact gatcatcagc aaggataact ccaagagcca agttttctta 240 aaactgaaca gtctgcaaac tgatgacaca gccacctact actgtaccaa aggctttact 300 tactggggcc aggggactct ggtcactgtc tctgca 336

<210> SEQ ID NO 186
<211> LENGTH: 319
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 186 caaattgttc tcacccagtc tccagcaatc atgtctgcat ctccagggga gaaggtcacc 60 atgacctgca gtgccagctc aagtgtaagt tacatgcact ggtaccagca gaagtcaggc 120 acctccccca aaagatggat ttttgacaca tccaaactgg cttctggagt ccctgctcgc 180 ttcagtggca gtgggtctgg gacctcttac tctctcacaa tcagcagcat ggaggctgaa 240 gatgctgcca cttattactg ccagcagtgg agtagtaacc tgctcacgtt cggtgctggg 300 accaagctgg agctgaaac 319

<210> SEQ ID NO 187
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 187 caggtgcagc tgcaggagtc aggacctggc ctggtggcgc cctcacagag cctgtccatc 60 acatgcactg tctcagggtt ctcattaatc agctatggtg taaactgggt tcgccagcct 120 ccaggaaagg gtctggagtg gctgggagtg atatggggtg acgggagcac aaattatcag 180 tcagctctca tatccagact gatcatcagc aaggataact ccaagagcca agttttctta 240 aaactgaaca gtctgcaaac tgatgacaca gccacgtact actgtaccaa aggctttgct 300 tactggggcc aagggactct ggtcactgtc tctgca 336

<210> SEQ ID NO 188
<211> LENGTH: 319
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 188 caaattgttc tcacccagtc tccagcaatc atgtctgcat ctccagggga gaaggtcacc 60 atgacctgca gtgccagctc aagtgtaagt tacatgcact ggttccagca gaagtcaggc 120 acctccccca aaagatggat ttatgacaca tccaaactgg cttctggagt ccctgctcgc 180 ttcagtggca gtgggtctgg gacctcttac tctctcacaa tcagcagcat ggaggctgaa 240 gatgctgcca cttattactg ccagcagtgg agtagtaacc tgctcacgtt cggtgctggg 300 accaagctgg agctgaaac 319

<210> SEQ ID NO 189
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 189 caggtgcagc tgaaggagtc aggacctggc ctggtggcgc cctcacagaa cctgtccatc 60 acatgcactg tctcagggtt ctcattaacc agttatggtg taaactgggt tcgccagcct 120 ccaggaaagg gtctggagtg gctgggagta atatggggtg acgggagcac aaattatcat 180 tcagctctca tttccagact gatcatcagc aaggaaaact ccaagagcca agttttctta 240 aaactgaaca gtctgcaaac taatgacaca gccacgtatt actgtaccaa aggctttgtt 300 tactggggcc aagggactct ggtcactgtc tctgca 336

<210> SEQ ID NO 190
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 190 caggtgcagc tgaaggagtc aggacctggc ctggtggcgc cctcacagag cctgtccatc 60 acatgcactg tctcagggtt ctcattaacc agctatggtg taagctgggt tcgccagcct 120 ccaggaaagg gtctggagtg gctgggagta atatggggtg acgggagcac aaattatcat 180 tcagctctca tatccagact gagcatcagc aaggataact ccaagagcca agttttctta 240 aaactgaaca gtctgcaaac tgatgacaca gccacgtact actgtgccaa agggggctac 300 tttgactact ggggccaagg caccactctc acagtctcct ca 342

<210> SEQ ID NO 191
<211> LENGTH: 319
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 191 caaattgttc tcacccagtc tccagcagtc atgtctgcat ctccagggga gaaggtcgcc 60 ataacctgca gtgccagctc aagtgtaagt tacatgcact ggttccagca gaagccaggc 120 acttctccca aactctggat ttatagcaca tccaacctgg cttctggagt ccctgctcgc 180 ttcagtggca gtggatctgg gacctcttac tctctcacaa tcagccgaat ggaggctgaa 240 gatgctgcca cttattactg ccagcaaagg agtagttacc cgtggacgtt cggtggaggc 300 accaagctgg aaatcaaac 319

<210> SEQ ID NO 192
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 192 caggttcagt tgctgcagta tgacgctgag ttggtgaaac ctgggggtc agtgaagata 60 tcgtgcaagg cctctggcta caccttcact gaccatgcta ttcactgggt gaagcagaag 120 cctgaacagg gcctggaatg gattggatat ttttctcccg gaaatgatga tattaagtac 180 agtgagaagt tcaagggcaa ggccacactg actgcagaca agtcctccag cactgcctac 240 atgcagctca acagcctgac atctgaggat tctgcagtgt atttctgtaa aagatccatt 300 actacgcctt actggggcca agggactctg gtcactgtct ctgca 345

<210> SEQ ID NO 193
<211> LENGTH: 319
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 193 gacatccaga tgaaccagtc tccatccagt ctgtctgcat cccttggaga cacaattacc 60 atcacttgcc atgccagtca gaacattaat gtttggttaa gctggtacca gcagaaacca 120 ggaaatattc ctaaactatt gatctataag gtttccaact tgcacacagg cgtcccatca 180 aggtttagtg gcagtggatc tggaacaggt ttcacattaa ccatcagcag cctgcagcct 240 gaagacattg ccacttacta ctgtcaacag gatcaaagtt atccgtacac gttcggaggg 300 gggaccaagc tgaaaaaaa 319

<210> SEQ ID NO 194
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 194 caggttcagc tgcagcagtc tgacgctgag ttggtgaaac ctggggcttc agtgaagata 60 tcctgcaagg cctctggcta caccttcact gaccatgcta ttcactgggt gaagcagaag 120 cctgaacagg gcctggaatg gattggatat atttctcccg gaaatgatga tattaagtac 180 aatgagaagt tcaagggcaa ggccacactg actgcagaca aatcctccag cactgcctac 240 atgcagctca acagcctgac atctgaggat tctgcagtgt atttctgtaa aagatccatt 300 actacgtctt actggggcca agggactctg gtcactgtct ctgca 345

<210> SEQ ID NO 195
<211> LENGTH: 323
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 195 aacattgtaa tgacccaatc tcccaaatcc atgtccatgt cagtaggaga gagggtcacc 60 ttgacctgca aggccagtga gaatgtggtt atttatgttt cctggtatca acagaaacca 120 gagcagtctc ctaaactgct gatatacggg gcatccaacc ggtacactgg ggtccccgat 180 cgcttcacag gcagtggatc tgcaacagat ttcactctga ccatcagcag tgtgcaggct 240 gaagaccttg cagattatca ctgtggacag ggttacagct atccgtacac gttcggaggg 300 gggaccaagc tggaaataaa acg 323

<210> SEQ ID NO 196
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196 caggttcagt tgcagcagtc tgacgctgag ttggtgaaac ctggggcttc agtgaagata 60 tcctgcaagg cttctggcta caccttcact gaccatgcca ttcattgggt gaagcagaag 120 cctgaacagg gcctggaatg gattggatat gtttctcccg gaaatggtga tattaagtac 180 aatgagaagt tcaagggcaa ggccacactg actgcagaca aatcctccag cactgcctac 240 atgcagctca acagcctgac atcggaggat tctgcagtgt atttctgtaa aagatcttta 300 attggagact attggggcca aggcaccact ctcacagtct cctca 345

<210> SEQ ID NO 197
<211> LENGTH: 322
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 197 gacattgtga tgacccagtc tcaaaaattc atgtcctcat cagtaggaga cagggtcacc 60 atcacctgca aggccagtca gaatgtgggt actgctgtag cctggtatca acagaaacca 120 ggacaatctc ctaaatttct gatttactcg gcatccaatc ggtacactgg agtccctgat 180 cgcttcacag gcagtggatc tgggacagat ttcactctca cgatcagcaa tatgcagtct 240 gaagacctgg cagattattt ctgccagcaa tatagcagct atcgtctgac gttcggtgga 300 ggcaccaagc tggaaatcaa ac 322

<210> SEQ ID NO 198
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 198 caggttcagc tgcagcagtc tgacgctgaa ttggtgaaac ctggggcttc agtgaagata 60 tcctgcaagg cttctggcta caccttcact gaccatgcta ttcactgggt gaagcagaag 120 cctgaacagg gcctggaatg gattggatat ctttctcccg gaaatgatga tattaagtac 180 agtgagaagt tcaaggacaa ggccacactg actgcagaca aatcctccag cactgcctac 240 atgcagctca acagcctgac atctgaggat tctgcagtgt atttctgtaa aagatccata 300 ggggggggacc actggggcca aggcaccact ctcacagtct cctca 345

<210> SEQ ID NO 199
<211> LENGTH: 323
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 199 gacatccaga tgaaccagtc tccatccagt ctgtctgcat cccttggaga cacaattacc 60 atcacttgcc atgccagtca gaacattaat gtttggttaa actggtacca gcagaaacca 120 ggaaatattc ctaaactatt gatctataag gcttccaact tgcacacagg cgtcccatca 180 aggtttagtg gcagtggatc tggaacaggt ttcacattaa ccatcggcag cctgcagcct 240 gaagacattg ccacttacta ctgtcaacag ggtcaaagtt atccgttcac gttcggaggg 300 gggaccaagc tggaaataaa acg 323

<210> SEQ ID NO 200
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 200 caggttcagc tgcagcagtc tgacgctgag ttggtgaaac ctggggcttc agtgaagata 60 tcctgcaagg cttctggcta caccttcact gaccatgcta ttcactgggt gaaacagaag 120 cctgaacagg gcctggaatg gattggatat atttctcccg gaaatggtga tattaagtat 180 aatgagaagt tcaagggcaa ggccacactg actgcagaca aatcctccag cactgcctac 240 atgcagctca acagcctgac atctgaggat tctgcagtgt atttctgtca aagacaactg 300 ggacaaggct actggggcca aggcaccact ctcacagtct cctca 345

<210> SEQ ID NO 201
<211> LENGTH: 338
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 201 gatgttgtga tgacccaaac tccactctcc ctgcctgtca gtcttggaga tcaagcctcc 60 atctcttgca gatctagtca gagccttgta cacagttatg gaaacaccta tttacattgg 120 tacctgcaga agccaggcca gtctccaaag ctcctgattt acaaagtttc caaccgattt 180 tctggggtcc cagacaggtt cagtggcagt ggatcaggga cagatttcac actcaagatc 240 agcagagtgg aggctgagga tctgggagtt tatttctgct ctcaaaatac acatgttccg 300 tacacgttcg gagggggggac caagctggaa ataaaacg 338

<210> SEQ ID NO 202
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 202 caggttcagc tgcagcagtc tgacgctgag ttggggaaac ctggggcttc agtgaagata 60 tcctgcaagg cttctggcta caccttcagt gaccatgcta ttcactgggt gaagcagaag 120 cctgaacagg gcctggaatg gattggatat atctctcccg gaaacgatga tattaagtac 180 aatgagaagt tcaagggcaa ggccacactg actgcagaca aatcctccag cactgcctac 240 atgcagctca acagcctgac atctgaggat tctgcagtgt atttctgtga aagatcgatg 300 attggggttt actggggcca agggactctg gtcactgtct ctgca 345

<210> SEQ ID NO 203
<211> LENGTH: 337
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203 gatgttgtga tgacccaaac tccactctcc ctgactgtca gtcttggcga tcaagcctcc 60 atctcttgca gatttagtca gagccttgta caaagtaatg gaaataccta tttacagtgg 120 tatctgcaga agccaggcca gtctccaaag ctcctgattt acaaagtctc caaccgattt 180 tgtggggtcc cagacaggtt cagtggcagt ggatcaggga cagatttcac actcaagatc 240 agcagagtgg aggctgagga tctgggagtt tatttctgct ctcaaagtac acatgctccg 300 ctcacgttcg gtgctgggac caagctggag ctgaaac 337

<210> SEQ ID NO 204
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 204 caggttcagc tgcagcagtc tgacgctgag ttggtgaaac ctggggcttc agtgaagata 60 tcctgcaaga cttctggcta caccttcact gaccatgcaa ttcactgggt gaagcagaag 120 cctgaacagg gcctggaatg gattggatat atttctcccg gaaatggtga tattaagtac 180 aatgagaagt tcaagggcaa ggccaccctg actgcagaca aatcctccag cactgcctat 240 atgcagctca gcagcctgac acctgaggat tctgcagtgt atttctgtaa aatatcttac 300 tacggtattt ggggccaagg caccactctc acagtctcct ca 342

<210> SEQ ID NO 205
<211> LENGTH: 322
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205 gacatccaga tgactcagtc tccagcctcc ctatctgtat ctgtgggaga gtctgtcacc 60 atcacatgtc gactaagtga agatatttac agtaatttag catggtttca gcagagaccg 120 ggaaaatctc ctcagctcct ggtttataaa gcaacaaact tagcagacgg tgtgccatca 180 aggttcagtg gcagtggatc aggcacacag tattccctca agatcaacag cctgcagtct 240 gaagattttg ggacttatta ctgtcaacat ttttggggta ctccattcac gttcggctcg 300 gggaccaagg tggaaataaa ac 322

<210> SEQ ID NO 206
<211> LENGTH: 342

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206 caggttcagc tgcagcagtc tgacgctgag ttggtgaaac ctggggcttc agtgaagata 60 tcctgcaagg cttctggcta caccttcact gaccatgcta ttcactgggt gaagcagaag 120 cctgaacagg gcctggaatg gattggatat ttttctcccg gaaatgatga tattaagtat 180 aatgagaagt tcaaggtcaa ggccacactg actgcagaca aatcctccag cactgcctac 240 atgcaactca ccagcctgac atctgaagat tctgcagtgt atttctgtaa aagatcttac 300 tacggtgatt ggggccaagg caccactctc acagtctcct ca 342

<210> SEQ ID NO 207
<211> LENGTH: 322
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207 gacatccaga tgactcagtc tccagcctcc ctatctgttt ctgtgggaga aactgtcacc 60 atcacatgtc gagcaagtga gaatatttac agtcatttag catggtatca acagaaacag 120 ggaaaatctc ctcaactcct ggtctatggt gcaactaact tagcagatgg tgtgccatca 180 aggttcagtg gcagtggatc aggcacacag ttttccctca agatccacag cctgcagtct 240 gaagattttg ggagttatta ctgtcaacat ttttggggtg ctccattcac gttcggctcg 300 gggacaaagt tggaaataaa ac 322

<210> SEQ ID NO 208
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 208 caaattcagc tgcagcagtc tgacgctgag ttggtgaaac ctgggacttc agtgaagatg 60 tcctgcaagg cttctggcta caccttcact gaccatgcta ttcactgggt gaagcagaag 120 cctgaacagg gcctggaatg gattggatat ttttctcccg gaaatgatga tattaagtat 180 aatgtgaagt tcaagggcaa ggccacactg actgcagaca aatcctccag cactgcctac 240 atgcagctca acagcctgac atctgaagat tctgcagtgt atttctgttc ggtgggatac 300 gcccttgact actggggcct aggcaccact ctcacagtct cctca 345

<210> SEQ ID NO 209
<211> LENGTH: 323
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 209 aacattgtaa tgacccaatc tcccaaatcc atgtccatgt cagtaggaga gagggtcacc 60

```
ttgacctgca aggccagtga gaatgtggtt acttatgttt cctggtatca acagaaacca    120

gagcagtctc ctaaactgct gatatacggg gcatccaacc ggtacactgg ggtccccgat    180

cgcttcacag gcagtggatc tgcaacagat ttcactctga ccatcagcag tgtgcaggct    240

gaagaccttg cagattatca ctgtggacag ggttacagct atccgtacac gttcggaggg    300

gggaccaagc tggaaataaa acg                                            323
```

<210> SEQ ID NO 210
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 210

```
caggttcagc tgcaacagtc tgacgctgag ttggtgaaac ctgggactac agtgaagata     60

tcctgcaagg cttctggcta cactttcact gaccatgcta ttcactgggt gaaggagaag    120

cctgaacagg gcctggaatg gatcggatat atttctcccg gaaatgatga tattaagtac    180

agtgagaagt tcaagggcaa ggccacactg actgcagaca aatcctccag cactgcttac    240

atgcagctca acagcctgac atctgatgat tctgcagtgt atttctgtaa aagatcgctt    300

agtacgcctt actggggcca agggactctg gtcactgtct ctgca                    345
```

<210> SEQ ID NO 211
<211> LENGTH: 477
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 211

```
tttttaatac gactccctat agggcaagca gtggtatcaa tgcagattac aagggggaaa     60

ggcatcagac cagcatgggc atcaaggtgg aatcacagac tctggtcttc atatccatac    120

tgtttgggtt atatggagct gatgggaaca cattaatgac ccaatctccc acatccatgt    180

acatgtcagt aggagagagg gtcaccttga cttgcaaggc cagtgagaat gagattaatt    240

atgtttcctg gtatcaacag aaaccagagc agtctcctaa actgttgata tacggggcat    300

ccaaccggta ctctggggtc cccgatcgct tcacaggcag tggatctgca acagatttca    360

ctctgaccat cagcagtgtg caggctgaag accttgcaga ttatccctgt ggagcaaggg    420

attaactagc tatccgtaca cgttcggagg ggggaccaag ctggaaataa aacgggc       477
```

<210> SEQ ID NO 212
<211> LENGTH: 341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 212

```
gacattgtga tgacacagtc tccatcctcc ctgactgtga cagcaggaga gaaggtcact     60

atgagctgca ggtccagtca gagtctgtta aacagtggaa atcaaaagaa ctacttgacc    120

tggtaccagc agaaaccagg gcagcctcct aaactgttga tctactgggc atccactagg    180

gaatctgggg tccctgatcg cttcacaggc agtggatctg gaacagattt cactctcacc    240
```

atcagcagtg tgcaggctga agacctggca gtttattact gtcagaatga ttatagttat 300 ccgtacacgt tcggaggggg gaccaagctg gaaataaaac g 341

<210> SEQ ID NO 213
<211> LENGTH: 343
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 213 caggttcagc tgcagcagtc tgacgctgag ttggtgaaac ctggggcttc agtgaagata 60 tcctgcaagg cttctggcta caccttcact gaccatgcta ttcactgggt gatgcagatg 120 cctgaacagg gcctggaatg gattggatat atttctcccg gaaatggtga tgttaagtac 180 agtgagaggt tcaagggcag ggccacactg actgcagaca aatcctccag ctctgcctac 240 atgcagctca acagcctgac atctgaggat tctgcagttt atttctgtaa aagatcgctt 300 agtacgcctt actggggcca agggactctg gtcactgtct ctg 343

<210> SEQ ID NO 214
<211> LENGTH: 341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 214 gacattgtga tgacacagtc tccatcctcc ctgactgtga cagcaggaga gagggtcact 60 atgagctgca agtccagtca gagtctgtta aacagtggaa atcaaaagag ctacttgacc 120 tggtaccagc agaaaccagg gcagcctcct aaactgttga tctcctgggc atccactagg 180 gattctgggg tccctgatcg cttcacaggc agtggatctg gaacagattt cactctcacc 240 atcagcagtg tgcaggctga agacctggca gtttattact gtcagagtga ttatagttat 300 ccgtacacgt tcggaggggg gaccaagctg gaaataaaac g 341

<210> SEQ ID NO 215
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (26)..(26)
<223> OTHER INFORMATION: a, c, g, t or not present
<220> FEATURE:
<221> NAME/KEY: modified_base
<222> LOCATION: (332)..(332)
<223> OTHER INFORMATION: a, c, g, t or not present

<400> SEQUENCE: 215 caggttcagc tgcagcagtc tgacgntgag ttggtgaaac cgggggcttc agtgaagata 60 tcctgtaagg cttctggcta caccttcact gaccatgcta ttcactgggt gaagcagaag 120 cctgaacagg gcctggaatg gattggatat ttttctcccg gaaatgatga tattaagtac 180 aatgagaagt ttaggggcaa ggccacactg actgcagaca aatcctccag cactgcctac 240 atgcagctca acagcctgtc atctgatgat tctgcagtgt atttctgtaa aagatcgctt 300 agtacgcctt actggggcca agggactctg gncactgtct ctgca 345

<210> SEQ ID NO 216
<211> LENGTH: 341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 216 gacattgtga tgacacagtc tccatcctcc ctgactgtga cagcaggaga gaaagtcact 60 atgagctgca agtccagtca gagtctgtta aaccgtggaa atcataagaa ctacttgacc 120 tggtaccggc agaaaccagg gctgcctcct aaactgttga tttactgggc atccactagg 180 gaatctgggg tccctgatcg cttcacaggc agtggatctg gaacagattt cgctctcacc 240 atcagcagtg ttcaggctga agacctggca gtttattact gtcagaatga ttatacttat 300 ccgtacacgt tcggaggggg gaccaagctg gagataaaac g 341

<210> SEQ ID NO 217
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 217 caggttcagc tgcagcagtc tgacgctgag ttggtgaaac ctggggcttc aatgaagatt 60 tcctgcaagg cttctggcta caccttcact gaccatgcta ttcactgggt gaagcagaag 120 cctgaacagg gcctggaatg gattggatat atttctcccg gaaatggtga tattaagtac 180 aatgagaagt tcaaggtcaa ggccacactg actgcagaca aatcctccag cactgcctac 240 atgcagctca acagcctgac atctgaggat tctgcagtgt atttctgtaa aagatcgatt 300 actacgcctt actggggcca agggactctg gtcactgtct ctgca 345

<210> SEQ ID NO 218
<211> LENGTH: 341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 218 gacattgtga tgacacagtc tccatcctcc ctgactgtga cagcaggaga gaaggtcact 60 atgagctgca agtccagtca gagtctgtta aacagtggaa aaacaaagaa ctacttgacg 120 tggtaccagc agaaaccagg gcagcctcct aaactgttga tctactgggc atccactagg 180 gaatctgggg tccctgatcg cttcacaggc agtggatctg gaacagattt cactctcacc 240 atcagcagtg tgcaggctga agacctggca gtttattact gtaagaatga ttatagttat 300 ccgtacacgt tcggaggggg gaccaagctg gaaataaaac g 341

<210> SEQ ID NO 219
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 219 caggttcagc tgcagcagtc tgacgctgaa ttggtgaagc ctggggcttc agtgaagata 60 tcctgcaaga cttctggcta caccttcact gaccatgcta ttcactgggt gaagcagaag 120 cctgaacagg gcctggaatg gattggatat atctctcccg gaaatgatga tattaagtac 180 actgagaagt tcaagggcaa ggtcacactg actgcagaca aatcctccag cactgcctac 240 atgcagctca acagcctgac atctgaggat tctgcagtct atttctgtaa aagatcgatt 300 actacgcctt actggggcca agggactctg gtcactgtct ctgca 345

<210> SEQ ID NO 220
<211> LENGTH: 480
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (153)..(153)
<223> OTHER INFORMATION: a, c, g, t or not present
<220> FEATURE:
<221> NAME/KEY: modified_base
<222> LOCATION: (285)..(286)
<223> OTHER INFORMATION: a, c, g, t or not present
<220> FEATURE:
<221> NAME/KEY: modified_base
<222> LOCATION: (289)..(289)
<223> OTHER INFORMATION: a, c, g, t or not present
<220> FEATURE:
<221> NAME/KEY: modified_base
<222> LOCATION: (297)..(298)
<223> OTHER INFORMATION: a, c, g, t or not present
<220> FEATURE:
<221> NAME/KEY: modified_base
<222> LOCATION: (332)..(332)
<223> OTHER INFORMATION: a, c, g, t or not present
<220> FEATURE:
<221> NAME/KEY: modified_base
<222> LOCATION: (405)..(405)
<223> OTHER INFORMATION: a, c, g, t or not present
<220> FEATURE:
<221> NAME/KEY: modified_base
<222> LOCATION: (412)..(412)
<223> OTHER INFORMATION: a, c, g, t or not present
<220> FEATURE:
<221> NAME/KEY: modified_base
<222> LOCATION: (429)..(429)
<223> OTHER INFORMATION: a, c, g, t or not present

<400> SEQUENCE: 220 tttttatacg ccactttcta atacgcctca ctatagggca agcagtggta tcaacgcaga 60 ttacaaaggg gaaaggaatc agaccgactc gcgcatcaag atggaatcac agactctggt 120 cttcatatcc agtacgctcg gggactatgg agnggaacag tacattttaa tgacccaatg 180 tcccaaaggc aagaacatgt cagtaggaga gagggtcact cagagtgcaa ggccaggaga 240 aatcaaaaca cttatgtttc ctggtatcaa cagaaaccag agcannctnt aaaatgnnga 300 ttacggggca tccaaccggg aatctggggt cnccgatcgc ttcacaggca gtggatctgg 360 aacagatttc actctcacca tcagcagtgt gcaggctgaa gaccnggcag tnttcactgt 420 ggacagggnt acagttatcc gtacacgttc ggagggggga ccaagctgaa aaaaacgggc 480

<210> SEQ ID NO 221
<211> LENGTH: 345
<212> TYPE: DNA
<213> ORGANISM: Artificial Sequence <220> FEATURE:
<223> OTHER INFORMATION: Description of Artificial Sequence: Synthetic
polynucleotide

<400> SEQUENCE: 221 caggttcagc tgcagcagtc tgacgctgag ttggtgaaac ctggggcttc agtgaagata 60 tcctgcaagg cttctggcta caccttcact gaccatgcta ttcactgggt gaagcagaag 120 cctgaacagg gcctggaatg gattggatat atttctcccg gaaatggtga tattaagtac 180 gatgagaagt ttaagggcaa ggccacactg actgcagaca aatcctcctc cactgcctac 240 atgcagctca acagcctgac atctgaagat tctgcagtgt atttctgtaa aagatcgatt 300 actacctctt actggggcca agggactctg gtcactgtct ctgca 345

<210> SEQ ID NO 222
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 222 caggttcagc tgcagcagtc tgacgctgag ttggtgaaac ctggggcttc agtgaagata 60 tcctgcaagg cttctggcta caccttcact gaccatgcta ttcactgggt gaagcagaag 120 cctgaacagg gcctggaatg gattggatat atttctcccg gaaatgatga tattaagtac 180 aatgagaagt tcaagggcaa ggccacactg actgcagaca agtcctccag cactgcctac 240 atgcagctca acagcctgac atctgaggat tctgcagtgt ttttctgtaa aagatcgatt 300 actacctctt actggggcca agggactctg gtcactgtct ctgca 345

<210> SEQ ID NO 223
<211> LENGTH: 483
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (3)..(3)
<223> OTHER INFORMATION: a, c, g, t or not present
<220> FEATURE:
<221> NAME/KEY: modified_base
<222> LOCATION: (137)..(137)
<223> OTHER INFORMATION: a, c, g, t or not present
<220> FEATURE:
<221> NAME/KEY: modified_base
<222> LOCATION: (193)..(193)
<223> OTHER INFORMATION: a, c, g, t or not present

<400> SEQUENCE: 223 ttnataggac tcaatatagg gcaagcagtg gtattaacgc cgagtacatg gggagggcaa 60 gggcagaaag tcactttcag tgaggataca ccatcagcat gagggtcctt gttgagctcc 120 tgggggggct ggtgttntgc tttttaggtg tgagatgtga catccagatg aaccagtctc 180 catccagtct gtntgcatcc tttggagaca caattaccat catttgccat tccagtcaga 240 acattaatgt ttggttaaga tggtaccagc agaaaccagg aaatattcct aaaatattga 300 tatataaggg ttccaacttg tacacaggcg tcccatcaag gtttagtggc agtggatttg 360 gaacaggttt cacattaacc atcagcagcg tgcagcggga agacattgcc acttactact 420 gtcaacagga tcaaagttat ccgtacacgt tcggaggggg gaccaagctg aaataaaacg 480 ggc 483

<210> SEQ ID NO 224
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 224 caggttcagc tgcagcagtc tgacgccgag ttggtgaaac ctggggcttc agtgaagata 60 tcctgcaagg cttctggcta catcttcact gaccatgcta ttcactgggt gaagcagaag 120 cctgaacagg gcctggaatg gattggatat atttctcccg gaaatggtga tattaagtac 180 aatgagaagt tcaagggcaa ggccacactg actgcagaca aatcctccag cactgcctac 240 atgcatctca acagcctgac atctgaggat tctgcagtgt atttctgtaa aagatcgatt 300 actacctctt actggggcca agggactctg gtcactgtct ctgca 345

<210> SEQ ID NO 225
<211> LENGTH: 323
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 225 gacatccaga tgaaccagtc cccatccagt ctgtctgcat cccttggaga cacaattacc 60 atcacttgcc atgccagtca gcacattaat ttttggttaa gctggtacca gcagaaacca 120 ggaaatattc ctaaactctt gatctataag gcttccaact tgcacacagg cgtcccatca 180 aggtttagtg gcagtggatc tggaacaggt ttcacattaa ccatcagcag cctgctgcct 240 gaagacgttg ccacttacta ctgtcaacag gatcaaagtt atccgtatat gttcggaggg 300 gggaccaagc tggaaataaa acg 323

<210> SEQ ID NO 226
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 226 caggttcagc tgcagcagtc tgacgctgag ttggtgaaac ctggggcttc agtgaagata 60 tcctgcaagg cttctggcta caccttcact gaccatgcta ttcactgggt gaagcagaag 120 cctgaacagg gcctggaatg gattggatat atttctcccg gaaatgatga tattaagtac 180 aatgagaagt ttaagggcaa ggccacactg actgcagaca aatcctccag cactgcctac 240 atgctgctca acagcctgac atctgaggat tctgcagtgt atttctgtaa aagatcgatt 300 actacctctt actggggcca agggactctg gtcactgtct ctgca 345

<210> SEQ ID NO 227
<211> LENGTH: 323
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 227 aacattgtaa tgacccaatc tcccaaatcc atgtccatgt cagtaggaga gagggtcacc 60 ttgacctgca aggccagtga gaatgtggtt acttatgttt cctggtatca acagaaacca 120 gagcagtctc ctaaactgct gatatacggg gcatccaacc ggtacactgg ggtccccgat 180 cgcttcacag gcagtggatc tgcaacagat ttcactttga ccatcagcag tgtgcaggct 240 gaagaccttg cagattatca ctgtggacag ggttacagct atccgtacac gttcggaggg 300 gggaccaagc tggaaataaa acg 323

<210> SEQ ID NO 228
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 228 caggttcaac tgcagcagtc tgacgctgag ttggtgaaac ctggggcttc agtgaagata 60 tcctgcaagg cttctggcta caccttcact gaccatgcta ttcactgggt gaagcagaag 120 cctgaacagg gcctggaatg gattggatat atttctcccg gaaatggtga tattaagtac 180 aatgagaagt tcaagggtaa ggccacactg actgcagaca cttcctccac cactgcctac 240 atgcagctca acagcctgac atctgaggat tctgcaatgt atttctgtaa aagatccatt 300 actacgtctt actggggcca agggactctg gtcactgtct ctgca 345

<210> SEQ ID NO 229
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 229 caggttcagc tgcagcagtc tgacgctgag ttggtgaaac ctggggcttc agtgaagata 60 tcctgcaagg cttctggcta catcttcact gaccatgcaa ttcactgggt gaagcagaag 120 cctgaacagg gcctggaatg gattggatat atttctcccg gaaatggtga tattaagtac 180 attgagaagt tcaggggcaa ggccacactg actgcagaca aatcctccag cactgcctac 240 atgcagctca acagcctgac atctgaggat tctgcagtgt atttctgtaa aagatcgctt 300 agtacgcctt actggggcca agggactctg gtcactgtct ctgca 345

<210> SEQ ID NO 230
<211> LENGTH: 329
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 230 aacattttaa tgacccaatc tcccaaatcc atgtccatgt cagtaggaga gagggtcacc 60 ttgacctgca aggccagtga gaatgtggtt aattatgttt cctggtatca acagaaacca 120 gagcagtctc ctaaactgct gatattcggg gcatccaacc ggtactctgg ggtccccgat 180

```
cgcttcacag gcagtggatc tgcaacagat ttcactctga ccatcagcag tgtgcaggct    240

gaagaccttg cagattatca ctgtggaagc aagtggatta ctagctatcc gtacacgttc    300

ggagggggga ccaagctgga aataaaacg                                      329


<210> SEQ ID NO 231
<211> LENGTH: 326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231

aacattttaa tgacccaatc tcccaaatcc atgtccatgt cagtaggaga gagggtcacc     60

ttgacctgca aggccagtga gaatgtggtt aattatgttt cctggtatca acagaaacca    120

gagcagtctc ctaaactgct gatatacggg gcatccaacc ggtactctgg ggtccccgat    180

cgcttcacag gcagtggatc tgcaacagat ttcactctga ccatcagcag tgtgcaggct    240

gaagaccttg cagattatca ctgtggagca agggttacta gctatccgta cacgttcgga    300

ggggggacca agctggaaat aaaacg                                         326


<210> SEQ ID NO 232
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232

caggttcagc tgcagcagtc tgacgctgag ttggtgaaac ctgggacttc agtgaagata     60

tcctgcaggg cttctggcta caccttcact gaccatgcta ttcactgggt gaagcagaag    120

cctgaacagg gcctggaatg gattggatat atttctcccg gaaatggtga tattaagtac    180

aatgagaagt tcaagggcaa ggccacactg actgcagaca aatcctccag cactgcctac    240

atgcagctca acagcctgac atctgacgat tctgcagtgt atttctgtaa aagatccatt    300

actacgcctt actggggcca aggcaccact ctcacagtct cctca                    345


<210> SEQ ID NO 233
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233

agttttgtga tgacccagac tcccaaattc ctgcttgtgt cagcaggaga cagggttacc     60

ataacctgca aggccagtca gagtgtgaat aataatgtag cttggtacca acagaagcca    120

gggcagtctc ctaaacagct gatatactat gcatccaatc gctacactgg agtccctgat    180

cgcttcactg gcagtggata tgggacggat ttcactttca ccatctacac tgtgcaggct    240

gaagacctgg cagtttattt ctgtcagcag ggttatagct ctccgtggac gttcggtgga    300

ggcaccaagc tgaaa                                                     315


<210> SEQ ID NO 234
<211> LENGTH: 330
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 234

Ala Lys Thr Thr Ala Pro Ser Val Tyr Pro Leu Ala Pro Val Cys Gly
1 5 10 15

Asp Thr Thr Gly Ser Ser Val Thr Leu Gly Cys Leu Val Lys Gly Tyr
20 25 30

Phe Pro Glu Pro Val Thr Leu Thr Trp Asn Ser Gly Ser Leu Ser Ser
35 40 45

Gly Val His Thr Phe Pro Ala Val Leu Gln Ser Asp Leu Tyr Thr Leu
50 55 60

Ser Ser Ser Val Thr Val Thr Ser Ser Thr Trp Pro Ser Gln Ser Ile
65 70 75 80

Thr Cys Asn Val Ala His Pro Ala Ser Ser Thr Lys Val Asp Lys Lys
85 90 95

Ile Glu Pro Arg Gly Pro Thr Ile Lys Pro Cys Pro Pro Cys Lys Cys
100 105 110

Pro Ala Pro Asn Leu Leu Gly Gly Pro Ser Val Phe Ile Phe Pro Pro
115 120 125

Lys Ile Lys Asp Val Leu Met Ile Ser Leu Ser Pro Ile Val Thr Cys
130 135 140

Val Val Val Asp Val Ser Glu Asp Asp Pro Asp Val Gln Ile Ser Trp
145 150 155 160

Phe Val Asn Asn Val Glu Val His Thr Ala Gln Thr Gln Thr His Arg
165 170 175

Glu Asp Tyr Asn Ser Thr Leu Arg Val Val Ser Ala Leu Pro Ile Gln
180 185 190

His Gln Asp Trp Met Ser Gly Lys Glu Phe Lys Cys Lys Val Asn Asn
195 200 205

Lys Asp Leu Pro Ala Pro Ile Glu Arg Thr Ile Ser Lys Pro Lys Gly
210 215 220

Ser Val Arg Ala Pro Gln Val Tyr Val Leu Pro Pro Pro Glu Glu Glu
225 230 235 240

Met Thr Lys Lys Gln Val Thr Leu Thr Cys Met Val Thr Asp Phe Met
245 250 255

Pro Glu Asp Ile Tyr Val Glu Trp Thr Asn Asn Gly Lys Thr Glu Leu
260 265 270

Asn Tyr Lys Asn Thr Glu Pro Val Leu Asp Ser Asp Gly Ser Tyr Phe
275 280 285

Met Tyr Ser Lys Leu Arg Val Glu Lys Lys Asn Trp Val Glu Arg Asn
290 295 300

Ser Tyr Ser Cys Ser Val Val His Glu Gly Leu His Asn His His Thr
305 310 315 320

Thr Lys Ser Phe Ser Arg Thr Pro Gly Lys
325 330

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 235

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

Thr Tyr Ser Met Ser Ser Thr Leu Thr Leu Thr Lys Asp Glu Tyr Glu
65 70 75 80

Arg His Asn Ser Tyr Thr Cys Glu Ala Thr His Lys Thr Ser Thr Ser
85 90 95

Pro Ile Val Lys Ser Phe Asn Arg Asn Glu Cys
100 105

<210> SEQ ID NO 236
<211> LENGTH: 446
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 236

Gln Val Gln Leu Gln Gln Ser Asp Ala Glu Leu Val Lys Pro Gly Ala
1 5 10 15

Ser Val Lys Ile Ser Cys Lys Ala Ser Gly Tyr Thr Phe Thr Asp His
20 25 30

Ala Ile His Trp Val Lys Gln Lys Pro Glu Gln Gly Leu Asp Trp Ile
35 40 45

Gly Tyr Ile Ser Pro Gly Asn Gly Asp Ile Lys Tyr Asn Glu Lys Phe
50 55 60

Lys Asp Lys Val Thr Leu Thr Ala Asp Lys Ser Ser Ser Thr Ala Cys
65 70 75 80

Met His Leu Asn Ser Leu Thr Ser Glu Asp Ser Ala Val Tyr Phe Cys
85 90 95

Lys Arg Ser Leu Leu Ala Leu Asp Tyr Trp Gly Gln Gly Thr Thr Leu
100 105 110

Thr Val Ser Ser Ala Lys Thr Thr Ala Pro Ser Val Tyr Pro Leu Ala
115 120 125

Pro Val Cys Gly Asp Thr Thr Gly Ser Ser Val Thr Leu Gly Cys Leu
130 135 140

Val Lys Gly Tyr Phe Pro Glu Pro Val Thr Leu Thr Trp Asn Ser Gly
145 150 155 160

Ser Leu Ser Ser Gly Val His Thr Phe Pro Ala Val Leu Gln Ser Asp
165 170 175

Leu Tyr Thr Leu Ser Ser Ser Val Thr Val Thr Ser Ser Thr Trp Pro
180 185 190

Ser Gln Ser Ile Thr Cys Asn Val Ala His Pro Ala Ser Ser Thr Lys
195 200 205

Val Asp Lys Lys Ile Glu Pro Arg Gly Pro Thr Ile Lys Pro Cys Pro
210 215 220

Pro Cys Lys Cys Pro Ala Pro Asn Leu Leu Gly Gly Pro Ser Val Phe
225 230 235 240

```
Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445


<210> SEQ ID NO 237
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237

atggagaccg acaccctgct gctctgggtg ctgctgctct gggtgcccgg ctccaccgga     60

caggttcagc tgcagcagtc tgacgctgag ttggtgaaac ctggggcttc agtgaagata    120

tcctgcaagg cttctggcta caccttcact gaccatgcta ttcactgggt gaagcaaaag    180

cctgaacagg gcctggactg gattggatat atttctcccg gaaatggtga tattaagtac    240

aatgagaagt tcaaggacaa ggtcacactg actgcagaca aatcctccag cactgcctgc    300

atgcacctca acagcctgac atctgaggat tctgcagtgt atttctgcaa aagatcccta    360

ctagctcttg actactgggg ccaaggcacc actctcacag tctcctcagc taaaacaaca    420

gccccatcgg tctatccact ggcccctgtg tgtggagata caactggctc ctcggtgact    480

ctaggatgcc tggtcaaggg ttatttccct gagccagtga ccttgacctg gaactctggt    540

tccctgtcca gtggtgtgca caccttccca gctgtcctgc agtctgacct ctacaccctc    600

agctcaagcg tgactgtaac cagctcgacc tggcccagcc agtccatcac ctgcaatgtg    660

gcccacccgg caagcagcac caaggtggac aagaaaattg agcccagagg gcccacaatc    720

aagccctgtc ctccatgcaa atgcccagca cctaacctct tgggtggacc atccgtcttc    780

atcttccctc caaagatcaa ggatgtactc atgatctccc tgagccccat agtcacatgt    840

gtagtcgttg atgtgagcga ggatgaccca gatgtccaga tcagctggtt tgtgaacaac    900
```

```
gtggaagtgc acactgctca gacacagacg catagagagg attacaacag tactctccgg    960

gttgtcagtg ccctccccat ccagcaccag gactggatga gtggcaagga gttcaaatgc   1020

aaggtcaaca acaaagacct cccagcgccc atcgagagaa ccatctcaaa acccaaaggg   1080

tcagtaagag ctccacaggt atatgtcttg cctccaccag aagaggagat gactaagaaa   1140

caggtcactc tgacctgcat ggtcacagac ttcatgcctg aagacattta cgtggagtgg   1200

accaacaacg ggaaaacaga gctaaactac aagaacactg aaccagtcct ggactctgat   1260

ggttcttact tcatgtacag caagctgaga gtggagaaga agaactgggt ggagagaaat   1320

agctactcct gttcagtggt ccacgagggt ctgcacaatc accacacgac taagagcttc   1380

tcccggactc cgggtaaata g                                             1401
```

<210> SEQ ID NO 238
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 238

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Asn
            20                  25                  30

Ile Ala Trp Tyr Gln Gln Lys Pro Gly Arg Ser Pro Lys Val Leu Ile
        35                  40                  45

Tyr Ser Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Ser Phe Pro Leu
                85                  90                  95

Thr Phe Gly Val Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 239
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 239 atggagaccg acaccctgct gctctgggtg ctgctgctct gggtgcccgg ctccaccgga 60 gacattgtga tgacccagtc tcacaaattc atgtccacat cagtaggaga cagggtcagc 120 atcacctgca aggccagtca ggatgtgggc actaatatag cctggtatca acagaaacca 180 ggccgatctc ctaaagtact gatttactcg gcatccaccc ggcacactgg agtccctgat 240 cgcttcacag gcagtggatc tgggacagat ttcactctca ccattagcaa tgtgcagtct 300 gaagacttga cagattattt ctgtcagcaa tatagcagct ttcctctcac gttcggtgtt 360 gggaccaagc tggagctgaa acgggcagat gctgcaccaa ctgtatccat cttcccacca 420 tccagtgagc agttaacatc tggaggtgcc tcagtcgtgt gcttcttgaa caacttctac 480 cccaaagaca tcaatgtcaa gtggaagatt gatggcagtg aacgacaaaa tggcgtcctg 540 aacagttgga ctgatcagga cagcaaagac agcacctaca gcatgagcag caccctcacg 600 ttgaccaagg acgagtatga acgacataac agctatacct gtgaggccac tcacaagaca 660 tcaacttcac ccattgtcaa gagcttcaac aggaatgagt gttga 705

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Cys Gln Phe Asp Leu Ser Thr Arg Arg Leu Lys Cys
1 5 10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Cys Gln Tyr Asn Leu Ser Ser Arg Ala Leu Lys Cys
1 5 10

<210> SEQ ID NO 242
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Lys Asp Glu Leu
1

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
peptide -continued

```
<400> SEQUENCE: 243

Glu Gln Lys Leu Ile Ser Glu Glu Asp Leu
1               5                   10


<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp Tyr Lys Asp Asp Asp Asp Lys
1               5
```

The invention claimed is:

1. A method of reducing tumor volume comprising administering an antibody that specifically binds to sialyl Tn antigen (STn) to a subject, wherein said subject has a tumor comprising STn, wherein said antibody is administered at a dose of from about 0.25 mg/kg to about 25 mg/kg, and wherein said antibody comprises:

a heavy chain variable domain (VH) comprising:

a complementarity determining region (CDR)-H1 comprising the amino acid sequence of SEQ ID NO: [143] *81*:

a CDR-H2 comprising the amino acid sequence of SEQ ID NO: [146] *84*; and a CDR-H3 comprising the amino acid sequence of SEQ ID NO: [153] *96*;

a light chain variable domain (VL) comprising:

a CDR-L1 comprising the amino acid sequence of SEQ ID NO: [161] *108*;

a CDR-L2 comprising the amino acid sequence of SEQ ID NO: 123; and a CDR-L3 comprising the amino acid sequence of SEQ ID NO: 135; and a conjugated cytotoxic agent, thereby reducing the volume of said tumor comprising STn in said subject.

2. The method of claim 1, wherein said antibody is a monoclonal antibody.

3. The method of claim 1, wherein said antibody comprises an IgG1 isotype.

4. The method of claim 1, wherein said antibody comprises an IgG2 isotype.

5. The method of claim 1, wherein said conjugated cytotoxic agent comprises monomethyl auristatin E.

6. The method of claim 1, wherein tumor volume in said subject is reduced by at least 20%.

7. The method of claim 6, wherein tumor volume in said subject is reduced by from about 80% to about 99%.

8. The method of claim 7, wherein said conjugated cytotoxic agent comprises monomethyl auristatin E.

9. A composition comprising:

(a) an antibody that specifically binds to sialyl Tn antigen (STn), said antibody comprising:

a VH comprising:

a CDR-H1 comprising the amino acid sequence of SEQ ID NO: [143] *81*;

a CDR-H2 comprising the amino acid sequence of SEQ ID NO: [146] *84*; and a CDR-H3 comprising the amino acid sequence of SEQ ID NO: [153] *96*; and a VL comprising:

a CDR-L1 comprising the amino acid sequence of SEQ ID NO: [161] *108*;

a CDR-L2 comprising the amino acid sequence of SEQ ID NO: 123; and a CDR-L3 comprising the amino acid sequence of SEQ ID NO: 135; and (b) an excipient, said excipient comprising from about 2 mM to about 100 mM citrate and from about 10 mM to about 300 mM NaCl.

10. The composition of claim 9, wherein said antibody is conjugated to a drug.

11. A method of treating cancer that expresses sialyl Tn antigen (STn) comprising administering a composition to a subject, wherein said subject comprises at least one cancer cell that expresses STn, and wherein said composition comprises:

(a) an antibody that specifically binds to STn comprising:

a VH comprising:

a CDR-H1 comprising the amino acid sequence of SEQ ID NO: [143] *81*;

a CDR-H2 comprising the amino acid sequence of SEQ ID NO: [146] *84*; and a CDR-H3 comprising the amino acid sequence of SEQ ID NO: [153] *96*;

a VL comprising:

a CDR-L1 comprising the amino acid sequence of SEQ ID NO: [161] *108*;

a CDR-L2 comprising the amino acid sequence of SEQ ID NO: 123; and a CDR-L3 comprising the amino acid sequence of SEQ ID NO: 135; and a conjugated cytotoxic agent; and (b) an excipient, said excipient comprising from about 2 mM to about 100 mM citrate and from about 10 mM to about 300 mM NaCl, thereby treating said cancer in said subject.

12. The method of claim 11, wherein said conjugated cytotoxic agent comprises monomethyl auristatin E.

13. The method of claim 1, wherein STn is present on the surface of at least one cell of said tumor comprising STn.

14. The method of claim 11, wherein STn is present on the surface of said at least one cancer cell that expresses STn.

15. A method of treating cancer that expresses sialyl Tn antigen (STn) comprising administering an antibody that specifically binds to STn to a subject, wherein said subject includes at least one cancer cell that expresses cell surface STn, wherein said antibody is administered at a dose of from about 0.25 mg/kg to about 25 mg/kg, and wherein said antibody comprises:

a VH comprising:

a CDR-H1 comprising the amino acid sequence of SEQ ID NO: [143] *81*;

a CDR-H2 comprising the amino acid sequence of SEQ ID NO: [146] *84*; and a CDR-H3 comprising the amino acid sequence of SEQ ID NO: [153] *96*;

a VL comprising:

a CDR-L1 comprising the amino acid sequence of SEQ ID NO: [161] *108*;

a CDR-L2 comprising the amino acid sequence of SEQ ID NO: 123; and a CDR-L3 comprising the amino acid sequence of SEQ ID NO: 135; and wherein said antibody comprises an Fc region capable of promoting antibody-dependent cell-mediated cytotoxicity, antibody-dependent cell phagocytosis, and/or complement-dependent cytotoxicity directed against said at least one cancer cell in said subject or wherein said antibody includes a conjugated cytotoxic agent, thereby treating said cancer in said subject.

16. The method of claim 15, wherein said antibody includes a conjugated cytotoxic agent, wherein said conjugated cytotoxic agent is conjugated directly or via a linker.

17. The method of claim 16, wherein said conjugated cytotoxic agent comprises a cytoskeletal inhibitor.

18. The method of claim 17, wherein said cytoskeletal inhibitor is monomethyl auristatin E.

19. The composition of claim 10, wherein said drug is conjugated directly or via a linker.

20. The composition of claim 19, wherein said drug is a cytotoxic agent.

21. The composition of claim 20, wherein said cytotoxic agent is monomethyl auristatin E.

* * * * *